(12) United States Patent
Cramer, Jr. et al.

(10) Patent No.: US 12,116,579 B2
(45) Date of Patent: Oct. 15, 2024

(54) COMPOSITIONS AND METHODS RELATED TO FUNGAL HYPOXIA RESPONSIVE MORPHOLOGY FACTOR A (HRMA) AND BIOFILM ARCHITECTURE FACTOR (BAF) PROTEINS

(71) Applicant: THE TRUSTEES OF DARTMOUTH COLLEGE, Hanover, NH (US)

(72) Inventors: Robert A. Cramer, Jr., Hanover, NH (US); Caitlin Kowalski, Hanover, NH (US)

(73) Assignee: THE TRUSTEES OF DARTMOUTH COLLEGE, Hanover, NH (US)

(*) Notice: Subject to any disclaimer, the term of this patent is extended or adjusted under 35 U.S.C. 154(b) by 0 days.

(21) Appl. No.: 17/642,592

(22) PCT Filed: Sep. 11, 2020

(86) PCT No.: PCT/US2020/050352
§ 371 (c)(1),
(2) Date: Mar. 11, 2022

(87) PCT Pub. No.: WO2021/050840
PCT Pub. Date: Mar. 18, 2021

(65) Prior Publication Data
US 2023/0135464 A1    May 4, 2023

Related U.S. Application Data

(60) Provisional application No. 62/899,660, filed on Sep. 12, 2019, provisional application No. 63/006,930, filed on Apr. 8, 2020.

(51) Int. Cl.
*C12N 15/80* (2006.01)
*C07K 14/38* (2006.01)
*C12N 15/52* (2006.01)

(52) U.S. Cl.
CPC ............ *C12N 15/80* (2013.01); *C07K 14/38* (2013.01); *C12N 15/52* (2013.01)

(58) Field of Classification Search
CPC ......... C12N 15/80; C12N 15/52; C07K 14/38
See application file for complete search history.

(56) References Cited

U.S. PATENT DOCUMENTS

| | | |
|---|---|---|
| 2010/0015663 A1 | 1/2010 | Lubeck et al. |
| 2015/0361471 A1 | 12/2015 | Panaccione et al. |
| 2016/0040202 A1 | 2/2016 | Hua et al. |
| 2017/0313997 A1 | 11/2017 | Udagawa |

FOREIGN PATENT DOCUMENTS

| | | |
|---|---|---|
| EP | 2 169 068 A1 | 3/2010 |
| JP | 2012-157315 A | 8/2012 |
| WO | 2008/053018 A2 | 5/2008 |
| WO | 2010/032230 A9 | 3/2010 |
| WO | 2014/114810 A1 | 7/2014 |

OTHER PUBLICATIONS

Heu et al. Nucleotide Sequence and Properties of the hrmA Locus Associated with the *Pseudomonas syringae* pv. syringae 61 hrp Gene Cluster. MPMI (1993), 6(5): 553-564. (Year: 1993).*
Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10: 8-9. (Year: 2002).*
Kaur et al. Biofilm formation by Aspergillus fumigatus. Medical Mycology (2014), 52: 2-9, Epub Aug. 21, 2013. (Year: 2013).*
Bennett et al. (1998) "Mycotechnology: the role of fungi in biotechnology", J Biotechnol. vol. 66, pp. 101-107.
Fong et al. (Apr. 2015) "Biofilm Matrix Proteins", Microbiology Spectrum, vol. 3, pp. 1-27.
Kowalski et al. (Sep. 2016) "Heterogeneity among Isolates Reveals that Fitness in Low Oxygen Correlates with Aspergillus fumigatus Virulence", MBio, vol. 7, pii: e01515-16.
Kowalski et al. (Sep. 2019) "Fungal biofilm morphology impacts hypoxia fitness and disease progression", Nature Microbiology, vol. 4, pp. 2430-2441.
Max et al. (Oct. 2010) "Biotechnological production of citric acid", Braz J Microbiol, vol. 41, pp. 862-875.
Show et al. (Apr. 2015) "Overview of citric acid production from Aspergillus niger" Frontiers in Life Science, vol. 8, pp. 271-283.

(Continued)

*Primary Examiner* — Iqbal H Chowdhury
(74) *Attorney, Agent, or Firm* — Cozen O'Connor

(57) ABSTRACT

Filamentous fungal host cells expressing hypoxia responsive morphology factor A (hrmA) and biofilm architecture factor (baf) proteins are provided. Methods of producing filamentous fungal host cells expressing hrmA and baf proteins are also provided. In one aspect, the disclosure provides a filamentous fungal host cell, comprising a nucleotide sequence encoding an *Aspergillus fumigatus* hypoxia responsive morphology factor A (hrmA) protein, or a homolog or ortholog thereof.

7 Claims, 67 Drawing Sheets
Specification includes a Sequence Listing.

(56) References Cited

OTHER PUBLICATIONS

International Search Report and Written Opinion received for PCT Patent Application No. PCT/US2020/050352, dated Feb. 9, 2021, 17 Pages.
Fedorova N.D.: "Genomic islands in the pathogenic filamentous fungus Aspergillus fumigatus", Jul. 26, 2016, XP093134735, URL: https://www.ncbi.blm.nih.gov/protein/E DP47808.I?report=genbank &log$=protalign&bl ast_rank=I&RID=XTDWG735013.
Pel H.J.: "Genome sequencing and analysis of th versatile cell factory Aspergillus niger CBS 513.88", Mar. 14, 2015 (Mar. 14, 2015), XP093134761, URL:https://www.ncbi.nlm.nih.gov/protein/C AK40077.I.
Extended European Search Report in corresponding EP Application No. 20862695.2, dated Mar. 18, 2024, 18 pages.

\* cited by examiner

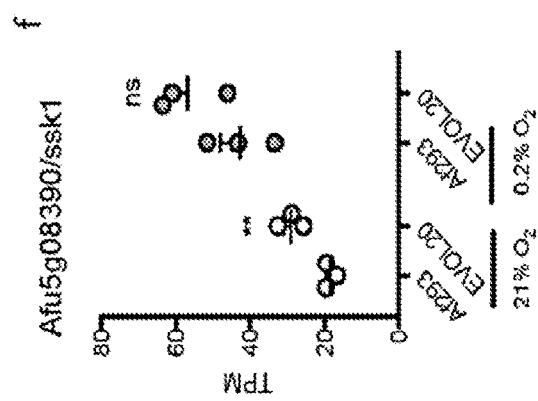
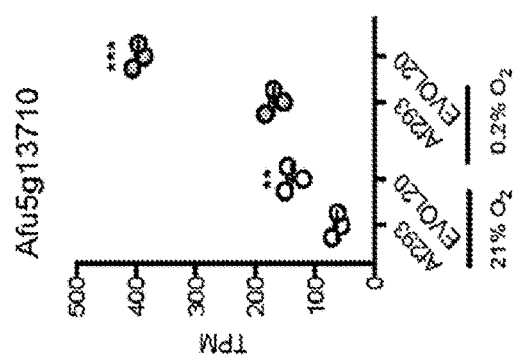
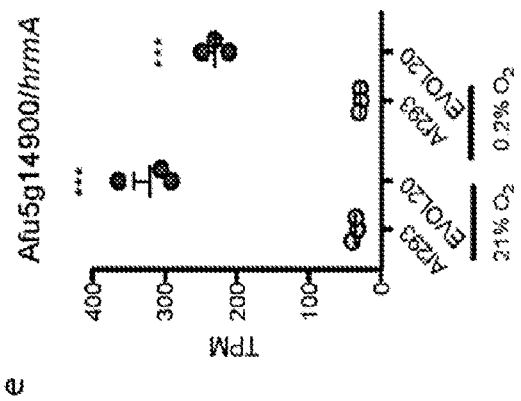
Fig. 2

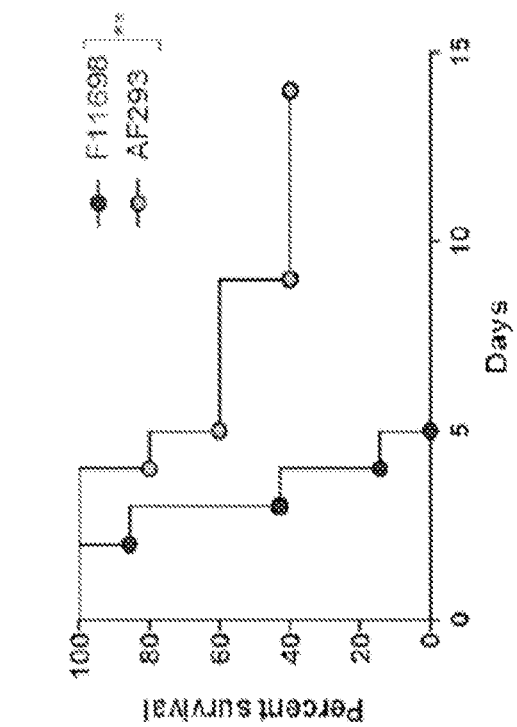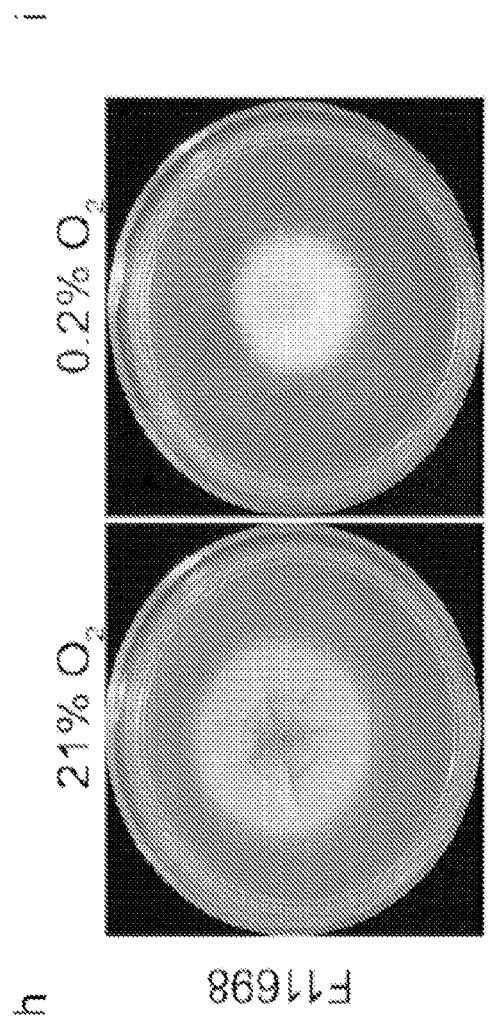
Fig. 5

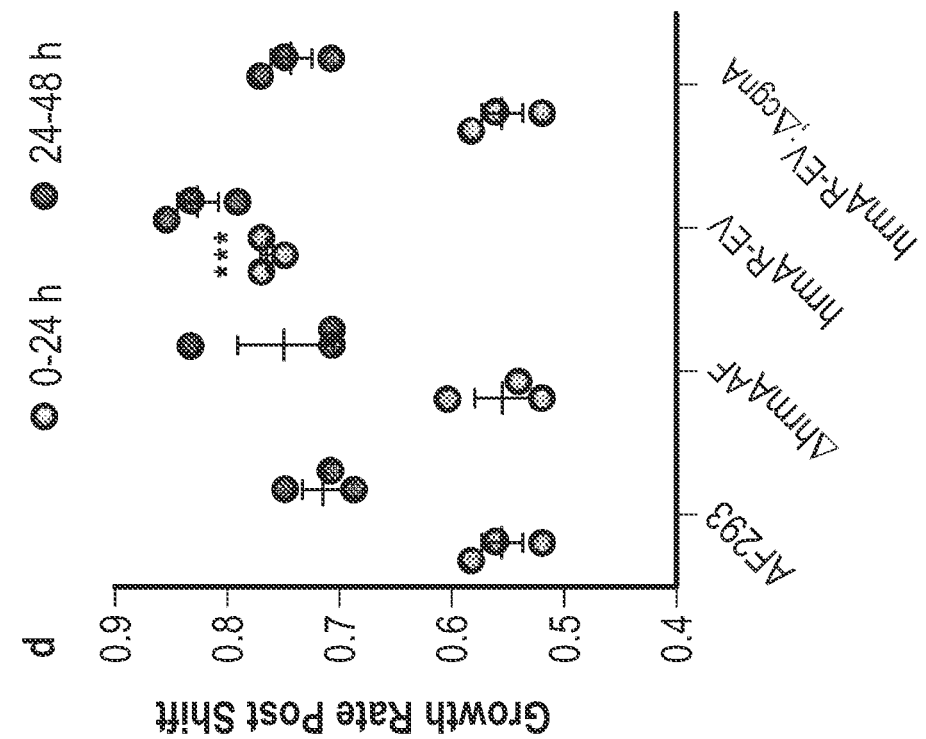
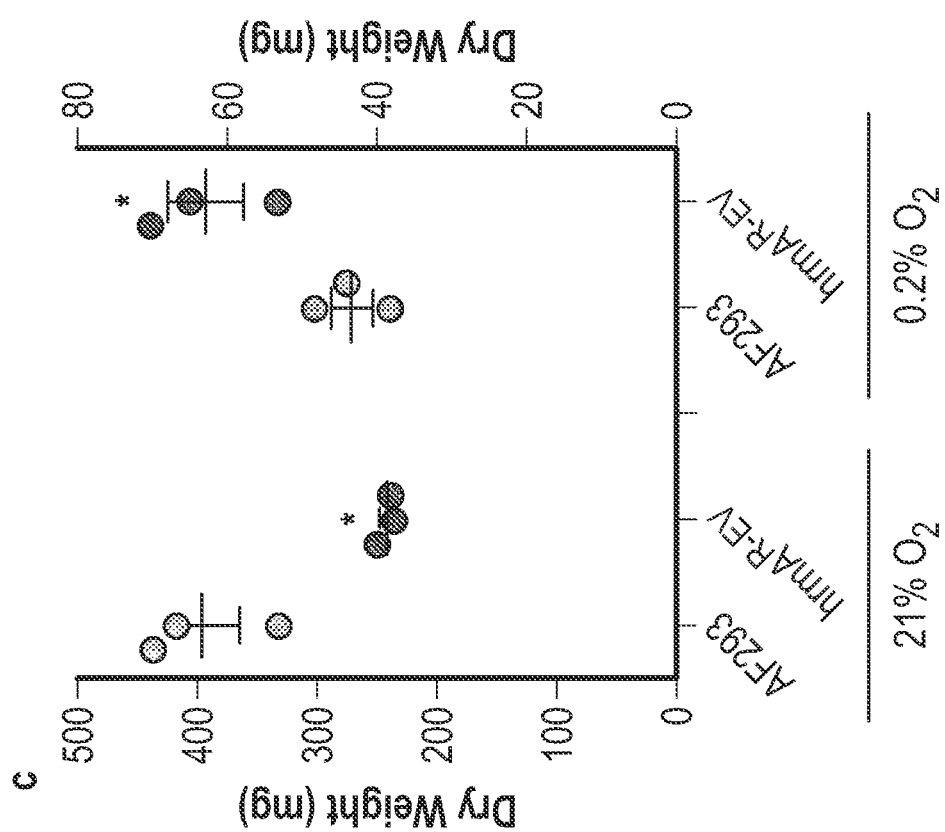
FIG. 8

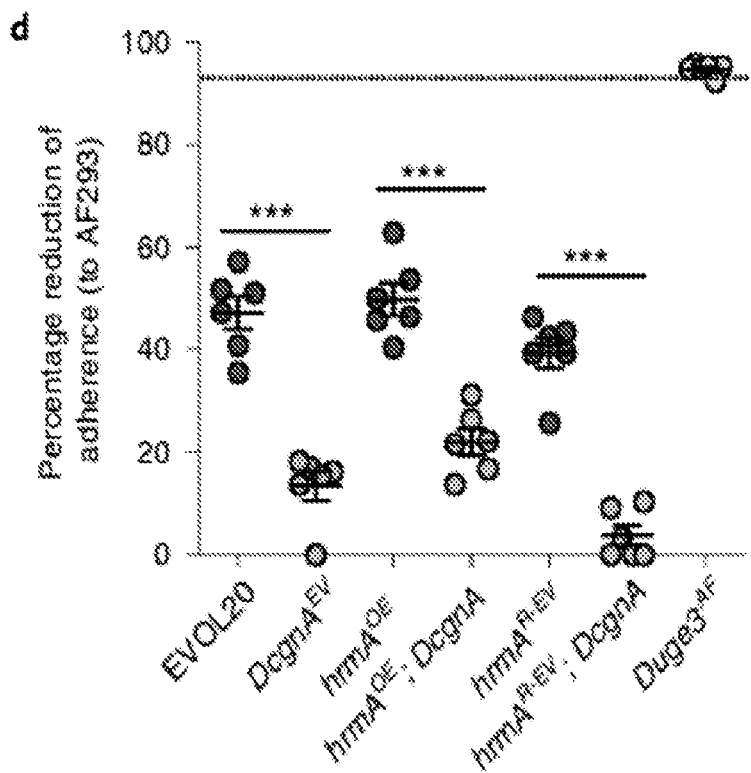
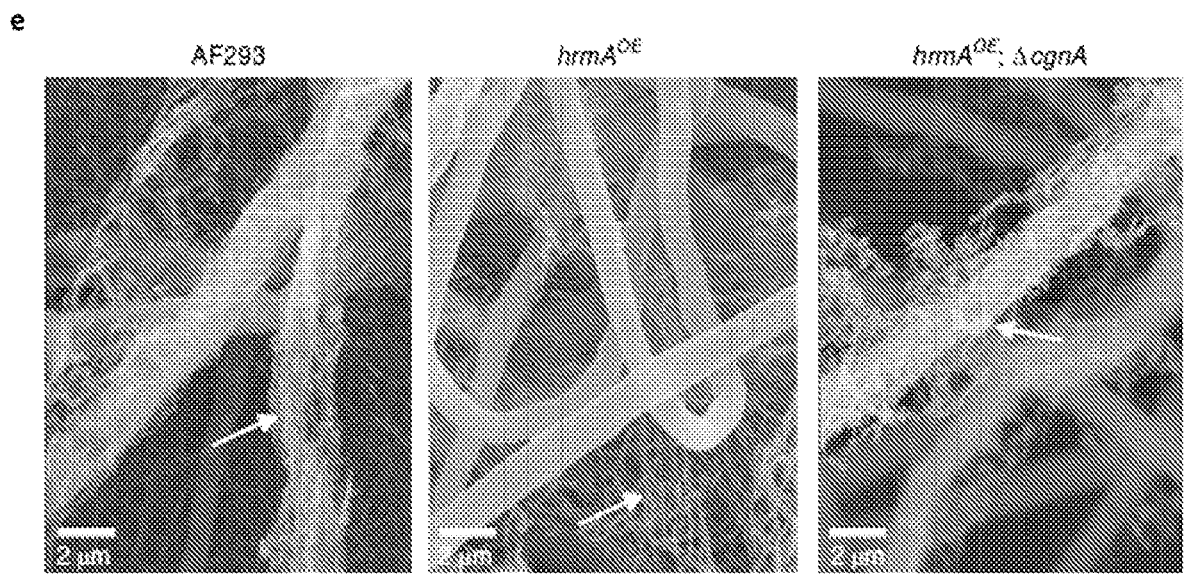
Fig. 12

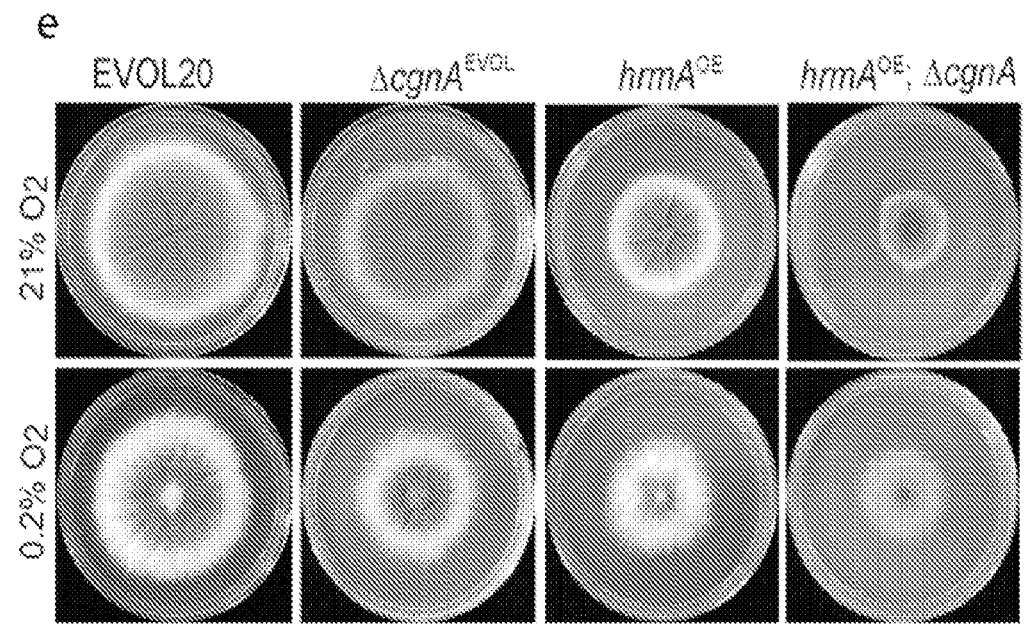
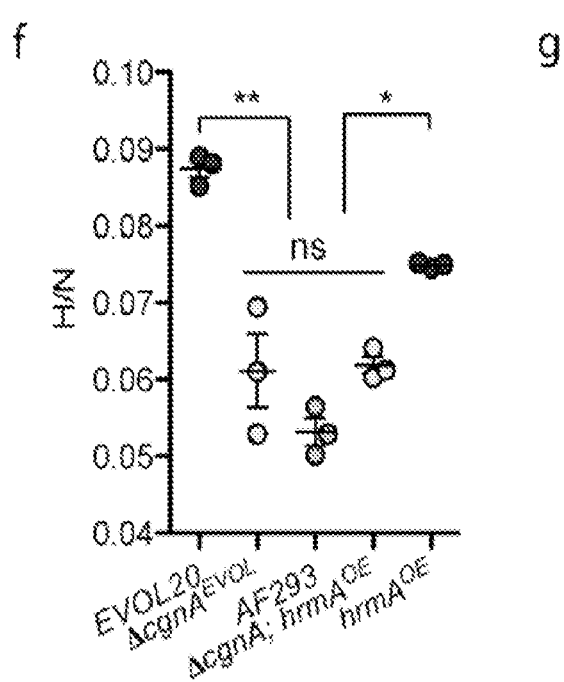
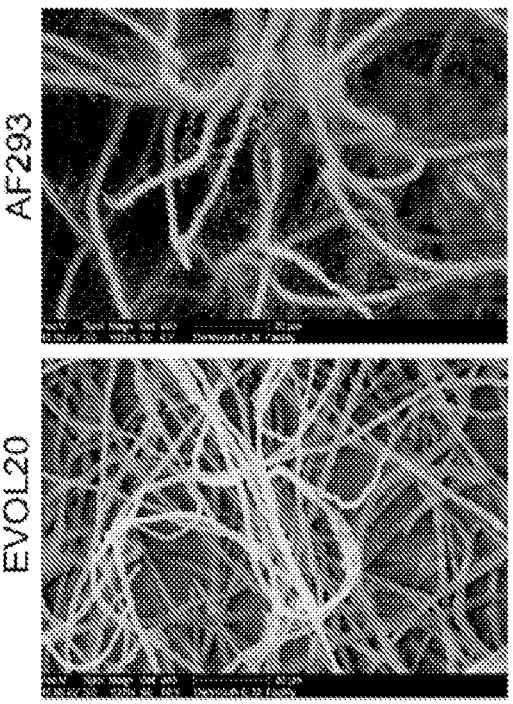
*Fig. 13*

FIG. 21

```
An08g12010    MAWYSALLPCMLWWRNLLWRNSTNRYRQSTDDLTSLTDKIPNLGERLPNL--LSFVNS----    56
AFUB_044360   MVWYRAILVCMPWWL--MGRNSTNEGKRSEGERAPMIDKVPTFEEMTITTSAKYVNGEKI    58
Afu5g14915    MAWYRALLPCIPLMRKVLGRNSTDEDGRSEDDLTSLSDKMPTFEET--TTSAKYINGEKI    58
              *.**.*:*: **      *..:   .   :  :  *****.:.*      ..:;*:.

An08g12010    -----------I--PDQ-------------------STTAGKINHKALRDPELFA       79
AFUB_044360   MEHTVVETKQIDNRGDTSVSNNDSNSTAETRHSGLSSVSHSDQSKVVEDANALEKPELFA   118
Afu5g14915    MEHTVVETKHIDERGDTSVSNGDSNSTAVTRHSGLSSVSLSDQSTIVEDANALEEPELFA   118
                            *   * .:                     . *       *****

An08g12010    IRSSCIDKSASKWMVSLYYEPPFSLDDLEIKNFGSRIPESEDDPIEAIFHYEGENIWVSV   139
AFUB_044360   VHSPYVDASTGKQMLRLYYELPVSLDDLEITGLESRIPESDDDSIEACFCYRGEKFWLHV   178
Afu5g14915    VHSPYVDDSTGEQMVRLYYELPVSLDDLEIIGLESRIPESDDDSIEARFRYRGEDFWLPV   178
              ::*  :**::.:: .:*** *.***** ****** . **     :.:.: :  *:.* *

An08g12010    PYLYARTRSLSSGLF     154    SEQ ID NO:16
AFUB_044360   PYSYAKARMVLMGVY     193    SEQ ID NO:32
Afu5g14915    RYSYAKARMVLTGVC     193    SEQ ID NO:33
              * **:;** :  *  :
```

Fig. 25

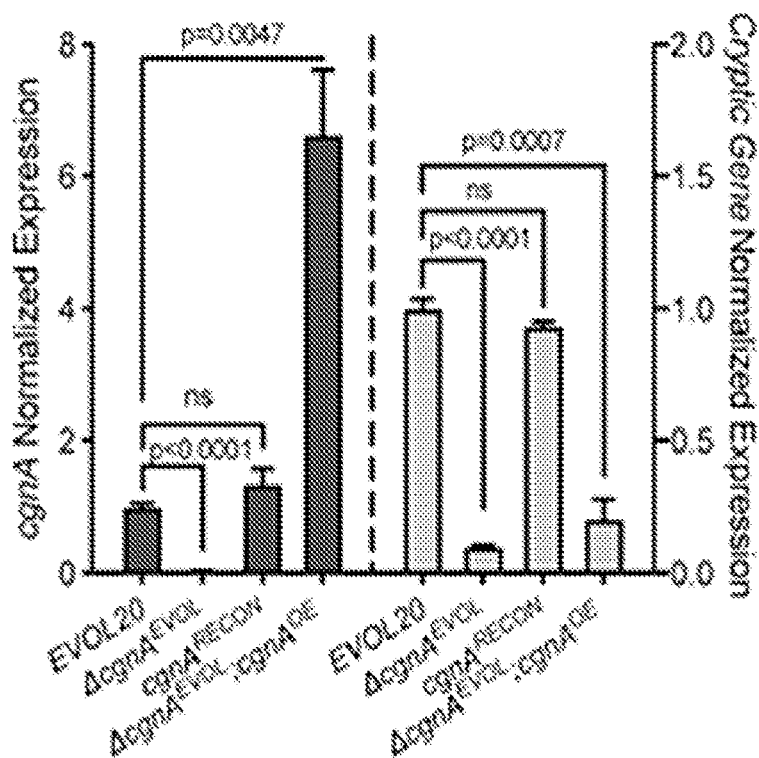
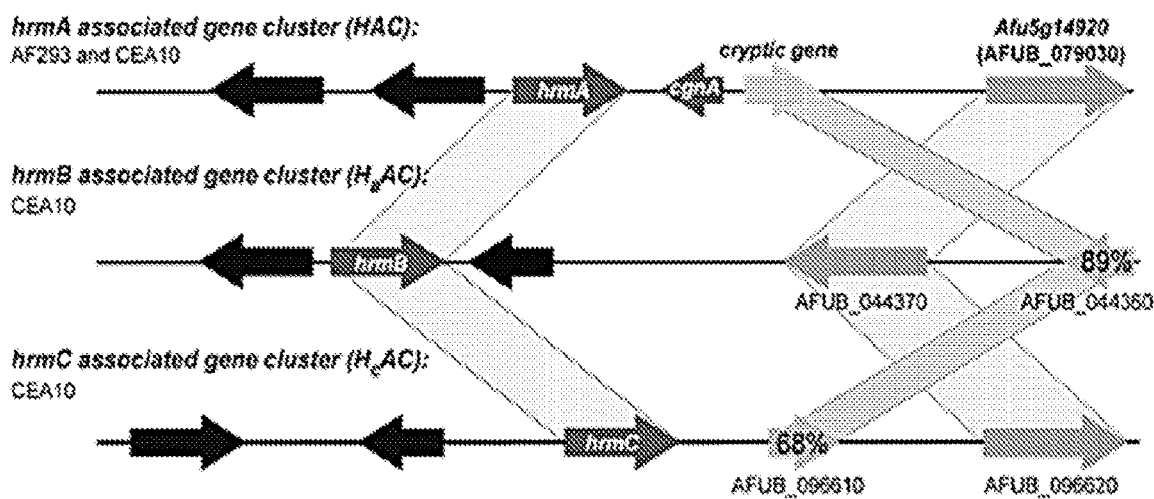
Fig. 28

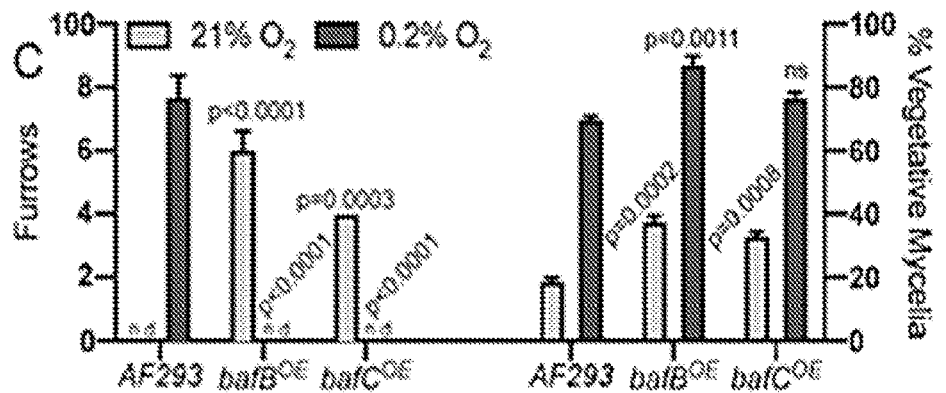
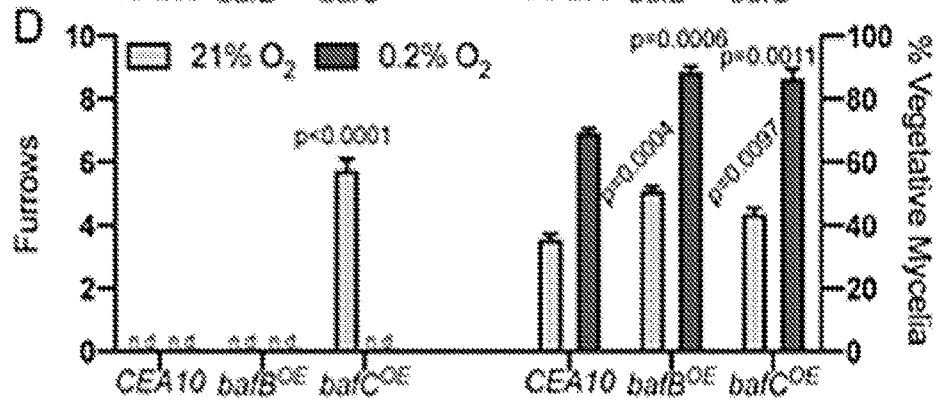
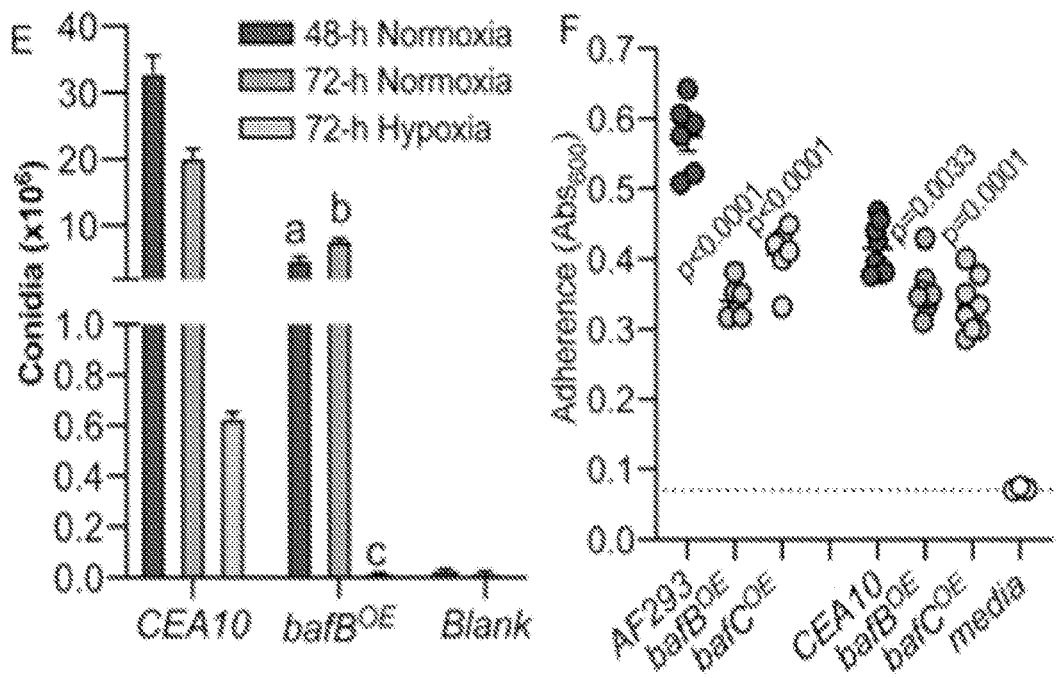
*Fig. 31*

C
An A1144
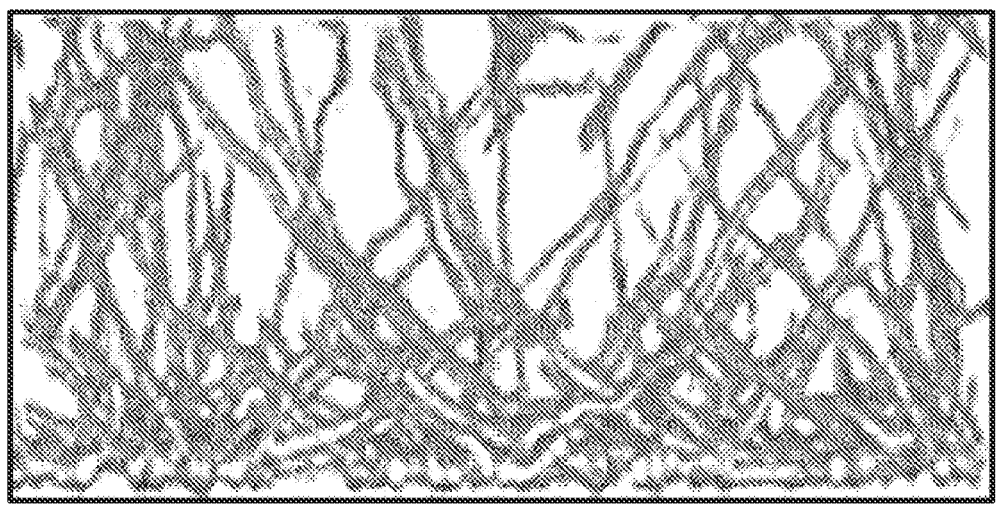
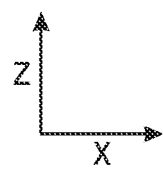
An Af*bafA*$^{OE}$
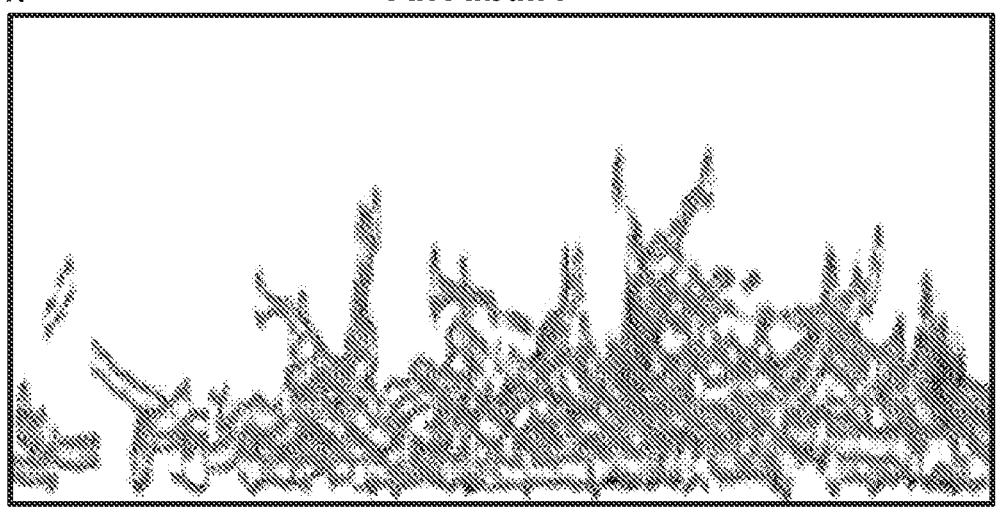
200 μm
FIG. 32

```
                         SEQUENCE LISTING

<160> NUMBER OF SEQ ID NOS: 33

<210> SEQ ID NO 1
<211> LENGTH: 1142
<212> TYPE: DNA
<213> ORGANISM: Artificial Sequence
<220> FEATURE:
<223> OTHER INFORMATION: Artificial polynucleotide sequence

<400> SEQUENCE: 1
atggcatcca caaagcccgc ttcgagtctc atttaccagg catggaacaa actcagtatc      60
aaccaaacca tccctagtga ctcccttgaa ttacttgggg agcgtttggc tattgccttc     120
gcacccaaac tcaaggagca acgaaggaat ggccggcgtc ggaatctgga atatgtggca    180
caacatcgac ggaagattgc tcgaaaaatc tacttggaga ttctggagaa agacccaaat    240
atctttcttc cttttatcct ggctgtttcc cctagagcat gcttatcctt tgatatctcg     300
agctttcttg aacagcacca aagccaagga agacatttcc tccgcaacaa tgccgaagcg    360
atcctctggg gtctcgcaaa gaaacatgac attgatggct ccctccattt caggaagctg    420
atgcgtgaga ttttccaact gtctcctcca gcgacagaag ccgaaggcaa ggagcattat    480
tcattgcatt taagcactct ccccgcaatc cgcaatgcct tcggtgatgt tatctttgac    540
gcaattgaac gttcccctac acaggtgaca gcgagagcta aaggttattt ctctgagaaa    600
accgaaagtg tttggacaaa agttccctac agaagttctc aagacgcaat catatctctt    660
gaagtagggt cggcaatcga gcttgcgaat gtgttgttcc caatcgcaac ccaaaaaatt    720
gtctctatcc tttccgcatg ttctcccact gtgcgccaga agaacttttc tgaggctatt    780
ctcggcccag accctcagga tacaccggca acatcatcag aaatcggtat gaagtttaag    840
gtacacatga ctgcagttgc taattccacc ctgtgctaga tgtggcgtat tttactctgc    900
gaggagcaac ggtctcggca attgaatcag tctttcgcgc tgatatttgc gaaggtatta    960
agggcagcga actgagaaac tgggaaaagg agcagctgct catcgacacg acagattgtg   1020
tcacgatgca gatatggcgg gcacaacctc aacatggaac catcaagttg cgtattggat   1080
tctatgcagc ggtgaatttg gcaaatcggc tgtatgcaga aacaccccaa gatcacatat   1140
ag                                                                  1142

<210> SEQ ID NO 2
<211> LENGTH: 8855
<212> TYPE: DNA
<213> ORGANISM: Artificial Sequence
<220> FEATURE:
<223> OTHER INFORMATION: Artificial polynucleotide sequence

<400> SEQUENCE: 2
cgccgtaacg taacaaagcg gggttggtag tgtttgcaaa tgcattcaca tggaccgatc      60 actttcttt ccagtctgtc cattctgtcc aatctgtccg atctgacctg cccagtctgt     120
ccagtctgtc ccttgtgtcg tccgatccaa gctggttatc atggcatcca caaagcccgc    180
ttcgagtctc atttaccagg catggaacaa actcagtatc aaccaaacca tccctagtga    240
```

```
ctcccttgaa ttacttgggg agcgtttggc tattgccttc gcacccaaac tcaaggagca    300
acgaaggaat ggccggcgtc ggaatctgga atatgtggca caacatcgac ggaagattgc    360
tcgaaaaatc tacttggaga ttctggagaa agacccaaat atctttcttc cttttatcct    420
ggctgtttcc cctagagcat gcttatcctt tgatatctcg agctttcttg aacagcacca    480
aagccaagga agacatttcc tccgcaacaa tgccgaagcg atcctctggg gtctcgcaaa    540
gaaacatgac attgatggct ccctccattt caggaagctg atgcgtgaga ttttccaact    600
gtctcctcca gcgacagaag ccgaaggcaa ggagcattat tcattgcatt taagcactct    660
ccccgcaatc cgcaatgcct tcggtgatgt tatctttgac gcaattgaac gttcccctac    720
acaggtgaca gcgagagcta aggttatttc tctgagaaaa accgaaagtg tttggacaaa    780
agttccctac agaagttctc aagacgcaat catatctctt gaagtagggt cggcaatcga    840
gcttgcgaat gtgttgttcc caatcgcaac ccaaaaaatt gtctctatcc tttccgcatg    900
ttctcccact gtgcgccaga agaactttc tgaggctatt ctcggcccag accctcagga    960
tacaccggca acatcatcag aaatcggtat gaagtttaag gtacacatga ctgcagttgc   1020
taattccacc ctgtgctaga tgtggcgtat tttactctgc gaggagcaac ggtctcggca   1080
attgaatcag tctttcgcgc tgatatttgc gaaggtatta agggcagcga actgagaaac   1140
tgggaaaagg agcagctgct catcgacacg acagattgtg tcacgatgca gatatggcgg   1200
gcacaacctc aacatggaac catcaagttg cgtattggat tctatgcagc ggtgaatttg   1260
gcaaatcggc tgtatgcaga aacaccccaa gatcacatat agtaacctt catcttttcg    1320 gccttcttaa atcattgcct ttctgtgagt cgcgactttc cacctttat gaatacacca    1380 ataccagggg gaagaacgat ttcaccgctt cccttggcaa tccatatagt tcccttctca   1440
ttctggaacc tgatttcatc gcagttgaag caatataaat tccttcgag gttttctgca    1500 ttgtagggat ggaatgggtg cgtgaaatat ttgtcgaaaa tagaagggtc cgaaagttct   1560
ttccaagctg cgcgctgaaa gttgttagcc catctttcga gcatatggtt tggcccacat   1620
acgagagatt cttttgtgat cggttgagat tcttccgtga tcggttctgt cattttcatt   1680
aagtcagaga gccctcttgt atgccggctt ttgctgtcgg atccggcgag ataatcgctc   1740
ctaagccagt cagtcaggga aaagcaaaga taaataaaat ataggcgagg agtacaacca   1800
ggcacgcgtc gtagactatt tttctgaaga gtttgtcacg taacctacct catatggatg   1860
ggtagttcga atacttgatt gacttgaccc gaggttctga aggcggcgga ggaaattgcc   1920
caaccccacc attgcatttt caggtatcaa tctctgccac actgtggcta aattcgtctt   1980
tatcgacacg tgatcacgtt ccctcttcca gccctggtat cagagaatca tcgagttatc   2040
gcttgtttca atttcgtctt gcaattagct tagggaataa gcatgtggtc acatcaacct   2100
acagagcgct accggtcttt gcgctgagac tctcagtgat ccgcccaaca gacaactaga   2160
ctttgaggtt gtcgatataa ccacaacaaa tggcctgtat atcaacgatg tccacgcaat   2220
tgtctcaagc ctcttcaccc gacttccagc actagcatcc aagcggcctc tcctcttctc   2280
ccatgtttct cgtagcgcgc ctgcatatac ttatatctgg agatatgtta aaggagctgg   2340
aagcctggag catacgctgg aagcctggag catacgcttc aagtgctgcc atattcagat   2400
agctgagtag gcacaattag gtctaagttc agggaattgc acctctcgct tcattgtccg   2460
tcgattcgta tcggtctcta gttctccccg tttatcactc tcactcggtg gacagtccgt   2520
ccagtccgtc cagtccgtcg agcctgtcca atctgtccaa tctgtccaat ctgtccaatc   2580
```

```
tgtccaatct gtccaatctg tccaatctgt ccaatctgtc caatctgtcc aatctgtcca    2640
atctgtccaa tctgtccaat ctgtccaatc tgtccaatct gtccaatctg tccactctgt    2700
ccactctgtc cactctgtcc aatctgtcca ctctgtcccc tctgtccact ctgtcccctc    2760
tgtccactct gtcccctctg tccaatcggt ccaatctgtc caatcttgat gatctcgatg    2820 atcaataccaa tttagcgagc gctagtgacg ccttacagcg ttgcggcgtc ttatggctta    2880
tacatcttcc gaatatcagt cgttcgatct ccagatcaca cctcggggtg aaacaagcgc    2940
catagttctt ggtgcgcctg agcttttccc tgcccggcca ctcagtcgtg atggcttccc    3000
agagtattcc ataagtcgaa accagagata ggccagcgga cggcaaatct cctctgctcc    3060
gttctcaacc aatactgcca aagtgagcaa tggaaagtgt tccaggagca ccgtggcctt    3120
taaaagcgcc agccttgtcc cagatcctca ccgcaattcg gcacagacca acgcagactt    3180
tcattgacca ttcttcattt ccagatcgct gcatagtttc cggtatggct tggtatagag    3240
ccttactccc gtgcataccg ttgtggcgga aggttctggg gcgtaacagc accgatgagg    3300
acggacggag tgaagacgac cttacttcat tgagcgataa aatgcctact tttgaagaaa    3360
cgacaactgt gagtactgtt cgtgaaattg cctccagctg tctaatgtct ccgtcggtca    3420
gatcacttct gcaaagtaca tcaacggtga aaaaatcatg gagcataccg ttgtggagac    3480
caagcacatt gacgaacgtg gagacaccag cgtcagtaac ggtgattcga acagcactgc    3540
ggtaaccaga cattctgggc ttagctctgt cagccttttca gatcaaagta caattgtcga    3600
ggacgcgaat gctctggaag aacctgaact ctttgctgtt cactctccat atgttgacga    3660
ctcaaccggc gagcagatgg ttagactcta ctacgagctc ccagtaagcc tcgatgatct    3720
tgagatcata ggccttgaat ctcgtattcc agagtctgac gatgattcaa ttgaggcccg    3780
ctttcgttat cgaggagagg atttttggct acctgttcgt tattcttatg ccaaagctcg    3840
aatggtttta acgggtgtat gctgaatggt ctgacttctt cactgttgtt atttttctatt   3900 tcccggctgc tggccactca atattatcgc aagcactata caaaataaat agtcctatct    3960
ctataacaga gtacgtcaca aacagcgttc gtccttggca agaatataaa tagtgtcaat    4020
ctgctgagaa aaggaggtat gaaatccact tcattcaagc aatggttccc ttcgtataca    4080
ttattatttg tatatggatg ggaactttcc ttgtcttagt tgccctgaac gcccgcttta    4140
agaagaagcg cattgctgat cctgagtctt ctgctgcctt cactgatcat ccccatcaag    4200
agtaacatgg attctgtatg tccctttggg catgtttatg tggcagttac taatatatta    4260
gatggaaact aggaagcggc aaaacacagg ggcaggaagg gaaggactca ttccaagaaa    4320
gaaggacaag gaagaacaca agagtgtaag gggtagcaat cctcattggc gtctactagc    4380
tgatgggtta aagcaagata caggtgttca tacgctccaa gacaacgatc ctgttgtcga    4440
gaagccgcca ttaatttaca ggagagctgg agaagcgccg aaacatgatt gggacaagaa    4500
gtcacccggt ttgcgcctta gacggtcctg ctgtagctgc gggaaggaag taccggtagg    4560
cctggtctgt cgtatttgtc accatgagtc ttgtcctgag tgcttgaaca tgcaaaagcg    4620
agattacgga tgttgatcag atacacgggc ccctatacta ggactagtta ccactaggat    4680
tgtactcaac cttaacagtg gcgtttggta cttcgttaca gctaagggga gaggacagtt    4740
cctactttca tgtgcttcaa gggagaggct cctccaacta ctgttgctag ggaggaaaga    4800
cactctattc ttagctgagg gctgcaggaa ttcgcatcca tgcagtcata ccatccatgg    4860
catgcaatct atgttgcatt agatgcaaga agtaggatag agaacccatg tacttgattc    4920
acgctagcag gacagagaga gataccatac ccgacgggag cccctgcatg acttcctgtc    4980
```

```
tgcagcttgt cgtgcgtgta tcattcccat gcgccacgaa ctcataggca gtggtagttc    5040
agaacactct ttttttttaa aaaaaaaaaa gataggaaaa taataattta ggggaagaaa    5100
agtaaaaatt aaaaagaaaa agttccagat ggcgcttcta cttctatatt cgatcgttat    5160
tcaatacccc agaggcacag gcattccgat ctctcatcgc caacactgaa aagcagccat    5220
tttcccccgt cttaaagctc caatcctcct tcttctcatc tacttcctcg ctccttcagg    5280
accttgagtg ttccgttgag ctattgggta acttctcacc tgtcaatcat cgattgtcct    5340
ttctcttgac ttgacttcgt gtcgccattc tcatttacga tacatatccc tggagcagaa    5400
aacaaagaaa agggccaatt actcttgatc tagttccaac tctgttgctg cttggaacat    5460
ccgcccatct gtgtggtgaa atcagatgcc agcatccatc ttgcagcttc tcccacttcc    5520
tgggccgatc ttgaatgttt gctctcgaac ctcgcttagt atttgatctc cattctcatc    5580
tgggtacatc ctgtgagtag catgtcgtca cttgtcacac atactacccg ctctcaaatc    5640
tgtttgatgg gagtcaatct gcctcgaaat ggctcgtctg ccttcacaag caaactacag    5700
cagatggcgg gggcatggac tcgagccaca gtgctggctc tcgcttgcat ctggaccttc    5760
ttattctttc tcattgctgt atcttttttcc cccttgaggc ttctggcgcg ctgcacccttt    5820 ccaagtatca aaccaaagct aatcaggggc gtttggcgtc ctgccatggc ttcactagac    5880
ctggatctct gcagcctcat caccatctcg gatcacctgg ttctgatcac cttggaagaa    5940
agcacaaaga ccttggagac aatacatatt gccgccatcg cagctccctc caatctcgac    6000
agcattttca tgtgtcgggc actatctacc tctcggcaat tcagtaaccg tactgcctga    6060
gaaacatcaa cctctcaaat tacacaatgg tgttcagcgc acctgctcct ggtgtgggct    6120
ccagtaaaag gccagcgtca tgcatgcagg acgatgttga tgagcgggat aatgtcccag    6180
taagtgatac cagcattgga aaggcagatg gagctgactc atctcctata tagcccatgg    6240
gtctatgcgt gcgttcatcg atcaacatcc cttacttcca ctacgccatg atctatctcg    6300
acaacatggg cagacttaag gtgatggaat ctccgtctat ccaggagcaa aatgagactg    6360
ttttcacaac cgaagtacgt gaaagatttt tggaaatcct tggtgccaag gtaggatatc    6420
aaccgcccat ggttcgaagt atgtaaacac tccgcgcaca agtacaatat tcttgctgat    6480
ctcaattgaa cagggttgtc agctgccggt gctacaccat acagctatga tcctcaacaa    6540
ccgcttggtt gcttgtctta ccgtcaaact aagcgggaca gaaattcccc agcccactct    6600
atgtacggtg tgccgccatc cgtccagttc tcagccccgg ttgaggaatc gccctcttgt    6660
ggatcagtgg acatggtcgg gctcgagatt ggtgatactc ctaatgtcct tgactactat    6720
gagagatcct taaagcactt tcggcaggtc aactgtcgcc agatcctaaa gacattcatt    6780
aagttcattg agccacgaaa gcaagccaag caccccctata atggaggtaa acccctgca    6840 ggagcccctc ctggtaagaa gggcgaccca gagaagacaa agcctgaatg gtggcccgcc    6900
aatgtggtcc acaaggagcc tgaccatctt cgaaaggatc gtacgtgtaa cccttcagaa    6960
aatcttcagt gtcaagtaac tttgctgaca gacttagaac gcctgtctct gttaattcat    7020
atcatccgca ggcttggaag atttggtatc accacggatc aattgcagga aattgcccac    7080
gactgcaagc ggcggctcag cgaccccac aaactccaaa tcttggacga ggtcttcaga    7140
gtgagaagga ttgaagaacg ctacgaaaga ggagaagttg gtaagcggca tcatctttcc    7200
atgaaattca ttttgacagc tgttgacgag cctcagatgc caacaagatc gtatatgttg    7260
tcaaccgaga gtcgaatcag aaagagaagg atggcgactc caacgtggat ccggaccaga    7320
```

| | |
|---|---|
| agcatgagca agaagacgat aatgcgcggg aggcacttcc cattctccac tccgagaaga | 7380 |
| actcaaccag cccgatgtcg aactcagccg agcacacggg catggcggca ccaagtcgtc | 7440 |
| caatgaatat gggaggtgac agaaaccagt tgtttccttt accggagtgg ccgagcttcg | 7500 |
| gtgagacacc ccaggatgat cgaattttct ttcccacgac ctctaagtat accgaagatt | 7560 |
| atgcatcgca gcagatgcct agaacacctg caacaacagc acttgtcagc actaatgaga | 7620 |
| cacatgcggc ctttgattat atgacacagg agtccatcac ctcctcctcc ccagagcaga | 7680 |
| cttcccacca ccgccaagca cccctgccca tgcagcactc ggccagcctc gacccttgga | 7740 |
| cccctacgtt ccgacataat ttcttcaacc caatggtgta tagtactgca ccccgtcacg | 7800 |
| ccatgtccca ggctactatg ttatctcagt ttcccaggtc cacgacgtct catggccagg | 7860 |
| aaatgcctca catggctcac ggcctgccga acctgcctca agacagacct tcaagcatgg | 7920 |
| atggcatgag catgagaggc ccttctttcc gcacaggatt tttgagtcat ccctgtgacc | 7980 |
| catcacagca ggctcctcat tctagcggat gcggccatcc tgacagttgg actcaaaata | 8040 |
| gaccacatgt ataatcttaa ctgattgatc cttgaccact gttttgaccc tcctgcagcc | 8100 |
| ttgaagcttc gtttcactga tgattgttct tcgactttgt ttctgtccct gactttgttg | 8160 |
| tcaatgcgga cttatccatg cggcttgttc cacgtcaagt gactaccagg acactccgtg | 8220 |
| gttttatatg gcaggtactg gcgatgactt tccaattctt cttcgtttag tatatatact | 8280 |
| cgtttcttgt tctatgttcg atcatgtctt tttccttata catacctcca aaaatcctgt | 8340 |
| tggagatggc gccagatggc atgagatgca aatatggatg atgttcttgt gtttgttcat | 8400 |
| ttcaatttct ttctcttaat catgatttga acaattggca gcgaggtatg gcggagctcg | 8460 |
| ttctctttgg atgccgatca gctgaatagg aggtaacgag gcatgagggt gtttcattat | 8520 |
| gactctctcc ggtgtttgtc atttaagggt gcgaggggga agtgtccgtt tcgatgtcct | 8580 |
| aggatatcga aaatctgagt agtagccacg tgaccctatg ctgacggctg ggctggaaga | 8640 |
| caagcaggtt gctgcttacg agaatatgtt gaggtattct cgttatcttc gtgaagaatg | 8700 |
| ccgtctcctt ggccctctag ccaaagtctg ggttgctgaa aggctagctg gaattgagaa | 8760 |
| tcgactgtct gcgtccgagt cgcctagagg tgggaaggcc ccctctttct catacatatg | 8820 |
| ctgactctgc agaccatacc aattcgctgc ccgaa | 8855 |

```
<210> SEQ ID NO 3
<211> LENGTH: 641
<212> TYPE: DNA
<213> ORGANISM: Aspergillus fumigatus

<400> SEQUENCE: 3
```

| | |
|---|---|
| atggcttggt atagagcctt actcccgtgc ataccgttgt ggcggaaggt tctggggcgt | 60 |
| aacagcaccg atgaggacgg acggagtgaa gacgacctta cttcattgag cgataaaatg | 120 |
| cctactttg aagaaacgac aactgtgagt actgttcgtg aaattgcctc cagctgtcta | 180 |
| atgtctccgt cggtcagatc acttctgcaa agtacatcaa cggtgaaaaa atcatggagc | 240 |
| ataccgttgt ggagaccaag cacattgacg aacgtggaga caccagcgtc agtaacggtg | 300 |
| attcgaacag cactgcggta accagacatt ctgggcttag ctctgtcagc ctttcagatc | 360 |
| aaagtacaat tgtcgaggac gcgaatgctc tggaagaacc tgaactcttt gctgttcact | 420 |
| ctccatatgt tgacgactca accggcgagc agatggttag actctactac gagctcccag | 480 |
| taagcctcga tgatcttgag atcataggcc ttgaatctcg tattccagag tctgacgatg | 540 |
| attcaattga ggcccgcttt cgttatcgag gagaggattt ttggctacct gttcgttatt | 600 |

```
cttatgccaa agctcgaatg gttttaacgg gtgtatgctg a                  641
```

<210> SEQ ID NO 4
<211> LENGTH: 635
<212> TYPE: DNA
<213> ORGANISM: Aspergillus fumigatus

<400> SEQUENCE: 4

```
atggtgtggt atagggccat actcgtttgc atgccgtggt ggctcatggg gcgtaacagc    60
accaatgagg gcaaacggag tgaaggcgaa cgggctccaa tgattgataa ggtgcccact   120
ttcgaagaaa tgacaattgt gagtactgtt ttgtggggtt gcctccagct gtctaatgct   180
tccttgcgca gaccacctct gcaaagtatg tcaacggtga aaaaatcatg gagcataccg   240
ttgtggagac caagcaaatt gacaaccgag gagacaccag cgtcagtaac aatgattcaa   300
acagcactgc ggaaaccaga cattctgggc ttagctccgt cagtcattca gatcaaagta   360
aagttgttga ggacgcgaat gccctggaaa aacctgaact ctttgctgtt cactctccat   420
atgttgacgc ctcaaccggc aagcagatgt taagactcta ctacgagctc ccagtaagcc   480
tcgatgatct tgagatcaca ggccttgaat ctcgtattcc agagtctgat gatgattcaa   540
ttgaggcctg cttttgttat cggggggaga aattttggct acatgttcct tattcttatg   600
ccaaagctcg aatggtttta atgggtgtat actga                             635
```

<210> SEQ ID NO 5
<211> LENGTH: 637
<212> TYPE: DNA
<213> ORGANISM: Aspergillus fumigatus

<400> SEQUENCE: 5

```
atggcttggt atgaagtctt cgagcaatgg gtgtactggt gctggcagcg catatggccc    60
ttcgacgaca gcaggaggga cggacgaaac gaagacgacc taacttcgtt aaccgataaa   120
atgcctgttt ttgaagataa gatcatcgtg agtactgtcc atgaggaggc ttccatctcc   180
ctaaccttgg cagaacacct ctgtcagata tgtcaatgga gagatcgcgg catatgtcgt   240
ccagacccag tatctcgata cccaagaggt ctcctctgct agggactctt attggaaaag   300
cgttgcggat atcaaaccgg gtgacttctg ctcccatagt atttcggatc agagcacaat   360
tgtcgaagaa aacgaagcga aggcgctgga aggacctgaa ccctttgctg ttcgcccttc   420
gtatattgga tccactggca aacgcacggt cgacttcttc tacaaggtct ctctaccact   480
ggatgatctt gagatgagag acaaggaatc gcgtgttccg gagtctagcg aagatctgat   540
tgaggctctc ttccactatc aaggggccga tatttgggta tatgttcctt attcgtacgc   600
caatgctcga atggtttcag gcggtcccac tgaatga                            637
```

<210> SEQ ID NO 6
<211> LENGTH: 640
<212> TYPE: DNA
<213> ORGANISM: Aspergillus niger

<400> SEQUENCE: 6

```
atggcttggt acagtgcttt actcccgtgc atgctatggt ggcggaacct cctgtggcgt    60
aacagcacca ataggtatag acagagtaca gacgacctta cttcactgac tgataagata   120
cctaatcttg gagaaagggt aagtgtaaat acttttttgag gtcgcttcta ggagtctaat   180
cactttggaa agacaactcc cacagataac atcgatggaa agagcttcgt ggcacatact   240
```

```
gtcgtgcaga ccaggcggat tggtgaccga gaacgttgct gcttcaatga ctcggatttg    300
aacagcggca cagttaccaa atttattgag ctttgttaat agcattccag atcagagtac    360
tactgccgga aaaattaatc acaaggccct gcgagatcct gagctctttg ctatccgctc    420
gtcatgcatc gacaaatcag ccagcaagtg gatggttagt ctctactacg aaccccccacc    480 cagccttgat gacctcgaga ttaagaactt cggatctcgt attccagagt cggaggatga    540
tccaattgag gctatctttc actatgaggg agagaacatt tgggtatctg ttccttatt    600 gtatgctaga actagaagcc tttcaagcgg tctgttctga                          640

<210> SEQ ID NO 7
<211> LENGTH: 582
<212> TYPE: DNA
<213> ORGANISM: Aspergillus fumigatus

<400> SEQUENCE: 7
atggcttggt atagagcctt actcccgtgc ataccgttgt ggcggaaggt tctggggcgt     60
aacagcaccg atgaggacgg acggagtgaa gacgacctta cttcattgag cgataaaatg    120
cctacttttg aagaaacgac aacttctgca aagtacatca acggtgaaaa aatcatggag    180
cataccgttg tggagaccaa gcacattgac gaacgtggac acccagcgt cagtaacggt    240 gattcgaaca gcactgcggt aaccagacat tctgggctta gctctgtcag cctttcagat    300
caaagtacaa ttgtcgagga gcgaatgct ctggaagaac ctgaactctt tgctgttcac    360
tctccatatg ttgacgactc aaccggcgag cagatggtta gactctacta cgagctccca    420
gtaagcctcg atgatcttga gatcataggc cttgaatctc gtattccaga gtctgacgat    480
gattcaattg aggcccgctt tcgttatcga ggagaggatt tttggctacc tgttcgttat    540
tcttatgcca aagctcgaat ggttttaacg ggtgtatgct ga                       582

<210> SEQ ID NO 8
<211> LENGTH: 582
<212> TYPE: DNA
<213> ORGANISM: Aspergillus fumigatus

<400> SEQUENCE: 8
atggtgtggt atagggccat actcgtttgc atgccgtggt ggctcatggg gcgtaacagc     60
accaatgagg gcaaacggag tgaaggcgaa cgggctccaa tgattgataa ggtgcccact    120
ttcgaagaaa tgacaattac cacctctgca aagtatgtca acggtgaaaa aatcatggag    180
cataccgttg tggagaccaa gcaaattgac aaccgaggag acaccagcgt cagtaacaat    240
gattcaaaca gcactgcgga aaccagacat tctgggctta gctccgtcag tcattcagat    300
caaagtaaag ttgttgagga gcgaatgcc ctggaaaaac ctgaactctt tgctgttcac    360
tctccatatg ttgacgcctc aaccggcaag cagatgttaa gactctacta cgagctccca    420
gtaagcctcg atgatcttga gatcacaggc cttgaatctc gtattccaga gtctgatgat    480
gattcaattg aggcctgctt tgttatcgg ggagagaaat tttggctaca tgttccttat    540
tcttatgcca aagctcgaat ggttttaatg ggtgtatact ga                       582

<210> SEQ ID NO 9
<211> LENGTH: 591
<212> TYPE: DNA
<213> ORGANISM: Aspergillus fumigatus

<400> SEQUENCE: 9
atggcttggt atgaagtctt cgagcaatgg gtgtactggt gctggcagcg catatggccc     60
```

```
ttcgacgaca gcaggaggga cggacgaaac gaagacgacc taacttcgtt aaccgataaa    120
atgcctgttt ttgaagataa gatcatcaac acctctgtca gatatgtcaa tggagagatc    180
gcggcatatg tcgtccagac ccagtatctc gatacccaag aggtctcctc tgctagggac    240
tcttattgga aaagcgttgc ggatatcaaa ccgggtgact tctgctccca tagtatttcg    300
gatcagagca caattgtcga agaaaacgaa gcgaaggcgc tggaaggacc tgaacccttt    360
gctgttcgcc cttcgtatat tggatccact ggcaaacgca cggtcgactt cttctacaag    420
gtctctctac cactggatga tcttgagatg agagacaagg aatcgcgtgt tccggagtct    480
agcgaagatc tgattgaggc tctcttccac tatcaagggg ccgatatttg ggtatatgtt    540
ccttattcgt acgccaatgc tcgaatggtt tcaggcggtc ccactgaatg a             591
```

<210> SEQ ID NO 10
<211> LENGTH: 465
<212> TYPE: DNA
<213> ORGANISM: Aspergillus niger

<400> SEQUENCE: 10

```
atggcttggt acagtgcttt actcccgtgc atgctatggt ggcggaacct cctgtggcgt     60
aacagcacca ataggtatag acagagtaca gacgacctta cttcactgac tgataagata    120
cctaatcttg gagaaaggtt accaaattta ttgagctttg ttaatagcat tccagatcag    180
agtactactg ccggaaaaat taatcacaag gccctgcgag atcctgagct ctttgctatc    240
cgctcgtcat gcatcgacaa atcagccagc aagtggatgg ttagtctcta ctacgaaccc    300
ccacccagcc ttgatgacct cgagattaag aacttcggat ctcgtattcc agagtcggag    360
gatgatccaa ttgaggctat cttcactat gagggagaga acatttgggt atctgttcct    420
tatttgtatg ctagaactag aagccttca agcggtctgt tctga                    465
```

<210> SEQ ID NO 11
<211> LENGTH: 362
<212> TYPE: PRT
<213> ORGANISM: Aspergillus fumigatus

<400> SEQUENCE: 11

```
Met Ala Ser Thr Lys Pro Ala Ser Ser Leu Ile Tyr Gln Ala Trp Asn
1               5                   10                  15

Lys Leu Ser Ile Asn Gln Thr Ile Pro Ser Asp Ser Leu Glu Leu Leu
            20                  25                  30

Gly Glu Arg Leu Ala Ile Ala Phe Ala Pro Lys Leu Lys Glu Gln Arg
        35                  40                  45

Arg Asn Gly Arg Arg Asn Leu Glu Tyr Val Ala Gln His Arg Arg
    50                  55                  60

Lys Ile Ala Arg Lys Ile Tyr Leu Glu Ile Leu Glu Lys Asp Pro Asn
65                  70                  75                  80

Ile Phe Leu Pro Phe Ile Leu Ala Val Ser Pro Arg Ala Cys Leu Ser
                85                  90                  95

Phe Asp Ile Ser Ser Phe Leu Glu Gln His Gln Ser Gln Gly Arg His
            100                 105                 110

Phe Leu Arg Asn Asn Ala Glu Ala Ile Leu Trp Gly Leu Ala Lys Lys
        115                 120                 125

His Asp Ile Asp Gly Ser Leu His Phe Arg Lys Leu Met Arg Glu Ile
    130                 135                 140

Phe Gln Leu Ser Pro Pro Ala Thr Glu Ala Glu Gly Lys Glu His Tyr
```

```
145                 150                 155                 160
Ser Leu His Leu Ser Thr Leu Pro Ala Ile Arg Asn Ala Phe Gly Asp
                165                 170                 175

Val Ile Phe Asp Ala Ile Glu Arg Ser Pro Thr Gln Val Thr Ala Arg
            180                 185                 190

Ala Lys Gly Tyr Phe Ser Glu Lys Thr Glu Ser Val Trp Thr Lys Val
        195                 200                 205

Pro Tyr Arg Ser Ser Gln Asp Ala Ile Ile Ser Leu Glu Val Gly Ser
    210                 215                 220

Ala Ile Glu Leu Ala Asn Val Leu Phe Pro Ile Ala Thr Gln Lys Ile
225                 230                 235                 240

Val Ser Ile Leu Ser Ala Cys Ser Pro Thr Val Arg Gln Lys Asn Phe
                245                 250                 255

Ser Glu Ala Ile Leu Gly Pro Asp Pro Gln Asp Thr Pro Ala Thr Ser
            260                 265                 270

Ser Glu Ile Asp Val Ala Tyr Phe Thr Leu Arg Gly Ala Thr Val Ser
        275                 280                 285

Ala Ile Glu Ser Val Phe Arg Ala Asp Ile Cys Glu Gly Ile Lys Asp
    290                 295                 300

Ser Glu Leu Arg Asn Trp Glu Lys Glu Gln Leu Leu Ile Asp Thr Thr
305                 310                 315                 320

Asp Cys Val Thr Met Gln Ile Trp Arg Ala Gln Pro Gln His Gly Thr
                325                 330                 335

Ile Lys Leu Arg Ile Gly Phe Tyr Ala Ala Val Asn Leu Ala Asn Arg
            340                 345                 350

Leu Tyr Ala Glu Thr Pro Gln Asp His Ile
        355                 360

<210> SEQ ID NO 12
<211> LENGTH: 362
<212> TYPE: PRT
<213> ORGANISM: Artificial Sequence
<220> FEATURE:
<223> OTHER INFORMATION: Artificial polypeptide sequence

<400> SEQUENCE: 12

Met Ala Ser Thr Lys Pro Ala Ser Ser Leu Ile Tyr Gln Ala Trp Asn
1               5                   10                  15

Lys Leu Ser Ile Asn Gln Thr Ile Pro Ser Asp Ser Leu Glu Leu Leu
            20                  25                  30

Gly Glu Arg Leu Ala Ile Ala Phe Ala Pro Lys Leu Lys Glu Gln Arg
        35                  40                  45

Arg Asn Gly Arg Arg Asn Leu Glu Tyr Val Ala Gln His Arg Arg
    50                  55                  60

Lys Ile Ala Arg Lys Ile Tyr Leu Glu Ile Leu Glu Lys Asp Pro Asn
65                  70                  75                  80

Ile Phe Leu Pro Phe Ile Leu Ala Val Ser Pro Arg Ala Cys Leu Ser
                85                  90                  95

Phe Asp Ile Ser Ser Phe Leu Glu Gln His Gln Ser Gln Gly Arg His
            100                 105                 110

Phe Leu Arg Asn Asn Ala Glu Ala Ile Leu Trp Gly Leu Ala Lys Lys
        115                 120                 125

His Asp Ile Asp Gly Ser Leu His Phe Arg Lys Leu Met Arg Glu Ile
    130                 135                 140

Phe Gln Leu Ser Pro Pro Ala Thr Glu Ala Glu Gly Lys Glu His Tyr
```

```
                145                 150                 155                 160
Ser Leu His Leu Ser Thr Leu Pro Ala Ile Arg Asn Ala Phe Gly Asp
                    165                 170                 175

Val Ile Phe Asp Ala Ile Glu Arg Ser Pro Thr Gln Val Thr Ala Arg
                    180                 185                 190

Ala Lys Gly Tyr Phe Ser Glu Lys Thr Glu Ser Val Trp Thr Lys Val
                    195                 200                 205

Pro Tyr Arg Ser Ser Gln Asp Ala Ile Ile Ser Leu Glu Val Gly Ser
        210                 215                 220

Ala Ile Glu Leu Ala Asn Val Leu Phe Pro Ile Ala Thr Gln Lys Ile
225                 230                 235                 240

Val Ser Ile Leu Ser Ala Cys Ser Pro Thr Val Arg Gln Lys Asn Phe
                    245                 250                 255

Ser Glu Ala Ile Leu Gly Pro Asp Pro Gln Asp Thr Pro Ala Thr Ser
                    260                 265                 270

Ser Glu Ile Asp Val Ala Tyr Phe Thr Leu Arg Gly Ala Thr Val Ser
                    275                 280                 285

Ala Ile Glu Ser Val Phe Arg Ala Asp Ile Cys Glu Gly Ile Lys Gly
            290                 295                 300

Ser Glu Leu Arg Asn Trp Glu Lys Glu Gln Leu Leu Ile Asp Thr Thr
305                 310                 315                 320

Asp Cys Val Thr Met Gln Ile Trp Arg Ala Gln Pro Gln His Gly Thr
                    325                 330                 335

Ile Lys Leu Arg Ile Gly Phe Tyr Ala Ala Val Asn Leu Ala Asn Arg
                    340                 345                 350

Leu Tyr Ala Glu Thr Pro Gln Asp His Ile
                355                 360

<210> SEQ ID NO 13
<211> LENGTH: 192
<212> TYPE: PRT
<213> ORGANISM: Aspergillus fumigatus

<400> SEQUENCE: 13

Met Ala Trp Tyr Arg Ala Leu Leu Pro Cys Ile Pro Leu Trp Arg Lys
1               5                   10                  15

Val Leu Gly Arg Asn Ser Thr Asp Glu Asp Gly Arg Ser Glu Asp Asp
                20                  25                  30

Leu Thr Ser Leu Ser Asp Lys Met Pro Thr Phe Glu Glu Thr Thr Thr
            35                  40                  45

Ser Ala Lys Tyr Ile Asn Gly Glu Lys Ile Met Glu His Thr Val Val
        50                  55                  60

Glu Thr Lys His Ile Asp Glu Arg Gly Asp Thr Ser Val Ser Asn Gly
65                  70                  75                  80

Asp Ser Asn Ser Thr Ala Val Thr Arg His Ser Gly Leu Ser Ser Val
                85                  90                  95

Ser Leu Ser Asp Gln Ser Thr Ile Val Glu Asp Ala Asn Ala Leu Glu
                100                 105                 110

Glu Pro Glu Leu Phe Ala Val His Ser Pro Tyr Val Asp Asp Ser Thr
            115                 120                 125

Gly Glu Met Val Arg Leu Tyr Tyr Glu Leu Pro Val Ser Leu Asp Asp
        130                 135                 140

Leu Glu Ile Ile Gly Leu Glu Ser Arg Ile Pro Glu Ser Asp Asp Asp
145                 150                 155                 160
```

```
Ser Ile Glu Ala Arg Phe Arg Tyr Arg Gly Glu Asp Phe Trp Leu Pro
                165                 170                 175

Val Arg Tyr Ser Tyr Ala Lys Ala Arg Met Val Leu Thr Gly Val Cys
            180                 185                 190

<210> SEQ ID NO 14
<211> LENGTH: 192
<212> TYPE: PRT
<213> ORGANISM: Aspergillus fumigatus

<400> SEQUENCE: 14

Met Val Trp Tyr Arg Ala Ile Leu Val Cys Met Pro Trp Trp Leu Met
1               5                   10                  15

Gly Arg Asn Ser Thr Asn Glu Gly Lys Arg Ser Glu Gly Glu Arg Ala
            20                  25                  30

Pro Met Ile Asp Lys Val Pro Thr Phe Glu Glu Met Thr Ile Thr Thr
        35                  40                  45

Ser Ala Lys Tyr Val Asn Gly Glu Lys Ile Met Glu His Thr Val Glu
    50                  55                  60

Thr Lys Gln Ile Asp Asn Arg Gly Asp Thr Ser Val Ser Asn Asn Asp
65                  70                  75                  80

Ser Asn Ser Thr Ala Glu Thr Arg His Ser Gly Leu Ser Ser Val Ser
                85                  90                  95

His Ser Asp Gln Ser Lys Val Val Glu Asp Ala Asn Ala Leu Glu Lys
            100                 105                 110

Pro Glu Leu Phe Ala Val His Ser Pro Tyr Val Asp Ala Ser Thr Gly
        115                 120                 125

Lys Gln Met Leu Arg Leu Tyr Tyr Glu Leu Pro Val Ser Leu Asp Asp
    130                 135                 140

Leu Glu Ile Thr Gly Leu Glu Ser Arg Ile Pro Glu Ser Asp Asp Asp
145                 150                 155                 160

Ser Ile Glu Ala Cys Phe Cys Tyr Arg Gly Glu Lys Phe Trp Leu His
                165                 170                 175

Val Pro Tyr Ser Tyr Ala Lys Ala Arg Met Val Leu Met Gly Val Tyr
            180                 185                 190

<210> SEQ ID NO 15
<211> LENGTH: 196
<212> TYPE: PRT
<213> ORGANISM: Aspergillus fumigatus

<400> SEQUENCE: 15

Met Ala Trp Tyr Glu Val Phe Glu Gln Trp Val Tyr Trp Cys Trp Gln
1               5                   10                  15

Arg Ile Trp Pro Phe Asp Asp Ser Arg Arg Asp Gly Arg Asn Glu Asp
            20                  25                  30

Asp Leu Thr Ser Leu Thr Asp Lys Met Pro Val Phe Glu Asp Lys Ile
        35                  40                  45

Ile Asn Thr Ser Val Arg Tyr Val Asn Gly Glu Ile Ala Ala Tyr Val
    50                  55                  60

Val Gln Thr Gln Tyr Leu Asp Thr Gln Glu Val Ser Ser Ala Arg Asp
65                  70                  75                  80

Ser Tyr Trp Lys Ser Val Ala Asp Ile Lys Pro Gly Asp Phe Cys Ser
                85                  90                  95

His Ser Ile Ser Asp Gln Ser Thr Ile Val Glu Glu Asn Glu Ala Lys
            100                 105                 110
```

Ala Leu Glu Gly Pro Glu Pro Phe Ala Val Arg Pro Ser Tyr Ile Gly
            115                 120                 125

Ser Thr Gly Lys Arg Thr Val Asp Phe Phe Tyr Lys Val Ser Leu Pro
        130                 135                 140

Leu Asp Asp Leu Glu Met Arg Asp Lys Glu Ser Arg Val Pro Glu Ser
145                 150                 155                 160

Ser Glu Asp Leu Ile Glu Ala Leu Phe His Tyr Gln Gly Ala Asp Ile
                165                 170                 175

Trp Val Tyr Val Pro Tyr Ser Tyr Ala Asn Ala Arg Met Val Ser Gly
                180                 185                 190

Gly Pro Thr Glu
        195

<210> SEQ ID NO 16
<211> LENGTH: 154
<212> TYPE: PRT
<213> ORGANISM: Aspergillus niger

<400> SEQUENCE: 16

Met Ala Trp Tyr Ser Ala Leu Leu Pro Cys Met Leu Trp Trp Arg Asn
1               5                   10                  15

Leu Leu Trp Arg Asn Ser Thr Asn Arg Tyr Arg Gln Ser Thr Asp Asp
                20                  25                  30

Leu Thr Ser Leu Thr Asp Lys Ile Pro Asn Leu Gly Glu Arg Leu Pro
            35                  40                  45

Asn Leu Leu Ser Phe Val Asn Ser Ile Pro Asp Gln Ser Thr Thr Ala
50                  55                  60

Gly Lys Ile Asn His Lys Ala Leu Arg Asp Pro Glu Leu Phe Ala Ile
65                  70                  75                  80

Arg Ser Ser Cys Ile Asp Lys Ser Ala Ser Lys Trp Met Val Ser Leu
                85                  90                  95

Tyr Tyr Glu Pro Pro Pro Ser Leu Asp Asp Leu Glu Ile Lys Asn Phe
            100                 105                 110

Gly Ser Arg Ile Pro Glu Ser Glu Asp Asp Pro Ile Glu Ala Ile Phe
        115                 120                 125

His Tyr Glu Gly Glu Asn Ile Trp Val Ser Val Pro Tyr Leu Tyr Ala
    130                 135                 140

Arg Thr Arg Ser Leu Ser Ser Gly Leu Phe
145                 150

<210> SEQ ID NO 17
<211> LENGTH: 38
<212> TYPE: DNA
<213> ORGANISM: Artificial Sequence
<220> FEATURE:
<223> OTHER INFORMATION: Artificial polynucleotide sequence

<400> SEQUENCE: 17
aaaaaaaagg cgcgccatgg catccacaaa gcccgctt                              38

<210> SEQ ID NO 18
<211> LENGTH: 45
<212> TYPE: DNA
<213> ORGANISM: Artificial Sequence
<220> FEATURE:
<223> OTHER INFORMATION: Artificial polynucleotide sequence

<400> SEQUENCE: 18
aaaaaaaagc ggccgcctat atgtgatctt ggggtgtttc tgcat                      45

```
<210> SEQ ID NO 19
<211> LENGTH: 9149
<212> TYPE: DNA
<213> ORGANISM: Artificial Sequence
<220> FEATURE:
<223> OTHER INFORMATION: Artificial polynucleotide sequence
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t

<400> SEQUENCE: 19
```

| | | | | | |
|---|---|---|---|---|---|
| ggccgcgaag | cttgagatcc | acttaacgtt | actgaaatca | tcaaacagct | tgacgaatct | 60 |
| ggatataaga | tcgttggtgt | cgatgtcagc | tccggagttg | agacaaatgg | tgttcaggat | 120 |
| ctcgataaga | tacgttcatt | tgtccaagca | gcaaagagtg | ccttctagtg | atttaatagc | 180 |
| tccatgtcaa | caagaataaa | acgcgttttc | gggtttacct | cttccagata | cagctcatct | 240 |
| gcaatgcatt | aatgcattga | ctgcaaccta | gtaacgcctt | ncaggctccg | gcgaagagaa | 300 |
| gaatagctta | gcagagctat | tttcattttc | gggagacgag | atcaagcaga | tcaacggtcg | 360 |
| tcaagagacc | tacgagactg | aggaatccgc | tcttggctcc | acgcgactat | atatttgtct | 420 |
| ctaattgtac | tttgacatgc | tcctcttctt | tactctgata | gcttgactat | gaaaattccg | 480 |
| tcaccagcnc | ctgggttcgc | aaagataatt | gcatgtttct | tccttgaact | ctcaagccta | 540 |
| caggacacac | attcatcgta | ggtataaacc | tcgaaatcan | ttcctactaa | gatggtatac | 600 |
| aatagtaacc | atgcatggtt | gcctagtgaa | tgctccgtaa | cacccaatac | gccggccgaa | 660 |
| acttttttac | aactctccta | tgagtcgttt | acccagaatg | cacaggtaca | cttgtttaga | 720 |
| ggtaatcctt | ctttggggat | ctgacagacg | ggcaattgat | tacgggatcc | cattggtaac | 780 |
| gaaatgtaaa | agctaggaga | tcgtccgccg | atgtcaggat | gatttcactt | gtttcttgtc | 840 |
| cggctcaccg | gtcaaagcta | agaggagca | aaaggaacgg | atagaatcgg | gtgccgctga | 900 |
| tctatacggt | atagtgccct | tatcacgttg | actcaaccca | tgctatttaa | ctcaaccct | 960 |
| ccttctgaac | cccaccatct | tcttccttt | cctctcatcc | cacacaattc | tctatctcag | 1020 |
| atttgaattc | caaagtcct | cggacgaaac | tgaacaagtc | ttcctccctt | cgataaacct | 1080 |
| ttggtgattg | gaataactga | ccatcttcta | tagttcccaa | accaaccgac | aatgtaaata | 1140 |
| cactcctcga | ttagccctct | agtatccttg | aagctgtccc | tgatggtcgt | catctacctg | 1200 |
| cctggacagc | atggcctgca | acgcgggcat | cccgatgccg | ccggaagcga | gaagaatcat | 1260 |
| aatggggaag | gccatccagc | ctcgcgtcga | gctttgaagt | tgctgcaagc | tggcttcaag | 1320 |
| ccatcccatc | cgaatgtgat | ggatgcgttc | tttctgggcc | gttgcgactt | tggggatcgt | 1380 |
| ctttcccgcg | cccttggttg | gaggccctgt | ctccggtgtc | ccttgtccct | tccaggcaag | 1440 |
| cgagcgaggt | ccattcagat | ggtgctccat | cagcgttggc | tttccgtctc | cattggctct | 1500 |
| tggcaattcg | gtcagcgggg | ctgactgcct | caggtggggc | agtgctagtg | tgtgtaccga | 1560 |
| cccgcaggat | tggtgctttg | cccagagctc | tacagaatag | cgcgcgcatc | catatgttag | 1620 |
| ttctgcaatt | ttcttgtatc | ggtgctgtga | ctcatacttc | cccctttggc | tggccttgcg | 1680 |

```
gcaaccaata agaacgcaca gtgaaatctt gcgggtgggg agtggatcca tggcgcctgc    1740
attggcttgg ggacgcgcac tgtcgcacac ttccatctga cctttcagaa gggtttcgtg    1800
gtgggcaagg accaaccggt tgcgcggccg tgcgtgggtg cctcgcccgg cactgccagg    1860
gccactgcag tggcagtttg ctgcctgata caaaatcctt ccctccgccc agttttccct    1920
ctttgacctt cctttctctt ctctgcaacc aaatccaccc tatcaaacca aacagtatc    1980 tcgaccgagt tatcaacctg aatcagcaac atcgtagcca gcatttgtct ccgtctctgc    2040
agaaccagcg agttgcaaac attatccagg caacagggca ccaactcact tcttcggctt    2100
tcaccaatcg gtacagctct tctcagaact cgcgtccgca acagttctac gcttcctcag    2160
caccttcttc agcttcaatc ctgaacactc agaaccgcgc acagcagcgc cctcctgttc    2220
ccttgtttcc caaagtacc ggtagtattt cgcacgaaa gcagggcaac aagatgttct    2280
caggtaccca tatgaaaaag cctgaactca ccgcgacgtc tgtcgagaag tttctgatcg    2340
aaaagttcga cagcgtctcc gacctgatgc agctctcgga gggcgaagaa tctcgtgctt    2400
tcagcttcga tgtaggaggg cgtggatatg tcctgcgggt aaatagctgc gccgatggtt    2460
tctacaaaga tcgttatgtt tatcggcact ttgcatcggc cgcgctcccg attccggaag    2520
tgcttgacat tggggaattc agcgagagcc tgacctattg catctcccgc cgtgcacagg    2580
gtgtcacgtt gcaagacctg cctgaaaccg aactgcccgc tgttctgcag ccggtcgcgg    2640
aggccatgga tgcgatcgct gcggccgatc ttagccagac gagcgggttc ggcccattcg    2700
gaccgcaagg aatcggtcaa tacactacat ggcgtgattt catatgcgcg attgctgatc    2760
cccatgtgta tcactggcaa actgtgatgg acgaccgt cagtgcgtcc gtcgcgcagg    2820
ctctcgatga gctgatgctt tgggccgagg actgccccga agtccggcac ctcgtgcacg    2880
cggatttcgg ctccaacaat gtcctgacgg acaatggccg cataacagcg gtcattgact    2940
ggagcgaggc gatgttcggg gattcccaat acgaggtcgc caacatcttc ttctggaggc    3000
cgtggttggc ttgtatggag cagcagacgc gctacttcga gcggaggcat ccggagcttg    3060
caggatcgcc gcggctccgg gcgtatatgc tccgcattgg tcttgaccaa ctctatcaga    3120
gcttggttga cggcaatttc gatgatgcag cttgggcgca gggtcgatgc gacgcaatcg    3180
tccgatccgg agccgggact gtcgggcgta cacaaatcgc ccgcagaagc gcggccgtct    3240
ggaccgatgc tgtgtagaa gtactcgccg atagtggaaa ccgacgcccc agcactcgtc    3300
cgagggcaaa ggaatagagt agatgccgac cgggatccac ttaacgttac tgaaatcatc    3360
aaacagcttg acgaatctgg atataagatc gttggtgtcg atgtcagctc cggagttgag    3420
acaaatggtg ttcaggatct cgataagata cgttcatttg tccaagcagc aaagagtgcc    3480
ttctagtgat ttaatagctc catgtcaaca gaataaaac gcgtttcggg tttacctctt    3540
ccagatacag ctcatctgca atgcattaat gcattggacc tcgcaaccct agtacgccct    3600
tcaggctccg gcgaagcaga agaatagctt agcagagtct attttcattt tcgggagacg    3660
agatcaagca gatcaacggt cgtcaagaga cctacgagac tgaggaatcc gctcttggct    3720
ccacgcgact atatatttgt ctctaattgt actttgacat gctcctcttc tttactctga    3780
tagcttgact atgaaaattc cgtcaccagc ccctgggttc gcaaagataa ttgcactgtt    3840
tcttccttga actctcaagc ctacaggaca cacattcatc gtaggtataa acctcgaaaa    3900
tcattcctac taagatgggt atacaatagt aaccatggtt gcctagtgaa tgctccgtaa    3960
cacccaatac gccggccgaa acttttttac aactctccta tgagtcgttt acccagaatg    4020
cacaggtaca cttgtttaga ggtaatcctt cttttctagct agaggatcct ctacgccgga    4080
```

```
cgcatcgtgg ccggcatcac cggcgccaca ggtgcggttg ctgactagaa taattatgtg   4140
taacaagaaa gacagtataa tacaaacaaa gatgcaagag cggctcatcg tcaccccatg   4200
atagctagag cttggcactg gccgtcgttt tacaacgtcg tgactgggaa acccctggcg   4260
ttacccaact taatcgcctt gcagcacatc ccccttcgc cagctggcgt aatagcgaag    4320
aggcccgcac cgatcgccct tcccaacagt tgcgcagcct gaatggcgaa tggcgcctga   4380
tgcggtattt tctccttacg catctgtgcg gtatttcaca ccgcatatgg tgcactctca   4440
gtacaatctg ctctgatgcc gcatagttaa gccagccccg acacccgcca cacccgctg    4500
acgcgccctg acgggcttgt ctgctcccgg catccgctta cagacaagct gtgaccgtct   4560
ccgggagctg catgtgtcag aggttttcac cgtcatcacc gaaacgcgcg agacgaaagg   4620
gcctcgtgat acgcctattt ttataggtta atgtcatgat aataatggtt tcttagacgt   4680
caggtggcac ttttcgggga atgtgcgcg gaacccctat tgtttatt ttctaaatac      4740
attcaaatat gtatccgctc atgagacaat aaccctgata aatgcttcaa taatattgaa   4800
aaaggaagag tatgagtatt caacatttcc gtgtcgccct tattccctt tttgcggcat    4860
tttgccttcc tgttttgct cacccagaaa cgctggtgaa agtaaaagat gctgaagatc    4920
agttgggtgc acgagtgggt tacatcgaac tggatctcaa cagcggtaag atccttgaga   4980
gttttcgccc cgaagaacgt tttccaatga tgagcacttt taaagttctg ctatgtggcg   5040
cggtattatc ccgtattgac gccgggcaag agcaactcgg tcgccgcata cactattctc   5100
agaatgactt ggttgagtac tcaccagtca cagaaaagca tcttacggat ggcatgacag   5160
taagagaatt atgcagtgct gccataacca tgagtgataa cactgcggcc aacttacttc   5220
tgacaacgat cggaggaccg aaggagctaa ccgcttttt gcacaacatg ggggatcatg   5280
taactcgcct tgatcgttgg gaaccggagc tgaatgaagc cataccaaac gacgagcgtg   5340
acaccacgat gcctgtagca atggcaacaa cgttgcgcaa actattaact ggcgaactac   5400
ttactctagc ttcccggcaa caattaatag actggatgga ggcggataaa gttgcaggac   5460
cacttctgcg ctcggccctt ccggctggct ggtttattgc tgataaatct ggagccggtg   5520
agcgtgggtc tcgcggtatc attgcagcac tggggccaga tggtaagccc tcccgtatcg   5580
tagttatcta cacgacgggg agtcaggcaa ctatggatga acgaaataga cagatcgctg   5640
agataggtgc ctcactgatt aagcattggt aactgtcaga ccaagtttac tcatatatac   5700
tttagattga tttaaaactt catttttaat ttaaaaggat ctaggtgaag atcctttttg   5760
ataatctcat gaccaaaatc ccttaacgtg agttttcgtt ccactgagcg tcagaccccg   5820
tagaaaagat caaaggatct tcttgagatc ctttttttct gcgcgtaatc tgctgcttgc   5880
aaacaaaaaa accaccgcta ccagcggtgg tttgtttgcc ggatcaagag ctaccaactc   5940
ttttccgaa ggtaactggc ttcagcagag cgcagatacc aaatactgtc cttctagtgt    6000
agccgtagtt aggccaccac ttcaagaact ctgtagcacc gcctacatac ctcgctctgc   6060
taatcctgtt accagtggct gctgccagtg gcgataagtc gtgtcttacc gggttggact   6120
caagacgata gttaccggat aaggcgcagc ggtcgggctg aacggggggt tcgtgcacac   6180
agcccagctt ggagcgaacg acctacaccg aactgagata cctacagcgt gagctatgag   6240
aaagcgccac gcttcccgaa gggagaaagg cggacaggta tccggtaagc ggcagggtcg   6300
gaacaggaga gcgcacgagg gagcttccag ggggaaacgc ctggtatctt tatagtcctg   6360
tcgggtttcg ccacctctga cttgagcgtc gatttttgtg atgctcgtca ggggggcgga   6420
```

```
gcctatggaa aaacgccagc aacgcggcct ttttacggtt cctggccttt tgctggcctt    6480
ttgctcacat gttctttcct gcgttatccc ctgattctgt ggataaccgt attaccgcct    6540
ttgagtgagc tgataccgct cgccgcagcc gaacgaccga gcgcagcgag tcagtgagcg    6600
aggaagcgga gagcgcccca atacgcaaac cgcctctccc cgcgcgttgg ccgattcatt    6660
aatgcagctg gcacgacagg tttcccgact ggaaagcggg cagtgagcgc aacgcaatta    6720
atgtgagtta gctcactcat taggcacccc aggctttaca ctttatgctt ccggctcgta    6780
tgttgtgtgg aattgtgagc ggataacaat ttcacacagg aaacagctat gaccatgatt    6840
acgaattccc ttgtatctct acacacaggc tcaaatcaat aagaagaacg gttcgtctt     6900 ttcgtttata tcttgcatcg tcccaaagct attggcggga tattctgttt gcagttggct    6960
gacttgaagt aatctctgca gatctttcga cactgaaata cgtcgagcct gctccgcttg    7020
gaagcggcga ggagcctcgt cctgtcacaa ctaccaacat ggagtacgat aagggccagt    7080
tccgccagct cattaagagc cagttcatgg gcgttggcat gatggccgtc atgcatctgt    7140
acttcaagta caccaacgct cttctgatcc agtcgatcc ccgctgaagg cgctttcgaa     7200
tctggttaag atccacgtct tcgggaagcc agcgactggt gacctccagc gtccctttaa    7260
ggctgccaac agctttctca gccagggcca gcccaagacc gacaaggcct ccctccagaa    7320
cgccgagaag aactggaggg gtggtgtcaa ggaggagtaa gctccttatt gaagtcggag    7380
gacggagcgg tgtcaagagg atattcttcg actctgtatt atagataaga tgatgaggaa    7440
ttggaggtag catagcttca tttggatttg ctttccaggc tgagactcta gcttggagca    7500
tagagggtcc tttggctttc aatattctca agtatctcga gtttgaactt attccctgtg    7560 aacctttat tcaccaatga gcattggaat gaacatgaat ctgaggactg caatcgccat     7620
gaggttttcg aaatacatcc ggatgtcgaa ggcttgggc acctgcgttg gttgaattta     7680
gaacgtggca ctattgatca tccgatagct ctgcaaaggg cgttgcacaa tgcaagtcaa    7740
acgttgctag cagttccagg tggaatgtta tgatgagcat tgtattaaat caggagatat    7800
agcatgatct ctagttagct caccacaaaa gtcagacggc gtaaccaaaa gtcacacaac    7860
acaagctgta aggatttcgg cacggctacg gaagacggag aagccacctt cagtggactc    7920
gagtaccatt taattctatt tgtgtttgat cgagacctaa tacagcccct acaacgacca    7980
tcaaagtcgt atagctacca gtgaggaagt ggactcaaat cgacttcagc aacatctcct    8040
ggataaactt taagcctaaa ctatacagaa taagataggt ggagagctta taccgagctc    8100
ccaaatctgt ccagatcatg gttgaccggt gcctggatct tcctatagaa tcatccttat    8160
tcgttgacct agctgattct ggagtgaccc agagggtcat gacttgagcc taaaatccgc    8220
cgcctccacc atttgtagaa aaatgtgacg aactcgtgag ctctgtacag tgaccggtga    8280
ctctttctgg catgcggaga gacggacgga cgcagagaga agggctgagt aataagccac    8340
tggccagaca gctctggcgg ctctgaggtg cagtggatga ttattaatcc gggaccggcc    8400 gccctccgc cccgaagtgg aaaggctggt gtgcccctcg ttgaccaaga atctattgca     8460
tcatcggaga atatggagct tcatcgaatc accggcagta agcgaaggag aatgtgaagc    8520
caggggtgta tagccgtcgg cgaaatagca tgccattaac ctaggtacag aagtccaatt    8580
gcttccgatc tggtaaaaga ttcacgagat agtaccttct ccgaagtagg tagagcgagt    8640
acccggcgcg taagctccct aattggccca tccggcatct gtagggcgtc caaatatcgt    8700
gcctctcctg ctttgcccgg tgtatgaaac cggaaaggcc gctcaggagc tggccagcgg    8760
cgcagaccgg gaacacaagc tggcagtcga cccatccggt gctctgcact cgacctgctg    8820
```

```
aggtccctca gtccctggta ggcagctttg cccgtctgt ccgccggtg tgtcggcggg    8880 gttgacaagg tcgttgcgtc agtccaacat ttgttgccat attttcctgc tctcccacc    8940 agctgctctt ttcttttctc tttcttttcc catcttcagt atattcatct tcccatccaa    9000
gaacctttat ttcccctaag taagtacttt gctacatcca tactccatcc ttcccatccc    9060
ttattccttt gaacctttca gttcgagctt tcccacttca tcgcagcttg actaacagct    9120
accccgcttg agcagacatc accatgggg                                      9149
```

<210> SEQ ID NO 20
<211> LENGTH: 8747
<212> TYPE: DNA
<213> ORGANISM: Artificial Sequence
<220> FEATURE:
<223> OTHER INFORMATION: Artificial polynucleotide sequence
<220> FEATURE:
<221> NAME/KEY: misc_feature
<222> LOCATION: (3754)..(3754)
<223> OTHER INFORMATION: n is a, c, g, or t
<220> FEATURE:
<221> NAME/KEY: misc_feature
<222> LOCATION: (3962)..(3962)
<223> OTHER INFORMATION: n is a, c, g, or t
<220> FEATURE:
<221> NAME/KEY: misc_feature
<222> LOCATION: (4053)..(4053)
<223> OTHER INFORMATION: n is a, c, g, or t

<400> SEQUENCE: 20

```
gaattccctt gtatctctac acacaggctc aaatcaataa gaagaacggt tcgtcttttt     60
cgtttatatc ttgcatcgtc ccaaagctat tggcgggata ttctgtttgc agttggctga    120
cttgaagtaa tctctgcaga tctttcgaca ctgaaatacg tcgagcctgc tccgcttgga    180
agcggcgagg agcctcgtcc tgtcacaact accaacatgg agtacgataa gggccagttc    240
cgccagctca ttaagagcca gttcatgggc gttggcatga tggccgtcat gcatctgtac    300
ttcaagtaca ccaacgctct tctgatccag tcgatcatcc gctgaaggcg ctttcgaatc    360
tggttaagat ccacgtcttc gggaagccag cgactggtga cctccagcgt cccttaagg    420 ctgccaacag ctttctcagc cagggccagc caagaccga caaggcctcc ctccagaacg    480
ccgagaagaa ctggaggggt ggtgtcaagg aggagtaagc tccttattga agtcggagga    540
cggagcggtg tcaagaggat attcttcgac tctgtattat agataagatg atgaggaatt    600
ggaggtagca tagcttcatt tggatttgct ttccaggctg agactctagc ttggagcata    660
gagggtcctt tggctttcaa tattctcaag tatctcgagt ttgaacttat tccctgtgaa    720
ccttttattc accaatgagc attggaatga acatgaatct gaggactgca atcgccatga    780
ggttttcgaa atacatccgg atgtcgaagg cttgggcac ctgcgttggt tgaatttaga    840
acgtggcact attgatcatc cgatagctct gcaaagggcg ttgcacaatg caagtcaaac    900
gttgctagca gttccaggtg gaatgttatg atgagcattg tattaaatca ggagatatag    960
catgatctct agttagctca ccacaaaagt cagacggcgt aaccaaaagt cacacaacac   1020
aagctgtaag gatttcggca cggctacgga agacggagaa gccaccttca gtggactcga   1080
gtaccattta attctatttg tgtttgatcg agacctaata cagcccctac aacgaccatc   1140
aaagtcgtat agctaccagt gaggaagtgg actcaaatcg acttcagcaa catctcctgg   1200
ataaacttta agcctaaact atacagaata agataggtgg agagcttata ccgagctccc   1260
aaatctgtcc agatcatggt tgaccggtgc ctggatcttc ctatagaatc atccttattc   1320
```

```
gttgacctag ctgattctgg agtgacccag agggtcatga cttgagccta aaatccgccg    1380
cctccaccat ttgtagaaaa atgtgacgaa ctcgtgagct ctgtacagtg accggtgact    1440
cttcctggca tgcggagaga cggacggacg cagagagaag ggctgagtaa taagccactg    1500
gccagacagc tctggcggct ctgaggtgca gtggatgatt attaatccgg accggccgc     1560
ccctccgccc cgaagtggaa aggctggtgt gcccctcgtt gaccaagaat ctattgcatc    1620
atcggagaat atggagcttc atcgaatcac cggcagtaag cgaaggagaa tgtgaagcca    1680
ggggtgtata gccgtcggcg aaatagcatg ccattaacct aggtacagaa gtccaattgc    1740
ttccgatctg gtaaaagatt caccgagatag taccttctcc gaagtaggta gagcgagtac    1800
ccggcgcgta agctccctaa ttggcccatc cggcatctgt agggcgtcca aatatcgtgc    1860
ctctcctgct ttgcccggtg tatgaaaccg gaaaggccgc tcaggagctg gccagcggcg    1920
cagaccggga acacaagctg gcagtcgacc catccggtgc tctgcactcg acctgctgag    1980
gtccctcagt ccctggtagg cagctttgcc ccgtctgtcc gcccggtgtg tcggcggggt    2040
tgacaaggtc gttgcgtcag tccaacattt gttgccatat tttcctgctc tccccaccag    2100
ctgctctttt cttttctctt tcttttccca tcttcagtat attcatcttc ccatccaaga    2160
accttattt ccccctaagta agtactttgc tacatccata ctccatcctt cccatccctt    2220
attcctttga acctttcagt tcgagctttc ccacttcatc gcagcttgac taacagctac    2280
cccgcttgag cagacatcac catggggcgc gccaaaaaaa aggcgcgcca tggcatccac    2340
aaagcccgct tcgagtctca tttaccaggc atggaacaaa ctcagtatca accaaaccat    2400
ccctagtgac tcccttgaat tacttgggga gcgtttggct attgccttcg cacccaaact    2460
caaggagcaa cgaaggaatg gccggcgtcg gaatctggaa tatgtggcac aacatcgacg    2520
gaagattgct cgaaaaatct acttggagat tctggagaaa gacccaaata tctttcttcc    2580
ttttatcctg gctgtttccc ctagagcatg cttatccttt gatatctcga gctttcttga    2640
acagcaccaa agccaaggaa gacatttcct ccgcaacaat gccgaagcga tcctctgggg    2700
tctcgcaaag aaacatgaca ttgatggctc cctccatttc aggaagctga tgcgtgagat    2760
tttccaactg tctcctccag cgacagaagc cgaaggcaag gagcattatt cattgcattt    2820
aagcactctc cccgcaatcc gcaatgcctt cggtgatgtt atctttgacg caattgaacg    2880
ttccccctaca caggtgacag cgagagctaa aggttatttc tctgagaaaa ccgaaagtgt    2940
ttggacaaaa gttccctaca gaagttctca agacgcaatc atatctcttg aagtagggtc    3000
ggcaatcgag cttgcgaatg tgttgttccc aatcgcaacc caaaaaattg tctctatcct    3060
ttccgcatgt tctcccactg tgcgccagaa gaacttttct gaggctattc tcggcccaga    3120
ccctcaggat acaccggcaa catcatcaga atcggtatg aagtttaagg tacacatgac     3180
tgcagttgct aattccaccc tgtgctagat gtggcgtatt ttactctgcg aggagcaacg    3240
gtctcggcaa ttgaatcagt cttttcgcgct gatatttgcg aaggtattaa gggcagcgaa    3300
ctgagaaact gggaaaagga gcagctgctc atcgacacga cagattgtgt cacgatgcag    3360
atatggcggg cacaacctca acatggaacc atcaagttgc gtattggatt ctatgcagcg    3420
gtgaatttgg caaatcggct gtatgcagaa acaccccaag atcacatata ggcggccgcg    3480
aagcttgaga tccacttaac gttactgaaa tcatcaaaca gcttgacgaa tctggatata    3540
agatcgttgg tgtcgatgtc agctccggag ttgagacaaa tggtgttcag gatctcgata    3600
agatacgttc atttgtccaa gcagcaaaga gtgccttcta gtgatttaat agctccatgt    3660
caacaagaat aaaacgcgtt ttcgggttta cctcttccag atacagctca tctgcaatgc    3720
```

```
attaatgcat tgactgcaac ctagtaacgc cttncaggct ccggcgaaga gaagaatagc   3780
ttagcagagc tattttcatt ttcgggagac gagatcaagc agatcaacgg tcgtcaagag   3840
acctacgaga ctgaggaatc cgctcttggc tccacgcgac tatatatttg tctctaattg   3900
tactttgaca tgctcctctt ctttactctg atagcttgac tatgaaaatt ccgtcaccag   3960
cnactgggtt cgcaaagata attgcatgtt tcttccttga actctcaagc ctacaggaca   4020
cacattcatc gtaggtataa acctcgaaat canttcctac taagatggta tacaatagta   4080
accatgcatg gttgcctagt gaatgctccg taacacccaa tacgccggcc gaaactttt   4140
tacaactctc ctatgagtcg tttacccaga atgcacaggt acacttgttt agaggtaatc   4200
cttctttcta gaggcctcaa acaatgctct tcaccctctt cgcgggtctg aaataccctc   4260
acctggcaac agcaattggc gcttcatggc tgtttttccg atctctctac ttgtacggct   4320
atgtgtactc gggtaagcca caaggcaagg gcagattgct gggaggtttc ttctggtttt   4380
ctcaaggcgc tctgtgggct ctgagtgtgt ttggtgttgc caaagacatg atctcttact   4440
gagagttatt ctgtgtctga cgaaatatgt tgtgtatata tatatatgta cgttaaaagt   4500
tccgtgggagt taccagtgat tgaccaatgt tttatcttct acagttctgc ctgtctaccc   4560
cattctagct gtacctgact acagaatagt ttaattgtgg ttgaccccac agtcggaggc   4620
ggaggaatac agcaccgatg tggcctgtct ccatccagat tggcacgcaa ttttacacg   4680
cggaaaagat cgagatagag tacgacttta aatttagtcc ccggcggctt ctattttaga   4740
atatttgaga tttgattctc aagcaattga tttggttggg tcaccctcaa ttggataata   4800
tacctcattg ctcggctact tcaactcatc aatcaccgtc ataccccgca tataaccctc   4860
cattcccacg atgtcgtcca agtcgcaatt gacttacggt gctcgagcca gcaagcaccc   4920
caatcctctg gcaaagagac tttttgagat tgccgaagca aagaagacaa acgttaccgt   4980
ctctgctgat gtgacgacaa cccgagaact cctggacctc gctgaccgta cggaagctgt   5040
tggatccaat acatatgccg tctagcaatg gactaatcaa cttttgatga tacaggtctc   5100
ggtccctaca tcgccgtcat caagacacac atcgacatcc tcaccgattt cagcgtcgac   5160
actatcaatg gcctgaatgt gctggctcaa aagcacaact ttttgatctt cgaggaccgc   5220
aaattcatcg acatcggcaa taccgtccag aagcaatacc acggcggtgc tctgaggatc   5280
tccgaatggg cccacattat caactgcagc gttctccctg gcgagggcat cgtcgaggct   5340
ctggcccaga ccgcatctgc gcaagacttc ccctatggtc ctgagagagg actgttggtc   5400
ctggcagaga tgacctccaa aggatcgctg gctacgggcg agtataccaa ggcatcggtt   5460
gactacgctc gcaaatacaa gaacttcgtt atgggtttcg tgtcgacgcg ggccctgacg   5520
gaagtgcagt cggatgtgtc ttcagcctcg gaggatgaag atttcgtggt cttcacgacg   5580
ggtgtgaacc tctcttccaa aggagataag cttggacagc aataccagac tcctgcatcg   5640
gctattggac gcggtgccga ctttatcatc gccggtcgag gcatctacgc tgctcccgac   5700
ccggttgaag ctgcacagcg gtaccagaaa gaaggctggg aagcttatat ggccagagta   5760
tgcggcaagt catgatttcc tcttggagca aaagtgtagt gccagtacga gtgttgtgga   5820
ggaaggctgc atacattgtg cctgtcatta acgatgagc tcgtccgtat tggcccctgt    5880
aatgccatgt tttccgcccc caatcgtcaa ggttttccct ttgttagatt cctaccagtc   5940
atctagcaag tgaggtaagc tttgccagaa acgccaaggc tttatctatg tagtcgataa   6000
gcaaagtgga ctgatagctt aatatggaag gtccctcagg gacaagtcga cctgtgcaga   6060
```

```
agagataaca gcttggcatc acgcatcagt gcctcctctc agacagaatc tagagcttgg    6120
cactggccgt cgttttacaa cgtcgtgact gggaaaaccc tggcgttacc caacttaatc    6180
gccttgcagc acatccccct ttcgccagct ggcgtaatag cgaagaggcc cgcaccgatc    6240
gcccttccca acagttgcgc agcctgaatg gcgaatggcg cctgatgcgg tattttctcc    6300
ttacgcatct gtgcggtatt tcacaccgca tatggtgcac tctcagtaca atctgctctg    6360
atgccgcata gttaagccag ccccgacacc cgccaacacc cgctgacgcg ccctgacggg    6420
cttgtctgct cccggcatcc gcttacagac aagctgtgac cgtctccggg agctgcatgt    6480
gtcagaggtt ttcaccgtca tcaccgaaac gcgcgagacg aaagggcctc gtgatacgcc    6540
tatttttata ggttaatgtc atgataataa tggtttctta gacgtcaggt ggcacttttc    6600
ggggaaatgt gcgcggaacc cctatttgtt tatttttcta atacattca aatatgtatc    6660 cgctcatgag acaataaccc tgataaatgc ttcaataata ttgaaaaagg aagagtatga    6720
gtattcaaca tttccgtgtc gcccttattc cctttttgc ggcatttgc cttcctgttt    6780 ttgctcaccc agaaacgctg gtgaaagtaa aagatgctga agatcagttg ggtgcacgag    6840
tgggttacat cgaactggat ctcaacagcg gtaagatcct tgagagtttt cgccccgaag    6900
aacgttttcc aatgatgagc acttttaaag ttctgctatg tggcgcggta ttatcccgta    6960
ttgacgccgg gcaagagcaa ctcggtcgcc gcatacacta ttctcagaat gacttggttg    7020
agtactcacc agtcacagaa aagcatctta cggatggcat gacagtaaga gaattatgca    7080
gtgctgccat aaccatgagt gataacactg cggccaactt acttctgaca acgatcggag    7140
gaccgaagga gctaaccgct ttttgcaca acatggggga tcatgtaact cgccttgatc    7200
gttgggaacc ggagctgaat gaagccatac caaacgacga gcgtgacacc acgatgcctg    7260
tagcaatggc aacaacgttg cgcaaactat taactggcga actacttact ctagcttccc    7320
ggcaacaatt aatagactgg atggaggcgg ataaagttgc aggaccactt ctgcgctcgg    7380
cccttccggc tggctggttt attgctgata aatctggagc cggtgagcgt gggtctcgcg    7440
gtatcattgc agcactgggg ccagatggta agccctcccg tatcgtagtt atctacacga    7500
cggggagtca ggcaactatg gatgaacgaa atagacagat cgctgagata ggtgcctcac    7560
tgattaagca ttggtaactg tcagaccaag tttactcata tactttag attgatttaa    7620 aacttcattt ttaatttaaa aggatctagg tgaagatcct ttttgataat ctcatgacca    7680
aaatccctta acgtgagttt tcgttccact gagcgtcaga ccccgtagaa aagatcaaag    7740
gatcttcttg agatcctttt tttctgcgcg taatctgctg cttgcaaaca aaaaaaccac    7800
cgctaccagc ggtggtttgt ttgccggatc aagagctacc aactctttt ccgaaggtaa    7860 ctggcttcag cagagcgcag ataccaaata ctgtccttct agtgtagccg tagttaggcc    7920
accacttcaa gaactctgta gcaccgccta catacctcgc tctgctaatc ctgttaccag    7980
tggctgctgc cagtggcgat aagtcgtgtc ttaccgggtt ggactcaaga cgatagttac    8040
cggataaggc gcagcggtcg ggctgaacgg ggggttcgtg cacacagccc agcttggagc    8100
gaacgaccta caccgaactg agatacctac agcgtgagct atgagaaagc gccacgcttc    8160
ccgaagggag aaaggcggac aggtatccgg taagcggcag ggtcggaaca ggagagcgca    8220
cgagggagct ccaggggga aacgcctggt atctttatag tcctgtcggg tttcgccacc    8280
tctgacttga gcgtcgattt ttgtgatgct cgtcaggggg gcggagccta tggaaaaacg    8340
ccagcaacgc ggcctttta cggttcctgg ccttttgctg gccttttgct cacatgttct    8400
ttcctgcgtt atcccctgat tctgtggata accgtattac cgcctttgag tgagctgata    8460
```

```
ccgctcgccg cagccgaacg accgagcgca gcgagtcagt gagcgaggaa gcggaagagc    8520
gcccaatacg caaaccgcct ctccccgcgc gttggccgat tcattaatgc agctggcacg    8580
acaggtttcc cgactggaaa gcgggcagtg agcgcaacgc aattaatgtg agttagctca    8640
ctcattaggc accccaggct ttacacttta tgcttccggc tcgtatgttg tgtggaattg    8700
tgagcggata caatttcac acaggaaaca gctatgacca tgattac                  8747
```

<210> SEQ ID NO 21
<211> LENGTH: 36
<212> TYPE: DNA
<213> ORGANISM: Artificial Sequence
<220> FEATURE:
<223> OTHER INFORMATION: Primer 3

<400> SEQUENCE: 21

```
aaaaggcgcg ccatggcttg gtacagtgct ttactc                               36
```

<210> SEQ ID NO 22
<211> LENGTH: 35
<212> TYPE: DNA
<213> ORGANISM: Artificial Sequence
<220> FEATURE:
<223> OTHER INFORMATION: Primer 4

<400> SEQUENCE: 22

```
aaaagcggcc gctcagaaca gaccgcttga aaggc                                35
```

<210> SEQ ID NO 23
<211> LENGTH: 9797
<212> TYPE: DNA
<213> ORGANISM: Artificial Sequence
<220> FEATURE:
<223> OTHER INFORMATION: Artificial polynucleotide sequence
<220> FEATURE:
<221> NAME/KEY: misc_feature
<222> LOCATION: (3236)..(3236)
<223> OTHER INFORMATION: n is a, c, g, or t
<220> FEATURE:
<221> NAME/KEY: misc_feature
<222> LOCATION: (3444)..(3444)
<223> OTHER INFORMATION: n is a, c, g, or t
<220> FEATURE:
<221> NAME/KEY: misc_feature
<222> LOCATION: (3535)..(3535)
<223> OTHER INFORMATION: n is a, c, g, or t

<400> SEQUENCE: 23

```
gaattcccctt gtatctctac acacaggctc aaatcaataa gaagaacggt tcgtcttttt    60
cgtttatatc ttgcatcgtc ccaaagctat ggcgggata ttctgtttgc agttggctga    120
cttgaagtaa tctctgcaga tctttcgaca ctgaaatacg tcgagcctgc tccgcttgga    180
agcggcgagg agcctcgtcc tgtcacaact accaacatgg agtacgataa gggccagttc    240
cgccagctca ttaagagcca gttcatgggc gttggcatga tggccgtcat gcatctgtac    300
ttcaagtaca ccaacgctct tctgatccag tcgatcatcc gctgaaggcg ctttcgaatc    360
tggttaagat ccacgtcttc gggaagccag cgactggtga cctccagcgt cccttttaagg    420 ctgccaacag ctttctcagc cagggccagc ccaagaccga caaggcctcc ctccagaacg    480
ccgagaagaa ctggagggggt ggtgtcaagg aggagtaagc tccttattga agtcggagga    540
cggagcggtg tcaagaggat attcttcgac tctgtattat agataagatg atgaggaatt    600
ggaggtagca tagcttcatt tggattttgct ttccaggctg agactctagc ttggagcata    660
```

```
gagggtcctt tggctttcaa tattctcaag tatctcgagt ttgaacttat tccctgtgaa    720
ccttttattc accaatgagc attggaatga acatgaatct gaggactgca atcgccatga    780
ggttttcgaa atacatccgg atgtcgaagg cttggggcac ctgcgttggt tgaatttaga    840
acgtggcact attgatcatc cgatagctct gcaaagggcg ttgcacaatg caagtcaaac    900
gttgctagca gttccaggtg aatgttatg atgagcattg tattaaatca ggagatatag     960
catgatctct agttagctca ccacaaaagt cagacggcg aaccaaaagt cacacaacac     1020
aagctgtaag gatttcggca cggctacgga agacggagaa gccaccttca gtggactcga    1080
gtaccattta attctatttg tgtttgatcg agacctaata cagcccctac aacgaccatc    1140
aaagtcgtat agctaccagt gaggaagtgg actcaaatcg acttcagcaa catctcctgg    1200
ataaacttta agcctaaact atacagaata agataggtgg agagcttata ccgagctccc    1260
aaatctgtcc agatcatggt tgaccggtgc ctggatcttc ctatagaatc atccttattc    1320
gttgacctag ctgattctgg agtgacccag agggtcatga cttgagccta aaatccgccg    1380
cctccaccat ttgtagaaaa atgtgacgaa ctcgtgagct ctgtacagtg accggtgact    1440
ctttctggca tgcggagaga cggacggacg cagagagaag ggctgagtaa taagccactg    1500
gccagacagc tctggcggct ctgaggtgca gtggatgatt attaatccgg gaccggccgc    1560
ccctccgccc cgaagtggaa aggctggtgt gcccctcgtt gaccaagaat ctattgcatc    1620
atcggagaat atggagcttc atcgaatcac cggcagtaag cgaaggagaa tgtgaagcca    1680
ggggtgtata gccgtcggcg aaatagcatg ccattaacct aggtacagaa gtccaattgc    1740
ttccgatctg gtaaaagatt caccgagatag taccttctcc gaagtaggta gagcgagtac    1800
ccggcgcgta agctccctaa ttggcccatc cggcatctgt agggcgtcca aatatcgtgc    1860
ctctcctgct ttgcccggtg tatgaaaccg gaaaggccgc tcaggagctg gccagcggcg    1920
cagaccggga acacaagctg gcagtcgacc catccggtgc tctgcactcg acctgctgag    1980
gtccctcagt ccctggtagg cagctttgcc ccgtctgtcc gcccggtgtg tcggcggggt    2040
tgacaaggtc gttgcgtcag tccaacattt gttgccatat tttcctgctc tccccaccag    2100
ctgctctttt cttttctctt tcttttccca tcttcagtat attcatcttc ccatccaaga    2160
acctttattt cccctaagta agtactttgc tacatccata ctccatcctt cccatccctt    2220
attcctttga acctttcagt tcgagctttc ccacttcatc gcagcttgac taacagctac    2280
cccgcttgag cagacatcac catggggcgc gccatggctt ggtacagtgc tttactcccg    2340
tgcatgctat ggtggcggaa cctcctgtgg cgtaacagca ccaataggta tagacagagt    2400
acagacgacc ttacttcact gactgataag atacctaatc ttggagaaag ggtaagtgta    2460
aatactttt gaggtcgctt ctaggagtct aatcactttg gaaagacaac tcccacagat     2520
aacatcgatg gaaagagctt cgtggcacat actgtcgtgc agaccaggcg gattggtgac    2580
cgagaacgtt gctgcttcaa tgactcggat ttgaacagcg gcacagttac caaatttatt    2640
gagctttgtt aatagcattc cagatcagag tactactgcc ggaaaaatta atcacaaggc    2700
cctgcgagat cctgagctct ttgctatccg ctcgtcatgc atcgacaaat cagccagcaa    2760
gtggatggtt agtctctact acgaaccccc acccagcctt gatgacctcg agattaagaa    2820
cttcggatct cgtattccag agtcggagga tgatccaatt gaggctatct ttcactatga    2880
gggagagaac atttgggtat ctgttcctta tttgtatgct agaactagaa gcctttcaag    2940
cggtctgttc tgagcggccg cgaagcttga gatccactta acgttactga aatcatcaaa    3000
cagcttgacg aatctggata taagatcgtt ggtgtcgatg tcagctccgg agttgagaca    3060
```

```
aatggtgttc aggatctcga taagatacgt tcatttgtcc aagcagcaaa gagtgccttc    3120
tagtgattta atagctccat gtcaacaaga ataaaacgcg ttttcgggtt tacctcttcc    3180
agatacagct catctgcaat gcattaatgc attgactgca acctagtaac gccttncagg    3240
ctccggcgaa gagaagaata gcttagcaga gctattttca ttttcgggag acagatcaa    3300 gcagatcaac ggtcgtcaag agacctacga gactgaggaa tccgctcttg ctccacgcg    3360 actatatatt tgtctctaat tgtactttga catgctcctc ttctttactc tgatagcttg    3420
actatgaaaa ttccgtcacc agcncctggg ttcgcaaaga taattgcatg tttcttcctt    3480
gaactctcaa gcctacagga cacacattca tcgtaggtat aaacctcgaa atcanttcct    3540
actaagatgg tatacaatag taaccatgca tggttgccta gtgaatgctc cgtaacaccc    3600
aatacgccgg ccgaaacttt tttacaactc tcctatgagt cgtttaccca gaatgcacag    3660
gtacacttgt ttagaggtaa tccttctttg gggatctgac agacgggcaa ttgattacgg    3720
gatcccattg gtaacgaaat gtaaaagcta ggagatcgtc cgccgatgtc aggatgattt    3780
cacttgtttc ttgtccggct caccggtcaa agctaaagag gagcaaaagg aacggataga    3840
atcgggtgcc gctgatctat acggtatagt gcccttatca cgttgactca acccatgcta    3900
tttaactcaa cccctccttc tgaaccccac catcttcttc cttttcctct catcccacac    3960
aattctctat ctcagatttg aattccaaaa gtcctcggac gaaactgaac aagtcttcct    4020
cccttcgata aacctttggt gattggaata actgaccatc ttctatagtt cccaaaccaa    4080
ccgacaatgt aaatacactc ctcgattagc cctctagtat ccttgaagct gtccctgatg    4140
gtcgtcatct acctgcctgg acagcatggc ctgcaacgcg ggcatcccga tgccgccgga    4200
agcgagaaga atcataatgg ggaaggccat ccagcctcgc gtcgagcttt gaagttgctg    4260
caagctggct tcaagccatc ccatccgaat gtgatggatg cgttctttct gggccgttgc    4320
gactttgggg atcgtctttc ccgcgccctt ggttggaggc cctgtctccg gtgtcccttg    4380
tcccttccag gcaagcgagc gaggtccatt cagatggtgc tccatcagcg ttggctttcc    4440
gtctccattg gctcttggca attcggtcag cggggctgac tgcctcaggt ggggcagtgc    4500
tagtgtgtgt accgacccgc aggattggtg ctttgcccag agctctacag aatagcgcgc    4560
gcatccatat gttagttctg caattttctt gtatcggtgc tgtgactcat acttcccct    4620 ttggctggcc ttgcggcaac caataagaac gcacagtgaa atcttgcggg tggggagtgg    4680
atccatggcg cctgcattgg cttggggacg cgcactgtcg cacacttcca tctgaccttt    4740
cagaagggtt tcgtggtggg caaggaccaa ccggttgcgc ggccgtgcgt gggtgcctcg    4800
cccggcactg ccagggccac tgcagtggca gtttgctgcc tgatacaaaa tccttccctc    4860
cgcccagttt tccctctttg accttccttt ctcttcctg caaccaaatc caccctatca    4920
aaccaaaaca gtatctcgac cgaggtatca acctgaatca gcaacatcgt agccagcatt    4980
tgtctccgtc tctgcagaac cagcgagttg caaacattat ccaggcaaca gggcaccaac    5040
tcacttcttc ggctttcacc aatcggtaca gctcttctca gaactcgcgt ccgcaacagt    5100
tctacgcttc ctcagcacct tcttcagctt caatcctgaa cactcagaac cgcgcacagc    5160
agcgccctcc tgttcccttg tttcccaaaa gtaccggtag tatttcgcac ggaaagcagg    5220
gcaacaagat gttctcaggt acccatatga aaaagcctga actcaccgcg acgtctgtcg    5280
agaagtttct gatcgaaaag ttcgacagcg tctccgacct gatgcagctc tcggagggcg    5340
aagaatctcg tgctttcagc ttcgatgtag gagggcgtgg atatgtcctg cgggtaaata    5400
```

```
gctgcgccga tggtttctac aaagatcgtt atgtttatcg gcactttgca tcggccgcgc   5460
tcccgattcc ggaagtgctt gacattgggg aattcagcga gagcctgacc tattgcatct   5520
cccgccgtgc acagggtgtc acgttgcaag acctgcctga aaccgaactg cccgctgttc   5580
tgcagccggt cgcggaggcc atggatgcga tcgctgcggc cgatcttagc cagacgagcg   5640
ggttcggccc attcggaccg caaggaatcg gtcaatacac tacatggcgt gatttcatat   5700
gcgcgattgc tgatccccat gtgtatcact ggcaaactgt gatggacgac accgtcagtg   5760
cgtccgtcgc gcaggctctc gatgagctga tgctttgggc cgaggactgc cccgaagtcc   5820
ggcacctcgt gcacgcggat ttcggctcca acaatgtcct gacggacaat ggccgcataa   5880
cagcggtcat tgactggagc gaggcgatgt tcggggattc ccaatacgag gtcgccaaca   5940
tcttcttctg gaggccgtgg ttggcttgta tggagcagca gacgcgctac ttcgagcgga   6000
ggcatccgga gcttgcagga tcgccgcggc tccggcgta tatgctccgc attggtcttg   6060
accaactcta tcagagcttg gttgacggca atttcgatga tgcagcttgg gcgcagggtc   6120
gatgcgacgc aatcgtccga tccggagccg ggactgtcgg gcgtacacaa atcgcccgca   6180
gaagcgcggc cgtctggacc gatggctgtg tagaagtact cgccgatagt ggaaaccgac   6240
gccccagcac tcgtccgagg gcaaaggaat agagtagatg ccgaccggga tccacttaac   6300
gttactgaaa tcatcaaaca gcttgacgaa tctggatata agatcgttgg tgtcgatgtc   6360
agctccggag ttgagacaaa tggtgttcag gatctcgata agatacgttc atttgtccaa   6420
gcagcaaaga gtgccttcta gtgatttaat agctccatgt caacaagaat aaaacgcgtt   6480
tcgggtttac ctcttccaga tacagctcat ctgcaatgca ttaatgcatt ggacctcgca   6540
accctagtac gcccttcagg ctccggcgaa gcagaagaat agcttagcag agtctatttt   6600
cattttcggg agacgagatc aagcagatca acggtcgtca agagacctac gagactgagg   6660
aatccgctct tggctccacg cgactatata tttgtctcta attgtacttt gacatgctcc   6720
tcttctttac tctgatagct tgactatgaa aattccgtca ccagcccctg ggttcgcaaa   6780
gataattgca ctgtttcttc cttgaactct caagcctaca ggacacacat tcatcgtagg   6840
tataaacctc gaaaatcatt cctactaaga tgggtataca atagtaacca tggttgccta   6900
gtgaatgctc cgtaacaccc aatacgccgg ccgaaacttt tttacaactc tcctatgagt   6960
cgtttaccca gaatgcacag gtacacttgt ttagaggtaa tccttctttc tagctagagg   7020
atcctctacg ccggacgcat cgtggccggc atcaccggcg ccacaggtgc ggttgctgac   7080
tagaataatt atgtgtaaca agaaagacag tataatacaa acaaagatgc aagagcggct   7140
catcgtcacc ccatgatagc tagagcttgg cactggccgt cgttttacaa cgtcgtgact   7200
gggaaaaccc tggcgttacc caacttaatc gccttgcagc acatccccct ttcgccagct   7260
ggcgtaatag cgaagaggcc cgcaccgatc gcccttccca acagttgcgc agcctgaatg   7320
gcgaatggcg cctgatgcgg tattttctcc ttacgcatct gtgcggtatt tcacaccgca   7380
tatggtgcac tctcagtaca atctgctctg atgccgcata gttaagccag ccccgacacc   7440
cgccaacacc cgctgacgcg ccctgacggg cttgtctgct cccggcatcc gcttacagac   7500
aagctgtgac cgtctccggg agctgcatgt gtcagaggtt ttcaccgtca tcaccgaaac   7560
gcgcgagacg aaagggcctc gtgatacgcc tatttttata ggttaatgtc atgataataa   7620
tggtttctta gacgtcaggt ggcacttttc ggggaaatgt gcgcggaacc cctatttgtt   7680
tatttttcta aatacattca aatatgtatc cgctcatgag acaataaccc tgataaatgc   7740
ttcaataata ttgaaaaagg aagagtatga gtattcaaca tttccgtgtc gcccttattc   7800
```

-continued

```
ccttttttgc ggcattttgc cttcctgttt ttgctcaccc agaaacgctg gtgaaagtaa      7860
aagatgctga agatcagttg ggtgcacgag tgggttacat cgaactggat ctcaacagcg      7920
gtaagatcct tgagagtttt cgccccgaag aacgttttcc aatgatgagc acttttaaag      7980
ttctgctatg tggcgcggta ttatcccgta ttgacgccgg gcaagagcaa ctcggtcgcc      8040
gcatacacta ttctcagaat gacttggttg agtactcacc agtcacagaa aagcatctta      8100
cggatggcat gacagtaaga gaattatgca gtgctgccat aaccatgagt gataacactg      8160
cggccaactt acttctgaca acgatcggag gaccgaagga gctaaccgct tttttgcaca      8220
acatggggga tcatgtaact cgccttgatc gttgggaacc ggagctgaat gaagccatac      8280
caaacgacga gcgtgacacc acgatgcctg tagcaatggc aacaacgttg cgcaaactat      8340
taactggcga actacttact ctagcttccc ggcaacaatt aatagactgg atggaggcgg      8400
ataaagttgc aggaccactt ctgcgctcgg cccttccggc tggctggttt attgctgata      8460
aatctggagc cggtgagcgt gggtctcgcg gtatcattgc agcactgggg ccagatggta      8520
agccctcccg tatcgtagtt atctacacga cggggagtca ggcaactatg gatgaacgaa      8580
atagacagat cgctgagata ggtgcctcac tgattaagca ttggtaactg tcagaccaag      8640
tttactcata tactttag attgatttaa aacttcattt ttaatttaaa aggatctagg      8700
tgaagatcct tttgataat ctcatgacca aaatccctta acgtgagttt tcgttccact      8760
gagcgtcaga ccccgtagaa aagatcaaag gatcttcttg agatcctttt tttctgcgcg      8820
taatctgctg cttgcaaaca aaaaaaccac cgctaccagc ggtggtttgt ttgccggatc      8880
aagagctacc aactcttttt ccgaaggtaa ctggcttcag cagagcgcag ataccaaata      8940
ctgtccttct agtgtagccg tagttaggcc accacttcaa gaactctgta gcaccgccta      9000
catacctcgc tctgctaatc ctgttaccag tggctgctgc cagtggcgat aagtcgtgtc      9060
ttaccgggtt ggactcaaga cgatagttac cggataaggc gcagcggtcg ggctgaacgg      9120
ggggttcgtg cacacagccc agcttggagc gaacgaccta caccgaactg agatacctac      9180
agcgtgagct atgagaaagc gccacgcttc ccgaagggag aaaggcggac aggtatccgg      9240
taagcggcag ggtcggaaca ggagagcgca cgagggagct tccaggggga aacgcctggt      9300
atctttatag tcctgtcggg tttcgccacc tctgacttga gcgtcgattt ttgtgatgct      9360
cgtcaggggg gcggagccta tggaaaaacg ccagcaacgc ggccttttta cggttcctgg      9420
ccttttgctg gccttttgct cacatgttct ttcctgcgtt atccctgat tctgtggata      9480 accgtattac cgcctttgag tgagctgata ccgctcgccg cagccgaacg accgagcgca      9540
gcgagtcagt gagcgaggaa gcggaagagc gcccaatacg caaaccgcct ctccccgcgc      9600
gttggccgat tcattaatgc agctggcacg acaggtttcc cgactggaaa gcgggcagtg      9660
agcgcaacgc aattaatgtg agttagctca ctcattaggc accccaggct ttacacttta      9720
tgcttccggc tcgtatgttg tgtggaattg tgagcggata caatttcac acaggaaaca      9780 gctatgacca tgattac                                                    9797
```

<210> SEQ ID NO 24
<211> LENGTH: 31
<212> TYPE: DNA
<213> ORGANISM: Artificial Sequence
<220> FEATURE:
<223> OTHER INFORMATION: Primer 5

<400> SEQUENCE: 24

```
aaaaagatct gccgtaacgt aacaaagcgg g                              31
```

<210> SEQ ID NO 25
<211> LENGTH: 36
<212> TYPE: DNA
<213> ORGANISM: Artificial Sequence
<220> FEATURE:
<223> OTHER INFORMATION: Primer 6

<400> SEQUENCE: 25

```
aaaagcggcc gcttcgggca gcgaattggt atggtc                         36
```

<210> SEQ ID NO 26
<211> LENGTH: 5068
<212> TYPE: DNA
<213> ORGANISM: Artificial Sequence
<220> FEATURE:
<223> OTHER INFORMATION: Artificial polynucleotide sequence

<400> SEQUENCE: 26

```
ctaaattgta agcgttaata ttttgttaaa attcgcgtta aattttttgtt aaatcagctc    60
attttttaac caataggccg aaatcggcaa aatcccttat aaatcaaaag aatagaccga   120
gatagggttg agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta atcggaacc ctaaagggag    300
cccccgattt agagcttgac ggggaaagcc ggcgaacgtg gcgagaaagg aagggaagaa   360
agcgaaagga gcgggcgcta gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcggcc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta gggcgaat tggagctcgg    660
cgcgccagat ctacgcgttt aattaaccgc ggtggcggcc gctctagaac tagtggatcc   720
cccgggctgc aggaattcga tatcaagctt atcgataccg tcgaggtctg agaggaggca   780
ctgatgcgct atcatggggt gacgatgagc cgctcttgca tctttgtttg tattatactg   840
tctttcttgt tacacataat tattctagaa tgccccaccg ttacatacgg gacacagcca   900
tttacatatg catgtggatt acgagctaac gagttcattc aaatctcaga actatcacat   960
aatcatcatt ccctatcgt caaagaccgt aagacaaatc cggttcatgc actgaaccca  1020
ttcgggtagt gagtcattta ctcagcacac tcgcgctgac gctcgtcgaa caccttcaat  1080
gcctcctcgg cagccttgac accactgaga accatggcac cgaaggtagg gcccatgcgg  1140
ttaaagccat caatttcaga cagctccata ccgccgatta tcaagccctt agtaacctcg  1200
cgggtgttct tgacgatggc atcctcggcc gagttcatgt cgagaccacg catgccacct  1260
agcttgtcga cgctgcccat ggacaccaag cgcttcgcac agaaggcgcc gaatgggcca  1320
tcgtgaccag tggtactgat gatgacagga gcgttgatag tgttggggtc catgcaggag  1380
tgatcatcgt ggtgaagggt gaccagcgtc cagttgacga caacaccagc aatctggggg  1440
ttgccgttct cggtcggacg ggtgatcaag tcctcaacag cggtagcatt gaagagcttg  1500
acattgggga aggagagaac cttcgacatg agtgtcgagg taaacaggga ggcgtgcttg  1560
acgacaacgt agttggggtt tgcgtcctct tcgtaaggaa cacccagctc gttcaggaag  1620
acttccgcgg gacggcgcat gaccatagca gaaaagagtt ggccacccaa ccaggcaccg  1680
```

```
ccacctattg cacgttagtt ccggaaagct gagtgcaagg caatccatca tggactactg    1740
accaggagag acgctggcct cgacgatagc aatcttcagg tccggacgag ccttggccaa    1800
gacgtacgca gtgctcagac cgcaggaacc agcaccaaca atgacaacgt cactttcagc    1860
gtacttgtcc aggtcctcaa agtaacgtct ggtcatggca cgagagacct ggctttcgcg    1920
gataggggcg aacttgaact cgtcccactt gccaccgaaa tggtccaaca gcttggtctg    1980
agaagctccc tcaacgggga cggtctcaga accacgacc ttacccttga ggccggtagc     2040
ggccacagtg ggttcgtaga tggcagctgg aggagacatg tttcaagttg caatgactat    2100
catctgttag ccattccatc aacaggaaga acgagagaag gcatgaccct tttcgctggt    2160
attatccaga tcaagtttta gccgtataat ctcagaacga acccagtcca tcgatgccat    2220
gtccttctag actaggatcc tagagtctag ggcccagctt agggagggca tgtgaatgca    2280
tcgatgactg ggaacgaaca ccggcccacg ccaaagacgt acctaagat accttgatca     2340 ttgtgagagt ccagccaaaa gtattccatg acttccatcg tatgccctct agagggctaa    2400
tcgaggagtg tatttacatt gtcggttggt ttgggaacta tagaagatgg tcagttattc    2460
caatcaccaa aggtttatcg aagggaggaa gacttgttca gtttcgtccg aggacttttg    2520
gaattcaaat ctgagataga gaattgtgtg ggatgagagg aaaaggaaga gatggtgggg    2580
gttcagaagg aggggttgag ttaaatagca tgggttgagt caacgtgata agggcactat    2640
accgtataga tcagcggcac ccgattctat ccgttccttt tgctcctctt tagctttgac    2700
cggtgagccg gacaagaaac aagtgaaatc atcctgacat cggcggacga tctcctagct    2760
tttacatttc gttaccaatg ggatcccgta atcaattgcc cgtctgtcag atccccagag    2820
cattgtttga ggcgaccggt ctcgacctcg agggggggcc cggtacccag cttttgttcc    2880
ctttagtgag ggttaattgc gcgcttggcg taatcatggt catagctgtt tcctgtgtga    2940
aattgttatc cgctcacaat tccacacaac atacgagccg gaagcataaa gtgtaaagcc    3000
tggggtgcct aatgagtgag ctaactcaca ttaattgcgt tgcgctcact gcccgctttc    3060
cagtcgggaa acctgtcgtg ccagctgcat taatgaatcg gccaacgcgc ggggagaggc    3120
ggtttgcgta ttgggcgctc ttccgcttcc tcgctcactg actcgctgcg ctcggtcgtt    3180
cggctgcggc gagcggtatc agctcactca aaggcggtaa tacggttatc cacagaatca    3240
ggggataacg caggaaagaa catgtgagca aaaggccagc aaaaggccag gaaccgtaaa    3300
aaggccgcgt tgctggcgtt tttccatagg ctccgccccc ctgacgagca tcacaaaaat    3360
cgacgctcaa gtcagaggtg gcgaaacccg acaggactat aaagatacca ggcgtttccc    3420
cctggaagct ccctcgtgcg ctctcctgtt ccgaccctgc cgcttaccgg atacctgtcc    3480
gcctttctcc cttcgggaag cgtggcgctt tctcatagct cacgctgtag gtatctcagt    3540
tcggtgtagg tcgttcgctc caagctgggc tgtgtgcacg aaccccccgt tcagcccgac    3600
cgctgcgcct tatccggtaa ctatcgtctt gagtccaacc cggtaagaca cgacttatcg    3660
ccactggcag cagccactgg taacaggatt agcagagcga ggtatgtagg cggtgctaca    3720
gagttcttga agtggtggcc taactacggc tacactagaa ggacagtatt tggtatctgc    3780
gctctgctga agccagttac cttcggaaaa agagttggta gctcttgatc cggcaaacaa    3840
accaccgctg gtagcggtgg tttttttgtt tgcaagcagc agattacgcg cagaaaaaaa    3900
ggatctcaag aagatccttt gatcttttct acggggtctg acgctcagtg gaacgaaaac    3960
tcacgttaag ggattttggt catgagatta tcaaaaagga tcttcaccta gatccttta    4020
```

```
aattaaaaat gaagttttaa atcaatctaa agtatatatg agtaaacttg gtctgacagt      4080
taccaatgct taatcagtga ggcacctatc tcagcgatct gtctatttcg ttcatccata      4140
gttgcctgac tccccgtcgt gtagataact acgatacggg agggcttacc atctggcccc      4200
agtgctgcaa tgataccgcg agacccacgc tcaccggctc cagatttatc agcaataaac      4260
cagccagccg gaagggccga gcgcagaagt ggtcctgcaa ctttatccgc ctccatccag      4320
tctattaatt gttgccggga agctagagta agtagttcgc cagttaatag tttgcgcaac      4380
gttgttgcca ttgctacagg catcgtggtg tcacgctcgt cgtttggtat ggcttcattc      4440
agctccggtt cccaacgatc aaggcgagtt acatgatccc ccatgttgtg caaaaaagcg      4500
gttagctcct tcggtcctcc gatcgttgtc agaagtaagt tggccgcagt gttatcactc      4560
atggttatgg cagcactgca taattctctt actgtcatgc catccgtaag atgcttttct      4620
gtgactggtg agtactcaac caagtcattc tgagaatagt gtatgcggcg accgagttgc      4680
tcttgcccgg cgtcaatacg ggataatacc gcgccacata gcagaacttt aaaagtgctc      4740
atcattggaa aacgttcttc ggggcgaaaa ctctcaagga tcttaccgct gttgagatcc      4800
agttcgatgt aacccactcg tgcacccaac tgatcttcag catcttttac tttcaccagc      4860
gtttctgggt gagcaaaaac aggaaggcaa aatgccgcaa aaaagggaat aagggcgaca      4920
cggaaatgtt gaatactcat actcttcctt tttcaatatt attgaagcat ttatcagggt      4980
tattgtctca tgagcggata catatttgaa tgtatttaga aaaataaaca atagggggtt      5040
ccgcgcacat ttccccgaaa agtgccac                                         5068

<210> SEQ ID NO 27
<211> LENGTH: 13900
<212> TYPE: DNA
<213> ORGANISM: Artificial Sequence
<220> FEATURE:
<223> OTHER INFORMATION: Artificial polynucleotide sequence

<400> SEQUENCE: 27
ctaaattgta agcgttaata ttttgttaaa attcgcgtta aattttttgtt aaatcagctc        60 attttttaac caataggccg aaatcggcaa atcccttat aaatcaaaag aatagaccga       120
gatagggttg agtgttgttc cagtttggaa caagagtcca ctattaaaga acgtggactc       180
caacgtcaaa gggcgaaaaa ccgtctatca gggcgatggc ccactacgtg aaccatcacc       240
ctaatcaagt tttttggggt cgaggtgccg taaagcacta aatcggaacc taaagggag       300 ccccccgattt agagcttgac ggggaaagcc ggcgaacgtg gcgagaaagg aagggaagaa       360
agcgaaagga gcgggcgcta gggcgctggc aagtgtagcg gtcacgctgc gcgtaaccac       420
cacacccgcc gcgcttaatg cgccgctaca gggcgcgtcc cattcgccat tcaggctgcg       480
caactgttgg gaagggcgat cggtgcgggc ctcttcgcta ttacgccagc tggcgaaagg       540
gggatgtgct gcaaggcgat taagttgggt aacgccaggg ttttcccagt cacgacgttg       600
taaaacgacg gccagtgagc gcgcgtaata cgactcacta tagggcgaat tggagctcgg       660
cgcgccagat ctgccgtaac gtaacaaagc ggggttggta gtgtttgcaa atgcattcac       720
atggaccgat cacttttctt tccagtctgt ccattctgtc caatctgtcc gatctgacct       780
gcccagtctg tccagtctgt cccttgtgtc gtccgatcca agctggttat catggcatcc       840
acaaagcccg cttcgagtct catttaccag gcatggaaca aactcagtat caaccaaacc       900
atccctagtg actcccttga attacttggg gagcgtttgg ctattgcctt cgcacccaaa       960
ctcaaggagc aacgaaggaa tggccggcgt cggaatctgg aatatgtggc acaacatcga      1020
```

```
cggaagattg ctcgaaaaat ctacttggag attctggaga aagacccaaa tatctttctt    1080 cctttatcc tggctgtttc ccctagagca tgcttatcct ttgatatctc gagctttctt    1140
gaacagcacc aaagccaagg aagacatttc ctccgcaaca atgccgaagc gatcctctgg    1200
ggtctcgcaa agaaacatga cattgatggc tccctccatt tcaggaagct gatgcgtgag    1260
attttccaac tgtctcctcc agcgacagaa gccgaaggca aggagcatta ttcattgcat    1320
ttaagcactc tccccgcaat ccgcaatgcc ttcggtgatg ttatctttga cgcaattgaa    1380
cgttccccta cacaggtgac agcgagagct aaaggttatt tctctgagaa aaccgaaagt    1440
gtttggacaa aagttcccta cagaagttct caagacgcaa tcatatctct tgaagtaggg    1500
tcggcaatcg agcttgcgaa tgtgttgttc ccaatcgcaa cccaaaaaat tgtctctatc    1560
ctttccgcat gttctcccac tgtgcgccag aagaactttt ctgaggctat tctcggccca    1620
gaccctcagg atacaccggc aacatcatca gaaatcggta tgaagtttaa ggtacacatg    1680
actgcagttg ctaattccac cctgtgctag atgtggcgta ttttactctg cgaggagcaa    1740
cggtctcggc aattgaatca gtctttcgcg ctgatatttg cgaaggtatt aagggcagcg    1800
aactgagaaa ctgggaaaag gagcagctgc tcatcgacac gacagattgt gtcacgatgc    1860
agatatggcg ggcacaacct caacatggaa ccatcaagtt gcgtattgga ttctatgcag    1920
cggtgaattt ggcaaatcgg ctgtatgcag aaacacccca agatcacata tagtaacctt    1980 tcatctttc ggccttctta aatcattgcc tttctgtgag tcgcgacttt ccacccttta    2040
tgaatacacc aataccaggg ggaagaacga tttcaccgct tcccttggca atccatatag    2100
ttcccttctc attctggaac ctgatttcat cgcagttgaa gcaatataaa ttcctttcga    2160
ggttttctgc attgtaggga tggaatgggt gcgtgaaata tttgtcgaaa atagaagggt    2220
ccgaaagttc tttccaagct gcgcgctgaa agttgttagc ccatctttcg agcatatggt    2280
ttggcccaca tacgagagat tcttttgtga tcggttgaga ttcttccgtg atcggttctg    2340
tcattttcat taagtcagag agccctcttg tatgccggct tttgctgtcg gatccggcga    2400
gataatcgct cctaagccag tcagtcaggg aaaagcaaag ataaataaaa tataggcgag    2460
gagtacaacc aggcacgcgt cgtagactat ttttctgaag agtttgtcac gtaacctacc    2520
tcatatggat gggtagttcg aatacttgat tgacttgacc cgaggttctg aaggcggcgg    2580
aggaaattgc ccaaccccac cattgcattt tcaggtatca atctctgcca cactgtggct    2640
aaattcgtct ttatcgacac gtgatcacgt tccctcttcc agccctggta tcagagaatc    2700
atcgagttat cgcttgtttc aatttcgtct tgcaattagc ttagggaata agcatgtggt    2760
cacatcaacc tacagagcgc taccggtctt tgcgctgaga ctctcagtga tccgcccaac    2820
agacaactag actttgaggt tgtcgatata accacaacaa atggcctgta tatcaacgat    2880
gtccacgcaa ttgtctcaag cctcttcacc cgacttccag cactagcatc caagcggcct    2940
ctcctcttct cccatgtttc tcgtagcgcg cctgcatata cttatatctg gagatatgtt    3000
aaaggagctg gaagcctgga gcatacgctg gaagcctgga gcatacgctt caagtgctgc    3060
catattcaga tagctgagta ggcacaatta ggtctaagtt cagggaattg cacctctcgc    3120
ttcattgtcc gtcgattcgt atcggtctct agttctcccc gttatcact ctcactcggt    3180 ggacagtccg tccagtccgt ccagtccgtc gagcctgtcc aatctgtcca atctgtccaa    3240
tctgtccaat ctgtccaatc tgtccaatct gtccaatctg tccaatctgt ccaatctgtc    3300
caatctgtcc aatctgtcca atctgtccaa tctgtccaat ctgtccaatc tgtccaatct    3360
```

```
gtccactctg tccactctgt ccactctgtc caatctgtcc actctgtccc ctctgtccac    3420
tctgtcccct ctgtccactc tgtcccctct gtccaatcgg tccaatctgt ccaatcttga    3480
tgatctcgat gatcaatacc atttagcgag cgctagtgac gccttacagc gttgcggcgt    3540
cttatggctt atacatcttc cgaatatcag tcgttcgatc tccagatcac acctcggggt    3600
gaaacaagcg ccatagttct tggtgcgcct gagcttttcc ctgcccggcc actcagtcgt    3660
gatggcttcc cagagtattc cataagtcga accagagat aggccagcgg acggcaaatc     3720
tcctctgctc cgttctcaac caatactgcc aaagtgagca atggaaagtg ttccaggagc    3780
accgtggcct ttaaaagcgc cagccttgtc ccagatcctc accgcaattc ggcacagacc    3840
aacgcagact ttcattgacc attcttcatt tccagatcgc tgcatagttt ccggtatggc    3900
ttggtataga gccttactcc cgtgcatacc gttgtggcgg aaggttctgg ggcgtaacag    3960
caccgatgag gacggacgga gtgaagacga ccttacttca ttgagcgata aaatgcctac    4020
ttttgaagaa acgacaactg tgagtactgt tcgtgaaatt gcctccagct gtctaatgtc    4080
tccgtcggtc agatcacttc tgcaaagtac atcaacggta aaaaatcat ggagcatacc     4140
gttgtggaga ccaagcacat tgacgaacgt ggagacacca gcgtcagtaa cggtgattcg    4200
aacagcactg cggtaaccag acattctggg cttagctctg tcagcctttc agatcaaagt    4260
acaattgtcg aggacgcgaa tgctctggaa gaacctgaac tctttgctgt tcactctcca    4320
tatgttgacg actcaaccgg cgagcagatg gttagactct actacgagct cccagtaagc    4380
ctcgatgatc ttgagatcat aggccttgaa tctcgtattc cagagtctga cgatgattca    4440
attgaggccc gctttcgtta tcgaggagag gattttttggc tacctgttcg ttattcttat    4500
gccaaagctc gaatggtttt aacgggtgta tgctgaatgg tctgacttct tcactgttgt    4560
tattttctat ttcccggctg ctggccactc aatattatcg caagcactat acaaaataaa    4620
tagtcctatc tctataacag agtacgtcac aaacagcgtt cgtccttggc aagaatataa    4680
atagtgtcaa tctgctgaga aaaggaggta tgaaatccac ttcattcaag caatggttcc    4740
cttcgtatac attattattt gtatatggat gggaactttt cttgtcttag ttgccctgaa    4800
cgcccgcttt aagaagaagc gcattgctga tcctgagtct tctgctgcct tcactgatca    4860
tccccatcaa gagtaacatg gattctgtat gtccctttgg gcatgtttat gtggcagtta    4920
ctaatatatt agatggaaac taggaagcgg caaaacacag gggcaggaag gaaggactc     4980
attccaagaa agaaggacaa ggaagaacac aagagtgtaa ggggtagcaa tcctcattgg    5040
cgtctactag ctgatgggtt aaagcaagat acaggtgttc atacgctcca agacaacgat    5100
cctgttgtcg agaagccgcc attaatttac aggagagctg gagaagcgcc gaaacatgat    5160
tgggacaaga agtcacccgg tttgcgcctt agacggtcct gctgtagctg cgggaaggaa    5220
gtaccggtag gcctggtctg tcgtatttgt caccatgagt cttgtcctga gtgcttgaac    5280
atgcaaaagc gagattacgg atgttgatca gatacacggg ccctatact aggactagtt     5340
accactagga ttgtactcaa ccttaacagt ggcgtttggt acttcgttac agctaagggg    5400
agaggacagt tcctactttc atgtgcttca agggagaggc tcctccaact actgttgcta    5460
gggaggaaag acactctatt cttagctgag ggctgcagga attcgcatcc atgcagtcat    5520
accatccatg gcatgcaatc tatgttgcat tagatgcaag aagtaggata gagaacccat    5580
gtacttgatt cacgctagca ggacagagag agataccata cccgacggga gcccctgcat    5640
gacttcctgt ctgcagcttg tcgtgcgtgt atcattccca tgcgccacga actcataggc    5700
agtggtagtt cagaacactc tttttttttta aaaaaaaaa agataggaaa ataataattt    5760
```

```
aggggaagaa aagtaaaaat taaaaagaaa aagttccaga tggcgcttct acttctatat    5820
tcgatcgtta ttcaataccc cagaggcaca ggcattccga tctctcatcg ccaacactga    5880
aaagcagcca ttttcccccg tcttaaagct ccaatcctcc ttcttctcat ctacttcctc    5940
gctccttcag gaccttgagt gttccgttga gctattgggt aacttctcac ctgtcaatca    6000
tcgattgtcc tttctcttga cttgacttcg tgtcgccatt ctcatttacg atacatatcc    6060
ctggagcaga aaacaaagaa aagggccaat tactcttgat ctagttccaa ctctgttgct    6120
gcttggaaca tccgcccatc tgtgtggtga atcagatgc cagcatccat cttgcagctt     6180
ctcccacttc ctgggccgat cttgaatgtt tgctctcgaa cctcgcttag tatttgatct    6240
ccattctcat ctgggtacat cctgtgagta gcatgtcgtc acttgtcaca catactaccc    6300
gctctcaaat ctgtttgatg ggagtcaatc tgcctcgaaa tggctcgtct gccttcacaa    6360
gcaaactaca gcagatggcg ggggcatgga ctcgagccac agtgctggct ctcgcttgca    6420
tctggacctt cttattcttt tcattgctg tatcttttc cccttgagg cttctggcgc        6480 gctgcacctt tccaagtatc aaaccaaagc taatcagggg cgtttggcgt cctgccatgg    6540
cttcactaga cctggatctc tgcagcctca tcaccatctc ggatcacctg gttctgatca    6600
ccttggaaga aagcacaaag accttggaga caatacatat tgccgccatc gcagctccct    6660
ccaatctcga cagcattttc atgtgtcggg cactatctac ctctcggcaa ttcagtaacc    6720
gtactgcctg agaaacatca acctctcaaa ttacacaatg gtgttcagcg cacctgctcc    6780
tggtgtgggc tccagtaaaa ggccagcgtc atgcatgcag gacgatgttg atgagcggga    6840
taatgtccca gtaagtgata ccagcattgg aaaggcagat ggagctgact catctcctat    6900
atagcccatg ggtctatgcg tgcgttcatc gatcaacatc ccttacttcc actacgccat    6960
gatctatctc gacaacatgg gcagacttaa ggtgatggaa tctccgtcta tccaggagca    7020
aaatgagact gttttcacaa ccgaagtacg tgaaagattt ttggaaatcc ttggtgccaa    7080
ggtaggatat caaccgccca tggttcgaag tatgtaaaca ctccgcgcac aagtacaata    7140
ttcttgctga tctcaattga acagggttgt cagctgccgg tgctacacca tacagctatg    7200
atcctcaaca accgcttggt tgcttgtctt accgtcaaac taagcgggac agaaaattcc    7260
cagcccactc tatgtacggt gtgccgccat ccgtccagtt ctcagccccg gttgaggaat    7320
cgccctcttg tggatcagtg gacatggtcg ggctcgagat tggtgatact cctaatgtcc    7380
ttgactacta tgagagatcc ttaaagcact ttcggcaggt caactgtcgc cagatcctaa    7440
agacattcat taagttcatt gagccacgaa agcaagccaa gcaccctat aatgaggta      7500 aaccccctgc aggagcccct cctggtaaga agggcgaccc agagaagaca aagcctgaat    7560
ggtggcccgc caatgtggtc cacaaggagc ctgaccatct tcgaaaggat cgtacgtgta    7620
acccttcaga aaatcttcag tgtcaagtaa cttttgctgac agacttagaa cgcctgtctc    7680
tgttaattca tatcatccgc aggcttggaa gatttggtat caccacggat caattgcagg    7740
aaattgccca cgactgcaag cggcggctca gcgaccccca caaactccaa atcttggacg    7800
aggtcttcag agtgagaagg attgaagaac gctacgaaag aggagaagtt ggtaagcggc    7860
atcatctttc catgaaattc attttgacag ctgttgacga gcctcagatg ccaacaagat    7920
cgtatatgtt gtcaaccgag agtcgaatca gaaagagaag gatggcgact ccaacgtgga    7980
tccggaccag aagcatgagc aagaagacga taatgcgcgg gaggcacttc ccattctcca    8040
ctccgagaag aactcaacca gcccgatgtc gaactcagcc gagcacacgg gcatggcggc    8100
```

```
accaagtcgt ccaatgaata tgggaggtga cagaaaccag ttgtttcctt taccggagtg    8160
gccgagcttc ggtgagacac cccaggatga tcgaattttc tttcccacga cctctaagta    8220
taccgaagat tatgcatcgc agcagatgcc tagaacacct gcaacaacag cacttgtcag    8280
cactaatgag acacatgcgg cctttgatta tatgacacag gagtccatca cctcctcctc    8340
cccagagcag acttcccacc accgccaagc acccctgccc atgcagcact cggccagcct    8400
cgacccttgg acccctacgt tccgacataa tttcttcaac ccaatggtgt atagtactgc    8460
accccgtcac gccatgtccc aggctactat gttatctcag tttcccaggt ccacgacgtc    8520
tcatggccag gaaatgcctc acatggctca cggcctgccg aacctgcctc aagacagacc    8580
ttcaagcatg gatggcatga gcatgagagg cccttctttc cgcacaggat ttttgagtca    8640
tccctgtgac ccatcacagc aggctcctca ttctagcgga tgcggccatc ctgacagttg    8700
gactcaaaat agaccacatg tataatctta actgattgat ccttgaccac tgttttgacc    8760
ctcctgcagc cttgaagctt cgtttcactg atgattgttc ttcgactttg tttctgtccc    8820
tgactttgtt gtcaatgcgg acttatccat gcggcttgtt ccacgtcaag tgactaccag    8880
gacactccgt ggttttatat ggcaggtact ggcgatgact ttccaattct tcttcgttta    8940
gtatatatac tcgtttcttg ttctatgttc gatcatgtct ttttccttat acatacctcc    9000
aaaaatcctg ttggagatgg cgccagatgg catgagatgc aaatatggat gatgttcttg    9060
tgtttgttca tttcaatttc tttctcttaa tcatgatttg aacaattggc agcgaggtat    9120
ggcggagctc gttctctttg gatgccgatc agctgaatag gaggtaacga ggcatgaggg    9180
tgtttcatta tgactctctc cggtgttgt catttaaggg tgcgaggggg aagtgtccgt    9240
ttcgatgtcc taggatatcg aaaatctgag tagtagccac gtgaccctat gctgacggct    9300
gggctggaag acaagcaggt tgctgcttac gagaatatgt tgaggtattc tcgttatctt    9360
cgtgaagaat gccgtctcct tggccctcta gccaaagtct gggttgctga aaggctagct    9420
ggaattgaga atcgactgtc tgcgtccgag tcgcctagag gtgggaaggc cccctctttc    9480
tcatacatat gctgactctg cagaccatac caattcgctg cccgaagcgg ccgctctaga    9540
actagtggat cccccgggct gcaggaattc gatatcaagc ttatcgatac cgtcgaggtc    9600
tgagaggagg cactgatgcg ctatcatggg gtgacgatga gccgctcttg catctttgtt    9660
tgtattatac tgtctttctt gttacacata attattctag aatgccccac cgttacatac    9720
gggacacagc catttacata tgcatgtgga ttacgagcta acgagttcat tcaaatctca    9780
gaactatcac ataatcatca ttccctatc gtcaaagacc gtaagacaaa tccggttcat    9840
gcactgaacc cattcgggta gtgagtcatt tactcagcac actcgcgctg acgtcgtcg    9900 aacaccttca atgcctcctc ggcagccttg acaccactga gaaccatggc accgaaggta    9960
gggcccatgc ggttaaagcc atcaatttca gacagctcca taccgccgat tatcaagccc    10020
ttagtaacct cgcgggtgtt cttgacgatg gcatcctcgg ccgagttcat gtcgagacca    10080
cgcatgccac ctagcttgtc gacgctgccc atggacacca agcgcttcgc acagaaggcg    10140
ccgaatggcc catcgtgacc agtggtactg atgatgacag gagcgttgat agtgttgggg    10200
tccatgcagg agtgatcatc gtggtgaagg gtgaccagcg tccagttgac gacaacacca    10260
gcaatctggg ggttgccgtt ctcggtcgga cgggtgatca agtcctcaac agcggtagca    10320
ttgaagagct tgacattggg gaaggagaga accttcgaca tgagtgtcga ggtaaacagg    10380
gaggcgtgct tgacgacaac gtagttgggg tttgcgtcct cttcgtaagg aacacccagc    10440
tcgttcagga agacttccgc gggacggcgc atgaccatag cagaaaagag ttggccaccc    10500
```

```
aaccaggcac cgccacctat tgcacgttag ttccggaaag ctgagtgcaa ggcaatccat   10560
catggactac tgaccaggag agacgctggc ctcgacgata gcaatcttca ggtccggacg   10620
agccttggcc aagacgtacg cagtgctcag accgcaggaa ccagcaccaa caatgacaac   10680
gtcactttca gcgtacttgt ccaggtcctc aaagtaacgt ctggtcatgg cacgagagac   10740
ctggctttcg cggatagggg cgaacttgaa ctcgtcccac ttgccaccga aatggtccaa   10800
cagcttggtc tgagaagctc cctcaacggg gacggtctca gaaaccacga ccttacccttt  10860 gaggccggta gcggccacag tgggttcgta gatggcagct ggaggagaca tgtttcaagt   10920
tgcaatgact atcatctgtt agccattcca tcaacaggaa gaacgagaga aggcatgacc   10980
cttttcgctg gtattatcca gatcaagttt tagccgtata atctcagaac gaacccagtc   11040
catcgatgcc atgtccttct agactaggat cctagagtct agggcccagc ttagggaggg   11100
catgtgaatg catcgatgac tgggaacgaa caccggccca cgccaaagac gttacctaag   11160
ataccttgat cattgtgaga gtccagccaa aagtattcca tgacttccat cgtatgccct   11220
ctagagggct aatcgaggag tgtatttaca ttgtcggttg gtttgggaac tatagaagat   11280
ggtcagttat tccaatcacc aaaggtttat cgaaggagg aagacttgtt cagtttcgtc     11340
cgaggacttt tggaattcaa atctgagata gagaattgtg tgggatgaga ggaaaaggaa   11400
gaagatggtg gggttcagaa ggaggggttg agttaaatag catgggttga gtcaacgtga   11460
taagggcact ataccgtata gatcagcggc acccgattct atccgttcct tttgctcctc    11520
tttagctttg accggtgagc cggacaagaa acaagtgaaa tcatcctgac atcggcggac   11580
gatctcctag cttttacatt tcgttaccaa tgggatcccg taatcaattg cccgtctgtc    11640
agatccccag agcattgttt gaggcgaccg gtctcgacct cgagggggg cccggtaccc    11700 agcttttgtt ccctttagtg agggttaatt gcgcgcttgg cgtaatcatg gtcatagctg   11760
tttcctgtgt gaaattgtta tccgctcaca attccacaca acatacgagc cggaagcata   11820
aagtgtaaag cctggggtgc ctaatgagtg agctaactca cattaattgc gttgcgctca   11880
ctgcccgctt tccagtcggg aaacctgtcg tgccagctgc attaatgaat cggccaacgc   11940
gcggggagag gcggtttgcg tattgggcgc tcttccgctt cctcgctcac tgactcgctg   12000
cgctcggtcg ttcggctgcg gcgagcggta tcagctcact caaaggcggt aatacggtta   12060
tccacagaat caggggataa cgcaggaaag aacatgtgag caaaaggcca gcaaaaggcc   12120
aggaaccgta aaaaggccgc gttgctggcg ttttttccata ggctccgccc cctgacgag    12180 catcacaaaa atcgacgctc aagtcagagg tggcgaaacc cgacaggact ataaagatac   12240
caggcgtttc cccctggaag ctccctcgtg cgctctcctg ttccgaccct gccgcttacc   12300
ggatacctgt ccgcctttct cccttcggga agcgtggcgc tttctcatag ctcacgctgt   12360
aggtatctca gttcggtgta ggtcgttcgc tccaagctgg gctgtgtgca cgaaccccc    12420 gttcagcccg accgctgcgc cttatccggt aactatcgtc ttgagtccaa cccggtaaga   12480
cacgacttat cgccactggc agcagccact ggtaacagga ttagcagagc gaggtatgta   12540
ggcggtgcta cagagttctt gaagtggtgg cctaactacg gctacactag aaggacagta   12600
tttggtatct gcgctctgct gaagccagtt accttcggaa aaagagttgg tagctcttga   12660
tccggcaaac aaaccaccgc tggtagcggt ggtttttttg tttgcaagca gcagattacg   12720
cgcagaaaaa aaggatctca agaagatcct ttgatctttt ctacggggtc tgacgctcag   12780
tggaacgaaa actcacgtta agggattttg gtcatgagat tatcaaaaag gatcttcacc   12840
```

```
tagatccttt taaattaaaa atgaagtttt aaatcaatct aaagtatata tgagtaaact    12900
tggtctgaca gttaccaatg cttaatcagt gaggcaccta tctcagcgat ctgtctattt    12960
cgttcatcca tagttgcctg actccccgtc gtgtagataa ctacgatacg ggagggctta    13020
ccatctggcc ccagtgctgc aatgataccg cgagacccac gctcaccggc tccagattta    13080
tcagcaataa accagccagc cggaagggcc gagcgcagaa gtggtcctgc aactttatcc    13140
gcctccatcc agtctattaa ttgttgccgg gaagctagag taagtagttc gccagttaat    13200
agtttgcgca acgttgttgc cattgctaca ggcatcgtgg tgtcacgctc gtcgtttggt    13260
atggcttcat tcagctccgg ttcccaacga tcaaggcgag ttacatgatc ccccatgttg    13320
tgcaaaaaag cggttagctc cttcggtcct ccgatcgttg tcagaagtaa gttggccgca    13380
gtgttatcac tcatggttat ggcagcactg cataattctc ttactgtcat gccatccgta    13440
agatgctttt ctgtgactgg tgagtactca accaagtcat tctgagaata gtgtatgcgg    13500
cgaccgagtt gctcttgccc ggcgtcaata cgggataata ccgcgccaca tagcagaact    13560
ttaaaagtgc tcatcattgg aaaacgttct tcggggcgaa aactctcaag gatcttaccg    13620
ctgttgagat ccagttcgat gtaacccact cgtgcaccca actgatcttc agcatctttt    13680
actttcacca gcgtttctgg gtgagcaaaa acaggaaggc aaaatgccgc aaaaaaggga    13740
ataagggcga cacggaaatg ttgaatactc atactcttcc ttttcaata ttattgaagc     13800 atttatcagg gttattgtct catgagcgga tacatatttg aatgtattta gaaaaataaa    13860
caaatagggg ttccgcgcac atttccccga aagtgccac                          13900
```

<210> SEQ ID NO 28
<211> LENGTH: 23
<212> TYPE: PRT
<213> ORGANISM: Artificial sequence
<220> FEATURE:
<223> OTHER INFORMATION: N-terminal bipartite NLS

<400> SEQUENCE: 28

Arg Arg Asn Gly Arg Arg Arg Asn Leu Glu Tyr Val Ala Gln His Arg
1               5                   10                  15
Arg Lys Ile Ala Arg Lys Ile
            20

<210> SEQ ID NO 29
<211> LENGTH: 23
<212> TYPE: PRT
<213> ORGANISM: Artificial sequence
<220> FEATURE:
<223> OTHER INFORMATION: N-terminal bipartite NLS

<400> SEQUENCE: 29

Ala Arg Asn Gly Ala Ala Ala Asn Leu Glu Tyr Val Ala Gln His Arg
1               5                   10                  15
Arg Lys Ile Ala Arg Lys Ile
            20

<210> SEQ ID NO 30
<211> LENGTH: 31
<212> TYPE: PRT
<213> ORGANISM: Artificial sequence
<220> FEATURE:
<223> OTHER INFORMATION: RRM domain sequence

<400> SEQUENCE: 30

Gly Lys Glu His Tyr Ser Leu His Leu Ser Thr Leu Pro Ala Ile Arg

```
                1               5                  10                 15
Asn Ala Phe Gly Asp Val Ile Phe Asp Ala Ile Glu Arg Ser Pro
            20                  25                 30

<210> SEQ ID NO 31
<211> LENGTH: 31
<212> TYPE: PRT
<213> ORGANISM: Artificial sequence
<220> FEATURE:
<223> OTHER INFORMATION: RRM domain sequence

<400> SEQUENCE: 31

Gly Lys Glu His Tyr Ser Leu His Leu Ser Thr Leu Pro Ala Ile Arg
1               5                   10                  15

Asn Ala Ala Gly Asp Val Ile Ala Asp Ala Ile Glu Arg Ser Pro
            20                  25                  30

<210> SEQ ID NO 32
<211> LENGTH: 193
<212> TYPE: PRT
<213> ORGANISM: Aspergillus fumigatus

<400> SEQUENCE: 32

Met Val Trp Tyr Arg Ala Ile Leu Val Cys Met Pro Trp Trp Leu Met
1               5                   10                  15

Gly Arg Asn Ser Thr Asn Glu Gly Lys Arg Ser Glu Gly Glu Arg Ala
            20                  25                  30

Pro Met Ile Asp Lys Val Pro Thr Phe Glu Glu Met Thr Ile Thr Thr
            35                  40                  45

Ser Ala Lys Tyr Val Asn Gly Glu Lys Ile Met Glu His Thr Val Val
    50                  55                  60

Glu Thr Lys Gln Ile Asp Asn Arg Gly Asp Thr Ser Val Ser Asn Asn
65                  70                  75                  80

Asp Ser Asn Ser Thr Ala Glu Thr Arg His Ser Gly Leu Ser Ser Val
                85                  90                  95

Ser His Ser Asp Gln Ser Lys Val Val Glu Asp Ala Asn Ala Leu Glu
            100                 105                 110

Lys Pro Glu Leu Phe Ala Val His Ser Pro Tyr Val Asp Ala Ser Thr
        115                 120                 125

Gly Lys Gln Met Leu Arg Leu Tyr Tyr Glu Leu Pro Val Ser Leu Asp
    130                 135                 140

Asp Leu Glu Ile Thr Gly Leu Glu Ser Arg Ile Pro Glu Ser Asp Asp
145                 150                 155                 160

Asp Ser Ile Glu Ala Cys Phe Cys Tyr Arg Gly Glu Lys Phe Trp Leu
                165                 170                 175

His Val Pro Tyr Ser Tyr Ala Lys Ala Arg Met Val Leu Met Gly Val
            180                 185                 190

Tyr

<210> SEQ ID NO 33
<211> LENGTH: 193
<212> TYPE: PRT
<213> ORGANISM: Aspergillus fumigatus

<400> SEQUENCE: 33

Met Ala Trp Tyr Arg Ala Leu Leu Pro Cys Ile Pro Leu Trp Arg Lys
1               5                   10                  15

Val Leu Gly Arg Asn Ser Thr Asp Glu Asp Gly Arg Ser Glu Asp Asp
```

-continued

```
                    20                  25                  30
Leu Thr Ser Leu Ser Asp Lys Met Pro Thr Phe Glu Glu Thr Thr Thr
        35                  40                  45

Ser Ala Lys Tyr Ile Asn Gly Glu Lys Ile Met Glu His Thr Val Val
    50                  55                  60

Glu Thr Lys His Ile Asp Glu Arg Gly Asp Thr Ser Val Ser Asn Gly
65                  70                  75                  80

Asp Ser Asn Ser Thr Ala Val Thr Arg His Ser Gly Leu Ser Ser Val
            85                  90                  95

Ser Leu Ser Asp Gln Ser Thr Ile Val Glu Asp Ala Asn Ala Leu Glu
            100                 105                 110

Glu Pro Glu Leu Phe Ala Val His Ser Pro Tyr Val Asp Asp Ser Thr
        115                 120                 125

Gly Glu Gln Met Val Arg Leu Tyr Tyr Glu Leu Pro Val Ser Leu Asp
    130                 135                 140

Asp Leu Glu Ile Ile Gly Leu Glu Ser Arg Ile Pro Glu Ser Asp Asp
145                 150                 155                 160

Asp Ser Ile Glu Ala Arg Phe Arg Tyr Arg Gly Glu Asp Phe Trp Leu
            165                 170                 175

Pro Val Arg Tyr Ser Tyr Ala Lys Ala Arg Met Val Leu Thr Gly Val
            180                 185                 190

Cys
```

COMPOSITIONS AND METHODS RELATED TO FUNGAL HYPOXIA RESPONSIVE MORPHOLOGY FACTOR A (HRMA) AND BIOFILM ARCHITECTURE FACTOR (BAF) PROTEINS

CROSS-REFERENCE TO RELATED APPLICATIONS

This application is a 35 U.S.C. § 371 filing of International Application No. PCT/US2020/050352 filed Sep. 11, 2020, which claims benefit of priority to U.S. Provisional Patent Application No. 62/899,660 filed on Sep. 12, 2019 and U.S. Provisional Patent Application No. 63/006,930 filed on Apr. 8, 2020, which is incorporated herein by reference in its entirety.

STATEMENT OF FEDERALLY SPONSORED RESEARCH

This invention was made with government support under Grant Nos. F31 AI138354 and R01 AI130128 awarded by the National Institutes of Health. The Government has certain rights in this invention.

FIELD OF THE INVENTION

This disclosure relates to compositions and methods of using fungal hypoxia responsive morphology factor A (hrmA) proteins and biofilm architecture factor (baf) proteins.

BACKGROUND

Fungi, from yeasts like *Saccharomyces* spp. to molds like *Aspergillus* spp., serve as efficient powerhouses for the mass production of many biological products (Bennett et al. J Biotechnol 66, 101-107, 1998). While many of these organisms have been genetically designed to carry out efficient production of diverse products, there remain important areas where biological improvements could significantly reduce costs of production scale fungal fermentation products. In particular, the dissolved oxygen requirements in many fungal fermentations have a significant impact on fermentation design, product yield, microbial biomass, and ultimately production costs (Show et al. Frontiers in Life Science 8, 271-283, 2015). For example, the production of citric acid through microbial fermentation requires an excess of not only glucose but also oxygen (Show, supra; Max et al. Braz J Microbiol 41, 862-875, 2010). Oxygen is an essential requirement for all fungi currently used in industrial fermentations. With yeast based fermentations, millions of cubic feet of air are introduced daily into fermentations at high cost. Moreover, the capacity to host air supply systems of sufficient size often imposes restrictions on the type of fermentations that can be conducted by a given facility.

While chemical production of citric acid has been around since the 1880's, the production efficiency hardly compares to the microbial fermentation yields (Show, supra). *Aspergillus niger*, introduced as a citric acid producer in 1916, is considered the microbe of choice in citric acid production due to its high yields and ability to ferment a variety of inexpensive carbon sources (Show, supra). Among molds, *A. niger* is also relatively tolerant to low oxygen tensions, however citric acid production by the fungus is irreversibly altered in the total absence of oxygen, and thus constant aeration is required at a rate of 0.2-1 vvm to maintain dissolved oxygen at approximately 20% of saturation (Max, supra). A reduction in the amount of oxygen required during citric acid production is expected to have significant cost benefits. The demand for citric acid in estimated to be growing annually at ~3.5-4%; a large portion of which is accounted for by both the food industry, where citric acid is an acidifier and major ingredient in soft drinks, and industrial applications, such as metal finishing (Show, supra).

*Aspergillus fumigatus* is also capable of producing abundant amounts of citric acid (Bhattacharjee et al. IOSR Journal of Environmental Science, Toxicology and Food Technology 9, 19-23, 2015); and between reference genomes, *A. fumigatus* and *A. niger* share ~69% genomic sequence similarity across orthologous protein-coding genes (Fedorova et al. PLoS Genet 4, e1000046, 2008). However, unlike *A. niger*, *A. fumigatus* is a major cause of pulmonary mycosis in immune compromised patient populations, making it ill-suited for use in biotechnological applications (Sugui et al. Cold Spring Harb Perspect Med 5, a019786, 2014). We propose herein to utilize an in vitro evolved allele of a sub-telomeric gene cluster discovered in *A. fumigatus* but also present in other *Aspergillus* species to reduce fungal oxygen consumption in *A. niger* and other industrial used fungi such as *Trichoderma* reesi, *A. oryzae*, and the yeast *Saccharomyces cerevisiae* among others, with the ultimate objective to reduce dissolved oxygen requirements in industrial scale fermentations and heterologous protein production cultures.

SUMMARY

Disclosed herein are compositions and methods of using fungal hypoxia responsive morphology factor A (hrmA) proteins and biofilm architecture factor (bat) proteins, including variants, homologs, and orthologs thereof.

In one aspect, the disclosure provides a filamentous fungal host cell, comprising a nucleotide sequence encoding an *Aspergillus fumigatus* hypoxia responsive morphology factor A (hrmA) protein, or a homolog or ortholog thereof.

In certain embodiments, the filamentous fungal host cell is not *Aspergillus fumigatus*.

In certain embodiments, the hrmA protein comprises at least 90% identity to the amino acid sequence of SEQ ID NO: 11. In certain embodiments, the hrmA protein comprises a D304G mutation relative to the amino acid sequence of SEQ ID NO: 11. In certain embodiments, the hrmA protein comprises at least 90% identity to the amino acid sequence of SEQ ID NO: 12. In certain embodiments, the hrmA protein comprises the amino acid sequence of SEQ ID NO: 12.

In certain embodiments, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Saccharomyces, Schizophyllum, Talaromyces, Thermoascus, Thielavia, Tolypocladium, Trametes* and *Trichoderma*.

In certain embodiments, the filamentous fungal host cell is an *Aspergillus* host cell. In certain embodiments, the host cell is selected from the group consisting of: *Aspergillus awamori, Aspergillus flavus, Aspergillus foetidus, Aspergillus japonicus, Aspergillus luchensis, Aspergillus nidulans, Aspergillus niger* or an *Aspergillus oryzae* host cell.

In certain embodiments, the production of any one or more of aconitate, malate, isocitrate, and citrate are increased relative to a fungal host cell that does not comprise the nucleotide sequence encoding the *Aspergillus fumigatus* hypoxia hrmA protein.

In certain embodiments, the fungal host cell is less adherent to plastic and glass surfaces relative to a fungal host cell that does not comprise the nucleotide sequence encoding the *Aspergillus fumigatus* hypoxia hrmA protein.

In another aspect, the disclosure provides a filamentous fungal host cell, comprising a nucleotide sequence encoding an *Aspergillus fumigatus* biofilm architecture factor (baf) protein, or a homolog or ortholog thereof.

In certain embodiments, the filamentous fungal host cell is not *Aspergillus fumigatus*.

In certain embodiments, the baf protein comprises bafA, or a homolog or ortholog thereof. In certain embodiments, the baf protein comprises bafB, or a homolog or ortholog thereof. In certain embodiments, the baf protein comprises bafC, or a homolog or ortholog thereof. In certain embodiments, the bafA protein comprises at least 90% identity to the amino acid sequence of SEQ ID NO: 13. In certain embodiments, the bafA protein comprises the amino acid sequence of SEQ ID NO: 13. In certain embodiments, the bafB protein comprises at least 90% identity to the amino acid sequence of SEQ ID NO: 14. In certain embodiments, the bafB protein comprises the amino acid sequence of SEQ ID NO: 14. In certain embodiments, the bafC protein comprises at least 90% identity to the amino acid sequence of SEQ ID NO: 15. In certain embodiments, the bafC protein comprises the amino acid sequence of SEQ ID NO: 15.

In certain embodiments, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Saccharomyces, Schizophyllum, Talaromyces, Thermoascus, Thielavia, Tolypocladium, Trametes* and *Trichoderma*.

In certain embodiments, the filamentous fungal host cell is an *Aspergillus* host cell. In certain embodiments, the host cell is selected from the group consisting of: *Aspergillus awamori, Aspergillus flavus, Aspergillus foetidus, Aspergillus japonicus, Aspergillus luchensis, Aspergillus nidulans, Aspergillus niger* or an *Aspergillus oryzae* host cell.

In certain embodiments, the fungal host cell is less adherent to plastic and glass surfaces relative to a fungal host cell that does not comprise the nucleotide sequence encoding the *Aspergillus fumigatus* baf protein, or a homolog or ortholog thereof.

In another aspect, the disclosure provides a filamentous fungal host cell, comprising a nucleotide sequence encoding an *Aspergillus niger* biofilm architecture factor (baf) protein, or a homolog or ortholog thereof.

In certain embodiments, the filamentous fungal host cell is not *Aspergillus niger*.

In certain embodiments, the filamentous fungal host cell is a modified *Aspergillus niger* and the baf protein or a homolog or ortholog thereof is expressed to a higher level than an unmodified *Aspergillus niger* host cell.

In certain embodiments, the baf protein comprises bafA, or a homolog or ortholog thereof. In certain embodiments, the bafA protein comprises at least 90% identity to the amino acid sequence of SEQ ID NO: 16. In certain embodiments, the bafA protein comprises the amino acid sequence of SEQ ID NO: 16.

In certain embodiments, the fungal host cell is less adherent to plastic and glass surfaces relative to a fungal host cell that does not comprise the nucleotide sequence encoding the *Aspergillus niger* baf protein, or a homolog or ortholog thereof.

In certain embodiments, the filamentous fungal host cell further comprises a heterologous polynucleotide encoding a secreted polypeptide of interest.

In certain embodiments, the filamentous fungal host cell produces one or more products of interest at a higher level than a filamentous fungal host cell that does not comprise a nucleotide sequence encoding an *Aspergillus fumigatus* hrmA protein, an *Aspergillus fumigatus* baf protein, an *Aspergillus niger* baf protein, or homologs or orthologs thereof.

In certain embodiments, the filamentous fungal host cell secretes one or more products of interest at a higher level than a filamentous fungal host cell that does not comprise a nucleotide sequence encoding an *Aspergillus fumigatus* hrmA protein, an *Aspergillus fumigatus* baf protein, an *Aspergillus niger* baf protein, or homologs or orthologs thereof.

In certain embodiments, the one or more products of interest comprise citric acid, gluconic acid, fumaric acid, kojic acid, lactic acid, itaconic acid, proteins, and secondary metabolites.

In certain embodiments, the secondary metabolites are selected from the group consisting of: β-lactams, compactin, cyclosporines, gibberellins, griseofulvin, lovastatin, mycophenolic acid, pigments, siderophores, and taxol.

In certain embodiments, the filamentous fungal host cell grows at a higher level in the presence of reduced oxygen than a filamentous fungal host cell that does not comprise a nucleotide sequence encoding an *Aspergillus fumigatus* hrmA protein, an *Aspergillus fumigatus* baf protein, an *Aspergillus niger* baf protein, or homologs or orthologs thereof.

In certain embodiments, the filamentous fungal host cell oxygen consumption is reduced compared to a filamentous fungal host cell that does not comprise a nucleotide sequence encoding an *Aspergillus fumigatus* hrmA protein, an *Aspergillus fumigatus* baf protein, an *Aspergillus niger* baf protein, or homologs or orthologs thereof.

In certain embodiments, the oxygen consumption is reduced by about 10% to about 90%. In certain embodiments, the oxygen consumption is reduced by about 10%, about 20%, about 30%, about 40%, or about 50%.

In one aspect, the disclosure provides an *Aspergillus niger* host cell that is modified to express a biofilm architecture factor (bat) protein at a higher level than an unmodified *Aspergillus niger* host cell.

In certain embodiments, the baf protein comprises bafA, or a homolog or ortholog thereof. In certain embodiments, the bafA protein comprises at least 90% identity to the amino acid sequence of SEQ ID NO: 16. In certain embodiments, the bafA protein comprises the amino acid sequence of SEQ ID NO: 16.

In one aspect, the disclosure provides a method of increasing fungal secretion of one or more products of interest, comprising introducing into a filamentous fungal host cell one or more polynucleotide sequences encoding one or both of an hrmA protein and a baf protein.

In another aspect, the disclosure provides a method of increasing the production of one or more products of interest, comprising introducing into a filamentous fungal host cell one or more polynucleotide sequences encoding one or both of an hrmA protein and a baf protein.

In another aspect, the disclosure provides a method of reducing oxygen consumption of a filamentous fungal host cell, comprising introducing into a filamentous fungal host cell one or more polynucleotide sequences encoding one or both of an hrmA protein and a baf protein.

In certain embodiments, the hrmA protein comprises the amino acid sequence of SEQ ID NO: 12.

In certain embodiments, the baf protein comprises the amino acid sequence of SEQ ID NO: 13, SEQ ID NO: 14, SEQ ID NO: 15, or SEQ ID NO: 16.

In certain embodiments, oxygen consumption is reduced by about 10% to about 90%. In certain embodiments, oxygen consumption is reduced by about 10%, about 20%, about 30%, about 40%, or about 50%.

In certain embodiments, the polynucleotide sequence is introduced into the filamentous fungal host cell via transformation.

In certain embodiments, the transformation comprises one or more of protoplast-mediated transformation, *Agrobacterium*-mediated transformation, electroporation, biolistic transformation, and shock-wave-mediated transformation In certain embodiments, the polynucleotide sequence is introduced into the filamentous fungal host cell transiently.

In certain embodiments, the polynucleotide sequence is stably integrated into the filamentous fungal host cell genome.

In certain embodiments, the polynucleotide sequence is introduced into the filamentous fungal host cell genome with a genetic-editing system.

In certain embodiments, the genetic-editing system comprises one or more of a meganuclease system, a ZFN system, a TALEN system, and a CRISPR system.

In certain embodiments, the polynucleotide sequence further comprises a promoter to express one or both of the hrmA protein and the baf protein. In certain embodiments, the promoter is inducible or constitutive. In certain embodiments, the inducible promoter is selected from the group consisting of: alcA, amyB, bphA, catR, cbhI, cre1, exy1A, gas, glaA, mir1, niiA, qa-2, Smxy1, tcu-1, thiA, vvd, xy11, xy1P, xyn1, or zeaR. In certain embodiments, the constitutive promoter comprises cDNA1, enol, gpdA, gpd1, pdc1, pki1, poliC, tef1, or rp2.

In one aspect, the disclosure provides an isolated polynucleotide, comprising a nucleotide sequence encoding an hnnA allele (D304G), or a homolog or ortholog thereof, of a fungi.

In one aspect, the disclosure provides an isolated hrmA polypeptide, encoded by the polynucleotide recited above.

In one aspect, the disclosure provides a vector comprising the isolated polynucleotide recited above.

In one aspect, the disclosure provides a fungus, comprising the isolated polynucleotide recited above.

In one aspect, the disclosure provides a culture comprising the fungus recited above.

In one aspect, the disclosure provides a method for producing a biological product, wherein the method comprises culturing a fungus recited above under oxygen replete conditions, and harvesting the biological product.

In one aspect, the disclosure provides a polynucleotide, polypeptide, vector, fungi, culture, or method recited above, wherein the fungi is an *Aspergillus*, a *Trichoderma*, or a *Saccharomyces*.

In one aspect, the disclosure provides a polynucleotide, polypeptide, vector, fungi, culture, or method recited above, wherein the fungi is an *Aspergillus niger*, an *Aspergillus oryzae*, a *Trichoderma reesi*, or a *Saccharomyces cerevisiae*.

In one aspect, the disclosure provides a polynucleotide, polypeptide, vector, fungi, culture, or method recited above, wherein the polynucleotide is an hrmA associated gene cluster.

In one aspect, the disclosure provides a polynucleotide, polypeptide, vector, fungi, culture, recited above wherein the polynucleotide comprises a sequence according to any of the hrmA protein-coding regions of the hrmA, or homolog, or ortholog thereof, polynucleotide sequences provided herein.

In one aspect, the disclosure provides a polynucleotide, polypeptide, vector, fungi, culture, or method recited above, wherein the polynucleotide comprises a sequence according to any of the hrmA, or homolog, or ortholog thereof, polynucleotide sequences provided herein.

In one aspect, the disclosure provides a polynucleotide, polypeptide, vector, fungi, culture, recited above, wherein the polynucleotide comprises an hrmA allele (D304G) of *Aspergillus*, or a homolog, or ortholog, thereof.

In one aspect, the disclosure provides a polynucleotide, polypeptide, vector, fungi, culture, or method recited above, wherein the polynucleotide comprises an hrmA allele (D304G) of *Aspergillus fumigatus* or *Aspergillus Niger*, or a homolog, or ortholog thereof.

In one aspect, the disclosure provides a polynucleotide, polypeptide, vector, fungi, culture, or method recited above, wherein the fungi is a recombinant fungus or an evolved fungus.

In one aspect, the disclosure provides a polynucleotide, polypeptide, vector, fungi, culture, or method recited above, wherein the fungus is a recombinant fungus and the polynucleotide is from a different fungal species than the recombinant fungus.

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIG. 1a. Environmental (n=29 biologically independent samples) and clinical (n=29 biologically independent samples) isolates of *A. fumigatus* strains plotted for morphotype characteristics (furrowing and percent vegetative mycelia) when grown at 0.2% $O^2$ or 21% $O^2$ (FIG. 1b). Two-way ANOVA shows oxygen tension significantly contributes to the variation of colony furrowing (31.67%, p<0.0001) (FIG. 1c) and percent vegetative mycelia (PVM) (55.77%, p<0.0001) (FIG. 1d) in clinical (n=29 biologically independent samples) and environment (n=29 biologically independent samples) strains. Dashed lines indicated the mean values per condition; error bars indicate standard error with measure of centre at the mean. FIG. 1e. Representative isolates with an increased PVM (white) and furrowing when cultured at 0.2% $O^2$ vs. 21% $O_2$. Images representative of three biologically independent experiments. FIG. 1f. Example clinical strains that adopt H-MORPH during growth at 21% $O^2$ (closed blue circles in b, c, d). Images representative of three biologically independent replicates.

FIG. 1g. Representative side-view slices of submerged fungal biofilms from A. fumigatus H-Morph clinical isolates in FIG. 1f. FIG. 1h shows the quantification of vertical alignment of filaments as a function of biofilm depth. FIG. 1i shows representative side-view slices of submerged fungal biofilms of AF293 and the H-MORPH EVOL20 at 21% $O^2$ (24 hours) and 0.2% $O^2$ (36 hours) with (FIG. 1j) vertical alignment quantification. For FIG. 1h and FIG. 1j each lane is a representative alignment from a minimum of three independent biological replicates. Biofilm images are sample volumes of approximately 300 μm (h)×500 μm (1)×200 μm (w) and represent a minimum of 3 biologically independent experiments.

FIG. 2a. Example identification and quantification of the morphological characteristics of interest: furrowing and PVM. This is a representative example of a single analysis that was repeated three times per sample and averaged. FIG. 2b. H-MORPH strains (CDC20.2, F11698, F16311) have significantly increased hypoxia fitness (*: $p<0.001$ by One-way ANOVA with Dunnett multiple comparison test) compared to AF293. n=3 biologically independent samples. Error bars indicate standard error around the mean (centre). FIG. 2c. Experimental evolution schematic. FIG. 2d. Following 20 passages in 0.2% $O^2$ heterogeneous population was sorted into individual clonal colonies. Images are representative of three independent experiments. FIG. 2e. Afu5g14900/hrmA, Afu5g08390/ssk1, Afu5g13710 have non-synonymous mutations in EVOL20 v. AF293. RNA-sequencing shows all three to be oxygen responsive. Two-tailed unpaired t tests show hrmA to be elevated in EVOL20 (*: $p<0.0001$) as well as AFu5g13710 (:$p=0.0020$, *: $p<0.0001$) and Afu5g08390/ssk1 (**:$p=0.0085$, NS=0.1350). n=3 independent biological samples. FIG. 2f. The SNP in hrmA (D304G) is only found in the EVOL20 clonal colony.

In FIG. 3a, FIG. 3b, FIG. 3c biofilms are 1400 pm×1400 pmX−500 μm. In FIG. 3d, biofilms are 665.5 pm×665.5 pmX−300 pm. Experiments were repeated a minimum of 3 times showing similar results.

FIG. 5a. Co-isolated clinical strains display N-MORPH and H-MORPH (representative of 3 independent experiments) FIG. 5b. IFM 59356-3 biofilm architecture has many horizontal filaments quantified as having greater deviation from the vertical compared to the N-MORPH IFM 59356-1 (FIG. 5c) FIG. 5d. IFM 59356-3 has reduced ECM attachment (representatives from 2 independent experiments) than IFM 59356-1. Fi. 5e. IFM 59356-3 adheres less well (***:$p=0.0002$ by two-tailed unpaired t test, n=5 biologically independent samples per group) compared to IFM 59356-1. Error bars indicate standard error around the mean (centre). FIG. 5f. IFM 59356-3 (n=10 biologically independent animals) has 40% greater mortality at 14 dpi compared to IFM 59356-1 (n=10 biologically independent animals) ($p=0.0651$ by Gehan-Breslow-Wilcoxon). FIG. 5g hrmA nor cgnA mRNA are elevated in IFM 59356-3 compared to IFM 59356-1 (n=3 biologically independent samples, error bars indicate standard error around the mean (centre)). FIG. 5h. F11698 shows H-MORPH (representative from 3 independent experiments). FIG. 5i. F11698 (n=7 biologically independent animals) is more virulent than AF293 (n=5 biologically independent animals) (*:$p=0.0128$ by Gehan-Breslow-Wilcoxon).

FIG. 6a. A hypoxia evolved allele of hrmA, from the hypoxia evolved strain EVOL20, is sufficient to generate H-MORPH in AF293 (hrmA$^{R-Ev}$) and necessary for H-MORPH in EVOL20. Images representative of three biologically independent experiments. FIG. 6b. Morphotype quantification indicates hrmA$^{R-Ev}$ and EVOL20 are above the mean (dashed lines) for furrowing and PVM regardless of oxygen tension but dependent on hrmA/cgnA. FIG. 6c. hrmA$^{R-Ev}$ (n=3 biologically independent samples per group) has increased fitness (a: $p=0.9942$, b: $p=0.0033$ by One-way ANOVA with Tukey's Multiple Comparison test) in low oxygen as determined by dry weight. Error bars indicate standard error with the center at the mean. FIG. 6d. Representative side-view slices of submerged fungal biofilms reveal altered biofilm architecture in hrmA$^{R-Ev}$ is dependent on cgnA and is quantified in FIG. 6e. FIG. 6f. Representative side-view slices of submerged fungal biofilms revealing hrmA and cgnA are necessary for the collapse in biofilm architecture observed with EVOL20 and is quantified in FIG. 6g. Colony and biofilm analysis are representative of three biological replicates. Biofilm images are sample volumes of approximately 300 inn (h)×500 μm (1)×200 μm (w).

FIG. 8a. A heat map of collapsed biological replicates showing top genes with $p<0.05$ (two-sided) and log 2 differential expression>1 with a minimum FPMK of 5. Significance was determined with DESeq2 which utilizes DESeq2 which utilizes the Wald test for differential expression and adjustments for multiple comparisons using Benjamini and Hochberg procedures. Within this subset, hrmA$^{R-Ev}$ vs. AF293 reveals large scale changes in both 21% and 0.2% $O^2$ as a result of the hypoxia-evolved hrmA allele. FIG. 8b. Classification of all genes increased or decreased by 2-fold in hrmA$^{R-Ev}$ AF293 at 21% $O_2$ or 0.2% $O_2$ reveals activation of the hypoxia transcriptional response at ambient oxygen and reduction in this response at low oxygen in hrmA$^{R-EV}$ FIG. 8c. The growth advantage of hrmA$^{R-Ev}$ at 0.2% O$^2$ (p=0.0282) coincides with a significant (p=0.0088) reduction in fungal growth at 21% O$_2$. Two-tailed unpaired t test performed on n=3 independent biological replicates with error bars showing standard error centered at the mean. FIG. 8d. A transition from 48 hours of growth at 21% O$^2$ to growth at 0.2% O$_2$ shows an initial increase (p<0.0001) in growth rate during the first 24 hours at 0.2% O$^2$ for hrmA$^{R-}$ $^{Ev}$ that is not present (ns, p=0.0789) 24-48 hours post shift to 0.2% O$_2$. One-way ANOVA with Tukey's Multiple Comparison Test performed on n=3 biologically independent samples. Error bars indicate standard error around the mean (centre).

FIG. 9a. hrmA transcripts are detected in vivo during murine invasive disease with WT *A. fumigatus* and increase in abundance from 24 to 72 hours post inoculation (n=8 biologically independent animals, unpaired two-tailed students t-test, p=0.0151). FIG. 9b. Introduction of the evolved allele of hrmA (hrmA$^{R-Ev}$) is sufficient to induce significantly increased mRNA levels of hrmA compared to AF293 (p=0.0290), and similar to EVOL20 (p=0.3066) (n=3 biologically independent samples). Students unpaired two-tailed t test performed, error bars indicated standard error around the mean (centre). FIG. 9c. In the hypoxia-evolved EVOL20, loss of hrmA leads to a significant reduction in mRNA for the gene cluster surrounding the hrmA native locus (HAC: hrmA-associated cluster) (n=3 biologically independent samples). Unpaired students two-tailed t test performed between EVOL20 and ΔhrmA$^{EV}$ with error bars representing standard error around the mean (centre) (Afu5g14880: p<0.0001, Afii5g14890: p<0.0001, hrmA: p<0.0001, cgnA: p=0.0017, Afu5g14920: p=0.0604). FIG. 9d. Ectopic integration of a constitutively over expression WT allele of hrmA in AF293 acts in trans to significantly increase mRNA levels HAC (n=3 biologically independent samples). Unpaired students two-tailed t test performed between AF293 and hrmA$^{OE}$ with error bars representing standard error around the mean (centre) (Afu5g14880: p=0.0002, Afu5g14890: p=0.0184, hrmA: p=0.0371, cgnA: p=0.0009, Afu5g14920: p<0.0001). FIG. 9e. In a minimum of 3 independent experiments, overexpression of hrmA (hrmA$^{OE-WT-GFP}$) generates H-MORPH independent of oxygen tension but dependent on an N-terminal NLS (FIG. 9f) and nuclear localization of HrmA (FIG. 9g, FIG. 9h). Scale bars=5 µm. FIG. 9i. Localization to the nucleus is necessary for the induction of the HAC gene cgnA (Afu5g14900) (n=3 biologically independent samples). Error bars indicate standard error around the mean (centre).

FIG. 10a. Heat map of co-regulated HAC genes from Afu5g14865 to Afu5g14930. FIG. 10b. Comparisons of HAC average gene size and exon GC content with the published averages for the AF293 genome reveal a slightly increased average gene size and a similar GC content to the genome. Error bars indicate standard error around the mean (centre). FIG. 10c. Closely related strains AF293 and A1163 have assembled genomes and reveal synteny within HAC across these two strains. A1163 also encodes two putativeorthologous clusters with putative hrmA orthologs: AFUB_044390/hrmB and AFUB 096600/hrmC.

FIG. 11a(SEQ ID NOs:28-31). Model of HrmA with an N-terminal bipartite NLS, a weakly predicted RRM domain (E-VALUE 0.01), EVOL20 SNP locale, and the GFP tag. Green residues are the result of site directed mutagenesis. FIG. 11b. Two conserved phenylalanine residues with the RRM domain are not necessary for nuclear localization (images: n=10 biologically independent samples from 3 independent experiments), but are necessary for induction of cgnA (n=3 biologically independent samples). Scale bars are 10 pm. Error bars indicate standard error around the mean (centre). FIG. 11c. The RRM mutant no longer adopts the H-MORPH characteristics of elevated PVM and furrowing (representative of 3 independent experiments). FIG. 11d. Quantification of the localization signal (representative of 5 independent experiments). FIG. 11e. iTASSER protein modeling of the RRM domain of HrmA (156-229 residues) maps to the structure of the chromatin remodeling protein Spt16 in *Saccharomyces cerevisiae* and Ashbya *gossypii*.

FIG. 12a. In a minimum of 3 independent experiments, loss of cgnA in hrmA$^{R-EV}$ abolishes H-MORPH generating a AF293-like oxygen-responsive morphotype in regards to furrows and PVM (FIG. 12b). FIG. 12c. Representative HAC gene cgnA is necessary for the elevated hypoxia fitness of hrmA$^{R-Ev}$ (n=3 biological independent samples, One-way ANOVA with Dunnett's Multiple Comparison test, *: p=0.0433 and ns: p=0.9847). FIG. 12d. Adherence to plastic is reduced in response to HAC induction (EVOL20, hrmA$^{OE}$, hrmA$^{R-Ev}$) and is dependent on cgnA. n=6 biologically independent biological samples from 2 independent experimental repetitions. One-way ANOVA with Sidak's Multiple Comparison test performed, *: p<0.0001. Error bars indicate standard error around the mean (centre). FIG. 12e. SEM of 24 hour submerged fungal biofilms reveal detachment of extracellular matrix from hrmA$^{OE}$ hyphae that is dependent on cgnA. White arrows indicate extracellular matrix. Representative images of 3 replicates. FIG. 12f. Addition of culture supernatants with secreted ECM to the non-adherent strain Δuge3$^{AF}$ significantly (*: p<0.0001) rescues adherence. n=8 biologically independent samples with One-way ANOVA with Tukey's Multiple Comparison Test. Error bars indicate standard error around the mean (centre). FIG. 12g. The cell walls of hrmA$^{R-Ev}$ and EVOL20 are significantly (a: p<0.001, b: p>0.9999, c: p=0.0334) thinner than that of AF293 or ΔcgnA$^{Ev}$. n=13 independent biological samples with One-way ANOVA and Tukey's Multiple Comparisons test. Error bars indicate standard error around the mean (centre). FIG. 12h hrmA$^{R-Ev}$ has reduced total chitin staining by CFW fluorescence (n=10 independent biological samples, a: p=0.0492, b: p=0.0049, c: p<0.0001) and increased (3-glucan staining by Dectin-1 (n=10 independent biological samples, a: p<0.0001, b: p=0.0006, c: p=0.0044) (FIG. 12g). One-way ANOVA with Sidak's Multiple Comparison test for significant; error bars indicate standard error around the mean (centre) (FIG. 12f and FIG. 12g).

FIG. 13a. Ectopic over expression of cgnA does not generate H-MORPH in AF293 (representative of 3 independent experiments), does not impact hrmA RNA levels (n=4 biologically independent samples, **: p=0.0014 and NS: p=0.3960 by two-tailed unpaired t test) (FIG. 13b), does not alter fungal growth at 21% O$_2$ or 0.2% O$_2$ (n=3 biologically independent samples) (FIG. 13c), and does not impact surface adherence of AF293

(n=6 biologically independent samples, NS: p=0.5347 by unpaired t test) (FIG. 13d). FIG. 13e. Loss of cgnA in the HAC inducing strains EVOL20 and hrmA$^{OE}$ results in a loss of H-MORPH (representative of 3 independent experiments) and a reduction in hypoxia fitness (n=3 biologically independent samples, **: p<0.0001, *: p=0.0134, NS: p=1103, p=0.1579, by One-way ANOVA with Sidak's multiple comparisons test) (FIG. 13l). FIG. 13g. ECM detachment from EVOL20 but not AF293 (representative of 2 independent experiments). Scale bars: 20 pm. All error bars indicate the standard error around the mean (centre).

FIG. 14c. Δuge3EVOL does not impact hypoxia fitness of EVOL20 (n=3 biologically independent samples, a: p=0.0294, b: p=0.0370, NS: p=0.9988 by One-way ANOVA with Tukey's Multiple Comparisons test) (FIG. 14d) nor hypoxia fitness of AF293 (n=3 biologically independent samples, NS: p=0.0672 by two-tailed unpaired t test). FIG. 14e. Loss of uge3 in AF293 does not impact biofilm architecture (representative of 3 independent experiments). All error bars indicate standard error around the mean (centre).

FIG. 16a. Calcofluor white (CFW) staining of hyphae and processed as SUM projections. FIG. 16b. Soluble Dectin-1 staining for detection of (3-glucan and processed as SUM projections. Scale bars are 5 pm. Images representative from 3 biologically independent experiments. FIG. 16c. At 21% or 0.2% O$_2$, H-MORPH hrmA$^{R-Ev}$ (n=7 biologically independent samples) is more sensitive to growth on CFW than hrmA$^{R-Ev}$;ΔcgnA (n=4 biologically independent samples) (a: p=0.0016, b: p=0.0037 by two-tailed unpaired t test). FIG. 16d. In contrast, there is no impact of hrmA/cgnA on fungal sensitivity to the Echinocandin Caspofungin (n=3 biologically independent samples, c: p=0.9313, d: p=0.4550 by two-tailed unpaired t test). All error bars indicate standard error around the mean (centre).

FIG. 17c. Nearest-neighbor algorithm shows significantly increased distances between intralesion filaments in AF293 and EVOL20 (**:p=0.0052) and hrmA$^{R-Ev}$ (a: p=0.0003, b: p=0.0068) (AF293 n=45, EVOL20 n=24, ΔhrmA n=25, hrmA$^{R-Ev}$ n=61, hrmA$^{R-Ev}$;ΔcgnA n-22 biologically independent samples). One-way ANOVA with Sidak's Multiple Comparison test. FIG. 17d. hrmA$^{R-Ev}$ (n=28 independent animals) is significantly more virulent (p=0.0346 by Gehan-Breslow—Wilcoxon test (GBW)) than AF293 (n=16 independent animals) and hrmA$^{R-Ev}$; ΔcgnA (n=10 independent animals, p=0.0417 by GBW). AF293 and hrmA$^{R-Ev}$; ΔcgnA do not differ in virulence (ns: p=0.2087 by GBW). FIG. 17e. EVOL20 (n=30 independent animals) is significantly more virulent than ΔhrmA$^{EV}$ (n=20 independent animals, p=0.0008 by GBW), ΔcgnA$^{EV}$ (n=10 independent animals, p=0.0353 by GBW), and AF293 (n=10 independent animals, p=0.0465 by GBW). AF293, ΔhrmA EV (p=0.1731 by GBW) nor ΔcgnA$^{EV}$ (p=0.7812 by GBW) differ in virulence. FIG. 17f. hrmA$^{R-Ev}$ does not increase fungal burden (a: p=0.4669, b: p=0.1322, c: p=0.7960, One-way ANOVA with Dunnett's Multiple Comparison test, n=5 independent animals each). FIG. 17g Histopathology (n=6 independent animals each from 2 separate preparations) at 4 DPI indicate a cgnA-dependent increase in cellular infiltrate within hrmA$^{R-Ev}$ lesions (Scale bar: 20 μm). FIG. 17h-FIG. 17k Mice inoculated with hrmA$^{R-Ev}$ (n=8 independent animals per group) at 60 hours post-inoculation show elevated (FIG. 17h) LDH (a: p<0.0001, b: p=0.0013, c: p=0.0009), (FIG. 17i) chemoattractant KC (a: p=0.0013, b: p=0.0052, c: p=0.0001), (FIG. 17j) BALF neutrophils (a: p<0.0001), and (k) spleen weight (a: p=0.0009, b: p=0.0191, c: p=0.0021). One-way ANOVA with Dunnett's Multiple Comparisons test for FIG. 17h-FIG. 17k. All Error bars indicate standard error centered at the mean.

FIG. 18a. AF293 lesions show complex interconnection between fungal filaments. FIG. 18b. EVOL20 lesions show diffuse fungal lesions at both day 4 and 5 post inoculation. FIG. 18c. AF293 lesions are compact in the airways while EVOL20 lesions are more diffuse. Scale bars—4 DPI: 10 μm, 5 DPI: 100 pm, histopathology: 20 pm. All images are representative from 5 biologically independent animals from 2 independent sample preparations.

FIG. 20c. Macrophages are significantly reduced between AF293 (n=8 biologically independent animals) and hrmA$^{R-Ev}$ (n=7 biologically independent animals) in the lung tissue (e:p=0.0002 by One-way ANOVA with Dunnett's Multiple Comparison test), but (FIG. 20d) hrmA$^{R-Ev}$ neutrophils (n=7 biologically independent animals) are significantly elevated relative to all groups (n=8 biologically independent animals per group) (a: p<0.0001 by One-way ANOVA with Dunnett's Multiple Comparison test). In BAL, total cells (a: p<0.0001 by One-way ANOVA with Dunnett's Multiple Comparison test) (FIG. 20e) and CD45+leukocytes (a: p<0.0001 One-way ANOVA with Dunnett's Multiple Comparison test) (FIG. 20f) are elevated in hrmA$^{R-EV}$ (n=8 biologically independent animals per group), but not macrophages (b: p=0.2356, c: p=0.0755, d: p=0.9774, by One-way ANOVA with Dunnett's Multiple Comparison test) (FIG. 20g). FIG. 20h. Deletion of cgnA in hrmA$^{R-Ev}$ does not impact hrmA mRNA in vitro (n=3 biologically independent samples) (NS: p=0.4508, **: p=0.0002, One-way ANOVA with Dunnett's Multiple Comparison test). All error bars indicate standard error around the mean (centre).

Figure 21:
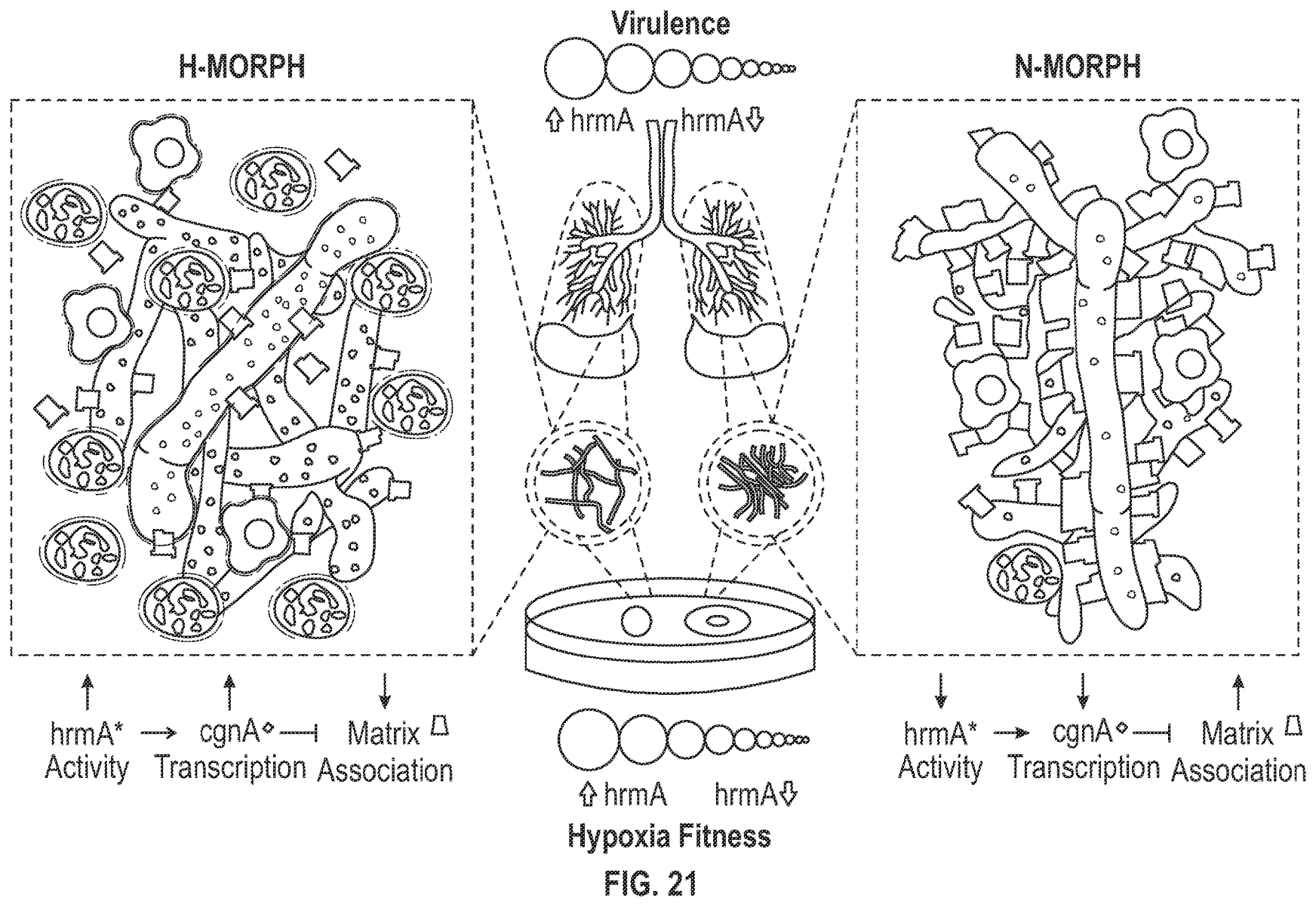

FIG. 21 depicts a model for the impact of macroscopic morphology of disease progression of *A. fumigatus*.

FIG. 23A. Agilent Seahorse XFe96 technology for basal oxygen consumption reveals significantly reduced oxygen consumption by the hypoxia-evolved strain of Aspergillus *fumigatus* EVOL20 (p<0.001 by Students t test). FIG. 23B. Unisense microelectrode technology (OX-25) with 5 mL of 12 hour planktonic cultures reveals reduced oxygen depletion by EVOL20 in fresh aerated media that is dependent on the hypoxia-evolved hrmA allele in EVOL20. FIG. 23C. The fungal biomass used in FIG. 23B to quantify the reduction in dissolved oxygen are not significantly different (p=0.08 by One-Way ANOVA with Tukey multiple comparisons test). Error bars indicate standard error around the mean.

FIG. 24A. 24 hours cultures of EVOL20 and AF293 were shifted from spent media at 21% oxygen to fresh media in 0.2% oxygen for 120 minutes. Following incubation, fungal tissue was collected, washed, quenched, and flash frozen. Unbiased metabolomics was performed at the University of California Davis Metabolomics Center. FIG. 24B. Adherence to polystyrene 96-well plates after 24 hour incubation at normal oxygen is significantly reduced (p<0.001, student's t test) in EVOL20 compared to AF293. Error bars indicate standard error around the mean.

FIG. 25 (SEQ ID NOs: 32 and 33) depicts *A. niger* putative HAC homolog alignments. Clustal omega alignment of A. *niger* CBS 513.88 AnO8g12010, A fumigatus A1163 AFUB 044360, and the uncharacterized, unannotated *A. fumigatus* AF293 HAC gene Afu5g14915 with open reading frame predictions based on RNA-sequencing and alignments with AFUB 044360.

FIG. 26A. Example plasmid for ectopic introduction and overexpression of *A. fumigatus* hrmA from EVOL20 into *A. niger* using Hygromycin as a dominant marker. FIG. 26B. Example plasmid for the ectopic introduction and overexpression of *A. niger* putative HAC ortholog An08g12010 with Hygromycin as a dominant marker. FIG. 26C. Example plasmid for the targeted introduction of a larger portion of HAC including the 3' 4 genes Afu5g14900/hrmA, Afu5g14910, Afu5g14915, and Afu5g14920. This plasmid encodes the dominant marker for pyrithiamine resistance (ptrA) and can be used in conjunction with phrmA_OE (A) to facilitate introduction and high expression of the HAC genes.

FIG. 27A. The *A. niger* strain with the overexpression of hrmA from *A. fumigatus* (evolved allele: D304G) or the over expression of the putative HAC homolog AnO8g12010 will result in *A. niger* strains that consume less oxygen in submerged cultures. FIG. 27B. These genetic changes will also result in increased, or unaltered, production of citrate, and these technologically-relevant phenotypes will not result in a significant reduction in fungal biomass (FIG. 27C).

(FIG. 28A) 96-hour colony biofilms in normoxia (21% $O_2$) and hypoxia (0.2% $O_2$). Images are representative of three independent biological samples. (FIG. 28B) Quantification of colony biofilm morphological features from three independent biological samples. One-way ANOVA with Dunnett's posttest for multiple comparisons was performed relative to EVOL20 within each oxygen environment. (FIG. 28C) The ratio of fungal biomass in hypoxia (0.2% $O_2$) relative to fungal biomass in normoxia (21% $O_2$) (H/N) in shaking flask cultures. One-way ANOVA with Dunnett's posttest for multiple comparisons was performed relative to EVOL20. n=3 independent biological samples. (FIG. 28D) Adherence to plastic measured through a crystal violet assay. Dashed line marks the mean value for media alone. One-way ANOVA with Dunnett's posttest for multiple comparisons was performed relative to ΔcgnAEVOL. n=6 independent biological replicates. (FIG. 28E) Schematics of DNA constructs utilized in generating the cgnAOE and cgnARECON strains in the ΔcgnAEVOL strain. The sequence for the gpdA promoter and trpC terminator are from *A. nidulans*. (FIG. 28F) Gene expression measured by qRT-PCR for cgnA and the cryptic ORF. n=3 independent biological replicates. One-way ANOVA with Tukey's multiple comparison test was performed. (FIG. 28G) Schematic alignment of the hrmA associated gene cluster (HAC) and the putative orthologous gene clusters identified in the strain CEA10. Grey boxes align putative orthologous genes. Not drawn to scale. Error bars indicate standard error around the mean. (ns: p>0.05, not significant).

(FIG. 29A) 96-hour colony biofilms from 21% $O^2$ where hypoxia-locked (H-MORPH) morphological features, furrows and vegetative mycelia, can be visualized. Images are representative of three independent biological samples. (FIG. 29B) Quantification of the H-MORPH features from colony biofilms of three independent biological samples. Student's two-tailed non-parametric t tests were performed between each isogenic strain set. (FIG. 29C) The ratio of fungal biomass in hypoxia (0.2% $O_2$) relative to fungal biomass in normoxia (21% $O_2$) (H/N) in shaking flask cultures. Student's two-tailed non-parametric t test performed between isogenic strain sets. n=3 independent biological samples. (FIG. 29D) Adherence to plastic measured through a crystal violet assay. Dashed line marks the mean value for media alone. Student's two-tailed non-parametric t test performed between isogenic strain sets. n=7 independent biological samples. (FIG. 29E) Gene expression measured by qRT-PCR for representative HAC genes as a result of bafB over expression at 21% $O_2$. n=3 independent biological samples. (FIG. 29F) Representative images (n=3 biological samples) of submerged biofilms on the orthogonal plane (XZ). Scale bar is 200 μm. Error bars indicate standard error around the mean.

(FIG. 30A) 96-hour colony biofilms in normoxia (21% $O_2$) and hypoxia (0.2% $O_2$) of AF293 and AF293 with the over expression of bafA. Images are representative of three independent biological samples. (FIG. 30B) 96-hour colony biofilms in normoxia (21% $O_2$) and hypoxia (0.2% $O_2$) of CEA10 and CEA10 with the over expression of bafA. Images are representative of three independent biological samples. (FIG. 30C) Quantification of the H-MORPH features from colony biofilms of three independent biological samples. Student's two-tailed non-parametric t tests were performed between each isogenic strain set. (FIG. 30D) Representative images of submerged biofilms (n=3 biological samples) on the orthogonal plane (XZ). Scale bar is 200 µm. (FIG. 30E) Adherence to plastic measured through a crystal violet assay. Dashed line marks the mean value for media alone. Student's two-tailed non-parametric t test performed between isogenic strain sets. n=6 independent biological samples. (FIG. 30F) The ratio of fungal biomass in hypoxia (0.2% $O_2$) relative to fungal biomass in normoxia (21% $O_2$) (FUN) in shaking flask cultures. Student's two-tailed non-parametric t test performed between isogenic strain sets. n=4 independent biological samples. (FIG. 30G) Gene expression measured by qRT-PCR for bafA, bafB, and bafC in AF293 and CEA10. n=3 independent biological samples. Error bars indicate standard error around the mean.

(FIG. 31A) 96-hour colony biofilms in normoxia (21% $O_2$) and hypoxia (0.2% $O_2$) of AF293 and AF293 with the over expression of bafB or bafC. Images are representative of three independent biological samples. (FIG. 31B) 96-hour colony biofilms in normoxia (21% $O_2$) and hypoxia (0.2% $O_2$) of CEA10 and CEA10 with the over expression of bafB or bafC. Images are representative of three independent biological samples. (FIG. 31C) Quantification of the H-MORPH features from colony biofilms of AF293, AF293 bafB$_{OE}$, and AF293 bafC$_{OE}$ with three independent biological samples. One-way ANOVA with Dunnett's posttest for multiple comparisons relative to AF293 were performed. (FIG. 31D) Quantification of the H-MORPH features from colony biofilms of CEA10, CEA10 bafB$_{OE}$, and CEA10 bafC$_{OE}$ with three independent biological samples. One-way ANOVA with Dunnett's posttest for multiple comparisons relative to CEA10 were performed. (FIG. 31E) Quantification of conidiation from three independent biological samples of CEA10 and CEA10 bafB$_{OE}$ in normoxia (21% $O_2$) or hypoxia (0.2% $O_2$). Student's two-tailed non parametric t tests were performed between CEA10 and CEA10 bafB$_{OE}$ for each time point. (a: p=0.0004, b: p=0.0006, c: p<0.0001). (FIG. 31F) Adherence to plastic measured through a crystal violet assay. Dashed line marks the mean value for media alone. One-way ANOVA with Dunnett's posttest for multiple comparisons was performed between isogenic strain sets relative to AF293 or CEA10. n=6 independent biological samples for AF293 strains and n=8 independent biological samples for CEA10 strains. (FIG. 31G) Representative images of submerged biofilms (n=3 biological samples) on the orthogonal plane (XZ) of AF293, AF293 bafB$_{OE}$, and AF293 bafC$_{OE}$. Scale bar is 200 µm. (FIG. 31H) Representative images of submerged biofilms (n=3 biological samples) on the orthogonal plane (XZ) of CEA10, CEA10 bafB$_{OE}$, and CEA10 bafC$_{OE}$. Scale bar is 200 µm.

(FIG. 32A) 96-hour colony biofilms in normoxia (21% $O_2$) and hypoxia (0.2% $O_2$) of *A. niger* reference strain A1144 and two independent strains of A1144 with the over expression of *A. fumigatus* bafA (AfbafA$_{OE}$). Images are representative of three independent biological samples. (FIG. 32B) Quantification of the H-MORPH features from colony biofilms of three independent biological samples in normoxia (21% $O_2$). One-way ANOVA with Dunnett's posttest for multiple comparisons relative to A1144. (FIG. 32C) Representative images of submerged biofilms (n=3 biological samples) on the orthogonal plane (XZ). Scale bar is 200 µm. (FIG. 32D) The ratio of fungal biomass in hypoxia (0.2% $O_2$) relative to fungal biomass in normoxia (21% $O_2$) (H/N) in shaking flask cultures. Student's two-tailed non-parametric t test performed between isogenic strain sets. n=3 independent biological samples. (FIG. 32E) Adherence to plastic measured through a crystal violet assay. Student's two-tailed non-parametric t test performed between samples within each media type. n=6 independent biological samples for minimal media and n=7 independent biological samples for complex media (minimal media with yeast extract).

DETAILED DESCRIPTION

Figure 1:
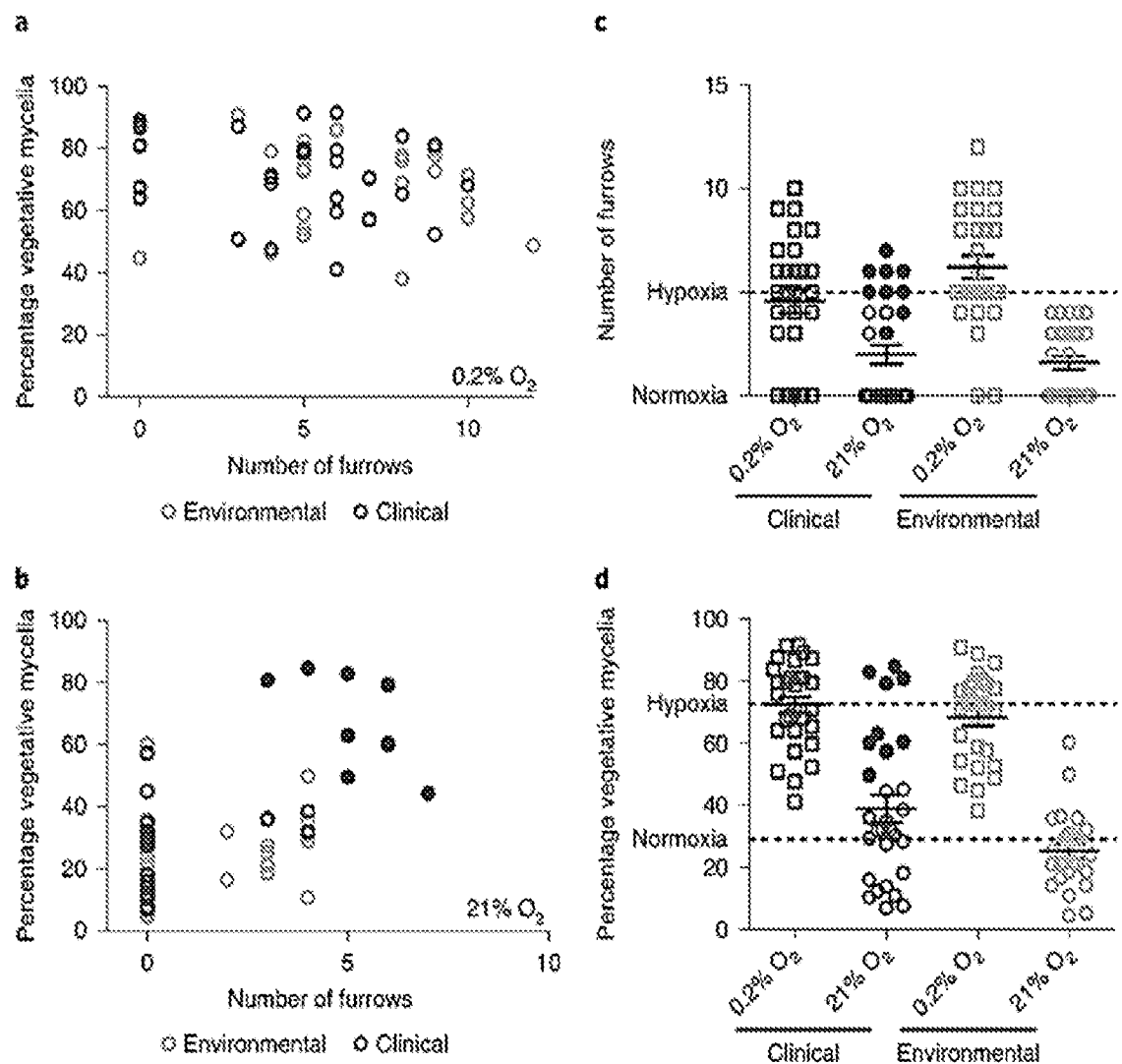
FIG. 1 depicts that the macroscopic morphotypes and biofilm architecture of *A. fumigatus* are influenced by oxygen tension.
Figure 1:
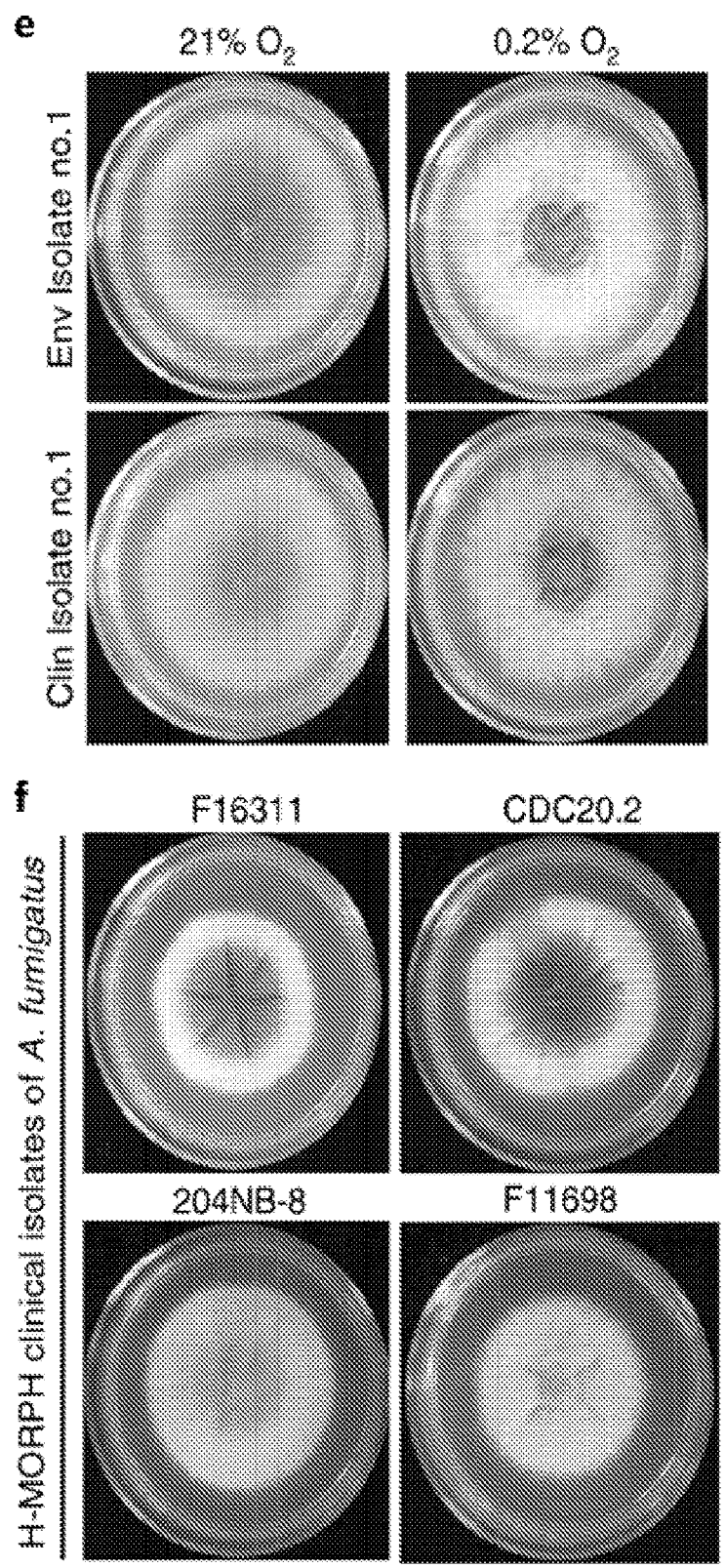
Figure 1:
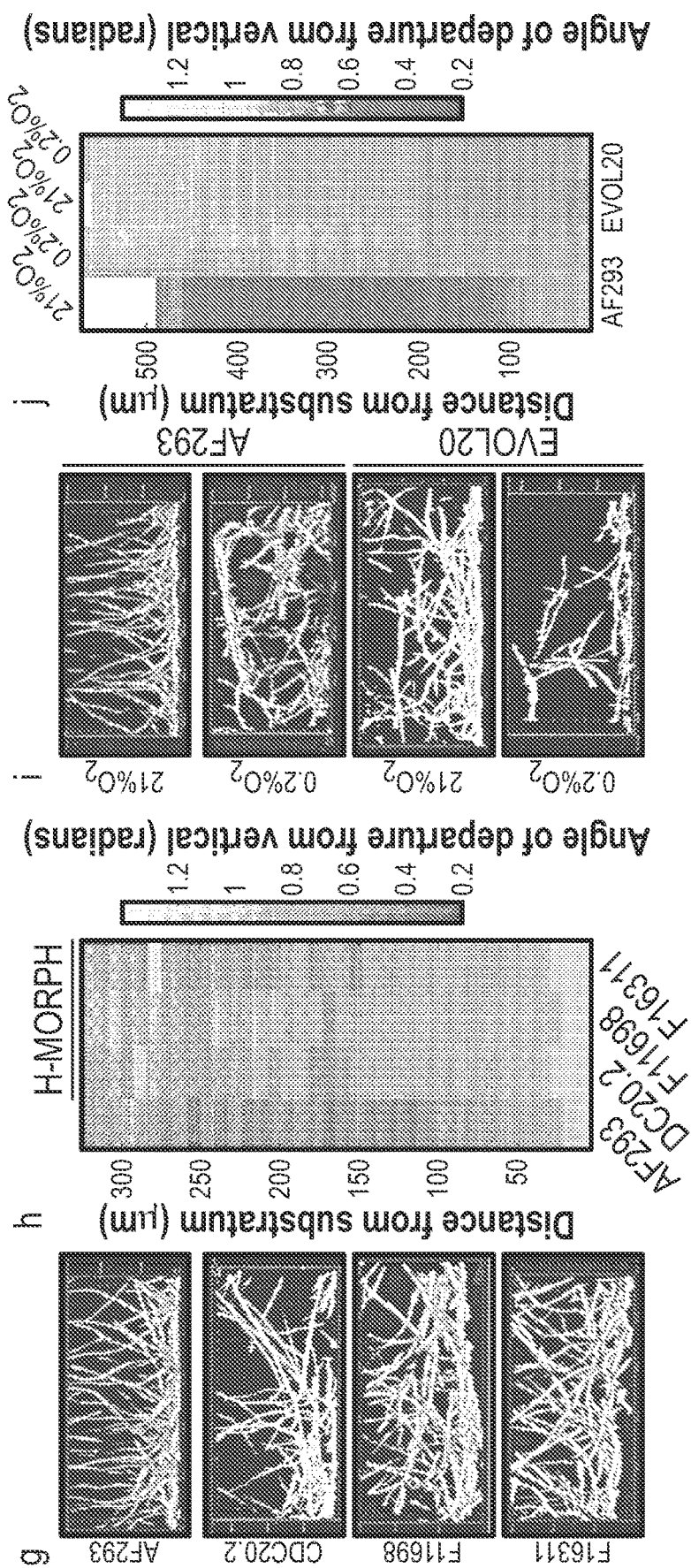

Filamentous fungal host cells engineered to express and/or overexpress an hrmA protein, or homolog, or ortholog thereof, are provided. Also provided are filamentous fungal host cells engineered to express and/or overexpress a baf protein, or homolog, or ortholog thereof.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

As used herein, the term "filamentous fungal host cell" refers to a fungal host cell that produces elongated and thread-like (filamentous) structures called hyphae. Filamentous fungal host cells are capable of secreting proteins and various metabolites, including many commercially relevant products, such as industrial enzymes. Non-limiting examples of filamentous fungal host cells include filamentous fungal host cells belonging to a genus selected from the group consisting of *Acremonium, Aspergillus, Aureoba-* sidium, *Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Saccharomyces, Schizophyllum, Talaromyces, Thermoascus, Thielavia, Tolypocladium, Trametes* and *Trichoderma*. In certain embodiments, the filamentous fungal host cell is an *Aspergillus* host cell. In certain embodiments, the filamentous fungal host cell is an *Aspergillus* host cell other than *Aspergillus fumigatus*.

In certain embodiments, the filamentous fungal host cell is a fungal species useful in industrial production of products of interest. In certain embodiments, the host cell is selected from the group consisting of: *Aspergillus awamori, Aspergillus flavus, Aspergillus foetidus, Aspergillus japonicus, Aspergillus luchensis, Aspergillus nidulans, Aspergillus niger* or an *Aspergillus oryzae* host cell.

Hypoxia Responsive Morphology Factor A (hrmA)

As used herein, the term "Hypoxia Responsive Morphology Factor A" or "hnnA" or "Afu5g14900" refers to a protein encoded by an *Aspergillus fumigatus* hrmA gene. In certain embodiments, the hrmA protein can be a homolog or ortholog of the *Aspergillus fumigatus* hrmA. In certain embodiments, the hrmA protein comprises at least 80%, at least 85%, at least 90%, or at least 95% identity to the amino acid sequence of SEQ ID NO: 11. In certain embodiments, the hrmA protein comprises or consists of the amino acid sequence of SEQ ID NO: 11. In certain embodiments, the hrmA protein comprises a D304G mutation relative to the amino acid sequence of SEQ ID NO: 11. In certain embodiments, the hrmA protein comprises at least 80%, at least 85%, at least 90%, or at least 95% identity to the amino acid sequence of SEQ ID NO: 12. In certain embodiments, the hrmA protein comprises or consists of the amino acid sequence of SEQ ID NO: 12.

It has been surprisingly discovered that expression (including overexpression) of hrmA in a filamentous fungal host cell promotes a hypoxia-specific morphology (H-MORPH) that is characterized, in part, by increased colony furrowing and high vegetative mycelia (white, non-conidiating mycelia) (PVM). In certain embodiments, a PVM of greater than about 30%, 35%, 40%, 45%, or 50% is considered indicative of a hypoxia-specific morphology. This morphology is associated with increased low oxygen fitness, increased production of products of interest, and increased secretion of products of interest.

In one aspect, the disclosure provides a filamentous fungal host cell, comprising a nucleotide sequence encoding an *Aspergillus fumigatus* hypoxia responsive morphology factor A (hrmA) protein, or a homolog or ortholog thereof.

In certain embodiments, the filamentous fungal host cell is not *Aspergillus fumigatus*. In certain embodiments, the filamentous fungal host cell is engineered to overexpress an hrmA protein, or homolog, or ortholog thereof. In certain embodiments, the filamentous fungal host cell is engineered to overexpress an hrmA protein that comprises at least 90% identity to the amino acid sequence of SEQ ID NO: 11. In certain embodiments, the filamentous fungal host cell is engineered to overexpress an hrmA protein that comprises at least 90% identity to the amino acid sequence of SEQ ID NO: 12. In certain embodiments, the filamentous fungal host cell is an engineered *Aspergillus fumigatus* host cell that overexpresses an hrmA protein, or homolog, or ortholog thereof. Overexpression of the hrmA protein, or homolog, or ortholog thereof, is relative to a wild-type, un-engineered *Aspergillus fumigatus* host cell. The engineered *Aspergillus fumigatus* host cell may overexpress the hrmA protein, or homolog, or ortholog thereof, by at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, or 1000-fold, relative to a wild-type *Aspergillus fumigatus* host cell.

The filamentous fungal host cell that can express (including overexpress) the hrmA protein can be any filamentous fungal host cell known in the art. In certain embodiments, the filamentous fungal host cell belongs to a fungal genus useful in industrial production of products of interest. In certain embodiments, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Saccharomyces, Schizophyllum, Talaromyces, Thermoascus, Thielavia, Tolypocladium, Trametes* and *Trichoderma*. In certain embodiments, the filamentous fungal host cell is an *Aspergillus* host cell. In certain embodiments, the filamentous fungal host cell is an *Aspergillus* host cell other than *Aspergillus fumigatus*.

In certain embodiments, the filamentous fungal host cell is a fungal species useful in industrial production of products of interest. In certain embodiments, the host cell is selected from the group consisting of: *Aspergillus awamori, Aspergillus flavus, Aspergillus foetidus, Aspergillus japonicus, Aspergillus luchensis, Aspergillus nidulans, Aspergillus niger* or an *Aspergillus oryzae* host cell.

In certain embodiments of the filamentous fungal host cell, the production of any one or more of aconitate, malate, isocitrate, and citrate are increased relative to a fungal host cell that does not comprise a nucleotide sequence encoding the *Aspergillus fumigatus* hrmA protein, or homolog, or ortholog thereof.

The filamentous fungal host cell expressing hrmA may comprise a hypoxia-specific morphology. In certain embodiments, the fungal host cell (e.g., the fungal host cell engineered to express or overexpress the hrmA protein, or homolog, or ortholog thereof) is less adherent to plastic and glass surfaces relative to a fungal host cell that does not comprise a nucleotide sequence encoding the *Aspergillus fumigatus* hrmA protein, or homolog, or ortholog thereof. Adherence may be reduced by about 10%, 20%, 30%, 40%, 50%, 60%, 70%, or 80%.

Biofilm Architecture Factor (baf)

As used herein, the term "Biofilm Architecture Factor" or "baf" refers to a class of proteins found in select fungal species that play a role in generating a hypoxia-specific morphology (H-MORPH) and promote biofilm architecture reorganization. In certain embodiments, the baf protein can be a homolog or ortholog of an *Aspergillus fumigatus* baf protein. In certain embodiments, the *Aspergillus fumigatus* baf protein is bafA, or homolog or ortholog thereof. In certain embodiments, the *Aspergillus fumigatus* baf protein is bafB, or homolog or ortholog thereof. In certain embodiments, the *Aspergillus fumigatus* baf protein is bafC, or homolog or ortholog thereof.

In certain embodiments, the bafA protein comprises at least 80%, at least 85%, at least 90%, or at least 95% identity to the amino acid sequence of SEQ ID NO: 13. In certain embodiments, the bafA protein comprises or consists of the amino acid sequence of SEQ ID NO: 13. In certain embodiments, the baf 13 protein comprises at least 80%, at least 85%, at least 90%, or at least 95% identity to the amino acid sequence of SEQ ID NO: 14. In certain embodiments, the bafB protein comprises or consists of the amino acid sequence of SEQ ID NO: 14. In certain embodiments, the bafC protein comprises at least 80%, at least 85%, at least 90%, or at least 95% identity to the amino acid sequence of SEQ ID NO: 15. In certain embodiments, the bafC protein comprises or consists of the amino acid sequence of SEQ ID NO: 15.

It has been surprisingly discovered that expression (including overexpression) of a baf protein in a filamentous fungal host cell promotes a hypoxia-specific morphology (H-MORPH) that is characterized, in part, by increased colony furrowing and high vegetative mycelia (white, non-conidiating mycelia) (PVM). In certain embodiments, a PVM of greater than about 30%, 35%, 40%, 45%, or 50% is considered indicative of a hypoxia-specific morphology. This morphology is associated with increased low oxygen fitness, increased production of products of interest, and increased secretion of products of interest.

In one aspect, the disclosure provides a filamentous fungal host cell, comprising a nucleotide sequence encoding an *Aspergillus fumigatus* biofilm architecture factor (baf) protein, or a homolog or ortholog thereof. In certain embodiments, the filamentous fungal host cell is not *Aspergillus fumigatus*. In certain embodiments, the filamentous fungal host cell is engineered to overexpress a baf protein, or homolog, or ortholog thereof. In certain embodiments, the filamentous fungal host cell is engineered to overexpress an baf protein that comprises at least 90% identity to the amino acid sequence of SEQ ID NO: 13. In certain embodiments, the filamentous fungal host cell is engineered to overexpress an baf protein that comprises at least 90% identity to the amino acid sequence of SEQ ID NO: 14. In certain embodiments, the filamentous fungal host cell is engineered to overexpress an baf protein that comprises at least 90% identity to the amino acid sequence of SEQ ID NO: 15. In certain embodiments, the filamentous fungal host cell is an engineered *Aspergillus fumigatus* host cell that overexpresses a baf protein, or homolog, or ortholog thereof. Overexpression of the baf protein, or homolog, or ortholog thereof, is relative to a wild-type, un-engineered *Aspergillus fumigatus* host cell. The engineered *Aspergillus fumigatus* host cell may overexpress the baf protein, or homolog, or ortholog thereof, by at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, or 1000-fold, relative to a wild-type *Aspergillus fumigatus* host cell.

In certain embodiments, the baf protein comprises bafA, or a homolog or ortholog thereof. In certain embodiments, the baf protein comprises bafB, or a homolog or ortholog thereof. In certain embodiments, the baf protein comprises bafC, or a homolog or ortholog thereof.

The filamentous fungal host cell that can express (including overexpress) a baf protein (such as bafA, bafB, and bafC) can be any filamentous fungal host cell known in the art. In certain embodiments, the filamentous fungal host cell belongs to a fungal genus useful in industrial production of products of interest. In certain embodiments, the filamentous fungal host cell is of a genus selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Saccharomyces, Schizophyllum, Talaromyces, Thermoascus, Thielavia, Tolypocladium,* *Trametes* and *Trichoderma*. In certain embodiments, the filamentous fungal host cell is an *Aspergillus* host cell. In certain embodiments, the filamentous fungal host cell is an *Aspergillus* host cell other than *Aspergillus fumigatus*.

In certain embodiments, the filamentous fungal host cell is a fungal species useful in industrial production of products of interest. In certain embodiments, the host cell is selected from the group consisting of: *Aspergillus awamori, Aspergillus flavus, Aspergillus foetidus, Aspergillus japonicus, Aspergillus luchensis, Aspergillus nidulans, Aspergillus niger* or an *Aspergillus oryzae* host cell.

In certain embodiments, of the filamentous fungal host cell, the production of any one or more of aconitate, malate, isocitrate, and citrate are increased relative to a fungal host cell that does not comprise the nucleotide sequence encoding an *Aspergillus fumigatus* baf protein (such as bafA, bafB, and bafC).

The filamentous fungal host cell expressing a baf protein may comprise a hypoxia-specific morphology. In certain embodiments, the fungal host cell is less adherent to plastic and glass surfaces relative to a fungal host cell that does not comprise the nucleotide sequence encoding an *Aspergillus fumigatus* baf protein (such as bafA, bafB, and bafC).

In another aspect, the disclosure provides a filamentous fungal host cell, comprising a nucleotide sequence encoding an *Aspergillus niger* biofilm architecture factor (baf) protein, or a homolog or ortholog thereof. In certain embodiments, the filamentous fungal host cell is not *Aspergillus niger*.

In certain embodiments, the baf protein comprises bafA, or a homolog or ortholog thereof. In certain embodiments, the bafA protein comprises at least 90% identity to the amino acid sequence of SEQ ID NO: 16. In certain embodiments, the bafA protein comprises or consists of the amino acid sequence of SEQ ID NO: 16. In certain embodiments, the fungal host cell is less adherent to plastic and glass surfaces relative to a fungal host cell that does not comprise the nucleotide sequence encoding the *Aspergillus niger* baf protein, or a homolog or ortholog thereof.

In one aspect, the disclosure provides a modified *Aspergillus niger* host cell, wherein the *Aspergillus niger* host cell is modified to express a biofilm architecture factor (baf) protein at a higher level than an unmodified *Aspergillus niger* host cell. In certain embodiments, the modified *Aspergillus niger* host cell is engineered to overexpress a baf protein, or homolog, or ortholog thereof, by at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 500-fold, or 1000-fold, relative to a unmodified *Aspergillus niger* host cell.

In certain embodiments, the baf protein comprises bafA, or a homolog or ortholog thereof. In certain embodiments, the bafA protein comprises at least 90% identity to the amino acid sequence of SEQ ID NO: 16. In certain embodiments, the bafA protein comprises or consists of the amino acid sequence of SEQ ID NO: 16.

Additional Filamentous Fungal Host Cell Features

In certain embodiments, the filamentous fungal host cell expressing one or more of an hrmA protein and baf protein further comprises a heterologous polynucleotide encoding a secreted polypeptide of interest. In certain embodiments, the polypeptide of interest is an enzyme.

In certain embodiments, the filamentous fungal host cell produces one or more products of interest at a higher level than a filamentous fungal host cell that does not comprise a nucleotide sequence encoding an *Aspergillus fumigatus* hrmA protein, an *Aspergillus fumigatus* baf protein, an *Aspergillus niger* baf protein, or homologs or orthologs thereof.

In certain embodiments, the filamentous fungal host cell secretes one or more products of interest at a higher level than a filamentous fungal host cell that does not comprise a nucleotide sequence encoding an *Aspergillus fumigatus* hrmA protein, an *Aspergillus fumigatus* baf protein, an *Aspergillus niger* baf protein, or homologs or orthologs thereof.

In certain embodiments, the one or more products of interest comprise citric acid, gluconic acid, fumaric acid, kojic acid, lactic acid, itaconic acid, proteins, and secondary metabolites.

As used herein, the term "secondary metabolites" refers a group of fungal-produced low-molecular weight compounds. The secondary metabolites generally are not directly involved in fundamental metabolic processes of growth and energy generation; however, they display varied biologic activities that contribute to the survival of the producing fungus under particular conditions. Secondary metabolites can belong to three broad classes, polyketides, non-ribosomal peptides, and terpenes. Non-limiting examples of secondary metabolites include, 0-lactams (such as cephalosporins and penicillin), compactin, cyclosporines (such as cyclosporine A), gibberellins (such as gibberelic acid), griseofulvin, lovastatin, mycophenolic acid, pigments (such as astaxanthin, 0-carotene, monascin, ankaflavin, monascorubrin, and rubropunctatin), siderophores, and taxol. In certain embodiments, the secondary metabolites are selected from the group consisting of: 0-lactams, compactin, cyclosporines, gibberellins, griseofulvin, lovastatin, mycophenolic acid, pigments, siderophores, and taxol. Additional description and examples of secondary metabolites may be found in Boruta (Bioengineered, 9(1): 12-16, 2018) and Hoffmeister et al. (Nat Prod Rep. 24(2):393-416, 2007).

In certain embodiments, the filamentous fungal host cell grows at a higher level in the presence of reduced oxygen than a filamentous fungal host cell that does not comprise a nucleotide sequence encoding an *Aspergillus fumigatus* hrmA protein, an *Aspergillus fumigatus* baf protein, an *Aspergillus niger* baf protein, or homologs or orthologs thereof.

In certain embodiments, filamentous fungal host cell oxygen consumption is reduced compared to a filamentous fungal host cell that does not comprise a nucleotide sequence encoding an *Aspergillus fumigatus* hrmA protein, an *Aspergillus fumigatus* baf protein, an *Aspergillus niger* baf protein, or homologs or orthologs thereof.

In certain embodiments, the oxygen consumption is reduced by about 10% to about 90%. In certain embodiments, the oxygen consumption is reduced by about 10%, about 15%, about 20%, about 25%, about 30%, about 35%, about 40%, about 45%, about 50%, about 55%, about 60%, about 65%, about 70%, about 75%, about 80%, about 85%, or about 90%.

In certain embodiments, the present disclosure provides a plasmid harboring a polynucleotide sequence encoding a hrmA protein or baf protein (such as bafA, bafB, or bafC). In certain embodiments, the plasmid is an expression vector harboring a polynucleotide sequence encoding a hrmA protein or baf protein (such as bafA, bafB, or bafC). In certain embodiments, the polynucleotide sequence further comprises a promoter to express one or both of the hrmA protein and the baf protein. In certain embodiments, the expression vector harboring the polynucleotide sequence further comprises a promoter to express one or both of the hrmA protein and the baf protein.

The promoter can be one chosen based on the filamentous fungal host cell being employed. For example, but in no way limiting, the promoter can be a naturally-occurring promoter in the filamentous fungal host cell being employed. In another non-limiting example, the promoter can be a heterologous promoter not found in the filamentous fungal host cell being employed.

In certain embodiments, the promoter is inducible or constitutive. In certain embodiments, the inducible promoter is selected from the group consisting of: alcA, amyB, bli-3, bphA, catR, cbhI, cre1, exy1A, gas, glaA, mir1, niiA, qa-2, Smxy1, tcu-I, thiA, vvd, xy11, xy1P, xyn1, or zeaR. In certain embodiments, the constitutive promoter comprises cDNA1, enol, gpdA, gpd1, pdc1, pki1, poliC, tef1, or rpt. Further details on fungal host cell promoters useful for the expression of genes of interest are described in Fitz et al. (Front. Bioeng. Biotechnol. 6: 135, 2018) and Kluge et al. (Appl Microbiol Biotechnol. 102(15):6357-6372, 2018), Polynucleotides encoding one or both of an hrmA protein and a baf protein (such as bafA, bafB, or bafC) of the disclosure may be introduced into the filamentous fungal host cells by any means known in the art, including via transformation.

As used herein, the term "transformation" refers to a non-viral method of DNA transfer in bacteria and non-animal eukaryotic cells, such as fungal cells. Numerous methods of fungal cell transformation are known in the art. Examples include, but are not limited to, protoplast-mediated transformation, *Agrobacterium*-mediated transformation, electroporation, biolistic transformation (i.e., particle bombardment), and shock-wave-mediated transformation. Methods of fungal host cell transformation are described in greater detail in Li et al. (Microb Cell Fact. 16: 168, 2017).

The polynucleotides encoding one or both of an hrmA protein and a baf protein may be introduced into the filamentous fungal host cells transiently or stably integrated into the host cell genome. If stable integration is employed, the polynucleotides can have homology arms at the 5' and 3' ends to facilitate integration.

Genomic modification of the filamentous fungal host cells may be performed with any known genetic editing technology. Non-limiting examples of genetic editing technologies include, meganucleases, zinc finger nucleases (ZFN), TALENs, and CRISPR.

The use of CRISPR genetic editing can be performed with CRISPR/Cas9-based systems or CRISPR/Cas12-based systems. The CRISPR system is composed of a CRISPR nuclease (such as Cas9 or Cas12) and a site-specific genome-targeting guide RNA (gRNA). The CRISPR system can be introduced via one or more expression cassettes that expresses the CRISPR nuclease and gRNA, such as a vector. The CRISPR nuclease and gRNA can be expressed off of a single expression cassette or separate expression cassettes. The CRISPR system can be introduced as a ribonucleoprotein (RNP) complex, where the CRISPR nuclease and gRNA form a complex in vitro (the CRISPR RNP), and the RNP is introduced into the filamentous fungal host cell. The filamentous fungal host cells can be transformed with a CRISPR system with any of the above recited transformation methods. The use of CRISPR genetic editing of fungal cells is described in greater detail in Dong et al. (J Microbiol Methods 163, 105655, 2019), Leynaud-Kieffer et al. (PLoS One 14, e0210243, 2019), and Song et al. (Appl Microbiol Biotechnol. 2019; 103(17): 6919-6932.).

The hrmA and baf proteins of the disclosure, and the polynucleotides that encode the same, are recited below in Table 1 and Table 2.

TABLE 1

Polynucleotide Sequences of the Disclosure. Lower case italicized sequences represent introns.

| Sequence Notes | Sequence |
| --- | --- |
| A. fumigatus hrmA/ Afu5g14900 hypoxia evolved genomic sequence Bold, underlined, and italicized "G" corresponds to the sequence change as a result of in vitro evolution in hypoxia to produce the hrmA D304G amino acid variant. (SEQ ID NO: 1) | ATGGCATCCACAAAGCCCGCTTCGAGTCTCATTTACC<br>AGGCATGGAACAAACTCAGTATCAACCAAACCATCC<br>CTAGTGACTCCCTTGAATTACTTGGGGAGCGTTTGGC<br>TATTGCCTTCGCACCCAAACTCAAGGAGCAACGAAG<br>GAATGGCCGGCGTCGGAATCTGGAATATGTGGCACA<br>ACATCGACGGAAGATTGCTCGAAAAATCTACTTGGA<br>GATTCTGGAGAAAGACCCAAATATCTTTCTTCCTTTT<br>ATCCTGGCTGTTTCCCCTAGAGCATGCTTATCCTTTGA<br>TATCTCGAGCTTTCTTGAACAGCACCAAAGCCAAGGA<br>AGACATTTCCTCCGCAACAATGCCGAAGCGATCCTCT<br>GGGGTCTCGCAAAGAAACATGACATTGATGGCTCCCT<br>CCATTTCAGGAAGCTGATGCGTGAGATTTTCCAACTG<br>TCTCCTCCAGCGACAGAAGCCGAAGGCAAGGAGCAT<br>TATTCATTGCATTTAAGCACTCTCCCCGCAATCCGCA<br>ATGCCTTCGGTGATGTTATCTTTGACGCAATTGAACG<br>TTCCCCTACACAGGTGACAGCGAGAGCTAAAGGTTAT<br>TTCTCTGAGAAAACCGAAAGTGTTTGGACAAAAGTTC<br>CCTACAGAAGTTCTCAAGACGCAATCATATCTCTTGA<br>AGTAGGGTCGGCAATCGAGCTTGCGAATGTGTTGTTC<br>CCAATCGCAACCCAAAAAATTGTCTCTATCCTTTCCG<br>CATGTTCTCCCACTGTGCGCCAGAAGAACTTTTCTGA<br>GGCTATTCTCGGCCCAGACCCTCAGGATACACCGGCA<br>ACATCATCAGAAATCG*gtatgaagtttaaggtacacatgactgcagttg<br>ctaattccaccctgtgctag*ATGTGGCGTATTTTACTCTGCGAGG<br>AGCAACGGTCTCGGCAATTGAATCAGTCTTTCGCGCT<br>GATATTTGCGAAGGTATTAAGGGCAGCGAACTGAGA<br>AACTGGGAAAAGGAGCAGCTGCTCATCGACACGACA<br>GATTGTGTCACGATGCAGATATGGCGGGCACAACCTC<br>AACATGGAACCATCAAGTTGCGTATTGGATTCTATGC<br>AGCGGTGAATTTGGCAAATCGGCTGTATGCAGAAAC<br>ACCCCAAGATCACATATAG |
| A. fumigatus 3' HAC region (Afu5g14900-Afu5g14920) Bold, underlined, and italicized "G" corresponds to the sequence change as a result of in vitro evolution in hypoxia to produce the hrmK D304G amino acid variant. (SEQ ID NO: 2) | CGCCGTAACGTAACAAAGCGGGGTTGGTAGTGTTTGC<br>AAATGCATTCACATGGACCGATCACTTTTCTTTCCAG<br>TCTGTCCATTCTGTCCAATCTGTCCGATCTGACCTGCC<br>CAGTCTGTCCAGTCTGTCCCTTGTGTCGTCCGATCCA<br>AGCTGGTTATCATGGCATCCACAAAGCCCGCTTCGAG<br>TCTCATTTACCAGGCATGGAACAAACTCAGTATCAAC<br>CAAACCATCCCTAGTGACTCCCTTGAATTACTTGGGG<br>AGCGTTTGGCTATTGCCTTCGCACCCAAACTCAAGGA<br>GCAACGAAGGAATGGCCGGCGTCGGAATCTGGAATA<br>TGTGGCACAACATCGACGGAAGATTGCTCGAAAAAT<br>CTACTTGGAGATTCTGGAGAAAGACCCAAATATCTTT<br>CTTCCTTTTATCCTGGCTGTTTCCCCTAGAGCATGCTT<br>ATCCTTTGATATCTCGAGCTTTCTTGAACAGCACCAA<br>AGCCAAGGAAGACATTTCCTCCGCAACAATGCCGAA<br>GCGATCCTCTGGGGTCTCGCAAAGAAACATGACATTG<br>ATGGCTCCCTCCATTTCAGGAAGCTGATGCGTGAGAT<br>TTTCCAACTGTCTCCTCCAGCGACAGAAGCCGAAGGC<br>AAGGAGCATTATTCATTGCATTTAAGCACTCTCCCCG<br>CAATCCGCAATGCCTTCGGTGATGTTATCTTTGACGC<br>AATTGAACGTTCCCCTACACAGGTGACAGCGAGAGC<br>TAAAGGTTATTTCTCTGAGAAAACCGAAAGTGTTTGG<br>ACAAAAGTTCCCTACAGAAGTTCTCAAGACGCAATC<br>ATATCTCTTGAAGTAGGGTCGGCAATCGAGCTTGCGA<br>ATGTGTTGTTCCCAATCGCAACCCAAAAAATTGTCTC<br>TATCCTTTCCGCATGTTCTCCCACTGTGCGCCAGAAG<br>AACTTTTCTGAGGCTATTCTCGGCCCAGACCCTCAGG<br>ATACACCGGCAACATCATCAGAAATCGGTATGAAGT<br>TTAAGGTACACATGACTGCAGTTGCTAATTCCACCCT<br>GTGCTAGATGTGGCGTATTTTACTCTGCGAGGAGCAA<br>CGGTCTCGGCAATTGAATCAGTCTTTCGCGCTGATAT<br>TTGCGAAGGTATTAAGGGCAGCGAACTGAGAAACTG<br>GGAAAAGGAGCAGCTGCTCATCGACACGACAGATTG<br>TGTCACGATGCAGATATGGCGGGCACAACCTCAACA<br>TGGAACCATCAAGTTGCGTATTGGATTCTATGCAGCG<br>GTGAATTTGGCAAATCGGCTGTATGCAGAAACACCCC<br>AAGATCACATATAGTAACCTTTCATCTTTTCGGCCTTC<br>TTAAATCATTGCCTTTCTGTGAGTCGCGACTTTCCACC<br>CTTTATGAATACACCAATACCAGGGGGAAGAACGAT<br>TTCACCGCTTCCCTTGGCAATCCATATAGTTCCCTTCT<br>CATTCTGGAACCTGATTTCATCGCAGTTGAAGCAATA<br>TAAATTCCTTTCGAGGTTTTCTGCATTGTAGGGATGG<br>AATGGGTGCGTGAAATATTTGTCGAAAATAGAAGGG<br>TCCGAAAGTTCTTTCCAAGCTGCGCGCTGAAAGTTGT |

TABLE 1-continued

Polynucleotide Sequences of the Disclosure. Lower case italicized sequences represent introns.

| Sequence Notes | Sequence |
|---|---|
| | TAGCCCATCTTTCGAGCATATGGTTTGGCCCACATAC<br>GAGAGATTCTTTTGTGATCGGTTGAGATTCTTCCGTG<br>ATCGGTTCTGTCATTTTCATTAAGTCAGAGAGCCCTC<br>TTGTATGCCGGCTTTTGCTGTCGGATCCGGCGAGATA<br>ATCGCTCCTAAGCCAGTCAGTCAGGGAAAAGCAAAG<br>ATAAATAAAATATAGGCGAGGAGTACAACCAGGCAC<br>GCGTCGTAGACTATTTTTCTGAAGAGTTTGTCACGTA<br>ACCTACCTCATATGGATGGGTAGTTCGAATACTTGAT<br>TGACTTGACCCGAGGTTCTGAAGGCGGCGGAGGAAA<br>TTGCCCAACCCCACCATTGCATTTTCAGGTATCAATC<br>TCTGCCACACTGTGGCTAAATTCGTCTTTATCGACAC<br>GTGATCACGTTCCCTCTTCCAGCCCTGGTATCAGAGA<br>ATCATCGAGTTATCGCTTGTTTCAATTTCGTCTTGCAA<br>TTAGCTTAGGGAATAAGCATGTGGTCACATCAACCTA<br>CAGAGCGCTACCGGTCTTTGCGCTGAGACTCTCAGTG<br>ATCCGCCCAACAGACAACTAGACTTTGAGGTTGTCGA<br>TATAACCACAACAAATGGCCTGTATATCAACGATGTC<br>CACGCAATTGTCTCAAGCCTCTTCACCCGACTTCCAG<br>CACTAGCATCCAAGCGGCCTCTCCTCTTCTCCCATGTT<br>TCTCGTAGCGCGCCTGCATATACTTTATATCTGGAGAT<br>ATGTTAAAGGAGCTGGAAGCCTGGAGCATACGCTGG<br>AAGCCTGGAGCATACGCTTCAAGTGCTGCCATATTCA<br>GATAGCTGAGTAGGCACAATTAGGTCTAAGTTCAGG<br>GAATTGCACCTCTCGCTTCATTGTCCGTCGATTCGTAT<br>CGGTCTCTAGTTCTCCCCGTTTATCACTCTCACTCGGT<br>GGACAGTCCGTCCAGTCCGTCAGTCCGTCGAGCCTG<br>TCCAATCTGTCCAATCTGTCCAATCTGTCCAATCTGTC<br>CAATCTGTCCAATCTGTCCAATCTGTCCAATCTGTCC<br>AATCTGTCCAATCTGTCCAATCTGTCCAATCTGTCCA<br>ATCTGTCCAATCTGTCCAATCTGTCCAATCTGTCCACT<br>CTGTCCACTCTGTCCACTCTGTCCAATCTGTCCACTCT<br>GTCCCCTCTGTCCACTCTGTCCCCTCTGTCCACTCTGT<br>CCCCTCTGTCCAATCGGTCCAATCTGTCCAATCTTGAT<br>GATCTCGATGATCAATACCATTTAGCGAGCGCTAGTG<br>ACGCCTTACAGCGTTGCGGCGTCTTATGGCTTATACA<br>TCTTCCGAATATCAGTCGTTCGATCTCCAGATCACAC<br>CTCGGGGTGAAACAAGCGCCATAGTTCTTGGTGCGCC<br>TGAGCTTTTCCCTGCCCGGCCACTCAGTCGTGATGGC<br>TTCCCAGAGTATTCCATAAGTCGAAACCAGAGATAG<br>GCCAGCGGACGGCAAATCTCCTCTGCTCCGTTCTCAA<br>CCAATACTGCCAAAGTGAGCAATGGAAAGTGTTCCA<br>GGAGCACCGTGGCCTTTAAAAGCGCCAGCCTTGTCCC<br>AGATCCTCACCGCAATTCGGCACAGACCAACGCAGA<br>CTTTCATTGACCATTCTTCATTTCCAGATCGCTGCATA<br>GTTTCCGGTATGGCTTGGTATAGAGCCTTACTCCCGT<br>GCATACCGTTGTGGCGGAAGGTTCTGGGGCGTAACA<br>GCACCGATGAGGACGGACGGAGTGAAGACGACCTTA<br>CTTCATTGAGCGATAAAATGCCTACTTTTGAAGAAAC<br>GACAACTGTGAGTACTGTTCGTGAAATTGCCTCCAGC<br>TGTCTAATGTCTCCGTCGGTCAGATCACTTCTGCAAA<br>GTACATCAACGGTGAAAAAATCATGGAGCATACCGT<br>TGTGGAGACCAAGCACATTGACGAACGTGGAGACAC<br>CAGCGTCAGTAACGGTGATTCGAACAGCACTGCGGT<br>AACCAGACATTCTGGGCTTAGCTCTGTCAGCCTTTCA<br>GATCAAAGTACAATTGTCGAGGACGCGAATGCTCTG<br>GAAGAACCTGAACTCTTTGCTGTTCACTCTCCATATG<br>TTGACGACTCAACCGGCGAGCAGATGGTTAGACTCTA<br>CTACGAGCTCCCAGTAAGCCTCGATGATCTTGAGATC<br>ATAGGCCTTGAATCTCGTATTCCAGAGTCTGACGATG<br>ATTCAATTGAGGCCCGCTTTCGTTATCGAGGAGAGGA<br>TTTTTGGCTACCTGTTCGTTATTCTTATGCCAAAGCTC<br>GAATGGTTTTAACGGGTGTATGCTGAATGGTCTGACT<br>TCTTCACTGTTGTTATTTTCTATTTCCCGGCTGCTGGC<br>CACTCAATATTATCGCAAGCACTATACAAAATAAATA<br>GTCCTATCTCTATAACAGAGTACGTCACAAACAGCGT<br>TCGTCCTTGGCAAGAATATAAATAGTGTCAATCTGCT<br>GAGAAAAGGAGGTATGAAATCCACTTCATTCAAGCA<br>ATGGTTCCCTTCGTATACATTATTATTTGTATATGGAT<br>GGGAACTTTTCTTGTCTTAGTTGCCCTGAACGCCCGC<br>TTTAAGAAGAAGCGCATTGCTGATCCTGAGTCTTCTG<br>CTGCCTTCACTGATCATCCCCATCAAGAGTAACATGG<br>ATTCTGTATGTCCCTTTGGGCATGTTTATGTGGCAGTT<br>ACTAATATATTAGATGGAAACTAGGAAGCGGCAAAA<br>CACAGGGGCAGGAAGGGAAGGACTCATTCCAAGAAA<br>GAAGGACAAGGAAGAACACAAGAGTGTAAGGGGTA |

TABLE 1-continued

Polynucleotide Sequences of the Disclosure. Lower case italicized sequences represent introns.

| Sequence Notes | Sequence |
|---|---|
| | GCAATCCTCATTGGCGTCTACTAGCTGATGGGTTAAA |
| | GCAAGATACAGGTGTTCATACGCTCCAAGACAACGA |
| | TCCTGTTGTCGAGAAGCCGCCATTAATTTACAGGAGA |
| | GCTGGAGAAGCGCCGAAACATGATTGGGACAAGAAG |
| | TCACCCGGTTTGCGCCTTAGACGGTCCTGCTGTAGCT |
| | GCGGGAAGGAAGTACCGGTAGGCCTGGTCTGTCGTA |
| | TTTGTCACCATGAGTCTTGTCCTGAGTGCTTGAACAT |
| | GCAAAAGCGAGATTACGGATGTTGATCAGATACACG |
| | GGCCCCTATACTAGGACTAGTTACCACTAGGATTGTA |
| | CTCAACCTTAACAGTGGCGTTTGGTACTTCGTTACAG |
| | CTAAGGGGAGAGGACAGTTCCTACTTTCATGTGCTTC |
| | AAGGGAGAGGCTCCTCCAACTACTGTTGCTAGGGAG |
| | GAAAGACACTCTATTCTTAGCTGAGGGCTGCAGGAAT |
| | TCGCATCCATGCAGTCATACCATCCATGGCATGCAAT |
| | CTATGTTGCATTAGATGCAAGAAGTAGGATAGAGAA |
| | CCCATGTACTTGATTCACGCTAGCAGGACAGAGAGA |
| | GATACCATACCCGACGGGAGCCCCTGCATGACTTCCT |
| | GTCTGCAGCTTGTCGTGCGTGTATCATTCCCATGCGC |
| | CACGAACTCATAGGCAGTGGTAGTTCAGAACACTCTT |
| | TTTTTTTAAAAAAAAAAAAGATAGGAAAATAATAAT |
| | TTAGGGGAAGAAAAGTAAAAATTAAAAAGAAAAAGT |
| | TCCAGATGGCGCTTCTACTTCTATATTCGATCGTTATT |
| | CAATACCCCAGAGGCACAGGCATTCCGATCTCTCATC |
| | GCCAACACTGAAAAGCAGCCATTTTCCCCCGTCTTAA |
| | AGCTCCAATCCTCCTTCTTCTCATCTACTTCCTCGCTC |
| | CTTCAGGACCTTGAGTGTTCCGTTGAGCTATTGGGTA |
| | ACTTCTCACCTGTCAATCATCGATTGTCCTTTCTCTTG |
| | ACTTGACTTCGTGTCGCCATTCTCATTTACGATACATA |
| | TCCCTGGAGCAGAAAACAAAGAAAAGGGCCAATTAC |
| | TCTTGATCTAGTTCCAACTCTGTTGCTGCTTGGAACAT |
| | CCGCCCATCTGTGTGGTGAAATCAGATGCCAGCATCC |
| | ATCTTGCAGCTTCTCCCACTTCCTGGGCCGATCTTGA |
| | ATGGGAGTCAATCTGCCTCGAAATGGCTCGTCTGCCT |
| | TTCTCATCTGGGTACATCCTGTGAGTAGCATGTCGTC |
| | ACTTGTCACACATACTACCCGCTCTCAAATCTGTTTG |
| | ATGGGAGTCAATCTGCCTCGAAATGGCTCGTCTGCCT |
| | TCACAAGCAAACTACAGCAGATGGCGGGGGCATGGA |
| | CTCGAGCCACAGTGCTGGCTCTCGCTTGCATCTGGAC |
| | CTTCTTATTCTTTCTCATTGCTGTATCTTTTTCCCCCTT |
| | GAGGCTTCTGGCGCGCTGCACCTTTCCAAGTATCAAA |
| | CCAAAGCTAATCAGGGGCGTTTGGCGTCCTGCCATGG |
| | CTTCACTAGACCTGGATCTCTGCAGCCTCATCACCAT |
| | CTCGGATCACCTGGTTCTGATCACCTTGGAAGAAAGC |
| | ACAAAGACCTTGGAGACAATACATATTGCCGCCATC |
| | GCAGCTCCCTCCAATCTCGACAGCATTTTCATGTGTC |
| | GGGCACTATCTACCTCTCGGCAATTCAGTAACCGTAC |
| | TGCCTGAGAAACATCAACCTCTCAAATTACACAATGG |
| | TGTTCAGCGCACCTGCTCCTGGTGTGGGCTCCAGTAA |
| | AAGGCCAGCGTCATGCATGCAGGACGATGTTGATGA |
| | GCGGGATAATGTCCCAGTAAGTGATACCAGCATTGG |
| | AAAGGCAGATGGAGCTGACTCATCTCCTATATAGCCC |
| | ATGGGTCTATGCGTGCGTTCATCGATCAACATCCCTT |
| | ACTTCCACTACGCCATGATCTATCTCGACAACATGGG |
| | CAGACTTAAGGTGATGGAATCTCCGTCTATCCAGGAG |
| | CAAAATGAGACTGTTTTCACAACCGAAGTACGTGAA |
| | AGATTTTTGGAAATCCTTGGTGCCAAGGTAGGATATC |
| | AACCGCCCATGGTTCGAAGTATGTAAACACTCCGCGC |
| | ACAAGTACAATATTCTTGCTGATCTCAATTGAACAGG |
| | GTTGTCAGCTGCCGGTGCTACACCATACAGCTATGAT |
| | CCTCAACAACCGCTTGGTTGCTTGTCTTACCGTCAAA |
| | CTAAGCGGGACAGAAATTCCCCAGCCCACTCTATGTA |
| | CGGTGTGCCGCCATCCGTCCAGTTCTCAGCCCCGGTT |
| | GAGGAATCGCCCTCTTGTGGATCAGTGGACATGGTCG |
| | GGCTCGAGATTGGTGATACTCCTAATGTCCTTGACTA |
| | CTATGAGAGATCCTTAAAGCACTTTCGGCAGGTCAAC |
| | TGTCGCCAGATCCTAAAGACATTCATTAAGTTCATTG |
| | AGCCACGAAAGCAAGCCAAGCACCCCTATAATGGAG |
| | GTAAACCCCTGCAGGAGCCCTCCTGGTAAGAAGG |
| | GCGACCCAGAGAAGACAAAGCCTGAATGGTGGCCCG |
| | CCAATGTGGTCCACAAGGAGCCTGACCATCTTCGAAA |
| | GGATCGTACGTGTAACCCTTCAGAAAATCTTCAGTGT |
| | CAAGTAACTTTGCTGACAGACTTAGAACGCCTGTCTC |
| | TGTTAATTCATATCATCCGCAGGCTTGGAAGATTTGG |
| | TATCACCACGGATCAATTGCAGGAAATTGCCCACGAC |
| | TGCAAGCGGCGGCTCAGCGACCCCCACAAACTCCAA |

TABLE 1-continued

Polynucleotide Sequences of the Disclosure. Lower case italicized sequences represent introns.

| Sequence Notes | Sequence |
|---|---|
| | ATCTTGGACGAGGTCTTCAGAGTGAGAAGGATTGAA<br>GAACGCTACGAAAGAGGAGAAGTTGGTAAGCGGCAT<br>CATCTTTCCATGAAATTCATTTTGACAGCTGTTGACG<br>AGCCTCAGATGCCAACAAGATCGTATATGTTGTCAAC<br>CGAGAGTCGAATCAGAAAGAGAAGGATGGCGACTCC<br>AACGTGGATCCGGACCAGAAGCATGAGCAAGAAGAC<br>GATAATGCGCGGGAGGCACTTCCCATTCTCCACTCCG<br>AGAAGAACTCAACCAGCCCGATGTCGAACTCAGCCG<br>AGCACACGGGCATGGCGGCACCAAGTCGTCCAATGA<br>ATATGGGAGGTGACAGAAACCAGTTGTTTCCTTTACC<br>GGAGTGGCCGAGCTTCGGTGAGACACCCCAGGATGA<br>TCGAATTTTCTTTCCCACGACCTCTAAGTATACCGAA<br>GATTATGCATCGCAGCAGATGCCTAGAACACCTGCA<br>ACAACAGCACTTGTCAGCACTAATGAGACACATGCG<br>GCCTTTGATTATATGACACAGGAGTCCATCACCTCCT<br>CCTCCCCAGAGCAGACTTCCCACCACCGCCAAGCACC<br>CCTGCCCATGCAGCACTCGGCCAGCCTCGACCCTTGG<br>ACCCCTACGTTCCGACATAATTTCTTCAACCCAATGG<br>TGTATAGTACTGCACCCCGTCACGCCATGTCCCAGGC<br>TACTATGTTATCTCAGTTTCCCAGGTCCACGACGTCTC<br>ATGGCCAGGAAATGCCTCACATGGCTCACGGCCTGCC<br>GAACCTGCCTCAAGACAGACCTTCAAGCATGGATGG<br>CATGAGCATGAGAGGCCCTTCTTTCCGCACAGGATTT<br>TTGAGTCATCCCTGTGACCCATCACAGCAGGCTCCTC<br>ATTCTAGCGGATGCGGCCATCCTGACAGTTGGACTCA<br>AAATAGACCACATGTATAATCTTAACTGATTGATCCT<br>TGACCACTGTTTTGACCCTCCTGCAGCCTTGAAGCTT<br>CGTTTCACTGATGATTGTTCTTCGACTTTGTTTCTGTC<br>CCTGACTTTGTTGTCAATGCGGACTTATCCATGCGGC<br>TTGTTCCACGTCAAGTGACTACCAGGACACTCCGTGG<br>TTTTATATGGCAGGTACTGGCGATGACTTTCCAATTC<br>TTCTTCGTTTAGTATATATACTCGTTTCTTGTTCTATG<br>TTCGATCATGTCTTTTTCCTTATACATACCTCCAAAAA<br>TCCTGTTGGAGATGGCGCCAGATGGCATGAGATGCA<br>AATATGGATGATGTTCTTGTGTTTGTTCATTTCAATTT<br>CTTTCTCTTAATCATGATTTGAACAATTGGCAGCGAG<br>GTATGCGGAGCTCGTTCTCTTTGGATGCCGATCAGC<br>TGAATAGGAGGTAACGAGGCATGAGGGTGTTTCATT<br>ATGACTCTCTCCGGTGTTTGTCATTTAAGGGTGCGAG<br>GGGGAAGTGTCCGTTTCGATGTCCTAGGATATCGAAA<br>ATCTGAGTAGTAGCCACGTGACCCTATGCTGACGGCT<br>GGGCTGGAAGACAAGCAGGTTGCTGCTTACGAGAAT<br>ATGTTGAGGTATTCTCGTTATCTTCGTGAAGAATGCC<br>GTCTCCTTGGCCCTCTAGCCAAAGTCTGGGTTGCTGA<br>AAGGCTAGCTGGAATTGAGAATCGACTGTCTGCGTCC<br>GAGTCGCCTAGAGGTGGGAAGGCCCCCTCTTTCTCAT<br>ACATATGCTGACTCTGCAGACCATACCAATTCGCTGC<br>CCGAA |
| *A. fumigatus*_AF293_bafA<br>(SEQ ID NO: 3) | ATGGCTTGGTATAGAGCCTTACTCCCGTGCATACCGT<br>TGTGGCGGAAGGTTCTGGGGCGTAACAGCACCGATG<br>AGGACGGACGGAGTGAAGACGACCTTACTTCATTGA<br>GCGATAAAATGCCTACTTTTGAAGAAACGACAACT*gtg*<br>*agtactgttcgtgaaattgcctccagctgtctaatgtctccgtcggtcagatc*ACTTC<br>TGCAAAGTACATCAACGGTGAAAAAATCATGGAGCA<br>TACCGTTGTGGAGACCAAGCACATTGACGAACGTGG<br>AGACACCAGCGTCAGTAACGGTGATTCGAACAGCAC<br>TGCGGTAACCAGACATTCTGGGCTTAGCTCTGTCAGC<br>CTTTCAGATCAAAGTACAATTGTCGAGGACGCGAATG<br>CTCTGGAAGAACCTGAACTCTTTGCTGTTCACTCTCC<br>ATATGTTGACGACTCAACCGGCGAGCAGATGGTTAG<br>ACTCTACTACGAGCTCCCAGTAAGCCTCGATGATCTT<br>GAGATCATAGGCCTTGAATCTCGTATTCCAGAGTCTG<br>ACGATGATTCAATTGAGGCCCGCTTTCGTTATCGAGG<br>AGAGGATTTTTGGCTACCTGTTCGTTATTCTTATGCCA<br>AAGCTCGAATGGTTTTAACGGGTGTATGCTGA |
| *A. fumigatus*_CEA10_bafB_<br>AFUB_044360<br>(SEQ ID NO: 4) | ATGGTGTGGTATAGGGCCATACTCGTTTGCATGCCGT<br>GGTGGCTCATGGGCGTAACAGCACCAATGAGGGCA<br>AACGGAGTGAAGGCGAACGGGCTCCAATGATTGATA<br>AGGTGCCCACTTTCGAAGAAATGACAATT*gtgagtactgttttt*<br>*gtggggttgcctccagctgtctaatgcttccttgcgcag*ACCACCTCTGCAA<br>AGTATGTCAACGGTGAAAAAATCATGGAGCATACCG<br>TTGTGGAGACCAAGCAAATTGACAACCGAGGAGACA<br>CCAGCGTCAGTAACAATGATTCAAACAGCACTGCGG |

TABLE 1-continued

Polynucleotide Sequences of the Disclosure. Lower case italicized sequences represent introns.

| Sequence Notes | Sequence |
| --- | --- |
| | AAACCAGACATTCTGGGCTTAGCTCCGTCAGTCATTC<br>AGATCAAAGTAAAGTTGTTGAGGACGCGAATGCCCT<br>GGAAAAACCTGAACTCTTTGCTGTTCACTCTCCATAT<br>GTTGACGCCTCAACCGGCAAGCAGATGTTAAGACTCT<br>ACTACGAGCTCCCAGTAAGCCTCGATGATCTTGAGAT<br>CACAGGCCTTGAATCTCGTATTCCAGAGTCTGATGAT<br>GATTCAATTGAGGCCTGCTTTTGTTATCGGGGGGAGA<br>AATTTTGGCTACATGTTCCTTATTCTTATGCCAAAGCT<br>CGAATGGTTTTAATGGGTGTATACTGA |
| A. fumigatus_CEA10_bafC_<br>AFUB_096610<br>(SEQ ID NO: 5) | ATGGCTTGGTATGAAGTCTTCGAGCAATGGGTGTACT<br>GGTGCTGGCAGCGCATATGGCCCTTCGACGACAGCA<br>GGAGGGACGGACGAAACGAAGACGACCTAACTTCGT<br>TAACCGATAAAATGCCTGTTTTTGAAGATAAGATCAT<br>C*gtgagtactgtccatgaggaggcttccatctccctaaccttggcag*AACACCT<br>CTGTCAGATATGTCAATGGAGAGATCGCGGCATATGT<br>CGTCCAGACCCAGTATCTCGATACCCAAGAGGTCTCC<br>TCTGCTAGGGACTCTTATTGGAAAAGCGTTGCGGATA<br>TCAAACCGGGTGACTTCTGCTCCCATAGTATTTCGGA<br>TCAGAGCACAATTGTCGAAGAAAACGAAGCGAAGGC<br>GCTGGAAGGACCTGAACCCTTTGCTGTTCGCCCTTCG<br>TATATTGGATCCACTGGCAAACGCACGGTCGACTTCT<br>TCTACAAGGTCTCTCTACCACTGGATGATCTTGAGAT<br>GAGAGACAAGGAATCGCGTGTTCCGGAGTCTAGCGA<br>AGATCTGATTGAGGCTCTCTTCCACTATCAAGGGGCC<br>GATATTTGGGTATATGTTCCTTATTCGTACGCCAATG<br>CTCGAATGGTTTCAGGCGGTCCCACTGAATGA |
| A. niger_CBS 513.88_<br>An08gl2010<br>(SEQ ID NO: 6) | ATGGCTTGGTACAGTGCTTTACTCCCGTGCATGCTAT<br>GGTGGCGGAACCTCCTGTGGCGTAACAGCACCAATA<br>GGTATAGACAGAGTACAGACGACCTTACTTCACTGAC<br>TGATAAGATACCTAATCTTGGAGAAAGG*gtaagtgtaaatac<br>tttttgaggtcgcttctaggagtctaatcactttggaaagacaactcccacagataacat<br>cgatgaaagagcttcgtggcacatactgtcgtgcagaccaggcggattggtgaccg<br>agaacgttgctgcttcaatgactcggatttgaacagcggcacag*TTACCAAAA<br>TTATTGAGCTTTGTTAATAGCATTCCAGATCAGAGTA<br>CTACTGCCGGAAAAATTAATCACAAGGCCCTGCGAG<br>ATCCTGAGCTCTTTGCTATCCGCTCGTCATGCATCGA<br>CAAATCAGCCAGCAAGTGGATGGTTAGTCTCTACTAC<br>GAACCCCCACCCAGCCTTGATGACCTCGAGATTAAGA<br>ACTTCGGATCTCGTATTCCAGAGTCGGAGGATGATCC<br>AATTGAGGCTATCTTTCACTATGAGGGAGAGAACATT<br>TGGGTATCTGTTCCTTATTTGTATGCTAGAACTAGAA<br>GCCTTTCAAGCGGTCTGTTCTGA |
| A. fumigatus_AF293_bafA-cDNA<br>(SEQ ID NO: 7) | ATGGCTTGGTATAGAGCCTTACTCCCGTGCATACCGT<br>TGTGGCGGAAGGTTCTGGGGCGTAACAGCACCGATG<br>AGGACGGACGGAGTGAAGACGACCTTACTTCATTGA<br>GCGATAAAATGCCTACTTTTGAAGAAACGACAACTTC<br>TGCAAAGTACATCAACGGTGAAAAAATCATGGAGCA<br>TACCGTTGTGGAGACCAAGCACATTGACGAACGTGG<br>AGACACCAGCGTCAGTAACGGTGATTCGAACAGCAC<br>TGCGGTAACCAGACATTCTGGGCTTAGCTCTGTCAGC<br>CTTTCAGATCAAAGTACAATTGTCGAGGACGCGAATG<br>CTCTGGAAGAACCTGAACTCTTTGCTGTTCACTCTCC<br>ATATGTTGACGACTCAACCGGCGAGCAGATGGTTAG<br>ACTCTACTACGAGCTCCCAGTAAGCCTCGATGATCTT<br>GAGATCATAGGCCTTGAATCTCGTATTCCAGAGTCTG<br>ACGATGATTCAATTGAGGCCCGCTTTCGTTATCGAGG<br>AGAGGATTTTGGCTACCTGTTCGTTATTCTTATGCCA<br>AAGCTCGAATGGTTTTAACGGGTGTATGCTGA |
| A. fumigatus_CEA10_bafB_<br>AFUB_044360-cDNA<br>(SEQ ID NO: 8) | ATGGTGTGGTATAGGGCCATACTCGTTTGCATGCCGT<br>GGTGGCTCATGGGCGTAACAGCACCAATGAGGGCA<br>AACGGAGTGAAGGCGAACGGGCTCCAATGATTGATA<br>AGGTGCCCACTTTCGAAGAAATGACAATTACCACCTC<br>TGCAAAGTATGTCAACGGTGAAAAAATCATGGAGCA<br>TACCGTTGTGGAGACCAAGCAAATTGACAACCGAGG<br>AGACACCAGCGTCAGTAACAATGATTCAAACAGCAC<br>TGCGGAAACCAGACATTCTGGGCTTAGCTCCGTCAGT<br>CATTCAGATCAAAGTAAAGTTGTTGAGGACGCGAAT<br>GCCCTGGAAAAACCTGAACTCTTTGCTGTTCACTCTC<br>CATATGTTGACGCCTCAACCGGCAAGCAGATGTTAAG<br>ACTCTACTACGAGCTCCCAGTAAGCCTCGATGATCTT<br>GAGATCACAGGCCTTGAATCTCGTATTCCAGAGTCTG |

TABLE 1-continued

Polynucleotide Sequences of the Disclosure. Lower case italicized sequences represent introns.

| Sequence Notes | Sequence |
|---|---|
| | ATGATGATTCAATTGAGGCCTGCTTTTGTTATCGGGG<br>GGAGAAATTTTGGCTACATGTTCCTTATTCTTATGCC<br>AAAGCTCGAATGGTTTTAATGGGTGTATACTGA |
| A. fumigatus_CEA10_bafC_<br>AFUB_096610-cDNA<br>(SEQ ID NO: 9) | ATGGCTTGGTATGAAGTCTTCGAGCAATGGGTGTACT<br>GGTGCTGGCAGCGCATATGGCCCTTCGACGACAGCA<br>GGAGGGACGGACGAAACGAAGACGACCTAACTTCGT<br>TAACCGATAAAATGCCTGTTTTTGAAGATAAGATCAT<br>CAACACCTCTGTCAGATATGTCAATGGAGAGATCGCG<br>GCATATGTCGTCCAGACCCAGTATCTCGATACCCAAG<br>AGGTCTCCTCTGCTAGGGACTCTTATTGGAAAAGCGT<br>TGCGGATATCAAACCGGGTGACTTCTGCTCCCATAGT<br>ATTTCGGATCAGAGCACAATTGTCGAAGAAAACGAA<br>GCGAAGGCGCTGGAAGGACCTGAACCCTTTGCTGTTC<br>GCCCTTCGTATATTGGATCCACTGGCAAACGCACGGT<br>CGACTTCTTCTACAAGGTCTCTCTACCACTGGATGAT<br>CTTGAGATGAGAGACAAGGAATCGCGTGTTCCGGAG<br>TCTAGCGAAGATCTGATTGAGGCTCTCTTCCACTATC<br>AAGGGGCCGATATTTGGGTATATGTTCCTTATTCGTA<br>CGCCAATGCTCGAATGGTTTCAGGCGGTCCCACTGAA<br>TGA |
| A. niger_CBS_513.88_<br>An08g12010-cDNA<br>(SEQ ID NO: 10) | ATGGCTTGGTACAGTGCTTTACTCCCGTGCATGCTAT<br>GGTGGCGGAACCTCCTGTGGCGTAACAGCACCAATA<br>GGTATAGATACAGAGTACAGACGACCTTACTTCACTGAC<br>TGATAAGATACCTAATCTTGGAGAAAGGTTACCAAAT<br>TTATTGAGCTTTGTTAATAGCATTCCAGATCAGAGTA<br>CTACTGCCGGAAAAATTAATCACAAGGCCCTGCGAG<br>ATCCTGAGCTCTTTGCTATCCGCTCGTCATGCATCGA<br>CAAATCAGCCAGCAAGTGGATGGTTAGTCTCTACTAC<br>GAACCCCCACCCAGCCTTGATGACCTCGAGATTAAGA<br>ACTTCGGATCTCGTATTCCAGAGTCGGAGGATGATCC<br>AATTGAGGCTATCTTTCACTATGAGGGAGAGAACATT<br>TGGGTATCTGTTCCTTATTTGTATGCTAGAACTAGAA<br>GCCTTTCAAGCGGTCTGTTCTGA |

In certain embodiments, the disclosure provides a filamentous fungal host cell that is modified through the introduction of any one or more of SEQ ID NOs 1-10 recited above. In certain embodiments, any one or more of SEQ ID NOs 1-10 can be integrated into the filamentous fungal host cell genome. In certain embodiments, any one or more of SEQ ID NOs 1-10 are incorporated into an expression vector comprising a promoter for expressing the one or more of SEQ ID NOs 1-10 in the filamentous fungal host cell.

TABLE 2

Amino Acid Sequences of the Disclosure.

| Sequence | Sequence |
|---|---|
| A. fumigatus_hrmA/<br>Afu5g14900<br>(SEQ ID NO: 11) | MASTKPASSLIYQAWNKLSINQTIPSDSLELLGERLAIAF<br>APKLKEQRRNGRRRNLEYVAQHRRKIARKIYLEILEKDP<br>NIFLPFILAVSPRACLSFDISSFLEQHQSQGRHFLRNNAE<br>AILWGLAKKHDIDGSLHFRKLMREIFQLSPPATEAEGKE<br>HYSLHLSTLPAIRNAFGDVIFDAIERSPTQVTARAKGYFS<br>EKTESVWTKVPYRSSQDAIISLEVGSAIELANVLFPIATQ<br>KIVSILSACSPTVRQKNFSEAILGPDPQDTPATSSEIDVAY<br>FTLRGATVSAIESVFRADICEGIKDSELRNWEKEQLLIDT<br>TDCVTMQIWRAQPQHGTIKLRIGFYAAVNLANRLYAET<br>PQDHI |
| A. fumigatus_hrmA/<br>Afu5g14900 D304G amino<br>acid variant<br>(SEQ ID NO: 12) | MASTKPASSLIYQAWNKLSINQTIPSDSLELLGERLAIAF<br>APKLKEQRRNGRRRNLEYVAQHRRKIARKIYLEILEKDP<br>NIFLPFILAVSPRACLSFDISSFLEQHQSQGRHFLRNNAE<br>AILWGLAKKHDIDGSLHFRKLMREIFQLSPPATEAEGKE<br>HYSLHLSTLPAIRNAFGDVIFDAIERSPTQVTARAKGYFS<br>EKTESVWTKVPYRSSQDAIISLEVGSAIELANVLFPIATQ<br>KIVSILSACSPTVRQKNFSEAILGPDPQDTPATSSEIDVAY<br>FTLRGATVSAIESVFRADICEGIKGSELRNWEKEQLLIDT |

TABLE 2-continued

Amino Acid Sequences of the Disclosure.

| Sequence | Sequence |
|---|---|
| | TDCVTMQIWRAQPQHGTIKLRIGFYAAVNLANRLYAET<br>PQDHI |
| A. fumigatus_AF293_BafA<br>(SEQ ID NO: 13) | MAWYRALLPCIPLWRKVLGRNSTDEDGRSEDDLTSLSD<br>KMPTFEETTTSAKYINGEKIMEHTVVETKHIDERGDTSV<br>SNGDSNSTAVTRHSGLSSVSLSDQSTIVEDANALEEPEL<br>FAVHSPYVDDSTGEMVRLYYELPVSLDDLEIIGLESRIPE<br>SDDDSIEARFRYRGEDFWLPVRYSYAKARMVLTGVC |
| A. fumigatus_CEA10_BafB_<br>AFUB_044360<br>(SEQ ID NO: 14) | MVWYRAILVCMPWWLMGRNSTNEGKRSEGERAPMID<br>KVPTFEEMTITTSAKYVNGEKIMEHTVETKQIDNRGDTS<br>VSNNDSNSTAETRHSGLSSVSHSDQSKVVEDANALEKP<br>ELFAVHSPYVDASTGKQMLRLYYELPVSLDDLEITGLES<br>RIPESDDDSIEACFCYRGEKFWLHVPYSYAKARMVLMG<br>VY |
| A. fumigatus_CEA10_BafC_<br>AFUB_096610<br>(SEQ ID NO: 15) | MAWYEVFEQWVYWCWQRIWPFDDSRRDGRNEDDLTS<br>LTDKMPVFEDKIINTSVRYVNGEIAAYVVQTQYLDTQE<br>VSSARDSYWKSVADIKPGDFCSHSISDQSTIVEENEAKA<br>LEGPEPFAVRPSYIGSTGKRTVDFFYKVSLPLDDLEMRD<br>KESRVPESSEDLIEALFHYQGADIWVYVPYSYANARMV<br>SGGPTE |
| A. niger_CBS_513.88_<br>An08g12010<br>(SEQ ID NO: 16) | MAWYSALLPCMLWWRNLLWRNSTNRYRQSTDDLTSL<br>TDKIPNLGERLPNLLSFVNSIPDQSTTAGKINHKALRDPE<br>LFAIRSSCIDKSASKWMVSLYYEPPPSLDDLEIKNFGSRI<br>PESEDDPIEAIFHYEGENIWVSVPYLYARTRSLSSGLF |

Methods of Use

In one aspect, the disclosure provides a method of increasing fungal secretion of one or more products of interest, comprising introducing into a filamentous fungal host cell one or more polynucleotide sequences encoding one or both of an hrmA protein and a baf protein.

In another aspect, the disclosure provides a method of increasing the production of one or more products of interest, comprising introducing into a filamentous fungal host cell one or more polynucleotide sequences encoding one or both of an hrmA protein and a baf protein.

In yet another aspect, the disclosure provides a method of reducing oxygen consumption of a filamentous fungal host cell, comprising introducing into a filamentous fungal host cell one or more polynucleotide sequences encoding one or both of an hrmA protein and a baf protein. In certain embodiments, a first polynucleotide sequence (e.g., a vector) encodes an hrmA protein and a second polynucleotide sequence (e.g., a vector) encodes a baf protein. In certain embodiments, more than one polynucleotide sequence is introduced into the filamentous fungal host cell, each polynucleotide sequence encoding for a different baf protein (e.g., a first polynucleotide sequence encoding the baf protein amino acid sequence of SEQ ID NO: 13 and a second polynucleotide sequence encoding the baf protein amino acid sequence of SEQ ID NO: 14).

In certain embodiments, the hrmA protein comprises or consists of the amino acid sequence of SEQ ID NO: 12. In certain embodiments, the baf protein comprises or consists of the amino acid sequence of SEQ ID NO: 13, SEQ ID NO: 14, SEQ ID NO: 15, or SEQ ID NO: 16.

In certain embodiments, oxygen consumption is reduced by about 10% to about 90%. In certain embodiments, oxygen consumption is reduced by about 10%, about 15%, about 20%, about 25%, about 30%, about 35%, about 40%, about 45%, about 50%, about 55%, about 60%, about 65%, about 70%, about 75%, about 80%, about 85%, or about 90%.

In certain embodiments, the polynucleotide sequence is introduced into the filamentous fungal host cell via transformation. In certain embodiments, the transformation comprises one or more of protoplast-mediated transformation, Agrobacterium-mediated transformation, electroporation, biolistic transformation, and shock-wave-mediated transformation.

In certain embodiments, the polynucleotide sequence is introduced into the filamentous fungal host cell transiently.

In certain embodiments, the polynucleotide sequence is stably integrated into the filamentous fungal host cell genome.

In certain embodiments, the polynucleotide sequence is introduced into the filamentous fungal host cell genome with a genetic-editing system.

In certain embodiments, the genetic-editing system comprises one or more of a meganuclease system, a ZFN system, a TALEN system, and a CRISPR system.

In certain embodiments, the polynucleotide sequence further comprises a promoter to express one or both of the hrmA protein and the baf protein. In certain embodiments, the promoter is inducible or constitutive. In certain embodiments, the inducible promoter is selected from the group consisting of: alcA, amyB, bli-3, bphA, catR, cbhI, cre1, exy1A, gas, glaA, mir1, niiA, qa-2, Smxy1, tcu-1, thiA, vvd, xy11, xy1P, xyn1, or zeaR. In certain embodiments, the constitutive promoter comprises cDNA1, eno1, gpdA, gpd1, pdc1, pki1, poliC, tef1, or rp2.

The following non-limiting examples are provided to further illustrate the present disclosure.

EXAMPLES

Example 1— Fungal Biofilm Morphology Impacts Hypoxia Fitness and Disease Progression Surface-dwelling microorganisms organize into macroscopic colonies of intricately structured populations. For bacteria and yeast, the inter- and intra-species heterogeneity of these macroscopic morphologies in vitro have been studied (Kuthan et al. Mol Microbiol 47, 745-754, 2003; Workentine et al. PLoS One 8, e60225, 2013); and microbial colony morphology (CM) variants are observed in clinical samples (Haussler et al. J Med Microbiol 52, 295-301, 2003; Hagiwara et al. J Clin Microbiol 52, 4202-4209, 2014). The challenge remains to determine how CM diversity reflects physiological variation and contributes to environmental fitness. CM is associated with changes in extracellular matrix (ECM) (Fong et al. J Bacteriol 189, 2319-2330, 2007), stress resistance (Drenkard et al. Nature 416, 740-743, 2002), reproduction (Miller et al. Cell 110, 293-302, 2002), and metabolism (Workentine et al. Environ Microbiol 12, 1565-1577, 2010).

Intraspecies CM variation can arise through accumulated genetic changes or through transcriptional rewiring resulting in phenotypic switching (Jain et al. FEMS Yeast Res 6, 480-488, 2006; Jain et al. Curr Fungal Infect Rep 2, 180-188, 2008). The human pathogenic mold *Aspergillus fumigatus* exhibits phenotypic plasticity at 0.2% $O_2$, where CM differs compared to 21% $O^2$ growth and is variable across strains (Kowalski et al. MBio 7, pii: e01515-16, 2016). Physiological changes and genetic mechanisms facilitating stable morphotype variants in *A. fumigatus* and other human pathogenic filamentous fungi are not well characterized, nor is their impact on pathogenesis and disease progression. Progress on understanding fungal CM and phenotypic variability has been limited in part by the underlying genetic complexity. Given the intraspecies CM variation found in *A. fumigatus* isolates and the impact of oxygen on CM, we sought to assess how a low oxygen CM variant impacts *A. fumigatus* pathogenesis and invasive aspergillosis (IA) disease progression and identify genetic factors involved in CM variation.

Example 1 Materials and Methods

Strains and growth conditions: *A. fumigatus* AF293 was used in the published experimental evolution approach that generated EVOL20 (Kowalski 2016, supra). Mutant strains were generated in AF293, the uracil/uridine auxotroph AF293.1, or EVOL20. IFM 59356-1 and IFM 59356-3 were kindly provided by Dr. D. Hagiwara (Hagiwara 2014, supra). Strains were cultured on 1% glucose minimal media (GMM) and collected for experimentation as previously described (Beattie et al. PLoS Pathog 13, e1006340, 2017).

Strain construction: Strain genotypes are provided in Table 3 below. Gene replacement mutants were generated as previously described using overlap extension PCR (Szewczyk et al. Nat Protoc 1, 3111-3120, 2006). The hrmA-GFP alleles were constructed through overlap extension PCR to tag HrmA at the C-terminus. Site-directed mutation of hrmA was carried out using QuikChange Site-Directed Mutagenesis (Agilent). Overexpression strains utilized the *A. nidulans* gpdA promoter for constitutive expression and was introduced ectopically. Fluorescent strains expressing tdtomato were transformed with linear constructs of gpdA-driven tdtomato. Protoplasting was done with *Trichoderma harzianum* (Sigma) lysing enzyme and strains were confirmed by Southern blotting as described previously (Grahl et al. PLoS Pathog 7, e1002145, 2011; Willger et al. PLoS Pathog 4, e1000200, 2008).

TABLE 3

*Aspergillus fumigatus* strains utilized in this disclosure, their genotypes, and their origination.

| Strain | Background strain | Genotype | Origin |
|---|---|---|---|
| AF293 | reference/Parent strain | n/a | Nierman et al. 2005 |
| EVOL20 | serially passed AF293 (27) | n/a | Kowalski et al. 2016 |
| AF293.1 | AF293 | pyrG− | Xue et al. 2004 |
| ΔhrmA$^{AF}$ | AF293.1 | hrmA−; pyrG+ | This study |
| ΔhrmA$^{EV}$ | EVOL20 | hrmA−; ptrA+ | This study |
| hrmA$^{R-EV}$ | ΔhrmA$^{AF}$ | hrmAEV+; pyrG+; ptrA+ | This study |
| hrmA$^{R-EV}$; ΔcgnA | hrmA$^{R-EV}$ | hrmAEV+; cgnA−; pyrG+; ptrA+; hyg+ | This study |
| hrmA$^{OE}$ | AF293.1 | gpdA-hrmA+; pyrG+ | This study |
| hrmA$^{OE}$-GFP | AF293.1 | gpdA-hrmA-GFP+; pyrG+ | This study |
| hrmA$^{OE/NLS}$-GFP | AF293.1 | gpdA-hrmA-NLS/GFP+; pyrG+ | This study |
| hrmA$^{OE}$; ΔcgnA | hrmA$^{OE}$ | gpdA-hrmA+; pyrG+; ΔcgnA; ptrA+ | This study |
| ΔcgnA$^{EV}$ | EVOL20 | cgnA−; ptrA+ | This study |
| Δuge3$^{AF}$ | AF293 | uge3−; ptrA+ | This study |
| Δuge3$^{EV}$ | EVOL20 | uge3−; ptrA+ | This study |
| hrmA$^{OE}$; Δuge3 | AF293.1 | gpdA-hrmA+; pyrG+ | This study |
| cgnA$^{OE}$ | AF293.1 | gpda-cgnA; pyrG+ | This study |
| EVOL20$^{tdtomato}$ | EVOL20 | gpdA-tdtomato; ptrA+ | This study |
| AF293$^{tdtomato}$ | AF293 | gpdA-tdtomato; ptrA+ | This study |
| IFM 59356-1 | clinical isolate | n/a | Hagiwara et al. 2017 |
| IFM 59356-3 | clinical isolate | n/a | Hagiwara et al. 2017 |
| ΔhrmA$^{AF-tdtomato}$ | ΔhrmA$^{AF}$ | hrmA−; pyrG+; gpda-tdtomato; hyg+ | This study |
| ΔhrmA$^{EV-tdtomato}$ | ΔhrmA$^{EV}$ | hrmA−; ptrA+; gpda-tdtomato; hyg+ | This study |
| hrmA$^{R-EV-tdtomato}$ | hrmA$^{R-EV}$ | hrmAEV+; pyrG+; ptrA+; gpda-tdtomato; hyg+ | This study |
| hrmA$^{R-EV-}$; ΔcgnA$^{tdtomato}$ | hrmA$^{R-EV}$; ΔcgnA | hrmAEV+; cgnA−; pyrG+; ptrA+; hyg+; phleo+; gpda-tdtomato | This study |
| ΔcgnA$^{EV-tdtomato}$ | ΔcgnA$^{EV}$ | cgnA−; ptrA+; gpda-tdtomato; hyg+ | This study |
| Δuge3$^{AF-GFP}$ | AF293 | gpdA-gfp; ptrA+; uge3−; hyg+ | This study |
| AF293$^{GFP}$ | AF293 | gpdA-gfp; ptrA+ | This study |
| F16311 | clinical isolate | n/a | Howard et al. 2009 |
| CDC20.2 | clinical isolate | n/a | This study |
| 204NB-8 | clinical isolate | n/a | This study |
| F11698/NCPF-7816 | clinical isolate | n/a | Howard et al. 2009 |

TABLE 3-continued

Aspergillus fumigatus strains utilized in this disclosure, their genotypes, and their origination.

| Strain | Background strain | Genotype | Origin |
|---|---|---|---|
| F1631$^{tdtomato}$ | F16311 | gpdA-tdtomato; hyg+ | This study |
| CDC20.2$^{tdtomato}$ | CDC20.2 | gpdA-tdtomato; hyg+ | This study |
| F11698/NCPF-7816$^{tdtomato}$ | F11698/ NCPF-7816 | gpdA-tdtomato; hyg+ | This study |

Growth and colony morphology assays: Growth assays were performed as previously described (Kowalski 2016, supra). Macroscopic morphology was quantified on GMM. 1000 spores were spotted at the center of the plates and grown for 72-96 hours at 21% $O^2$ or 0.2% $O_2$. Representative images are of 3 biological replicates. Statistics were performed with One-Way ANOVA with Tukey Post Test for multiple comparisons or two-tailed Students t-test. Error bars indicate standard error of the mean (StEM) centered at the mean. For shift experiments, cultures were started as described at 21% $O^2$ for 48 hours then shifted to 0.2% $O^2$ for 48 hours.

Figure 2:
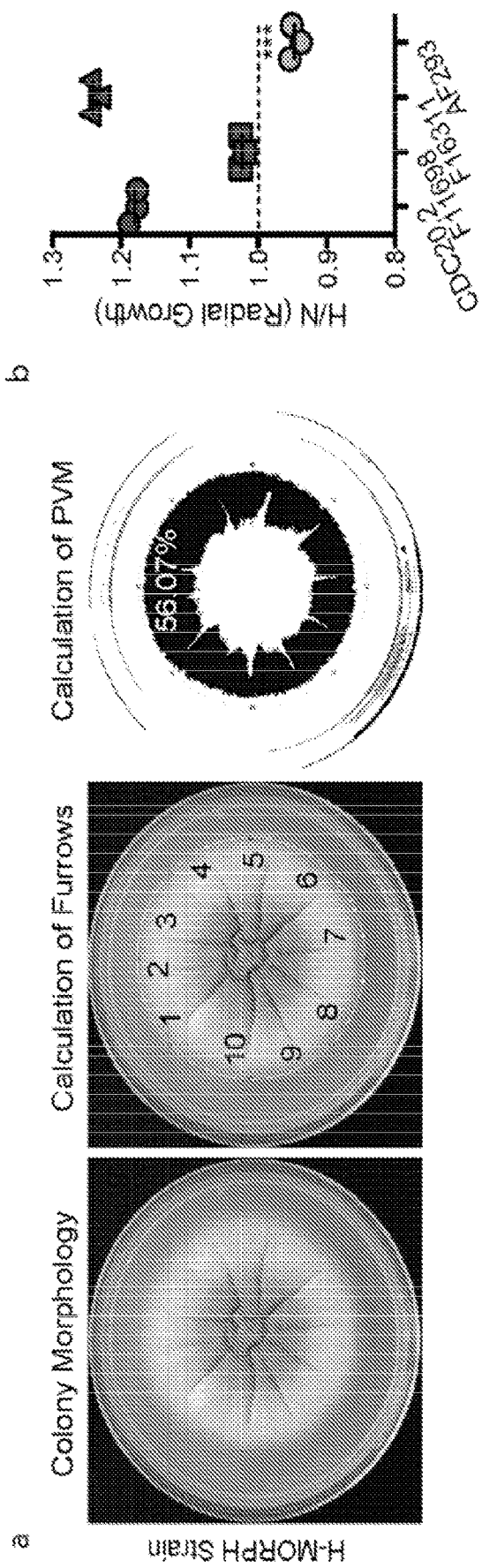
FIG. 2 depicts that whole genome sequencing and RNA sequencing of the hypoxia-evolved EVOL20 identified three nonsynonymous mutations.
Figure 2:
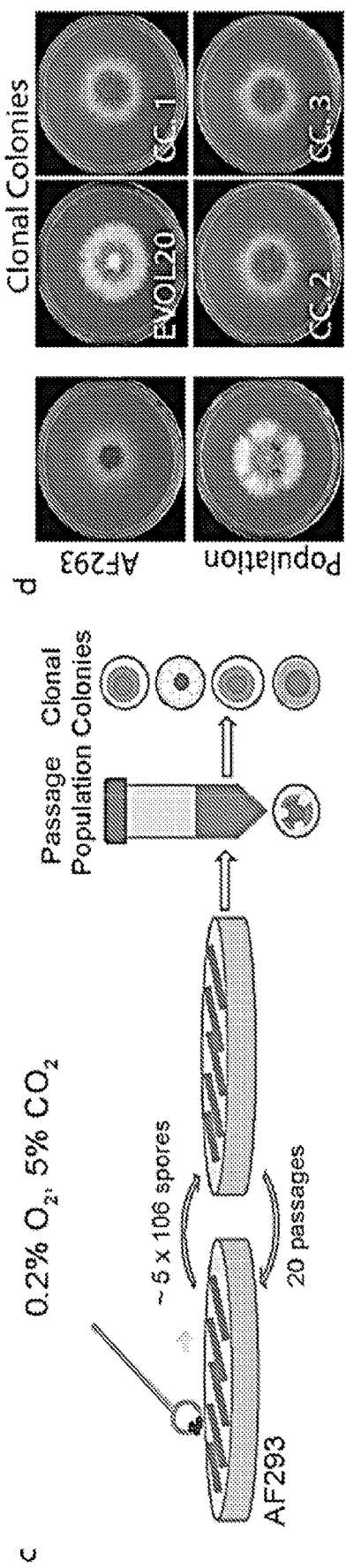

Macroscopic Morphology Quantification: Colonies were imaged with a Canon PowerShot SX40 HS. In Fiji (ImageJ) images were converted to 8-bit. Colony perimeter was selected and a Color Threshold was set to quantify percent of the colony that was 'white'. Furrows were counted by selecting only those that radiated away from the point of inoculation. A 'branched' furrow counted as a single furrow (FIG. 2). The influence of oxygen on morphology was measured with a Two-Way ANOVA (GraphPad Prism).

RNA extraction and qRT-PCR: Mycelia from liquid shaking cultures was flash frozen (~50 mg) and bead beat for 1 minute with 2.3 mm beads in 200 µl of Trisure (Bioline Reagents). Homogenate was brought to a total volume of 1 mL Trisure and RNA was extracted as previously described (Beattie 2017, supra). For RNA-sequencing and qRT-PCR, 50 mL cultures of 10 6 spores/mL were grown in normoxia (21% $O_2$) at 37° C. at 200 rpm for 18 hours before being shifted to low oxygen (0.2% $O_2$). When necessary, 25 mL of the culture was collected at 18 hours for the normoxia samples. For qRT-PCR and RNA-sequencing, 5 µg of RNA was DNAse treated with Ambion Turbo DNAse (Life Technologies) according to the manufacturer's instruction. For qRT-PCR DNase treated-RNA was processed as previously described (Beattie 2017, supra). mRNA levels were normalized to actA and tub2 for all qRT-PCR analyses. Statistical analysis for n>2 was performed with One-Way ANOVA with Dunnet Post Test for multiple comparisons. Error bards indicate StEM. qRT-PCR data was collected on a CFX Connect Real-Time PCR Detection System (Bio-Rad) with CFX Maestro Software (Bio-Rad).

RNA-sequencing and analysis: RNA-sequencing and RNA library preparation was carried out by SeqMatic LLC (Fremont, CA). Briefly, DNAse treated RNA (400-600 ng/L) were sent for QC using RNA Screen Tape Analysis (Agilent) and RNA library preparation using an Illumina TruSeq Standard mRNA library preparation kit with Poly A mRNA enrichment. RNA-sequencing was performed as Illumina NextSeq High Output Run with single end reads at 1×75 bp. Analysis of RNA-Seq was performed by aligning sequence reads to the annotated genome of A. fumigatus strain Af293 obtained from FungiDB (release 35) with GSNAP (2018-$O_2$-12) with splice-aware, single-ended mode. The alignments were processed with Picard (v2.14.1) to clean, sort, and assign read groups (tools CleanSam, AddOrReplaceReadGroups) (http://broadinstitute.github.io/picard/). Sequence read counts overlapping genes were computed with featureCount tool in the Subread package (v1.6.2). The read count table was processed in R using the DESeq2 (3.8) to identify differentially regulated genes and generate heat maps. Pipeline BASH scripts for the alignment, read count pipeline, and R analysis is available in github repository (https://github.comistajichlab/Afum_RNASeq_hrmA; BioProject PRJNA551460). Heatmaps were drawn using collapsed replicates showing top DESeq2 with a P-value<0.05 and log of differential expression>1 and a minimum FPKM of 5.

Surface attachment assays: Briefly, 10 4 spores seeded per well in a round-bottom 96-well polystyrene plate were incubated for 24 hours at 37° C. at ambient oxygen in 1% GMM. Wells were washed 2× with water and stained for 10 min. with 0.1% (wt/vol) crystal violet. Following 2× washes with water, remaining crystal violet was dissolved in 100% ethanol and absorbance was quantified at 600 nm. For matrix complementation experiments, matrix donating strains were cultured in RPMI 1640 (Gibco) at 5×10 7 spores/mL in 100 mL for 24 hours at 37° C. at ambient oxygen. Cultures were filtered through Miracloth to remove fungus, and supernatants were further filtered through a 0.22 µm PVDF sterile filter syringe. Filtered supernatants containing secreted GAG were diluted to 40% in fresh RPMI 1640 and used to perform the adherence assay with the attachment-deficient strain Δuge3.

Murine Virulence assays

Survival: Female CD-1 outbred mice (Charles River Laboratory, Raleigh, NC), grams were immune-suppressed with a single dose of triamcinolone acetonide (Kenalong-10, Bristol-Myer Squibb) at 40 mg/kg 24 hours prior to inoculation. Mice were inoculated with $10^5$ spores/401.d, sterile PBS, as previously described (Kowalski 2016, supra) and monitored for end-point criteria. Kaplan-Meier curves were generated and Log-rank Mantel-Cox tests and Gehan-Breslow-Wilcoxon tests performed.

Histopathology, fungal burden, and nearest neighbor calculation: Lungs from mice immune-suppressed as described were harvested on 4 days post-inoculation (dpi). Lungs were prepared for Gömöri methenamine silver (GMS) and hematoxylin and eosin (H&E) staining or fungal burden quantification as described (Beattie 2017, supra). A nearest neighbor calculation was applied to GMS images. In Matlab (MathWorks Inc.), binary images were generated and filaments defined as objects. Lesions within airways were analyzed blindly. Mean distances between each object in a lesion and its 30 nearest neighbors was calculated. For nearest neighbor calculations four murine lungs were processed per experimental group with two histopathology slides prepared per animal. For fungal burden 4-5 animals were used per group.

FunPACT sample preparation: Lungs from mice immune-suppressed as described above were harvested on day 4 and day 5 post-inoculation. Lungs were harvested and perfused with 1% paraformaldehyde and fixed for 24 hours at room temperature. Following fixation, lobes of fixed lungs were separated with 1 lobe per 1.75 mL microcentrifuge tube. Lobes were washed with PBS and embedded in 4% (vol/vol) 29:1 acrylamide:bis-acrylamide (Bio-Rad) and 0.25% (wt/vol) VA-044 (Wako) in PBS. To facilitate polymerization, tubes were left open at 0.2% $O_2$ at 37° C. for 1 hour, and then closed and incubated at 37° C. in a water bath for 4 hours. Embedded lobes were maintained at 4° C. or were processed for PACT tissue clearing. To clear the lobes, embedded lobes were trimmed of excess polymer and cut into 1 mm cubes using a stereomicroscope. Cubes were incubated in 20 mL of 8% (wt/vol) sodium dodecyl sulfate (SDS) in PBS shaking at 150 rpm at 37° C. for 6-8 weeks in the dark. When cubes became transparent, they were processed for staining and imaging.

After clearing, the cubes were washed 3× with PBS for 1 hour each. A subset of cubes was then transferred to a 1.75 mL microcentrifuge tube and stained for 48 hours with FITC-Soy Bean Agglutinin at 20 µg/mL (SBA) (Vector Labs). Lectin labeled cubes were washed in PBS for 24 hours to remove excess lectin, and cubes were placed in a refractive index matching solution (RIMS) (40 g HistoDenz: Sigma, in 30 mL PBS) with DAPI (10 µg/mL). Stained cubes in RIMS+DAPI were mounted on standard 24×40×1.5 glass slides with a Press-to-Seal™ Silicone Isolator (Invitrogen: P24744).

Cellularity and Immunological Studies: Mice were immune suppressed and inoculated as described above with 8 mice per group. After 60 hpi, animals were sacrificed using a lethal dose of pentobarbital and bronchoalveolar lavage (BAL) was performed and BAL fluid (BALF) and cells, lungs and spleens were collected. Cells from BAL and lungs were prepared for staining. Lung tissue was minced and digested with 2.2 mg/mL Collagenase IV (Worthington), 1U/mL DNase 1 (Zymo Research) and 5% FBS at 37° C. for 45 minutes. BALF was centrifuged to isolate cells and suspended in red blood cell (RBC) lysis buffer. Re-suspended cells from lung homogenate were also treated for RBC lysis. Cell numbers were enumerated with Trypan Blue staining. For cellularity analysis, the cells were stained with Fixable Viability Dye (eFluor™ 780, eBioscience), anti-CD45 (Pacific orange, Invitrogen), anti-CD11b (PECy5, BioLegend), anti-Ly6G (FITC, BioLegend) anti-SiglecF (BV421, BD bioscience) and analyzed on a MacsQuant VYB cytometer. The neutrophils were identified as $CD45^+ SiglecF^- Ly6G^+ CD11b^+$ cells and alveolar macrophages as $CD45^+ SigletrCD11b^{dim}$ cells. Samples were run on a MacsQuant VYB cytometer and analyzed with FlowJo version 9.9.6. BALF was used to quantify host cell damage and KC through the use of LDH-Cytotoxicity Colorimetric assay (BioVision #K311) and Mouse CXCL1/KC DuoSet ELISA (R&D Systems #DY453), respectively.

Fungal Biofilm Sample Preparation: Biofilms for imaging were cultured in MatTek dishes (MatTek #P35G-1.0-14-C) by seeding $10^5$ spores/mL of GMM with 2 mL per dish for 24 hours at 37° C. with 5% $CO_2$ at 21% $O^2$ or 0.2% $O_2$. Calcofluor white stain (CFW) (Sigma) was used to visualize the hyphae at a final concentration of 25 µg/mL for 15 minutes.

Fluorescent Microscopy: Fluorescent confocal microscopy was performed on an Andor W1 Spinning Disk Confocal with a Nikon Eclipse Ti inverted microscope stand with Perfect Focus, a Zeiss LSM880 with two multi-alkali photomultiplier tubes, GaAsP detector, and a transmitted light detector, or a Zeiss LSM800 AxioObserver.

HrmA Localization Studies: Fungi were cultured on coverslips in GMM at 30° C. for 18 hours until short hyphae, were washed, UV fixed, stained with 5 µg/mL DAPI (Life Technologies), and mounted on slides. Images were acquired with a 100× oil immersion objective at 488 nm (GFP) and 405 nm (DAPI) on the Andor W1 Spinning Disk Confocal. Z-stacks were assembled in Fiji (ImageJ) with sum intensity projections. Images are representative of at least 10 images. Quantification was performed as previously described (Danhof et al. *Infect Immun* 83, 4416-4426, 2015).

Fungal Biofilm Imaging and Quantification: Biofilms were imaged in MatTek dishes with a 20× multi-immersion objective (Nikon) or 10× multi-immersion objective (Zeiss, C-Apochromat 10×/0.45 W M27) using water. CFW biofilms were imaged at 405 nm and tdtomato biofilms were imaged at 561 nm at depths from 300-500 nm. 3D projections were generated in Nikon NIS-Elements Viewer (Nikon) or Zeiss Blue (Zeiss). For quantification of biofilm architecture strains expressed tdtomato and were imaged on the Zeiss LSM880 AxioObserver with the exception of IFM 59356-1 and IFM 59356-3 which were stained with CFW (25 µg/mL). For quantification see supplemental methods. To quantify the branch length and branch density distribution of the hyphae network image stacks were processed in BiofilmQ (https://drescherlab.org/data/biofilmQ/) as follows: First, noise and background fluorescence where removed by local averaging, i.e. Tophat-filtering, respectively. Second, the hyphae structure was binarized by thresholding using Otsu's method (Liao et al. *J Inf Sci Eng* 17, 713-727, 2001). Third, the obtained data was skeletonized with a custom BiofilmQ analysis module and all branches above a threshold length were considered for further investigation. Visualization of branch features was performed in BiofilmQ.

FunPACT Imaging: Mounted samples for funPACT were imaged on the Andor W1 Spinning Disk Confocal with a 20× multi-immersion objective lens used with oil or a 40× oil-immersion objective. Areas of fungal growth were identified by manual scanning at 561 nm. Lesions were imaged at 405 nm, 488, and 561 nm at various depths. Images were processed in Nikon NIS-Elements Viewer for deconvolution and 3D rendering.

Cell wall staining: Hyphae were generated as described for localization studies. Filaments were stained with 25 mg/mL calcofluor white (Fluorescent Brightener 28-Sigma) for 15 min. or soluble Dectin-1 as described previously (Shepardson et al. *Microbes Infect* 15, 259-269, 2013). 10 hyphae images were processed per strain.

Scanning and transmission electron microscopy: Fungal biofilms for scanning and transmission electron microscopy were grown on 12 mm sterile glass coverslips in 6-well plates for 24 hours at 37° C. at 21% $O_2$ with 10 6 spores/mL in RPMI 1640 (Gibco). Two coverslips were generated per sample. Samples were processed for SEM though a critical point drying method. Briefly, media was removed and replaced with fixative (2% GTA/2% PF in NaCacodylate pH 7.4) for 15 minutes at room temperature. Fresh fixative was then added for 24 hours. Coverslips were then washed 3× (0.05M NaCacodylate pH 7.4 for 5 min) and then incubated for 1 hour at room temperature in 1% $OsO_4$ in 0.05M NaCacodylate before 3× washings as before. Samples were then ethanol dehydrated for 10 min. in each 30%, 50%, 70%, and 85% ethanol, and were then washed 3× in 100% ethanol. Coverslips were then transferred to a CPD holder and incubated in 100% hexamethyldisilazane 2× for 10 min. each. Samples were then mounted on AI SEM stubs and coated with osmium plasma coater (4 nm) and were stored in a desiccator prior to imaging. SEM images were acquired on an FEI (Thermo Fisher Scientific) Scios2 LoVac dual bean FEG/FIB Scanning Electron Microscope with a Schottky emitter source. Images were acquired at 15.0 kV with 3 nm spot size.

Transmission electron microscopy and cell wall measurements: For transmission electron microscopy fungal biofilms were fixed in 5 mL 2× fixative (2% GTA/2% PF in 0.05M NaCacodylate pH 7.4) for 1 hour and then replaced with fresh fixative. Biofilms were scraped from coverslips and hyphae were pelleted and excess fixative removed. Hyphae were transferred to 100 μl 2% molten agar and solidified. Agar drops were trimmed to removed excess agar and transferred to 1 mL fresh fixative and rotated for 3 hours at room temperature then 48 hours at 4° C. Pellet was rinsed in 0.1M NaCac/0.1M Sucrose to remove GTA and then post-fix treated with 2% $OsO_4$ in 0.1M NaCac/0.07M Sucrose for 2 hours. Soft agar pellet was then rinsed twice with $dH_2O$ and then transferred to En-bloc stain with 1% Uranyl Acetate for 2 hours at room temperature in the dark. Pellet was then dehydrated through ethanol series at room temperature with 30%, 50%, 70% for 30 minutes each, then on a rotator for two days, followed by further dehydration with 85% then 95% ethanol for 30 minutes and then 100% ethanol for 6 rinses over 6 hours. Samples were then left at 4° C. for 48 hours. Samples were then incubated 2× in propylene oxide for 30 minutes each, then immersed in 1:1 LX112 (LADD, Inc. Burlington, VT):PO for 1 hour at room temperature and then in 1.5:1 LX112:PO for 18 hours. LX112 from LADD epoxy solution used in 6A:4B for medium hard block. Excess fluid was removed and samples were placed in vacuum desiccator for 24 hours before being transferred to BEEM capsules with fresh LX112, centrifuged for 30 min at 1500 rpm and returned to vacuum desiccator for 12 hours. Samples were polymerized at 45° C. for 24 hours, 60° C. for 24 hours, and then cooled and thin sectioned and places in 2% UAmem for 10 minutes followed by 3% Reynolds lead citrate for 2-3 minutes. Protocol was based on Burghardt & Droleskey (Burghardt et al. Curr Protoc Microbiol Chapter 2, Unit 2B 1, 2006). Samples were imaged on JEOL JEM 1010 transmission electron microscope at 100.0 kV. To determine cell wall size, ImageJ was used to open images files and for each cross-section of a filament 10 measurements of cell wall thickness, disregarding the electron-dense ECM, were averaged per filament.

Statistics and Reproducibility: All statistical analysis was performed in GraphPad Prism 5, GraphPad Prism 8, and R. Unless otherwise noted, all statistical analyses were performed with a minimum of three biologically independent samples. All images are representative of a minimum of three biologically independent samples that represent a minimum of three independent experimentations unless otherwise noted. funPact images are representative of five independent animals, but to reduce the use of animals, samples for funPact images were generated from two independent sample preparations. For comparisons between two groups two-tailed unpaired t-tests were performed. For comparisons between greater than two groups One-Way ANOVA with Tukey, Sidak, or Dunnett post tests for multiple comparisons were performed. All error bars indicate standard error and are centered around the mean.

Oxygen Tension Significantly Influences Fungal Colony Morphology and Biofilm Architecture

*A. fumigatus* CM is heterogeneous in response to oxygen tension (Kowalski 2016, supra). A screen of 58 isolates at 0.2% $O_2$ for two morphological features (1) colony furrowing and (2) percent vegetative mycelia (white, non-conidiating mycelia) (PVM) revealed abundant furrowing (mean: 5.30) and a high PVM (mean: 70.4%) (FIG. 1a, FIG. 2a). Colonies at 21% $O^2$ have significantly fewer furrows (mean: 1.85, p<0.0001) and significantly reduced PVM (mean: 32%, p<0.0001) (FIG. 1b). Oxygen tension is a significant source of variation for both colony furrowing (31.67%, p<0.0001) and PVM (55.77%, p<0.0001) (FIG. 1c, FIG. 1d). Most isolates screened have low furrowing and low PVM at normal oxygen (N-MORPH) and elevated furrowing and PVM at low oxygen (hypoxia) (H-MORPH) (FIG. 1e). A strain was considered to be H-MORPH if furrows are greater than 3 and PVM is greater than 40% when grown in the above described culture conditions. A subset of clinical strains adopt H-MORPH even at 21% $O^2$ (filled circles FIG. 1b, FIG. 1c, FIG. 1d, FIG. 10. Three such strains, CDC20.2, F11698, and F16311, have significantly increased low oxygen fitness (H/N) relative to the N-MORPH reference AF293 (FIG. 1f, FIG. 2b).

Figure 3:
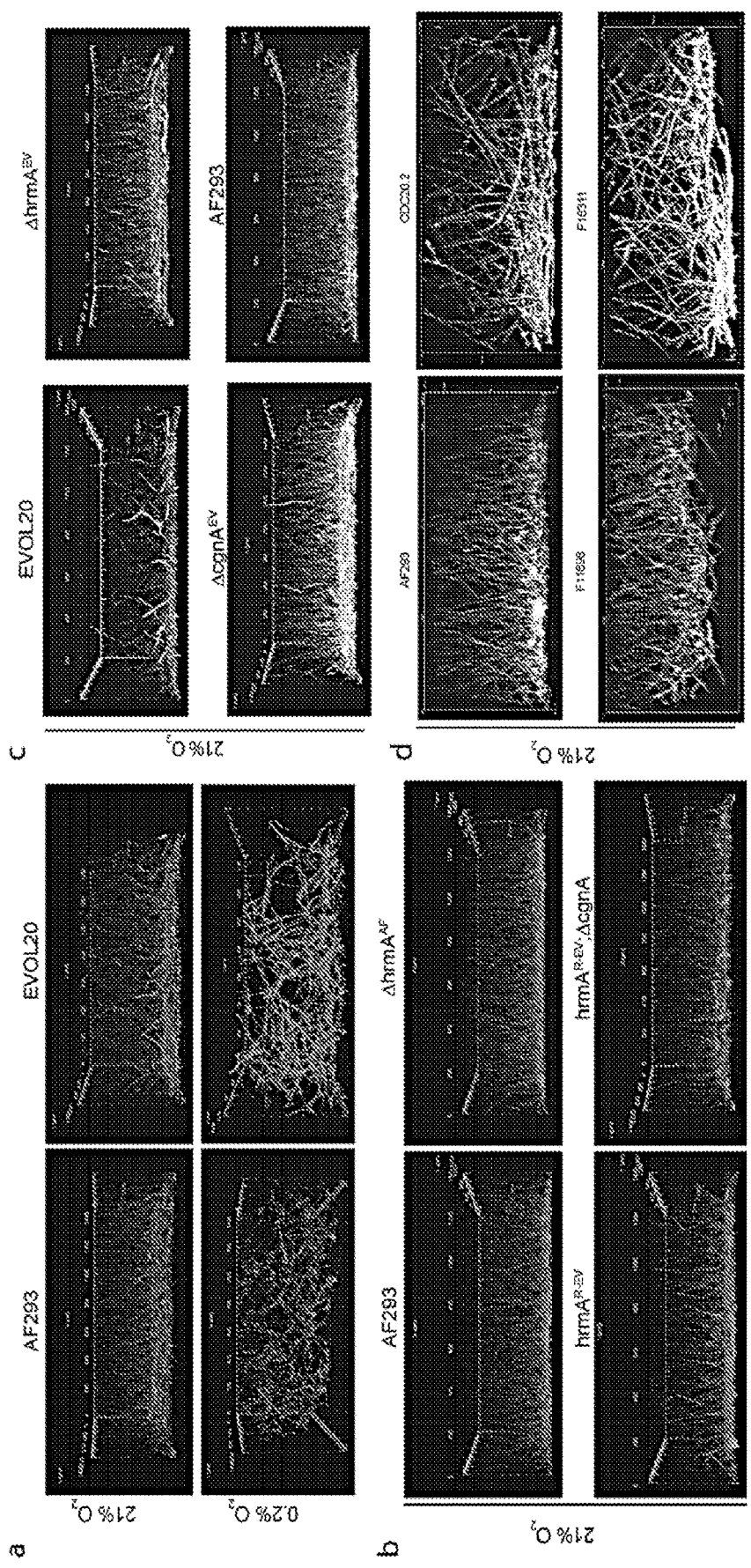
FIG. 3 depicts the full field of view biofilm images used in alignment analysis. Full volume view of the submerged fungal biofilms (XZ plane) with constitutively fluorescent fungi or biofilms dyed with calcofluor white.

H-MORPH submerged fungal biofilms have altered biofilm architecture compared to AF293 (FIG. 1g). AF293 biofilms have a mat of filaments at the base perpendicular to the vertical axis. Above −50 filaments grow polarized toward the air liquid interface with little deviation from the vertical axis (FIG. 1h). The N-MORPH strain AF293 cultured at 21% $O^2$ formed an organized biofilm with straight filaments growing toward the air-liquid interface. Clinical H-MORPH strains are similar within the first −50 1.1m, but the remaining volume contains filaments that deviate from the vertical axis (FIG. 1h, FIG. 3). This pattern of altered architecture is similar to AF293 cultured at 0.2% $O_2$, which forms a highly disorganized biofilm with many filaments that divert from the vertical, and in the AF293 hypoxia-evolved H-MORPH strain EVOL20 independent of oxygen tension, which forms a highly disorganized biofilm with many filaments that divert from the vertical at both 21% $O^2$ and 0.2% $O^2$ (FIG. 1i, FIG. 1j, FIG. 2c, FIG. 3). These data suggest that CM is an indicator of microscopic biofilm architecture impacted by oxygen.

H-MORPH occurs throughout genetically diverse strains of *A. fumigatus*

Figure 4:
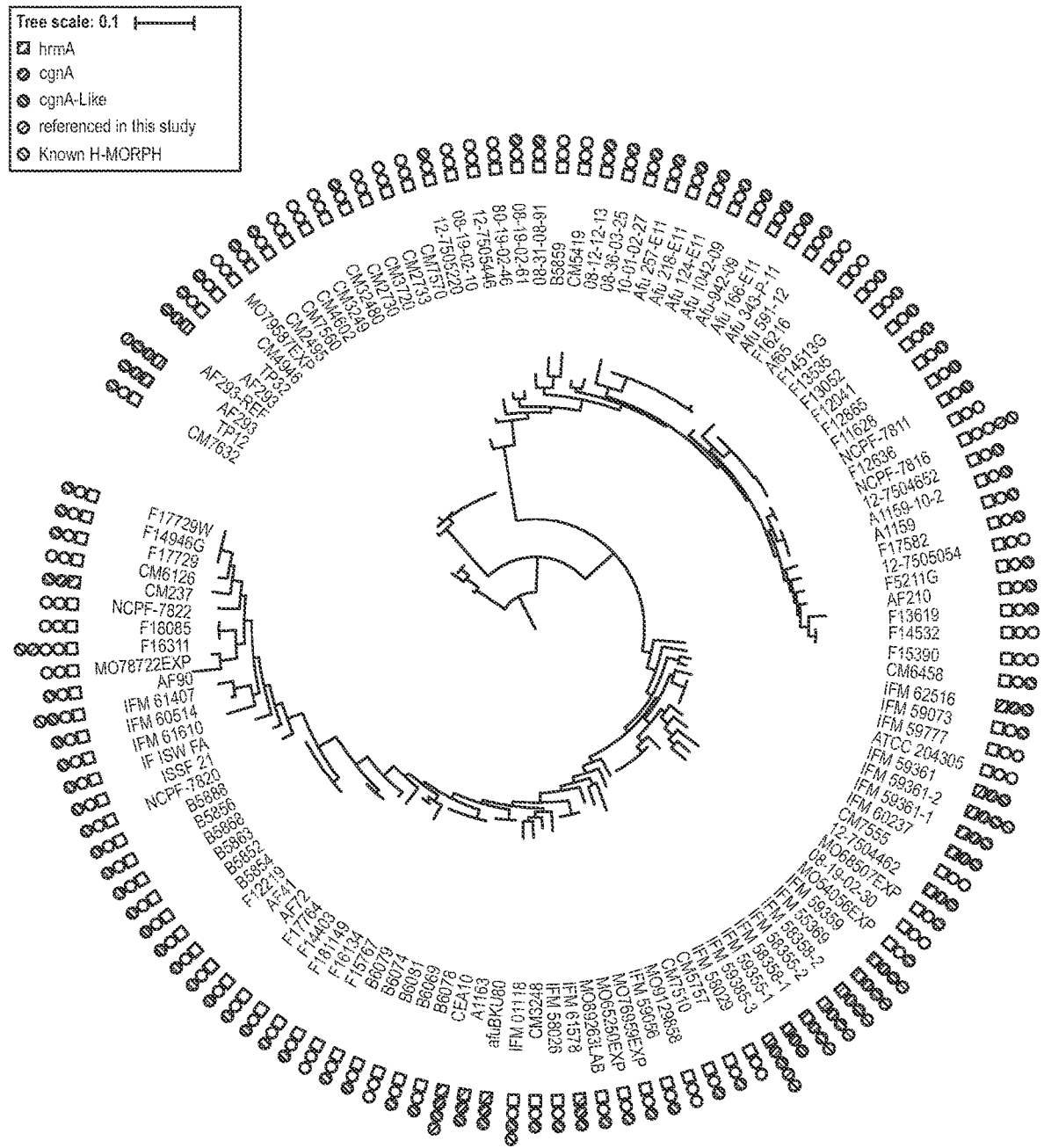
FIG. 4 depicts the Aspergillus fumigatus phylogeny of publicly available genomes depicting presence and absence of hrmA and cgnA. A. fumigatus species phylogeny indicates the presence of hrmA (red square, 95% ID) and cgnA (purple circle, 95% ID detected within same contig as hrmA) in a genetically diverse set of strains, while the majority of strains encode least one cgnA-like sequence (blue circle). Strains investigated further in this study are indicated with black circles and known H-morph strains are indicated with green circles.
Figure 5:
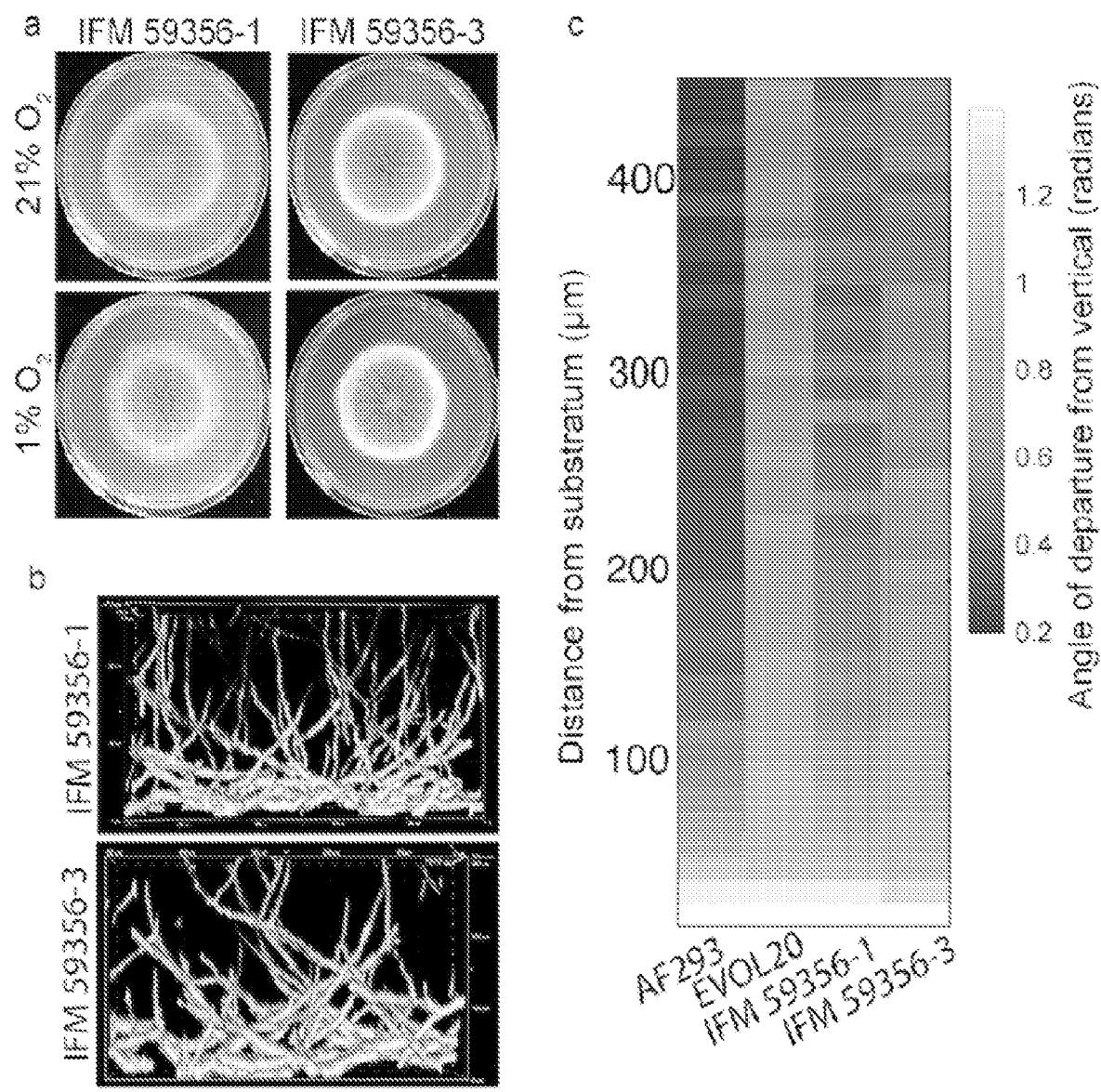
FIG. 5 depicts the phenotypic characterization of H-MORPH clinical strains.
Figure 5:
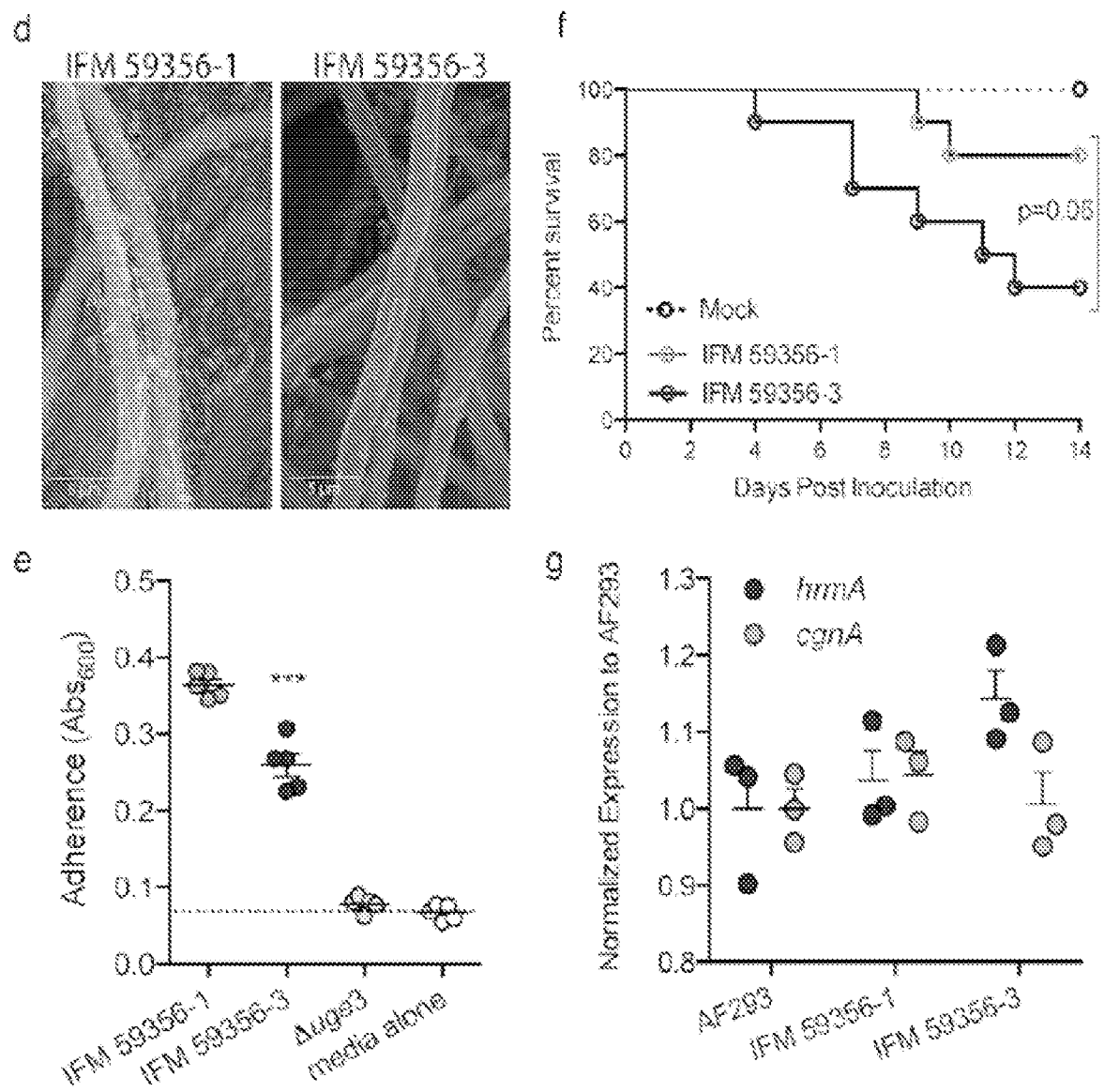

H-MORPH is not segregated by Glade within the *A. fumigatus* phylogeny (FIG. 4). Two H-MORPH clinical strains, F11698/NCPF-7816 and F13611, represent the abundant *A. fumigatus* genetic diversity with one present in each of the two major clades (FIG. 4). Genetically similar, co-isolated clinical strains, IFM 59356-3 and IFM 59356-1, have H-MORPH and N-MORPH respectively (FIG. 5a). Consistent with H-MORPH (FIG. 1g, FIG. 1h), IFM 59356-3 has a biofilm with greater filament deviation from the vertical relative to its N-MORPH counterpart IFM 59356-1 (FIG. 5b, FIG. 5c). The lack of clustering of H-MORPH within the phylogeny and the ability to generate this CM suggest multiple genetic mechanisms likely exist through which *A. fumigatus* evolves these morphological features.

A Sub-Telomeric Gene hrmA Allele is Sufficient to Generate H-MORPH

Figure 20:
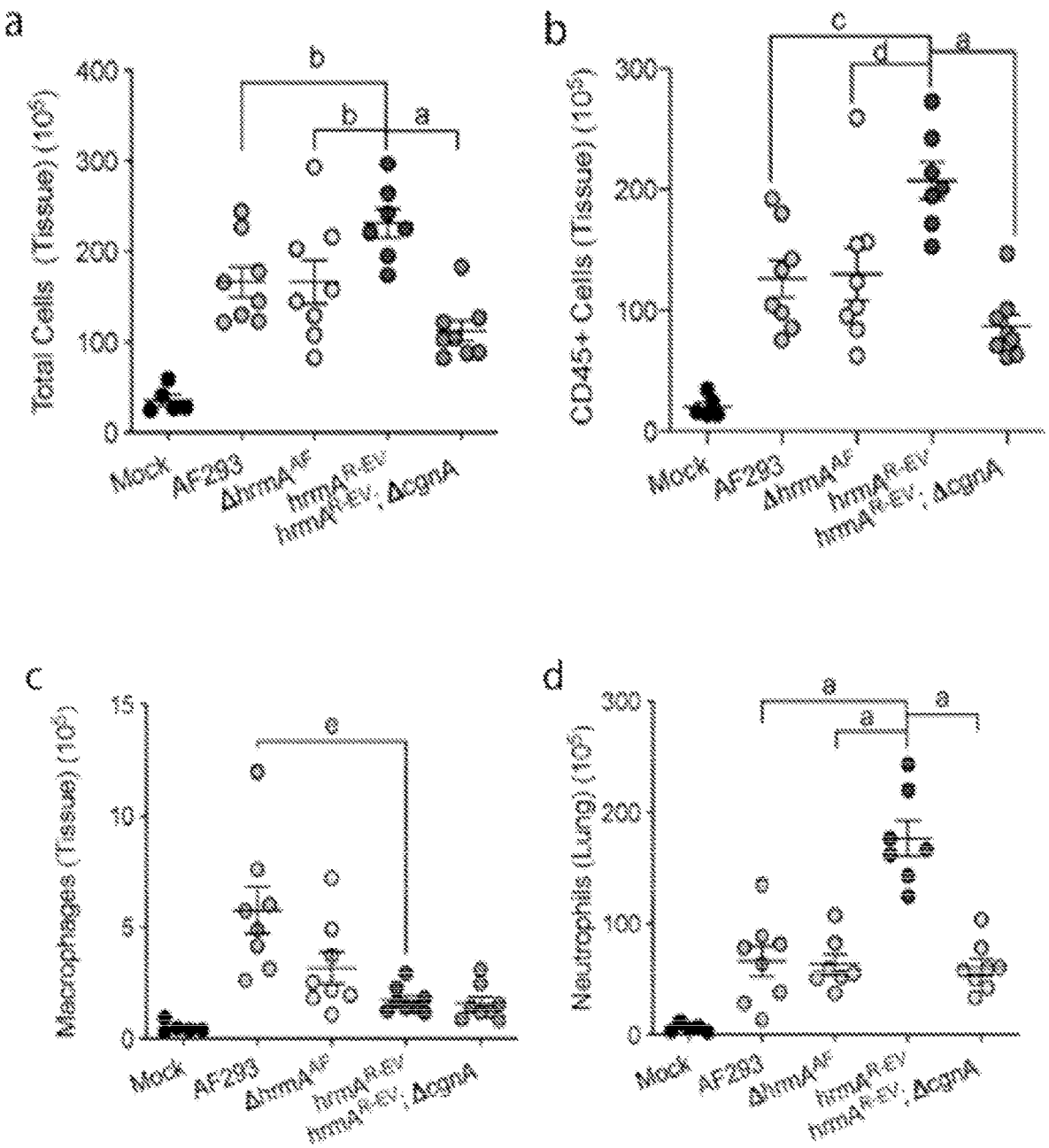
FIG. 20 depicts cellularity from tissue and histopathology. In murine lung tissue total cells (a: p<0.0001, b: p=0.0384 by One-way ANOVA with Dunnett's Multiple Comparison test) (FIG. 20a) and CD45+leukocytes (a: p<0.0001, c: p=0.0033, d: p=0.0049 One-way ANOVA with Dunnett's Multiple Comparison test) (FIG. 20b) are elevated at 60 hpi with hrmA$^{R-Ev}$ (n=7 biologically independent animals) relative to the other strains (n=8 biologically independent animals per group).
Figure 20:
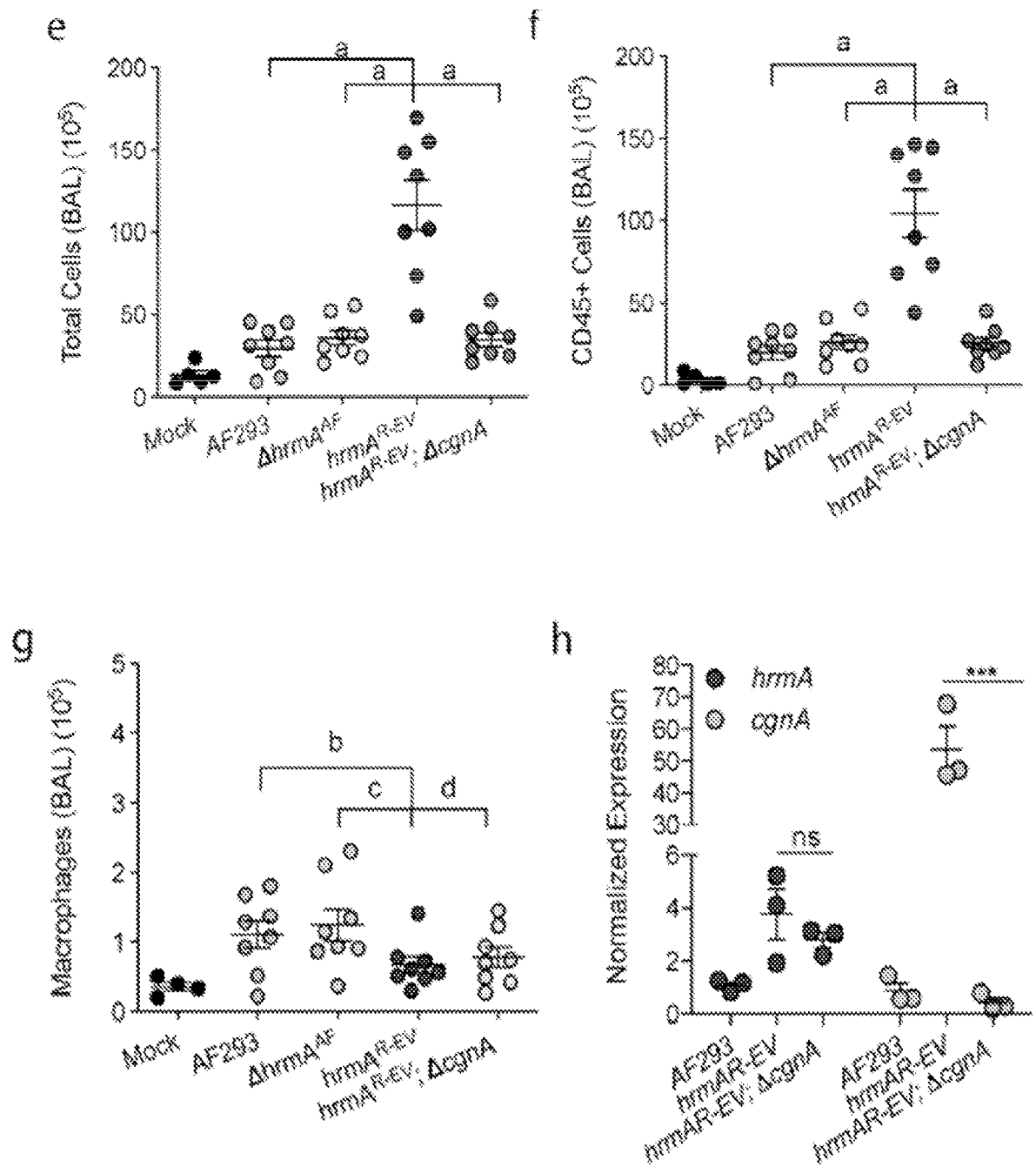
Figure 20I:
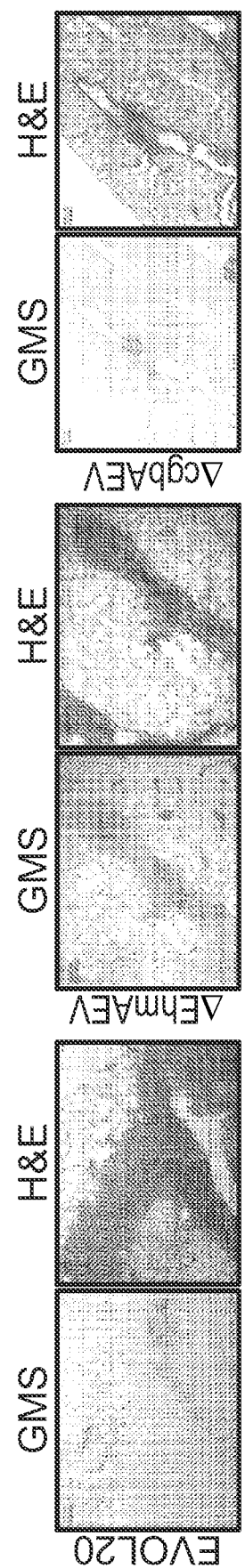
FIG. 20i. GMS and H&E histopathology of airway lesions of EVOL20, ΔhrmA$^{EV}$, and ΔcgnA$^{EV}$ (Scale bars: 20 pm). Images are representative of 5 biologically independent animals from 2 independent experiments.
Figure 22:
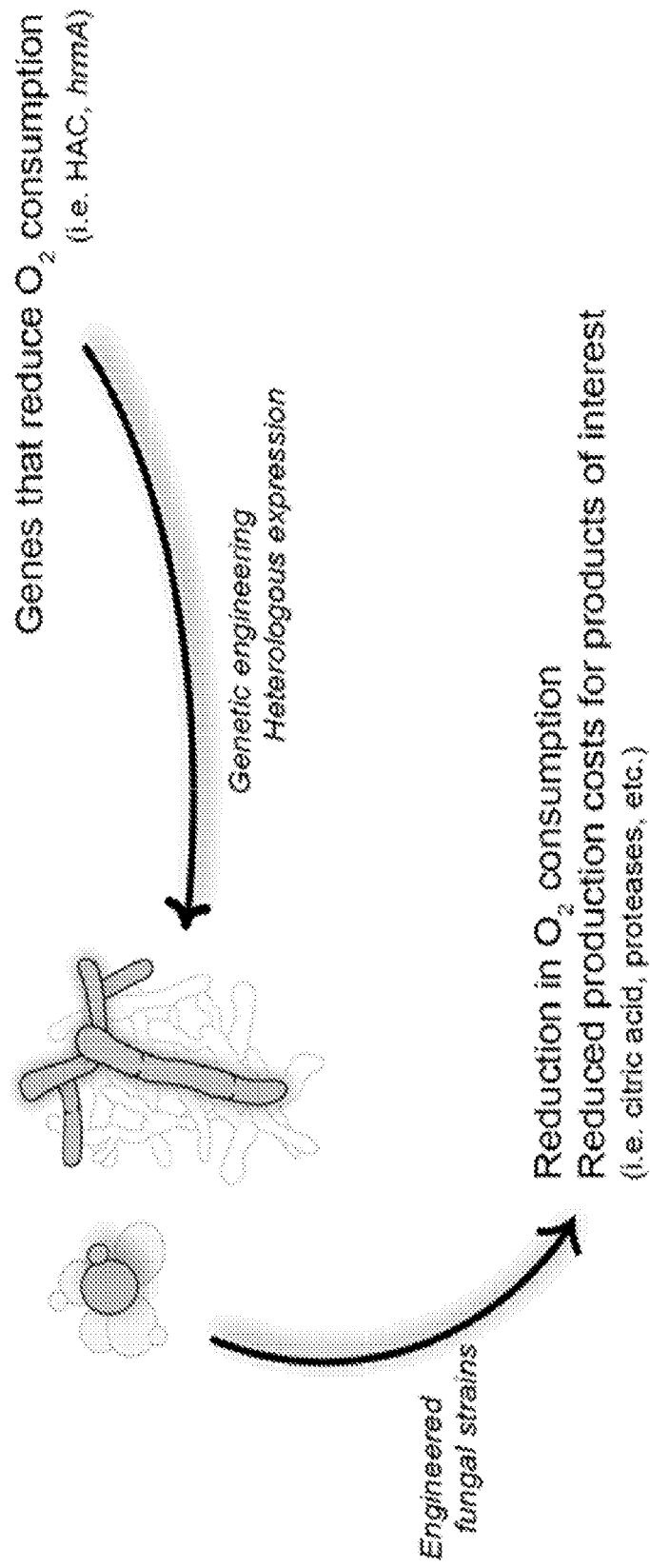
FIG. 22 depicts a conceptual overview of oxygen consumption modulation technology in industrial relevant fungi.

An in vitro experimental evolution approach with AF293 in 0.2% $O^2$ generated the strain EVOL20 that adopts H-MORPH independent of oxygen tension (FIG. 2c, FIG. 2d). Whole genome sequence analysis of EVOL20 revealed three non-synonymous mutations compared to AF293, including a missense mutation in an uncharacterized hypothetical protein Afu5g14900. This single nucleotide polymorphism (SNP) (D304G) was only identified in H-MORPH EVOL20 from the passaged population (FIG. 20. RNA sequencing indicates that Afu5g14900 transcript is significantly elevated in EVOL20 relative to AF293 in both normal (p=0.0002) and low oxygen conditions (p<0.0001) (FIG. 2e). Due to the generation of H-MORPH in EVOL20 the gene Afu5g14900 is named hypoxia responsive morphology factor A, hrmA.

In AF293, hrmA loss ($\Delta hrmA^{AF}$) did not alter in vitro CM in terms of furrowing and PVM, however, reconstitution of $\Delta hrmA^{AF}$ with the EVOL20 allele of hrmA ($hrmA^{R-EV}$) was sufficient to generate H-MORPH independent of oxygen tension (FIG. 6a, FIG. 6b). hrmA$^{R-EV}$ has hypoxia fitness equivalent to EVOL20 (FIG. 6c). Conversely, hrmA loss in EVOL20 (ΔhrmA$^{EV}$) resulted in a loss of H-MORPH during growth at 21% O$^2$ (FIG. 6a, FIG. 6b), and a reduction in hypoxia fitness (FIG. 6c). Similar to H-MORPH locked clinical isolates (FIG. 1g) and EVOL20, hrmA$^{R-Ev}$ generated a biofilm with vertically misaligned filaments above the first ~50 µm (FIG. 6d, FIG. 6e). Loss of hrmA in EVOL20 restored AF293-like biofilm architecture (FIG. 2f, FIG. 2g). Thus, the hypoxia-evolved allele of hrmA is shown herein to be sufficient and necessary to generate H-MORPH in AF293 and EVOL20, respectively.

Figure 7:
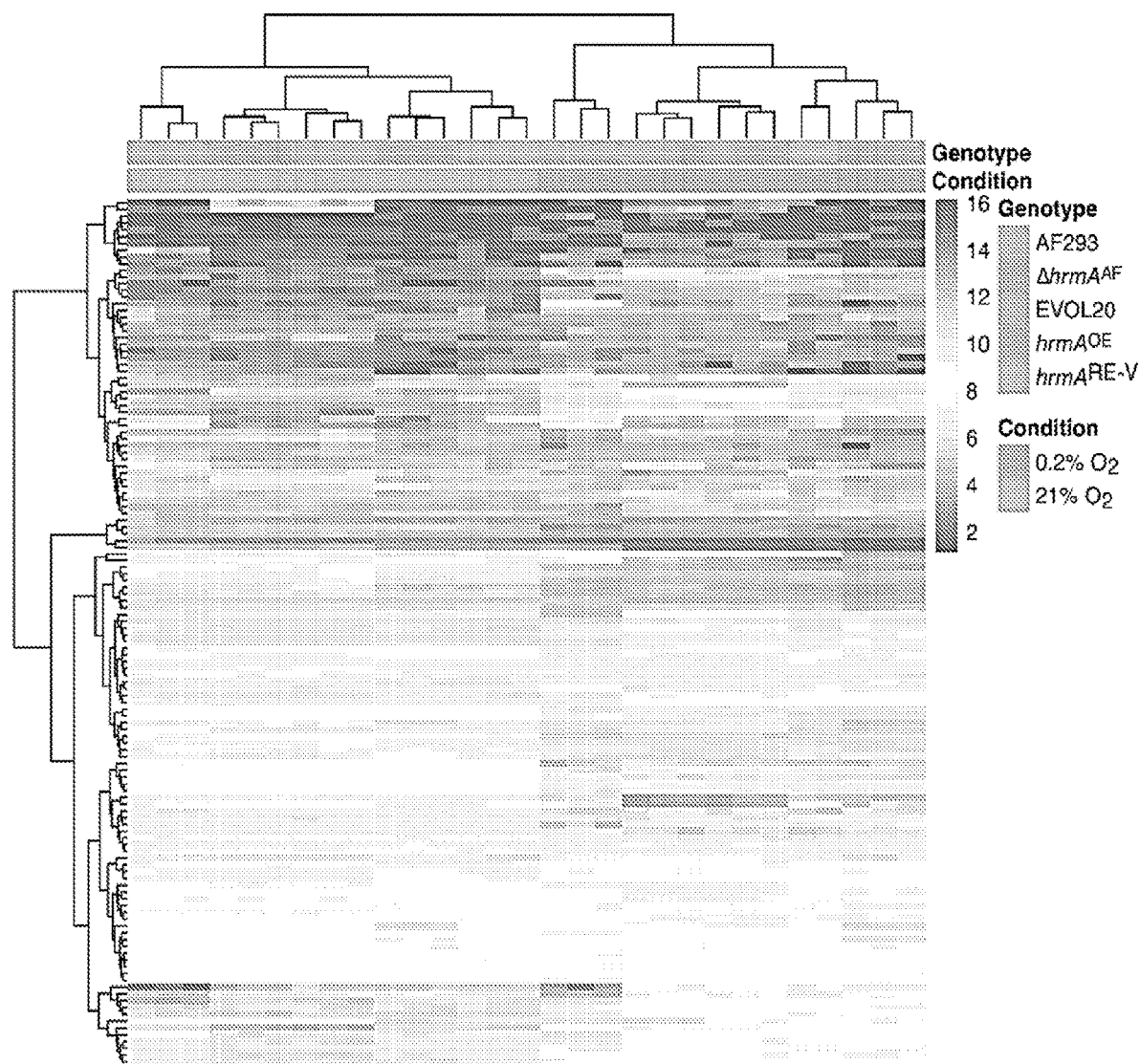
FIG. 7 depicts that the transcriptional profiles cluster overexpression of the reference allele of hrmA (hrmA$^{OE}$) with expression of the hypoxia-evolved allele (hrmA$^{R-Ev}$). All genes were plotted that have differential expression across the genotypes with $p<0.05$ (two-sided) as determined through DESeq2 which utilizes Wald test for differential expression and adjusted for multiple comparisons using Benjamini and Hochberg procedures. Any genes where total FPKM<1 were excluded. These data indicate that AF293 and ΔhrmA$^{AF}$ cluster closely together at 0.2% $O^2$ and 21% $O_2$. The hrmA$^{R-EV}$ and hrmA$^{OE}$ cluster together in normoxia and hypoxia indicating that these strains have similar transcriptional profiles despite the differences in the hrmA allele. EVOL20 has a more complex genetic background and clusters separately.
Figure 8:
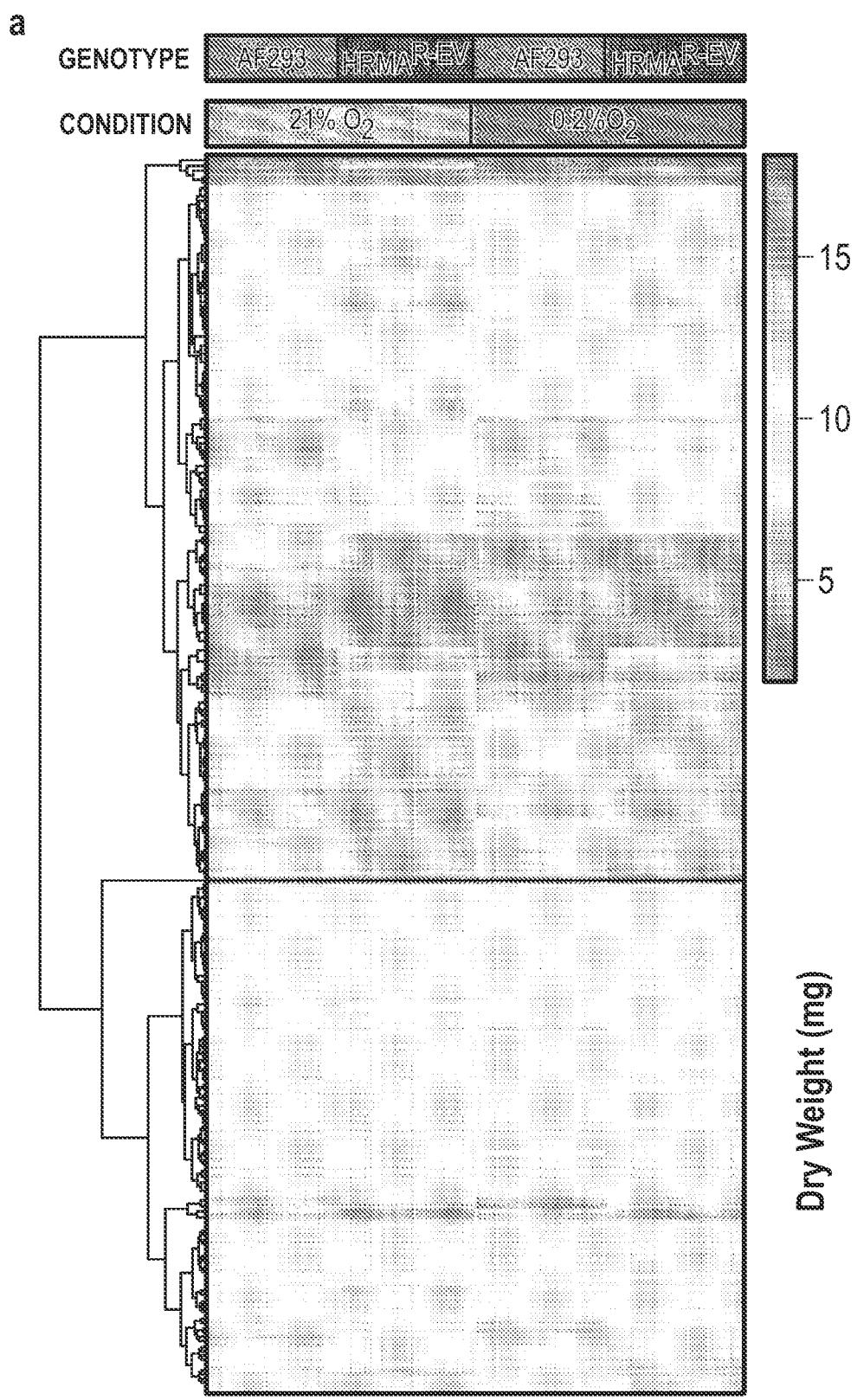
FIG. 8 depicts that the transcriptional rewiring of the hypoxia response is dependent on the hypoxia-evolved allele of hrmA and primes for improved growth in low oxygen.
Figure 8:
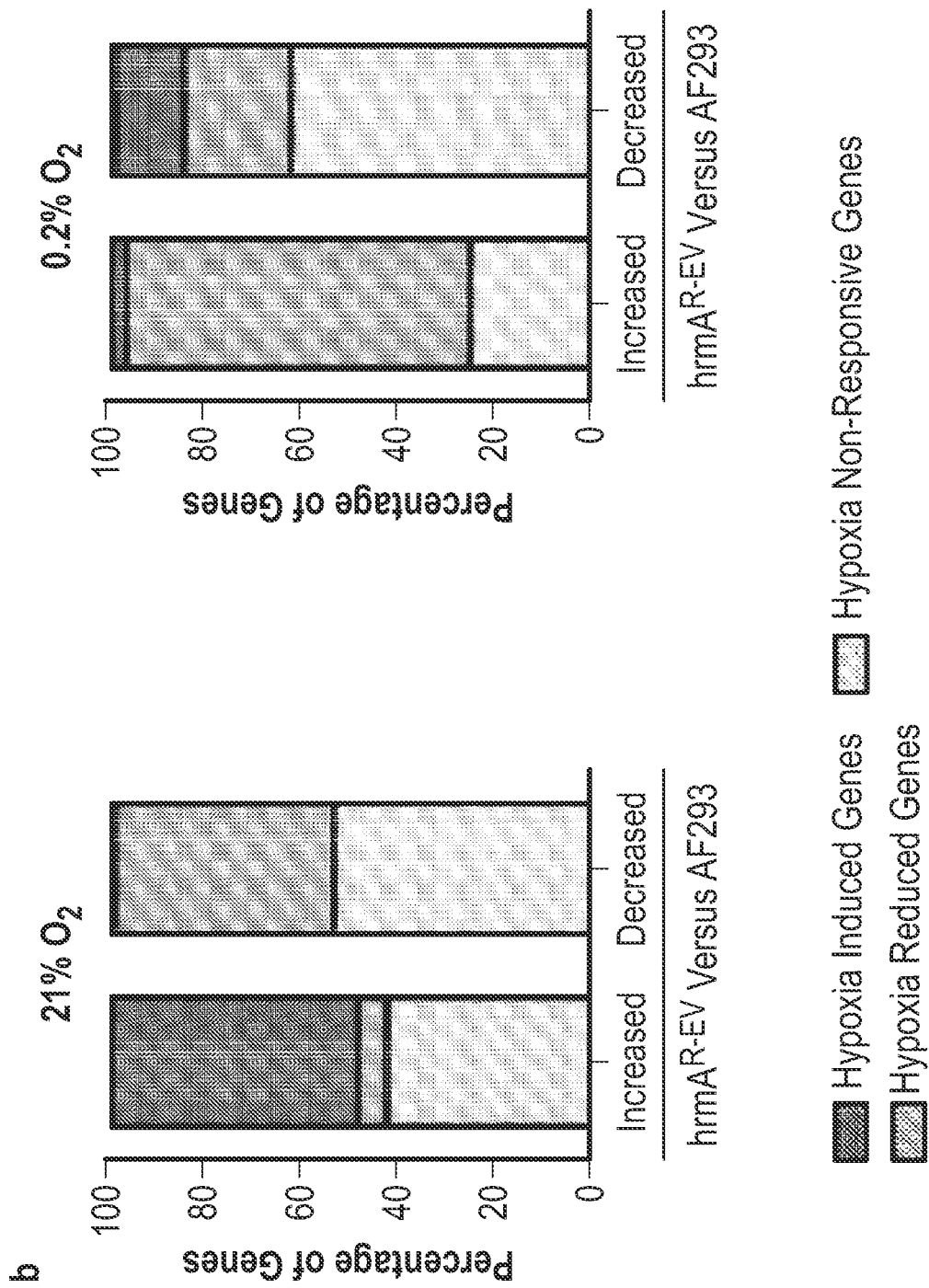

H-MORPH Coincides with the Initiation of the Hypoxia Transcriptional Response at Ambient Oxygen Tensions RNA sequencing was utilized to visualize broad consequences of H-MORPH at normal and low oxygen tensions. Hierarchical clustering of the transcriptomes reveals H-MORPHs hrmA$^{R-EV}$ and hrmA$^{OE}$ (over expression of the AF293 allele in AF293) cluster independently from N-MORPHs AF293 and ΔhrmA$^{AF}$ (FIG. 7). Of the differentially expressed transcripts between hrmA$^{R-EV}$ and AF293 in 21% and 0.2% 0 2, 58% are oxygen-response genes in AF293 (FIG. 8a). The Gene Ontology Functional Categories GO:0016491 Oxidoreductase Activity (32/904) and GO:0005506 Iron Ion Binding (7/142) are significantly enriched in the differentially expressed genes between hrmA$^{R-Ev}$ and AF293; two categories shown previously to be enriched during the hypoxia response (Barker et al. BMC Genomics 13, 62, 2012).

Transcripts with an increase or decrease of at least 4-fold between AF293 and hrmA$^{R-Ev}$ were categorized as "Hypoxia Induced Genes" (H/N>4), "Hypoxia Reduced Genes" (H/N<−4), or "Hypoxia Non-Responsive Genes" (4>H/N<−4). At 21% 02, 51% of the transcripts increased in hrmA$^{R-Ev}$ compared to AF293 are "Hypoxia Induced Genes"; conversely, 45% of the transcripts reduced in hrmA$^{R-Ev}$ compared to AF293 are "Hypoxia Reduced Genes" (FIG. 8b). Thus, H-MORPH strains, mediated by hrmA, activate the transcriptional hypoxic response despite oxygen replete conditions. At 0.2% O$^2$ where hrmA$^{R-EV}$ is more fit than AF293, 71.8% of increased transcripts are "Hypoxia Reduced Transcripts" further supporting an altered physiological response to hypoxic stress in H-MORPH strains (FIG. 8b). The inverted hypoxia response of hrmA$^{R-Ev}$ coincides with reduced fungal biomass at 21% O$^2$ and increased biomass at 0.2% O$^2$ (FIG. 8c). However, following a shift from ambient oxygen to low oxygen the H-MORPH hrmA$^{R-Ev}$ has increased growth rate compared to the N-MORPH AF293 (FIG. 8d).

Figure 9:
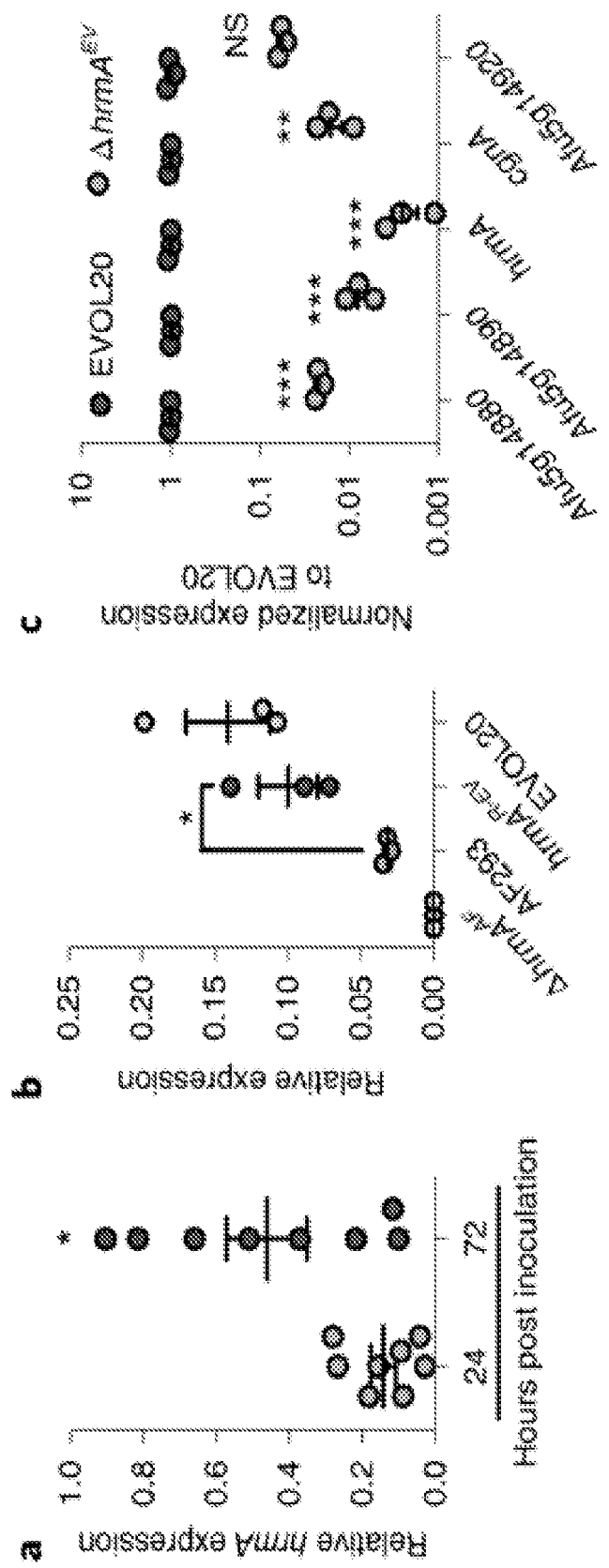
FIG. 9 depicts that HrmA localizes to the nucleus where it facilitates induction of a sub-telomeric gene cluster.
Figure 9:
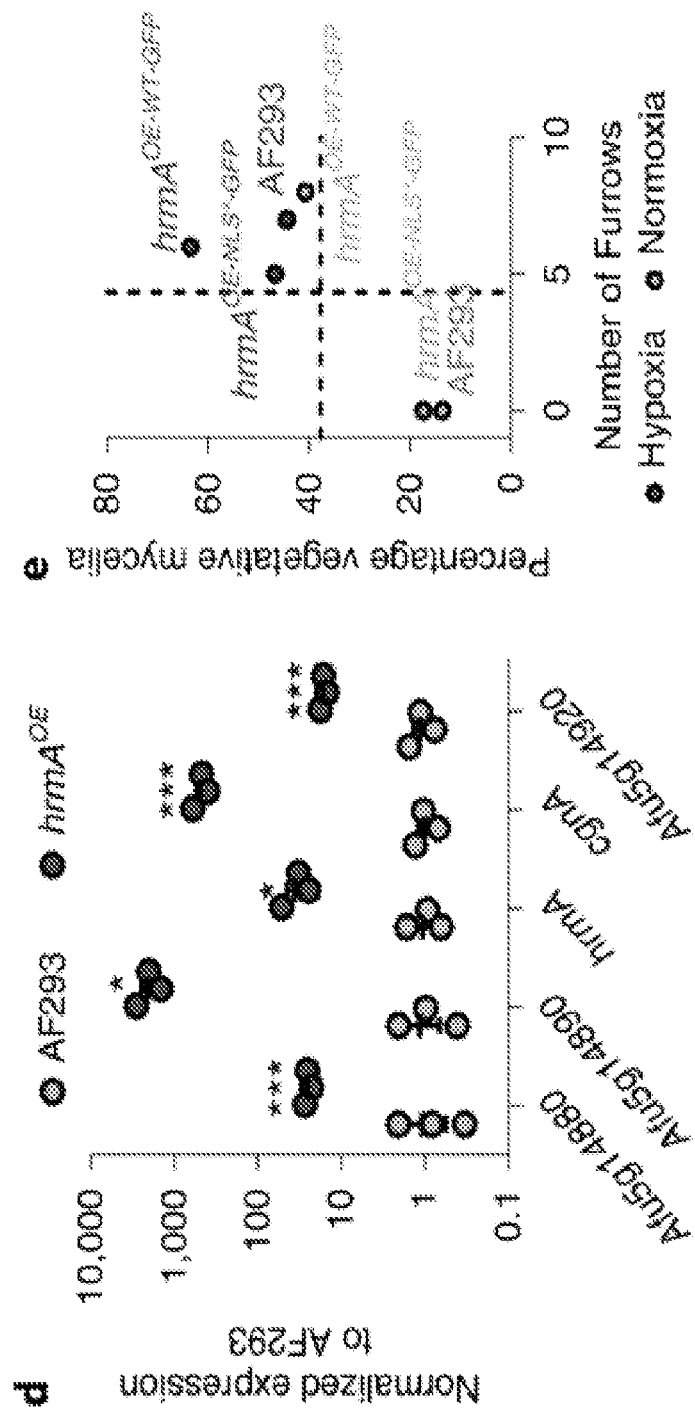
Figure 9:
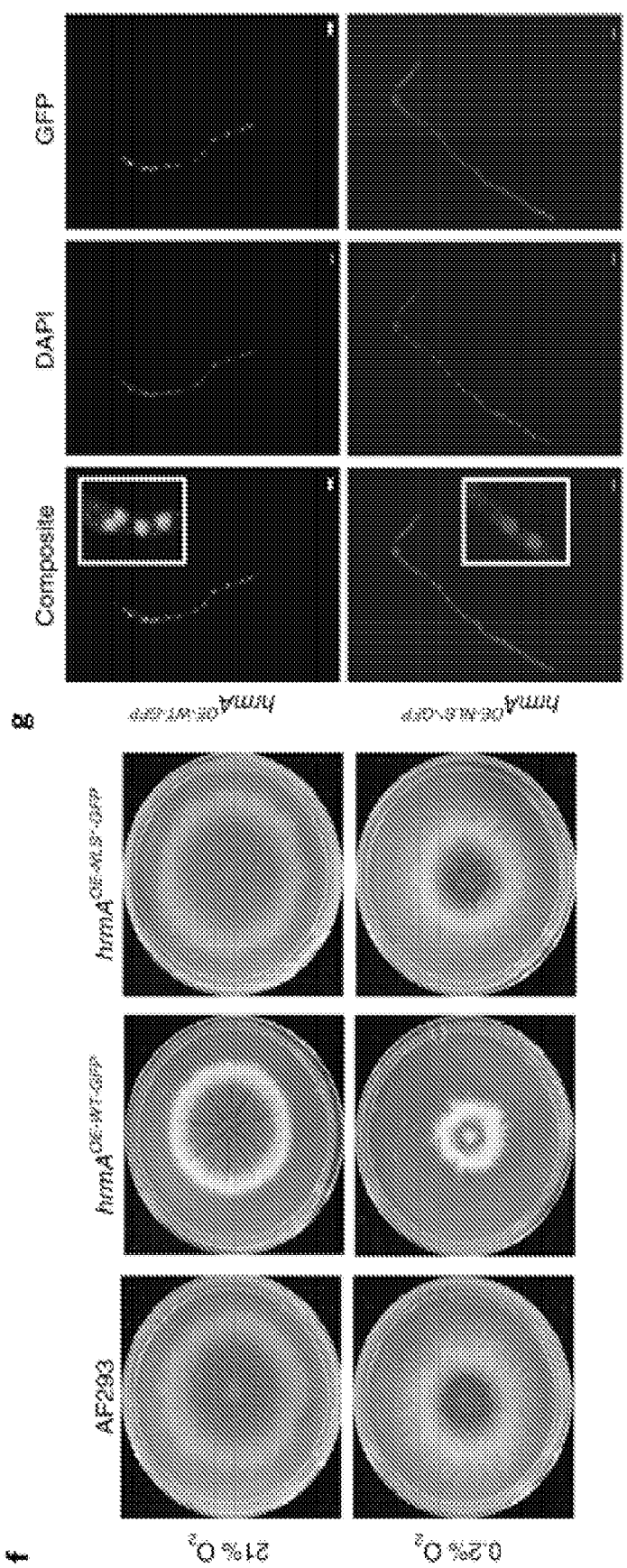
Figure 9:
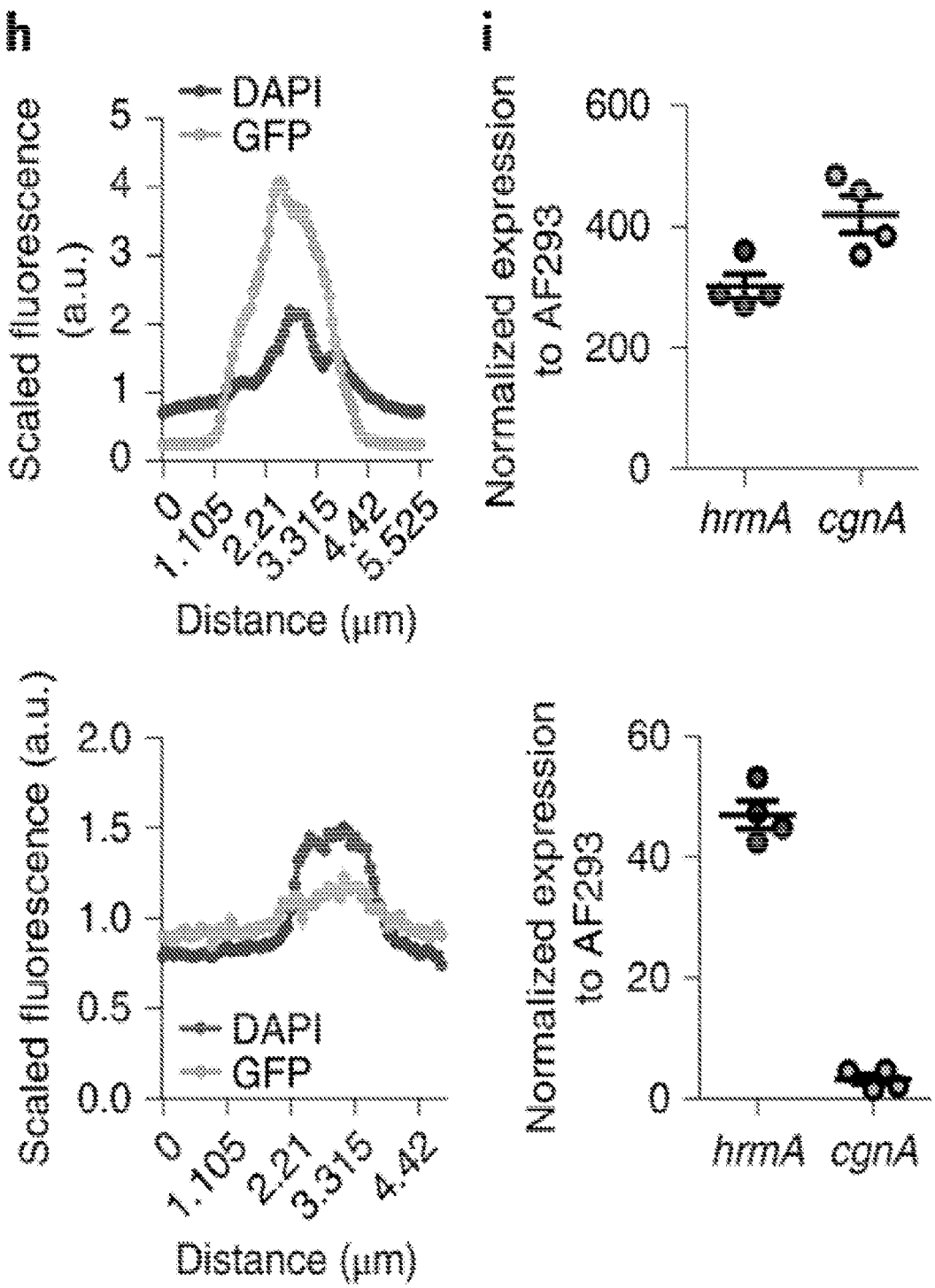
Figure 10:
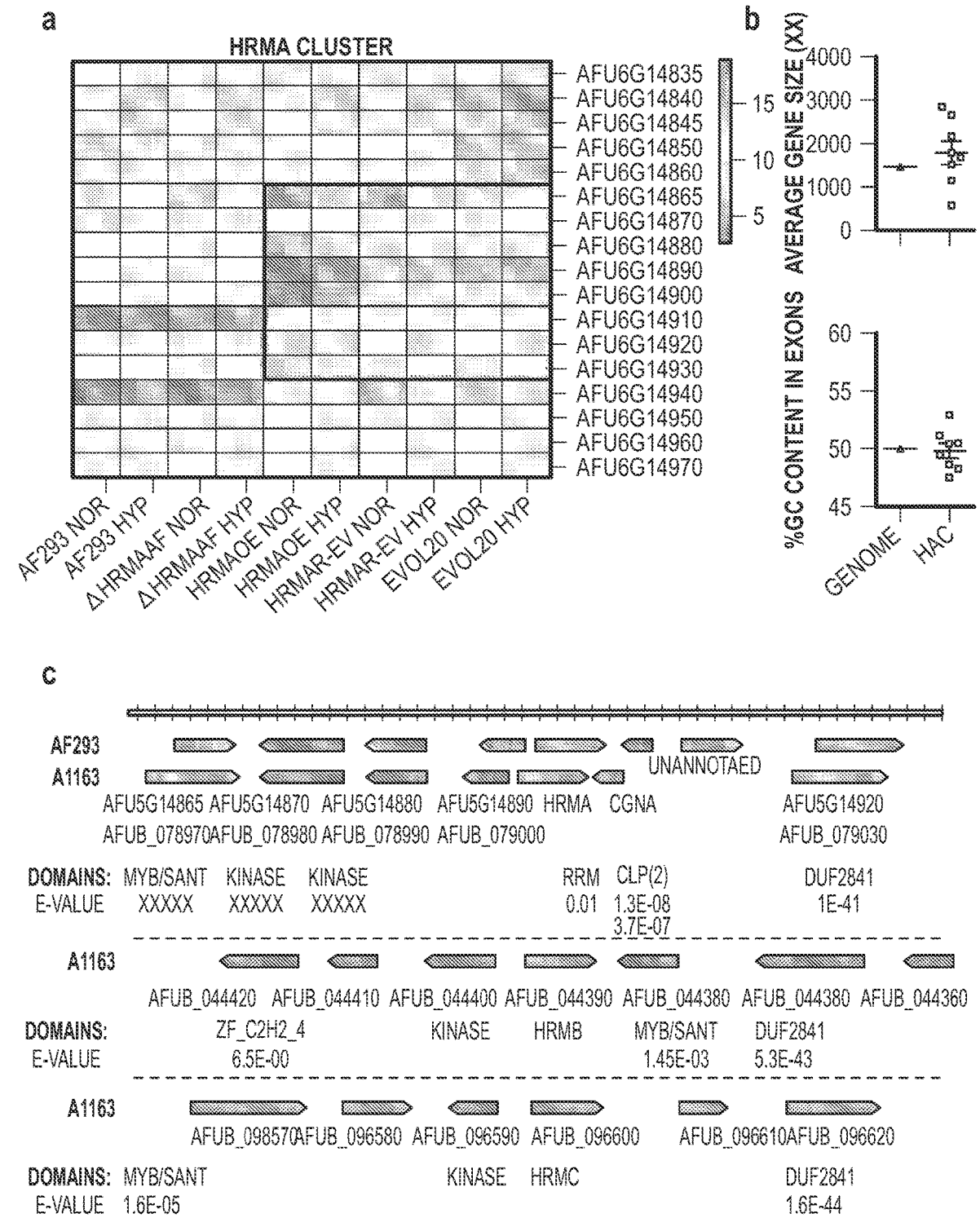
FIG. 10 depicts that HAC is conserved in A1163, a strain that additionally encodes 2 putative orthologous gene clusters.

HrmA is Induced During Murine Pulmonary Aspergillosis and Facilitates the Expression of a Sub-Telomeric Gene Cluster Previous reports suggest increased hrmA expression in vivo in a triamcinolone murine model of IA (Kale et al. Sci Rep 7, 17096, (2017). In that model, hrmA transcript levels significantly increase from 24 to 72 hours post fungal inoculation (hpi) (FIG. 9a). An increase in hrmA transcript in hrmA$^{R-Ev}$ (at the native locus) is also observed (FIG. 9b). HrmA is a member of a sub-telomeric gene cluster that responds to nitrogen starvation, a laboratory condition that transcriptionally correlates with a host-adaptation transcriptional response (McDonagh et al. PLoS Pathog 4, e1000154, 2008). Consistent with the assignment of hrmA to a sub-telomeric gene cluster, an influence of hrmA on transcript levels of genes surrounding its native locus was observed, termed here the hrmA associated cluster (HAC). In ΔhrmA$^{EV}$ the mRNA levels of three surrounding genes (Afu5g14880, Afu5g14890, Afu5g14910) are significantly reduced compared to EVOL20 (FIG. 9c). Ectopic overexpression of the AF293 allele of hrmA (hrmA$^{OE}$) acts in trans to facilitate an increase in transcripts of four HAC genes (Afu5g14880, Afu5g14890, Afu4g14910, Afu5g14920) (FIG. 9d).

Analysis of co-regulated transcripts from RNA-sequencing predicts that HAC extends from Afu5g14865 to Afu5g14920, and includes a putative unannotated ORF 3' to Afu5g14910 (Supplementary FIG. 10a, FIG. 10c). The average gene size and % GC content of HAC is not different from the AF293 genomic average (FIG. 10b) (Fedorova et al. PLoS Genet 4, e1000046, 2008); but in the hypoxia-fit strain A1163 (Kowalski 2016, supra), there is a sub-telomeric HAC that is syntenic to AF293 HAC and two additional putative homologous clusters that are not present in AF293 (FIG. 10c). The presence of these potential homologous clusters in a distantly related A. fumigatus strain suggests intragenomic movement of this genomic region. The clusters share certain genic components including genes encoding a MyB/SANT domain, a kinase domain, a DUF2841 domain, and putative hrmA paralogs (hrmB: AFUB_044390, hrmC: AFUB_096600). Analysis of HAC across sequenced strains indicates heterogeneous abundance of the original and homologous gene clusters (FIG. 4, alignment: https://github.com/stajichlab/Afum_hrmA_cluster_evolution; DOI: potentially highlighting a role for these homologous clusters in H-MORPH generation where HAC is absent. Other Ascomycetes encode genes similar to hrmA, including the human fungal pathogens Histoplasma capsulatum and Coccidioides immitis (http s://gi thub.com/staj ichlab/A fum_hrmA_clusterevoluti on).

HrmA Nuclear Localization is Necessary for the Induction of HAC

The HrmA protein sequence reveals a predicted N-terminal bipartite nuclear localization signal (NLS) (http://nls-mapper.iab.keio.ac.jp/) and a weakly predicted RNA Recognition Motif (RRM) domain (E-value: 0.01) (FIG. 11a). Overexpression of the parental allele of hrmA with a C-terminal GFP tag in AF293 generates oxygen-independent H-MORPH (FIG. 9e, FIG. 9f). In contrast, over expression of hrmA with a disrupted NLS is unable to generate H-MORPH (FIG. 4e, FIG. 4f) despite elevated levels of hrmA transcript (FIG. 9i). Confocal imaging reveals GFP signal enriched in the same location as the nuclear DAPI stain for the WT allele but a lack of this enrichment for the NLS mutant (FIG. 9g, FIG. 9h). Without localization to the nucleus or nuclear region, HrmA is unable to facilitate HAC induction as shown by the cluster gene cgnA (Afu5g14910) (FIG. 9i).

Despite low sequence similarity in the alignment to the RRM domain in HrmA, there are two conserved phenylalanine residues within this domain that are also present within hrmB and hrmC in strain A1163. When these conserved phenylalanine residues are each mutated to alanine, overexpression of this allele cannot generate H-MORPH despite observing hrmA nuclear region localization (FIG. 11b, FIG. 11c, FIG. 1id). Aromatic residues are critical in many RRM protein structures for direct interaction with nucleic acids (Law et al. Nucleic Acids Res 33, 2917-2928, 2005).

H-MORPH is Generated Through HrmA-Mediated Induction of HAC

Figure 6:
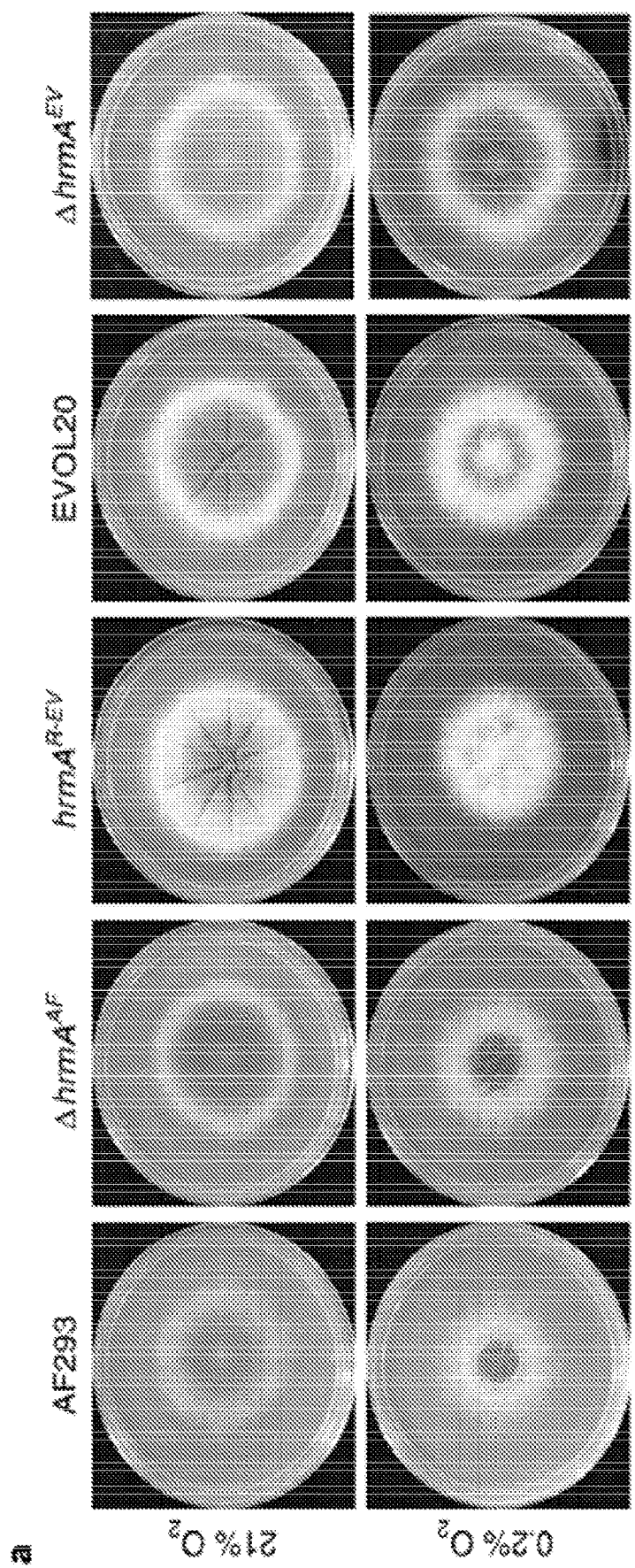
FIG. 6 depicts that the hypoxia-evolved allele of the sub-telomeric gene hrmA is sufficient to generate H-MORPH and collapse biofilm architecture.
Figure 6:
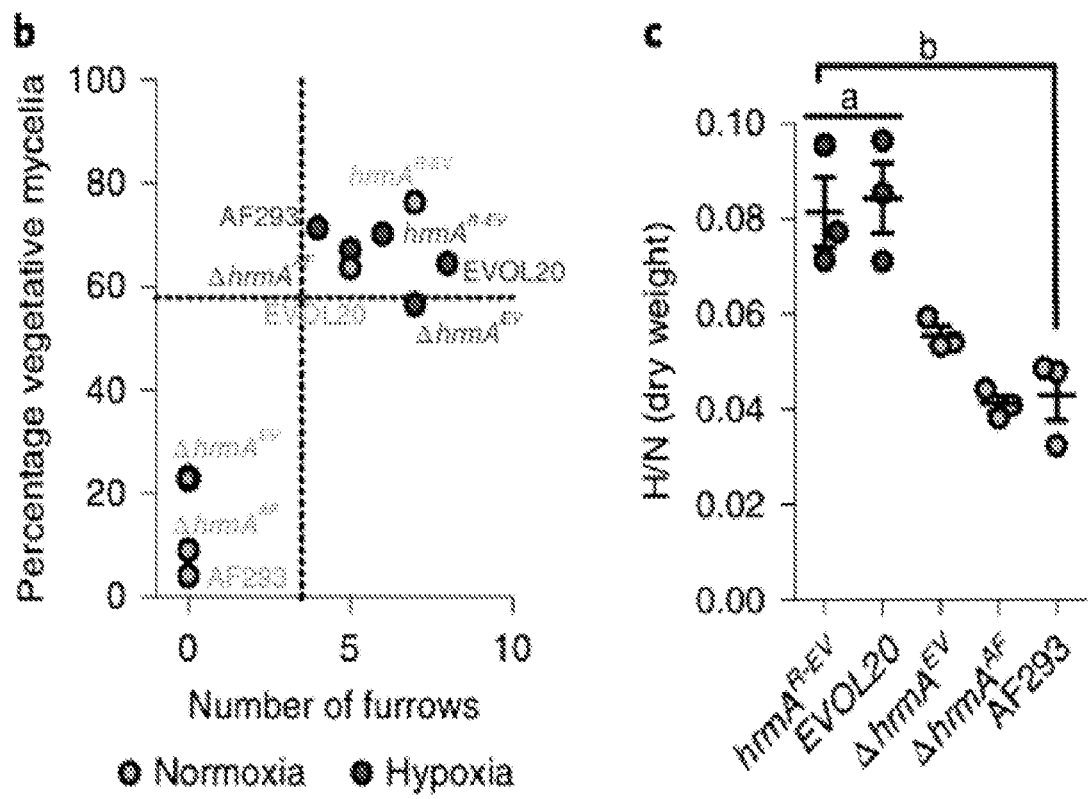
Figure 6:
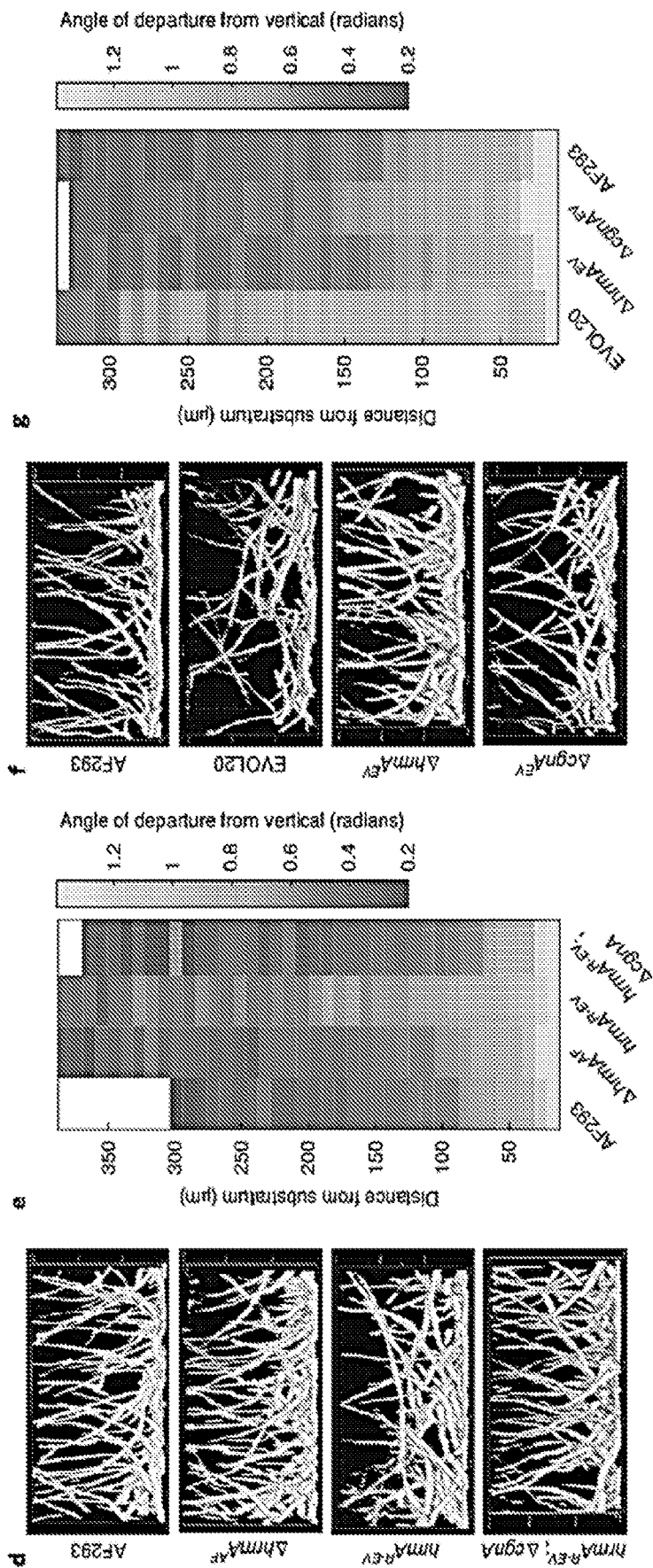
Figure 11:
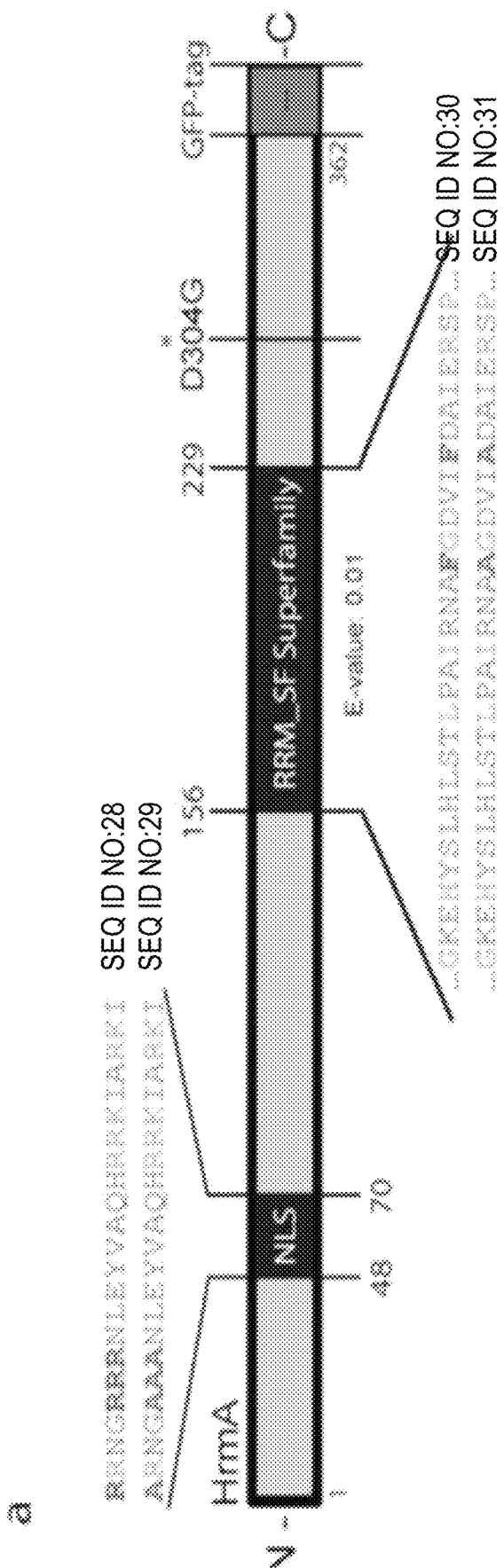
FIG. 11 depicts that HrmA has a RNA recognition motif (RRM) with two conserved phenylalanine residues necessary for H-MORPH.
Figure 11:
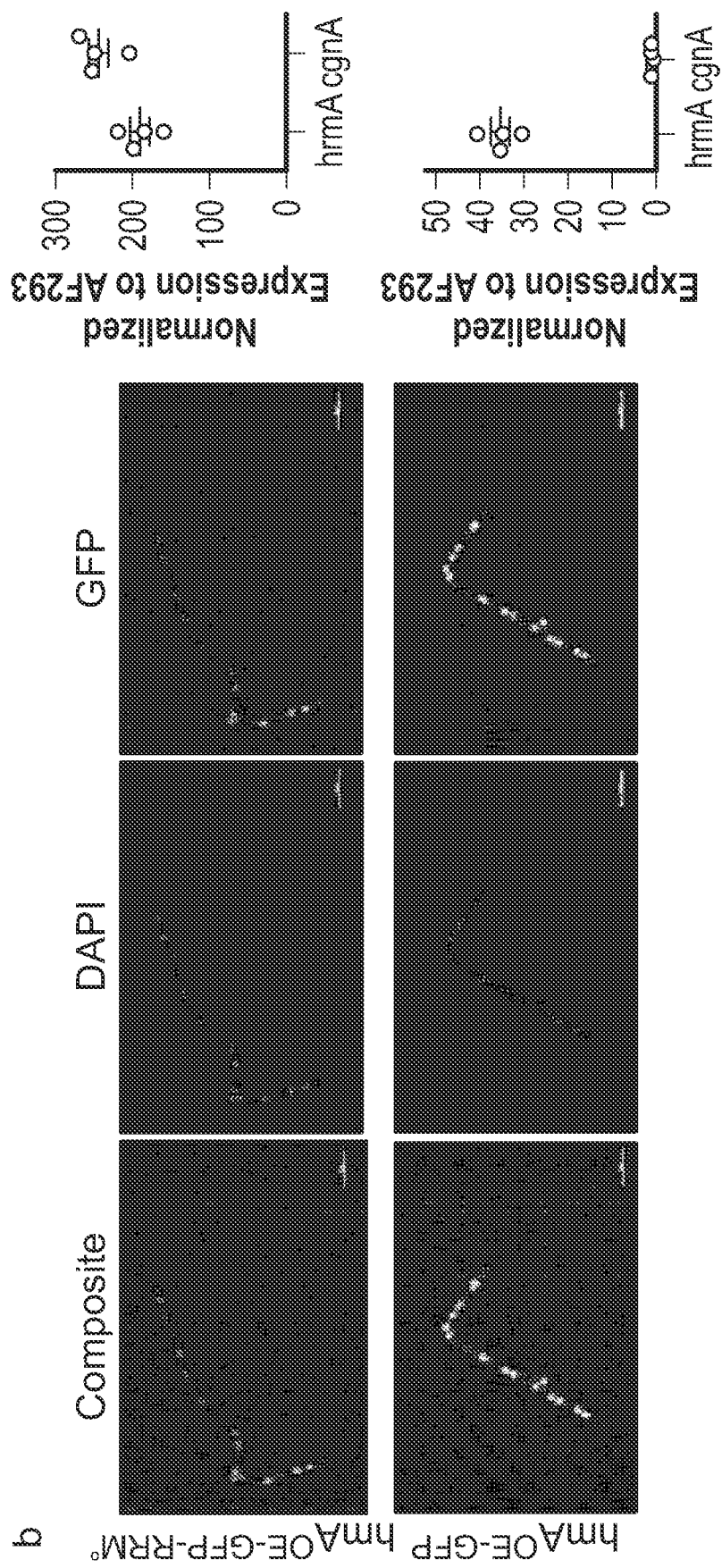
Figure 11:
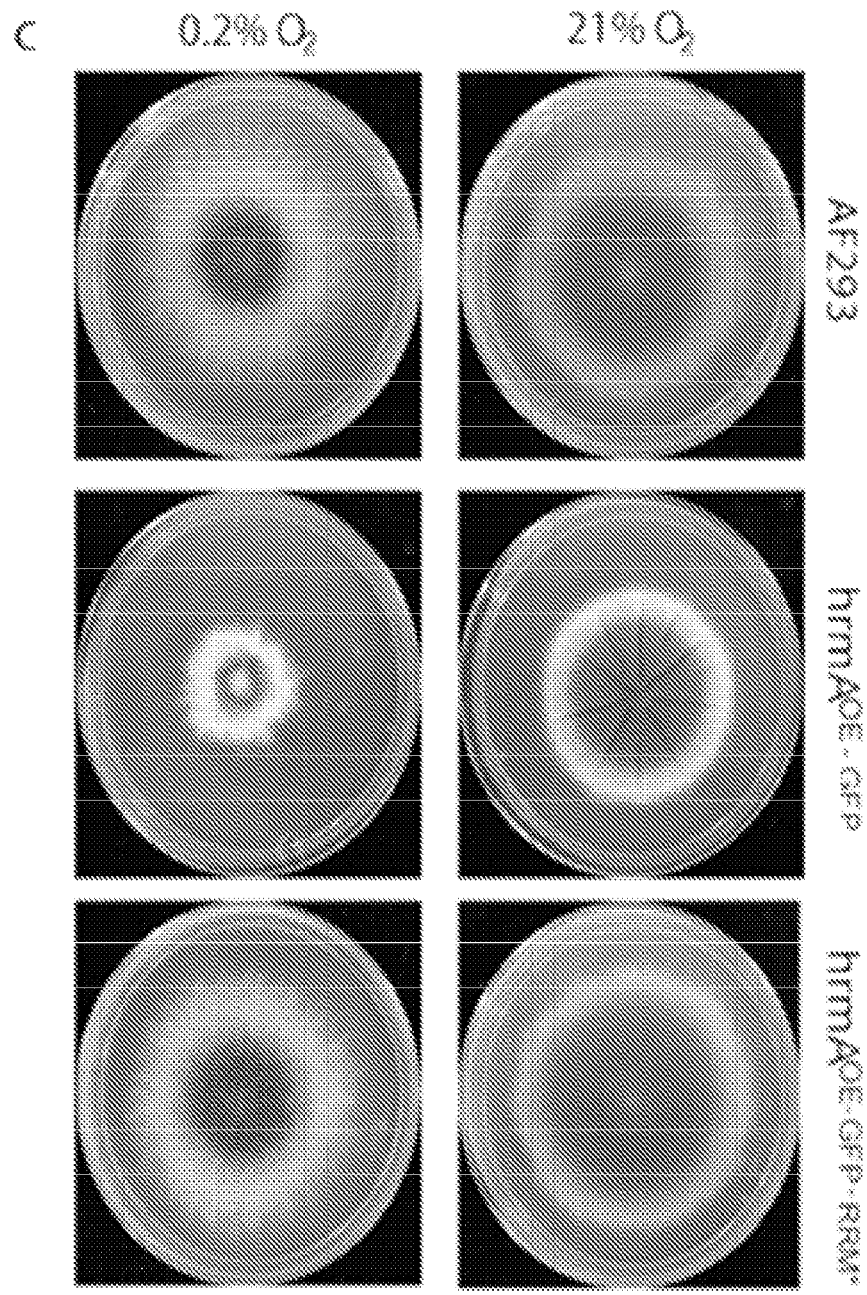
Figure 11:
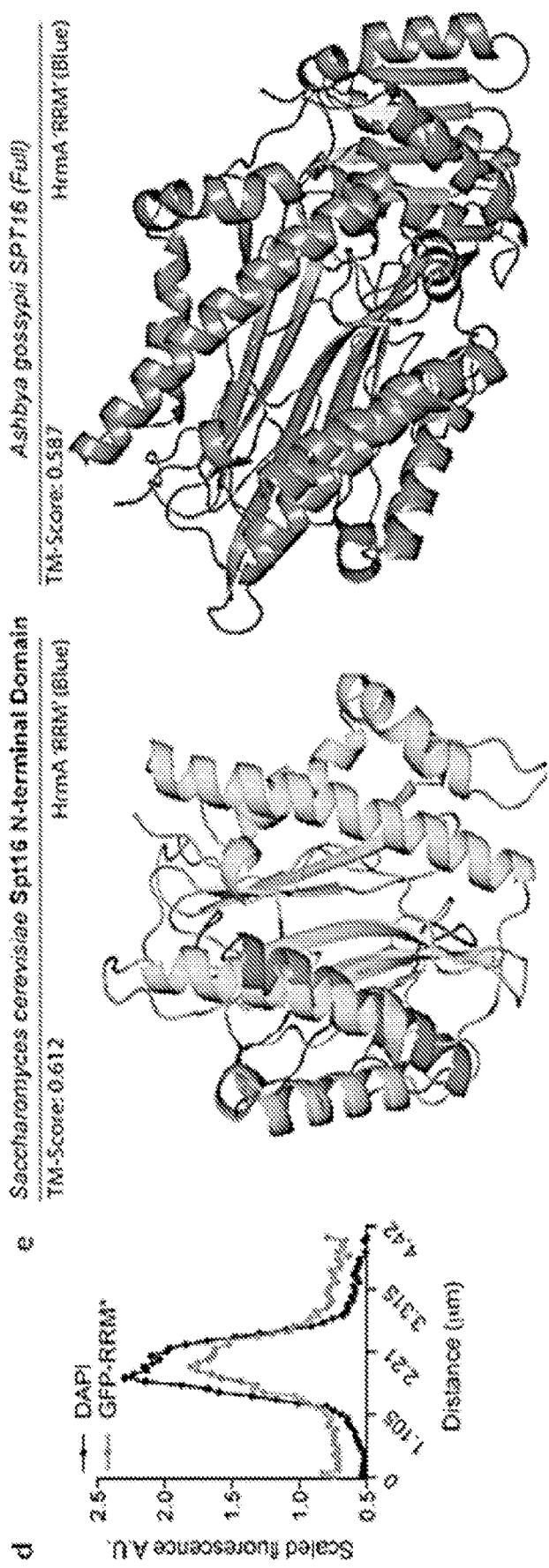
Figure 12:
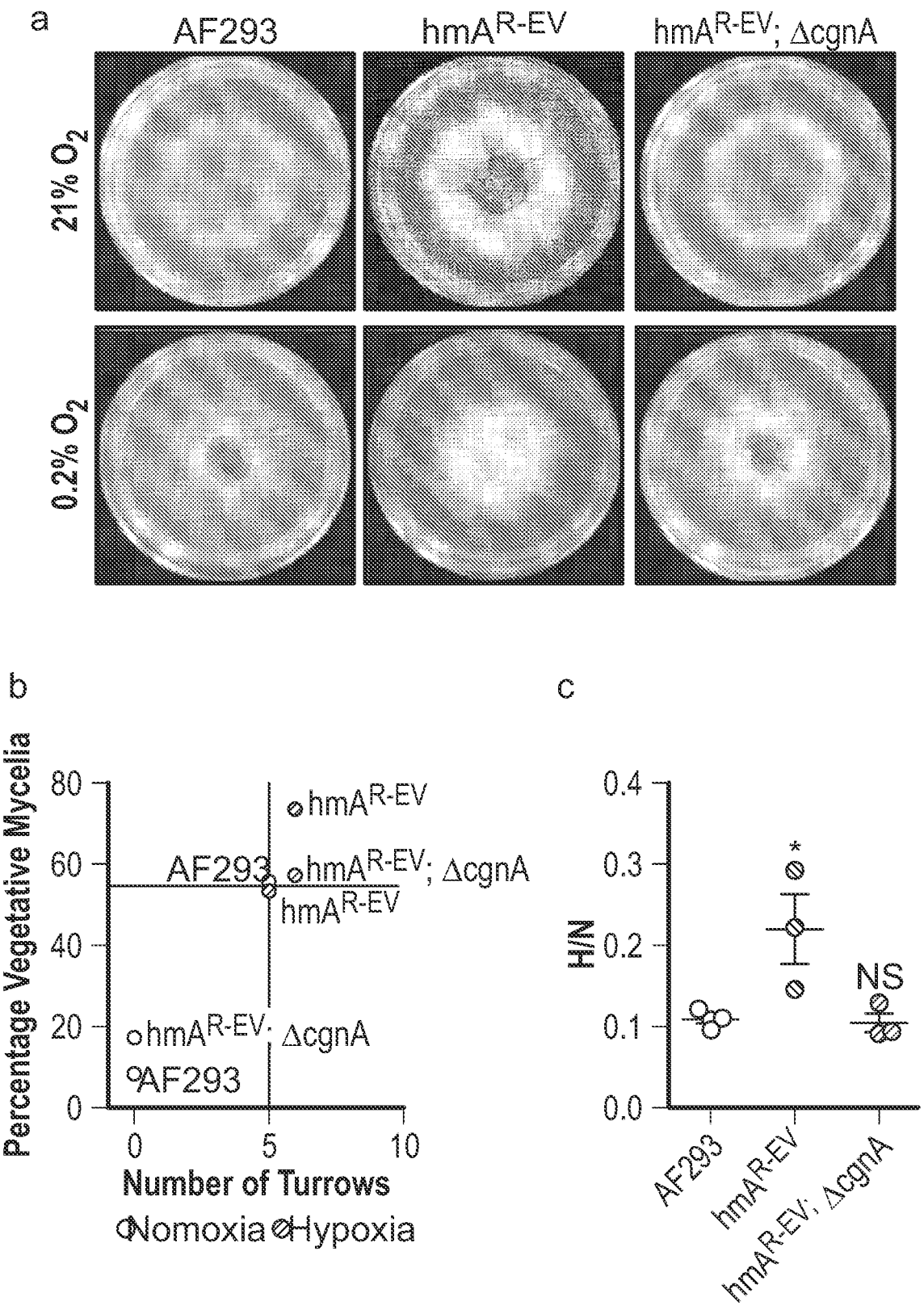
FIG. 12 depicts that HrmA-facilitated induction of the surrounding sub-telomeric gene cluster leads to increased hypoxia fitness and a modified hyphal surface.
Figure 12:
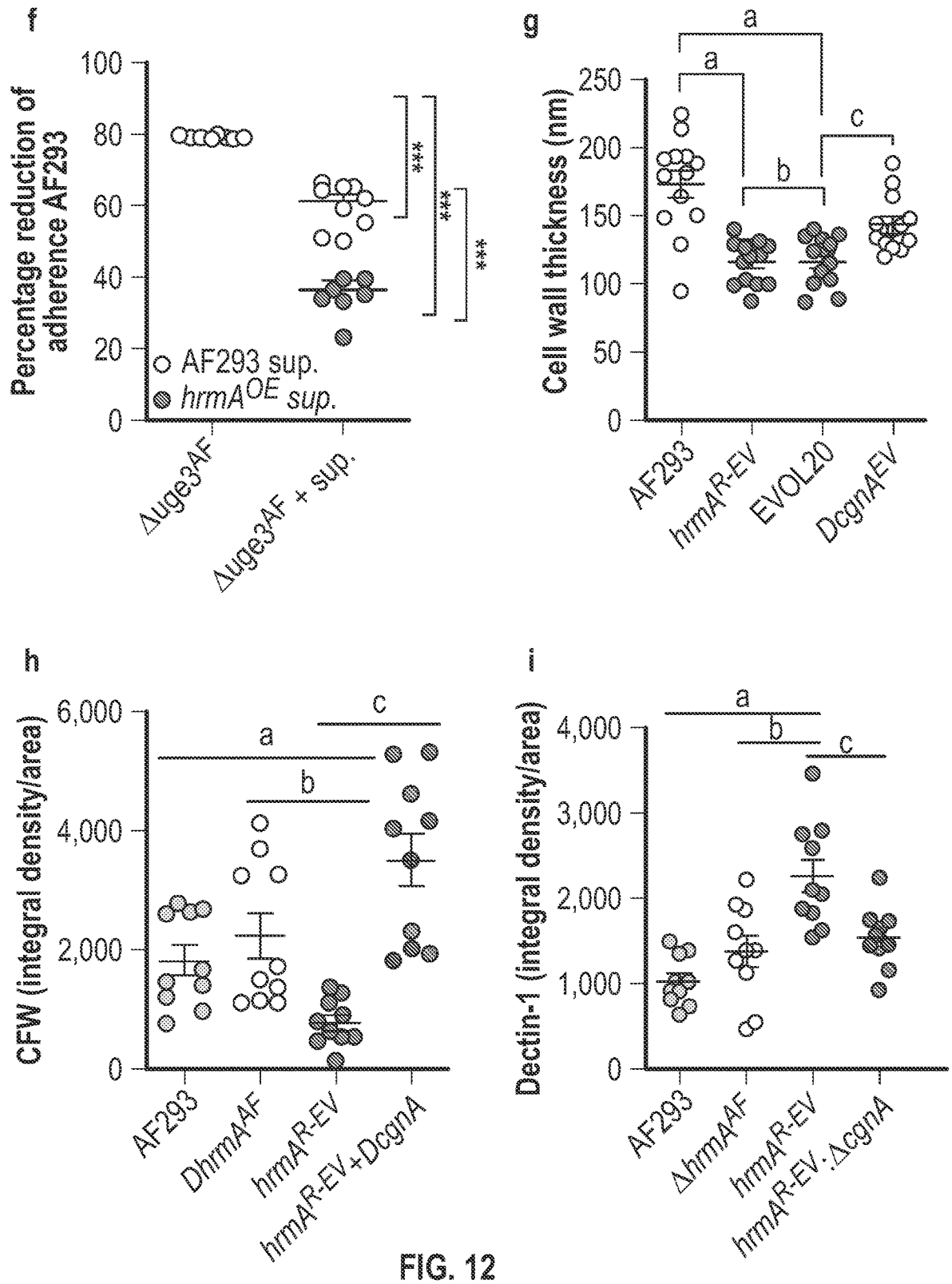
Figure 13:
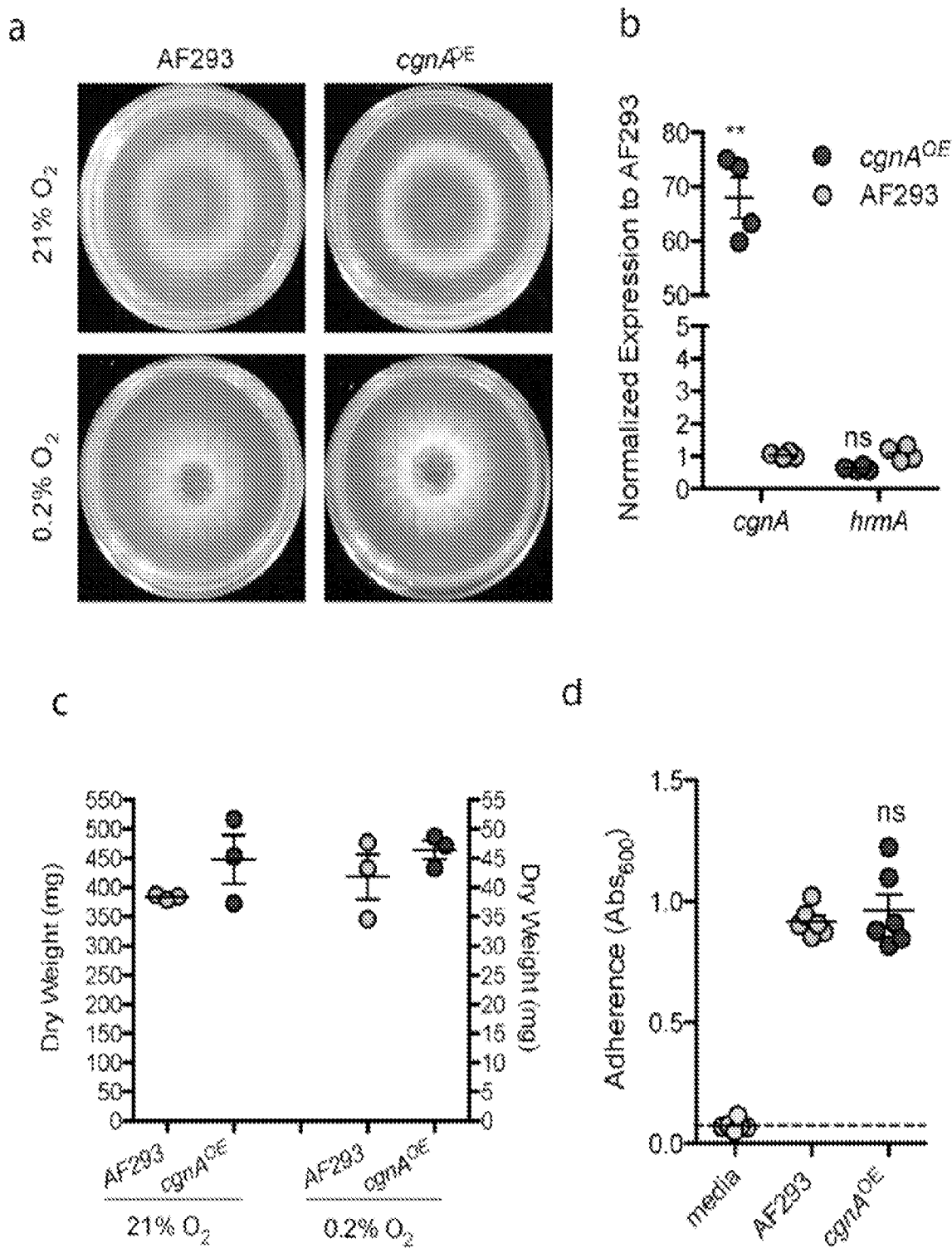
FIG. 13 depicts that overexpression of cgnA alone is not sufficient to generate H-MORPH.

Loss of HAC induction abolishes H-MORPH indicating HAC is necessary for this morphotype and increased hypoxia fitness (FIG. 12, FIG. 11). Expression of the HAC gene Afu5g14910, cgnA, is an indicator of HrmA downstream effects and encodes a predicted collagen-like protein (CLP), a class of proteins present but unstudied in other fungi. In *A. fumigatus*, CgnA has a tripeptide G-X-Y repeat of G-Q-I and G-Q-S, and lacks a canonical secretion signal. Despite induction of cgnA greater than 100-fold relative to AF293 in hrmA$^{OE}$. (FIG. 9d; morphology FIG. 13e), comparative levels of cgnA over expression in the absence of elevated hrmA (cgnA$^{OE}$). does not induce H-MORPH nor alter the hypoxic growth of AF293 (FIG. 13). Loss of cgnA in the context of elevated HAC abolishes H-MORPH, indicating a role for cgnA, and possibly other HAC genes, in the generation of H-MORPH (FIG. 12a, FIG. 12b; FIG. 13e). Loss of cgnA in HAC-induced strains EVOL20, and hrmA$^{R-Ev}$ reduces the hypoxia fitness of these strains (FIG. 12c, FIG. 130, and restores the N-MORPH biofilm architecture and filament alignment to that of AF293 (FIG. 6).

Figure 14:
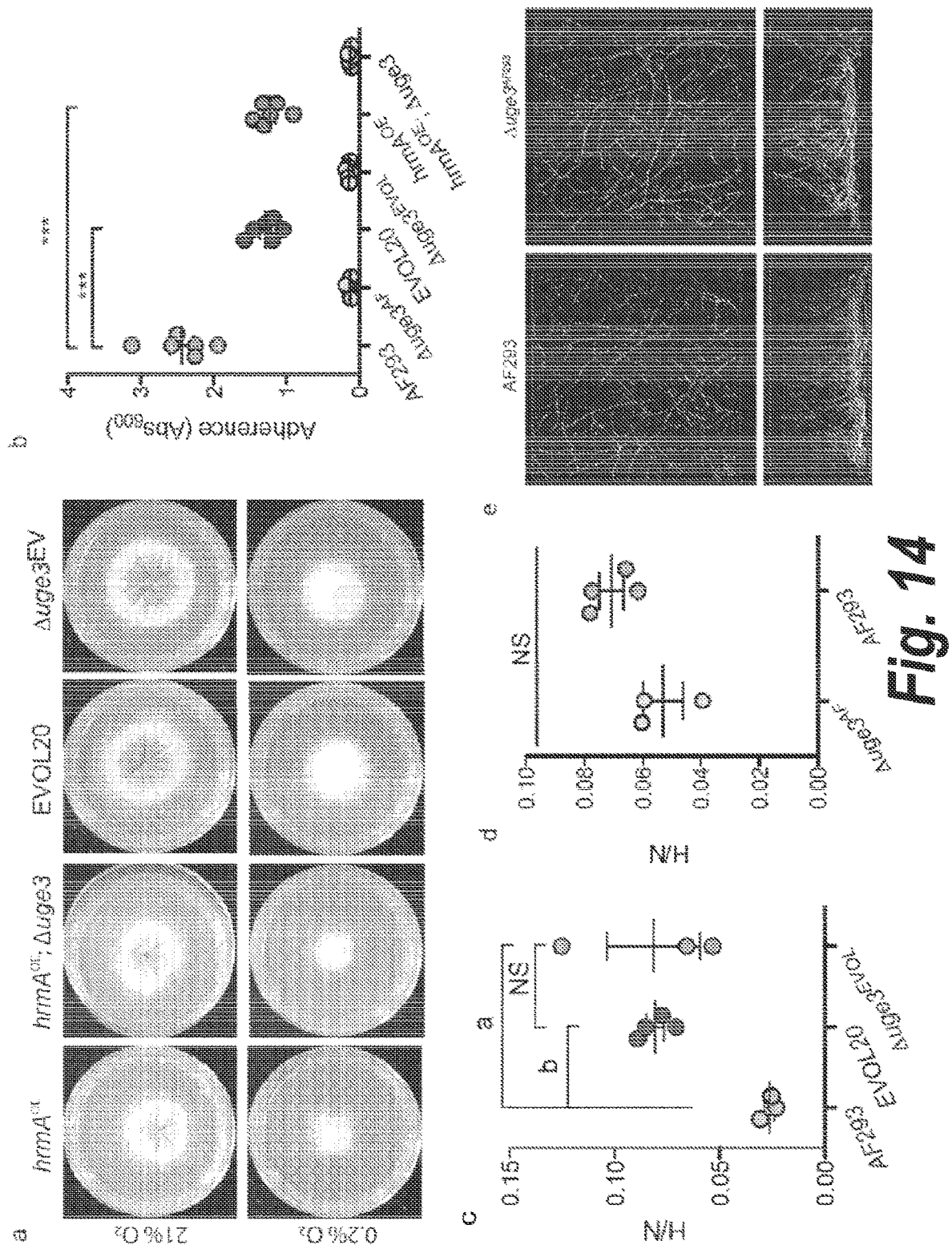
FIG. 14 depicts that loss of uge3 does not impact H-MORPH or hypoxia fitness. Deletion of uge3 from hrmA$^{OE}$ or EVOL20 does not impact the macroscopic H-MORPH (representative of 3 independent experiments) (FIG. 14a), but as expected reduces adherence of the strains (n=6 independent biological samples, ***: p<0.0001 One-way ANOVA with Dunnett multiple comparisons test) (FIG. 14b).

To further characterize the role of cgnA and HAC in the generation of H-MORPH, the features of the hyphal surface were assessed, as surface alteration and adhesion are associated with other microbial CLPs (Abdel-Nour et al. Appl Environ Microbiol 80, 1441-1454, 2014; Chen et al. BMC Microbiol 10, 320, 2010; Wang et al. Proc Natl Acad Sci USA 103, 6647-6652, 2006). Loss of cgnA and regeneration of N-MORPH increases surface adherence of H-MORPH strains (FIG. 12d), likely the consequence of ECM detachment from the H-MORPH strains (Supplementary FIG. 13g, FIG. 12e) that is dependent on cgnA. In the clinical strains IFM 59356-1 (N-MORPH) and IFM 59356-3 (H-MORPH), matrix detachment and reduced surface adherence is observed in H-MORPH (FIG. 5d, FIG. 5e). Matrix detachment from the H-MORPH filaments is not a defect in ECM production as it is still visibly secreted into the biofilms (FIG. 12e). A significant component of the ECM is galactosaminogalactan (GAG), and loss of GAG through deletion of the UDP-Glucose-4-epimerase uge3 abolishes surface adherence. Chemical modifications of GAG also prevents attachment of matrix to the hyphae, so the ability of secreted GAG from hrmA$^{OE}$. to complement the adherence defect of the GAG deficient strain Δuge3$^{AF}$ was investigated. Culture supernatants containing secreted GAG from AF293 and hrmA were both able to significantly increase adherence of Δuge3$^{AF}$ (FIG. 12O). These data suggest that HAC/cgnA modifies the hyphal surface mediating matrix/GAG detachment. To determine if GAG secretion was necessary for H-MORPH, uge3 deletions in hrmA$^{OE}$ and EVOL20 were generated; as a result, CM did not change but surface adherence was abolished (FIG. 14a, FIG. 14b). Loss of GAG production in AF293 does not impact hypoxia fitness nor the biofilm architecture (Supplementary FIG. 14d, FIG. 14e).

Figure 15:
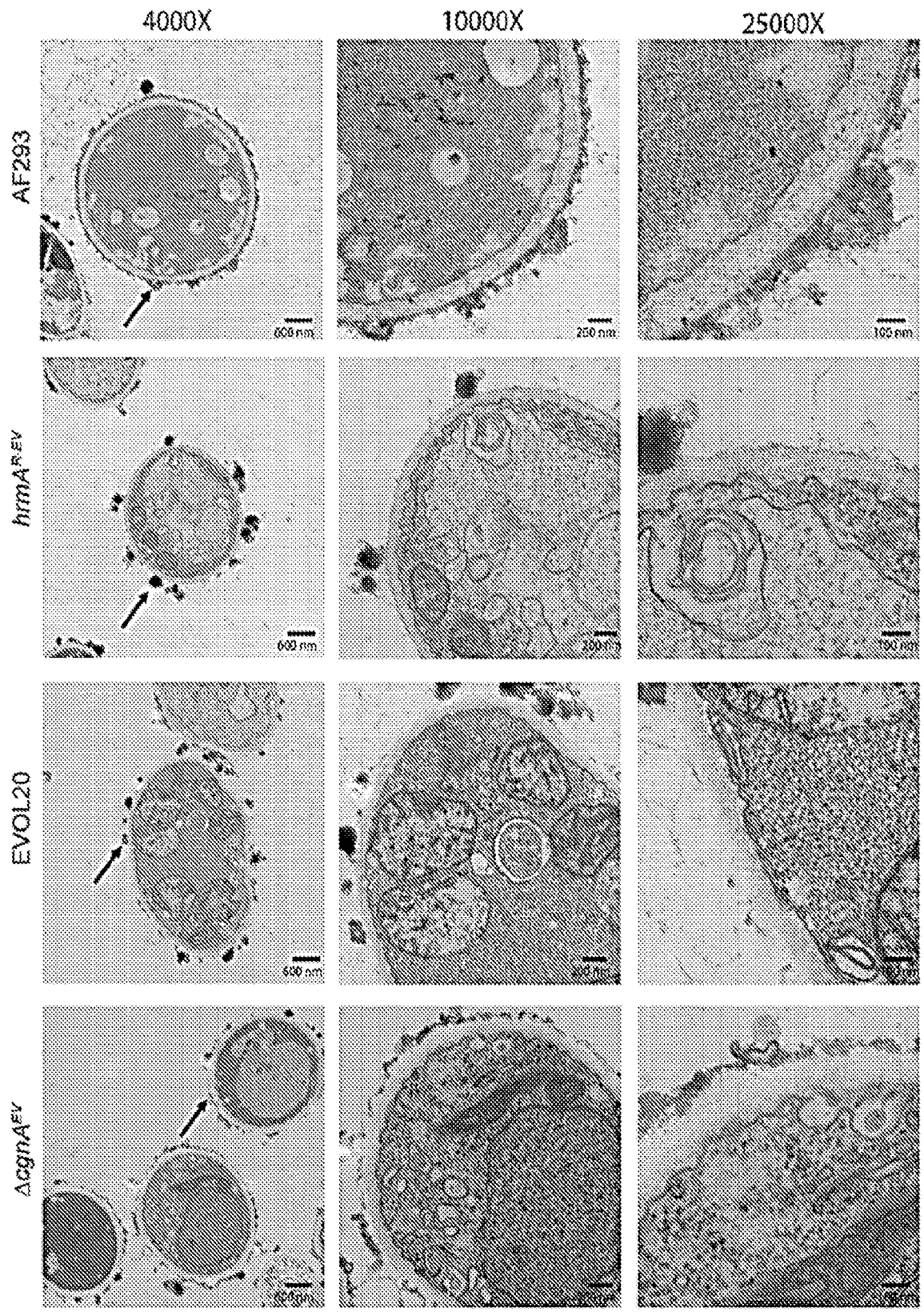
FIG. 15 depicts representative TEM images used for cell wall thickness analysis. Black arrows indicate electron-dense material presumed to be the extracellular matrix that is aggregated in the hrmA$^{R-Ev}$ and EVOL20 H-MORPH strains. Scale bars for 4000× images are 600 μm, for 10000× images are 200 μm, and for 25000× images are 100 pm. Images are representative of 13 biologically independent samples from 2 biologically independent experiment.
Figure 16:
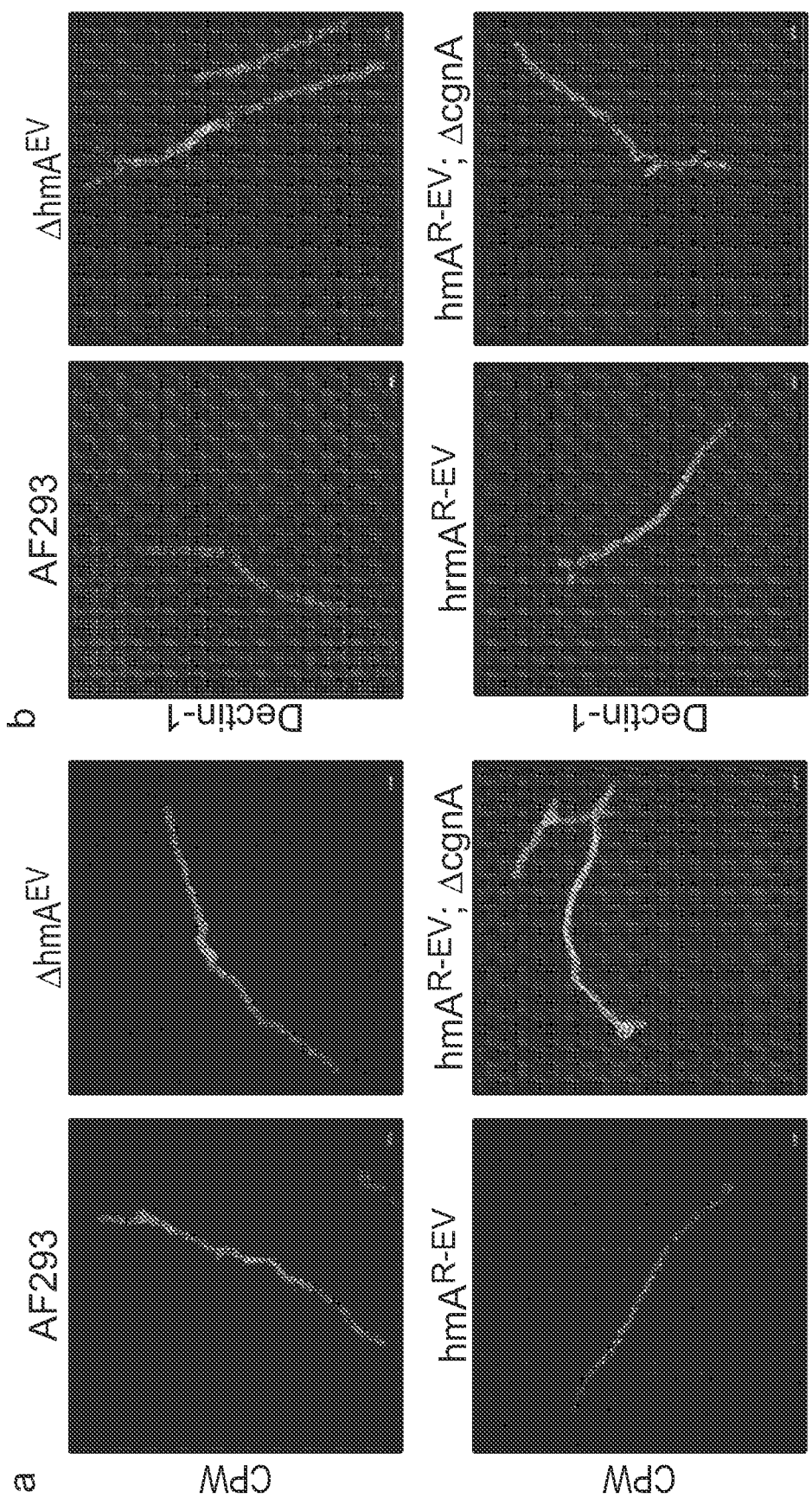
FIG. 16 depicts cell wall staining and cell wall perturbing agents.
Figure 16:
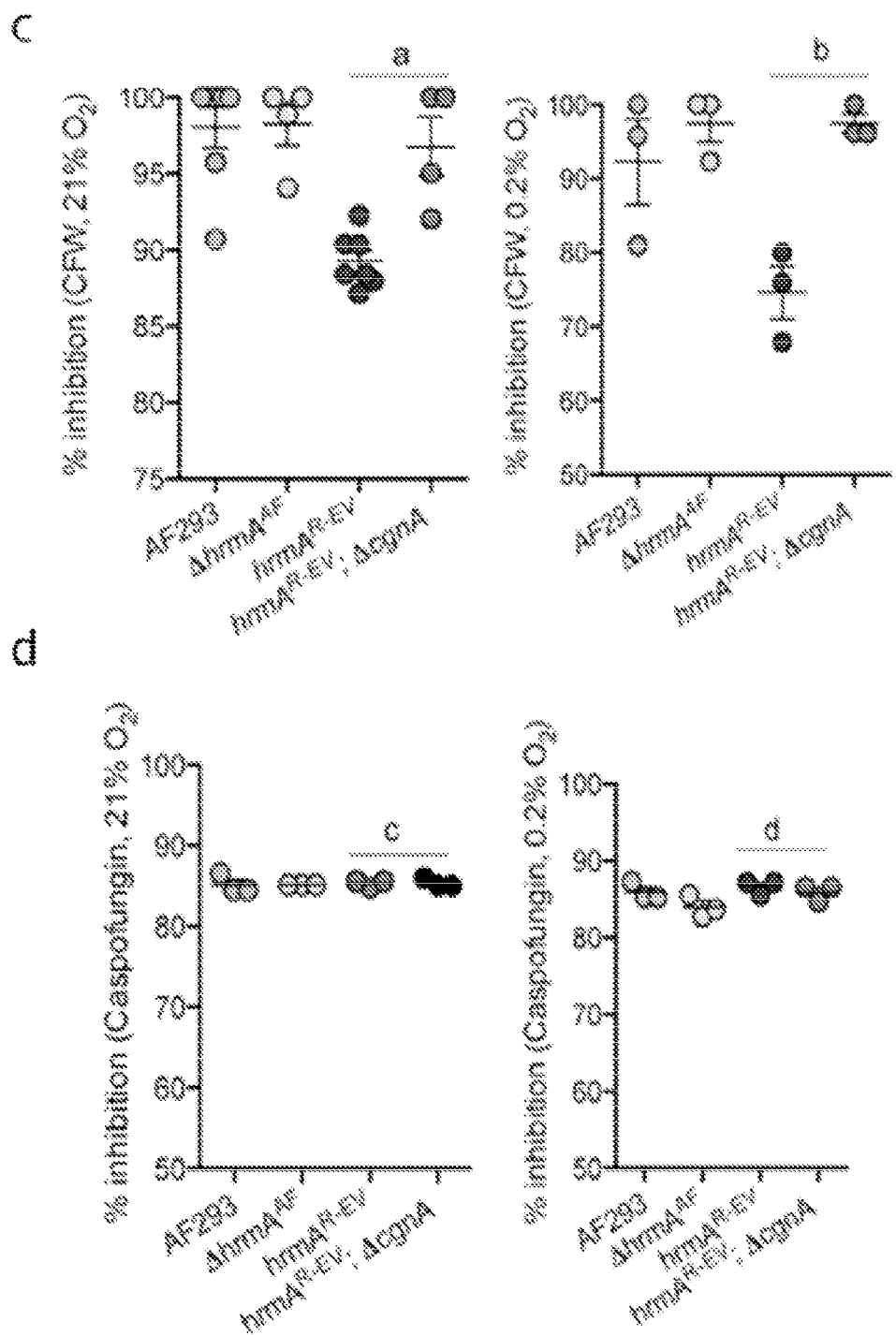

H-MORPHs hrmA$^{R-Ev}$ and EVOL20 have significantly thinner cell walls than the N-MORPH AF293, and in EVOL20 this is dependent on cgnA (FIG. 12g, FIG. 15). To determine if the cell wall architecture is altered, we imaged cell wall components through the use of calcofluor white (CFW) for chitin detection and soluble Dectin-1 for 13-glucan detection. H-MORPH hrmA$^{R-Ev}$ has reduced total chitin that is dependent on the induction of cgnA (FIG. 12h, FIG. 16a). In contrast, hrmA$^{R-Ev}$ has significantly increased cgnA-dependent β-glucan exposure (FIG. 12i, FIG. 16b). hrmA$^{R-Ev}$ is also more sensitive to growth on CFW in both normal and low oxygen compared to AF293, ΔhrmA$^{AF}$, and hrmA$^{R-Ev}$; ΔcgnA (FIG. 16c). No difference in sensitivity to the β-glucan synthase inhibitor caspofungin was observed (FIG. 16d). These surface changes appear to alter matrix attachment and inter-hyphal interactions within the developing biofilms resulting in a loss of vertically aligned polarized growing filaments.

H-MORPH Altered Biofilm Architecture Occurs In Vivo.

Figure 17:
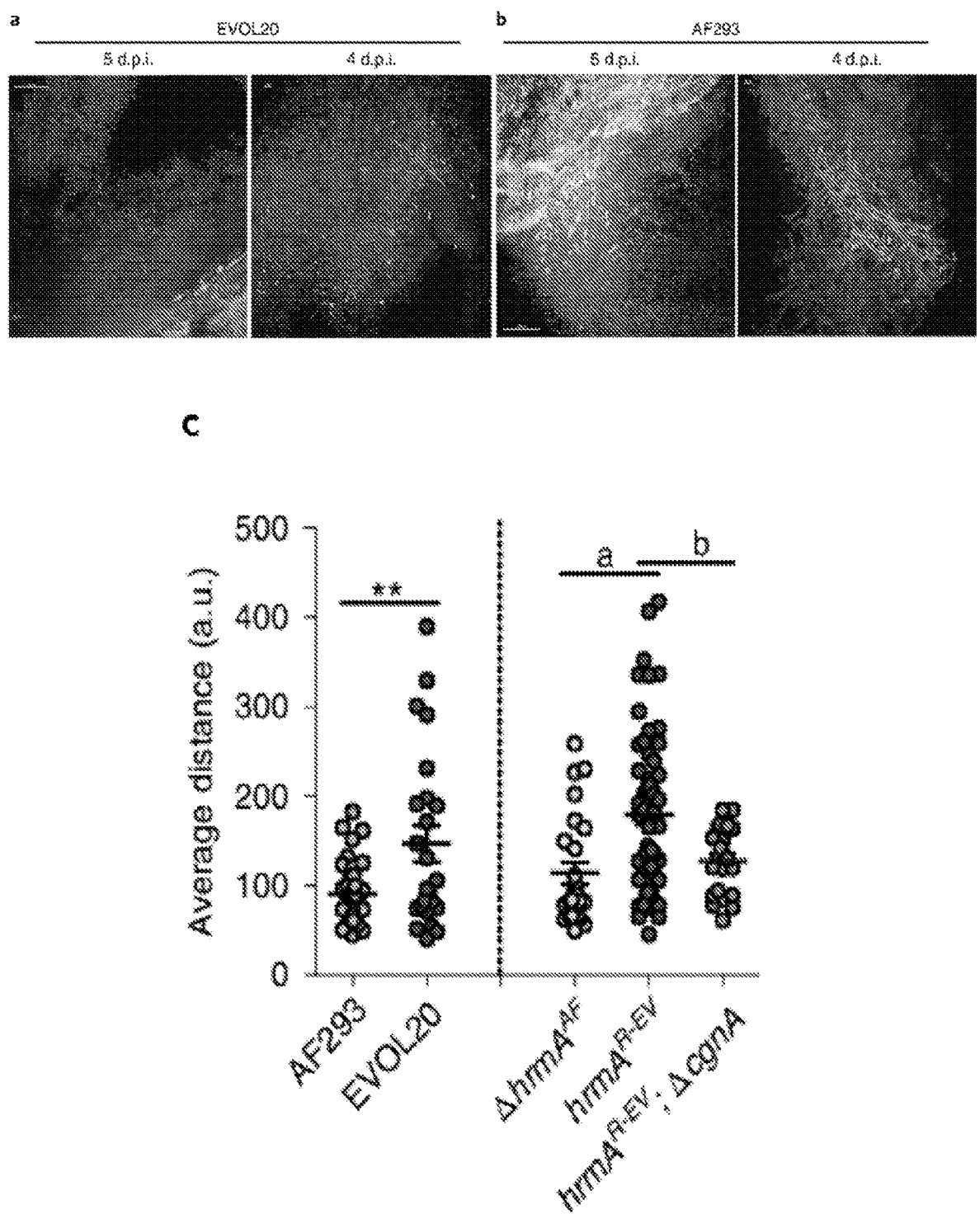
FIG. 17 depicts that H-MORPH contributes to increased virulence through increased inflammation and diffuse lesion morphology. AF293$^{tdtomato}$ (FIG. 17a) or EVOL20$^{tdtomato}$ (FIG. 17b) murine lesions stained with DAPI and FITC-SBA. Scale bars: 4 DPI: 10 μm, 5 DPI: 100 μm. Represents 5 independent animals from 2 independent preparations.
Figure 17:
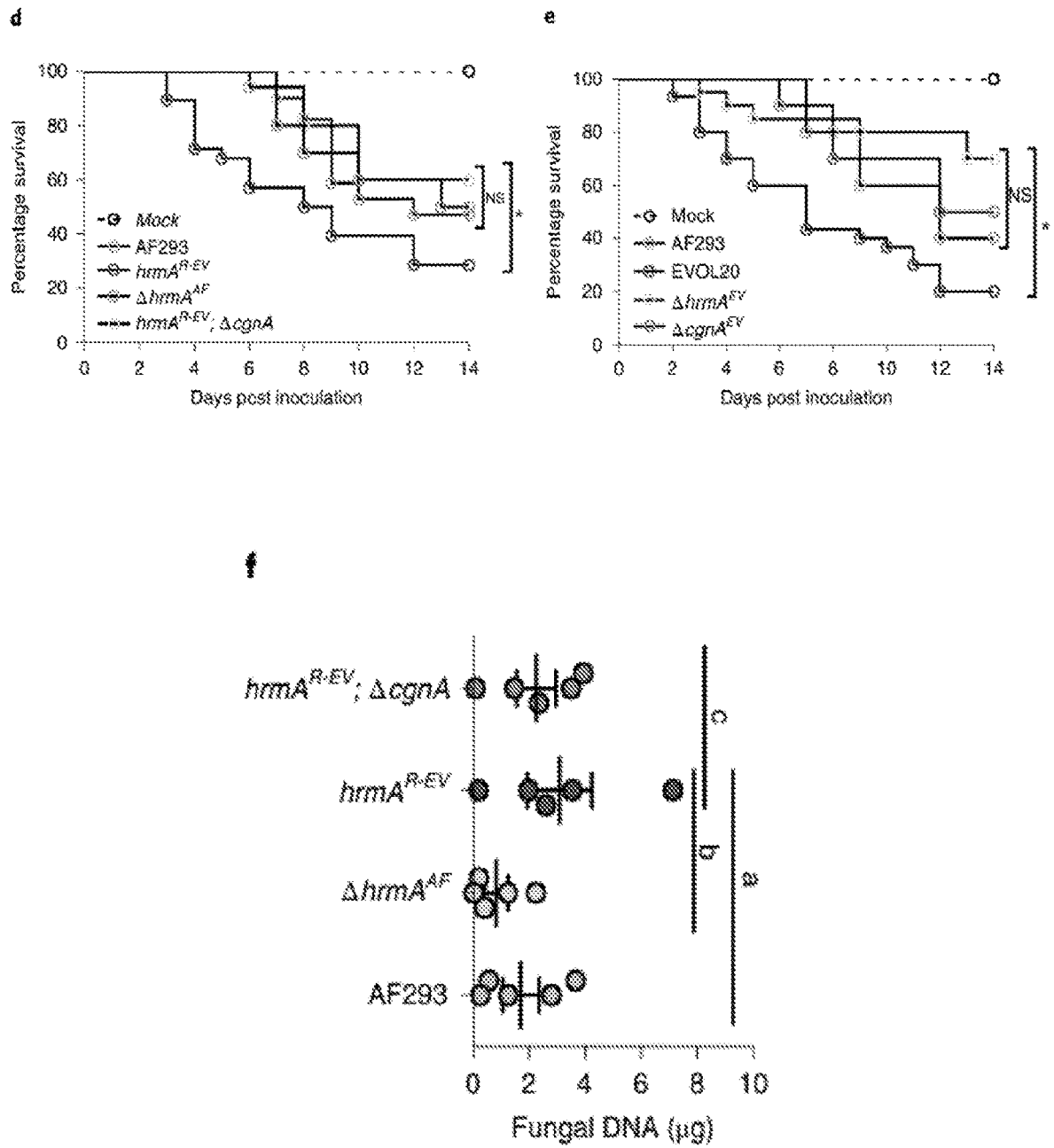
Figure 17:
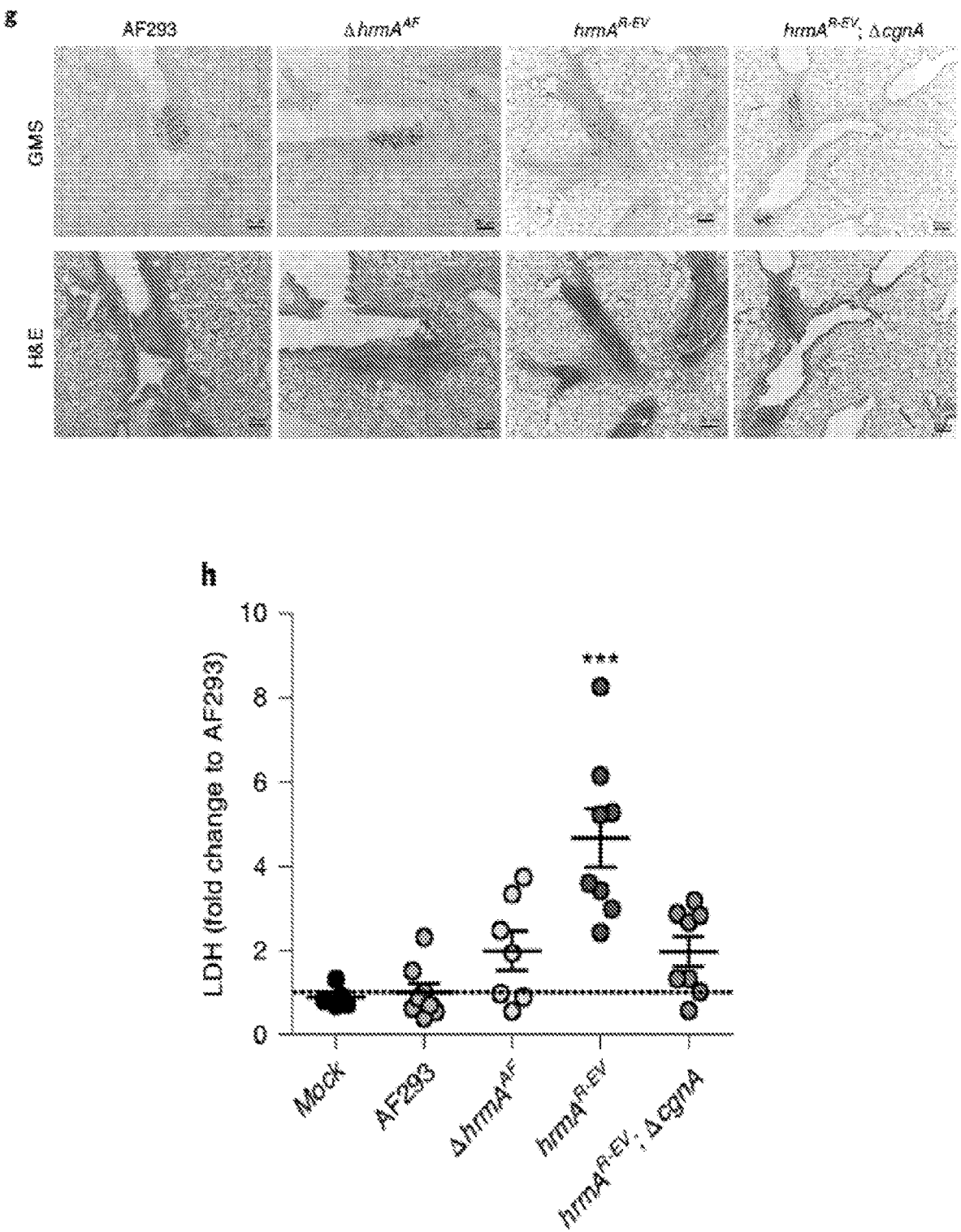
Figure 17:
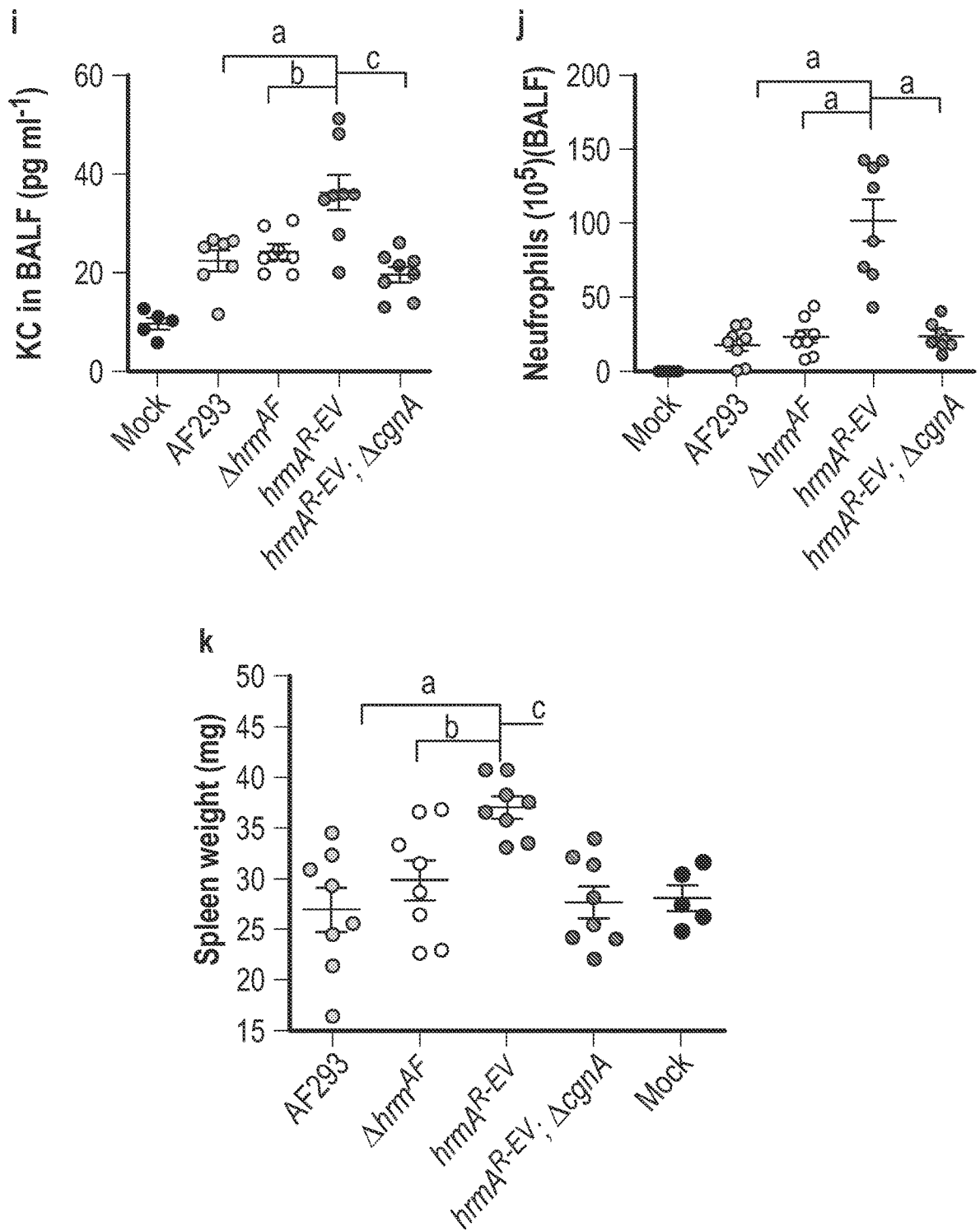
Figure 18:
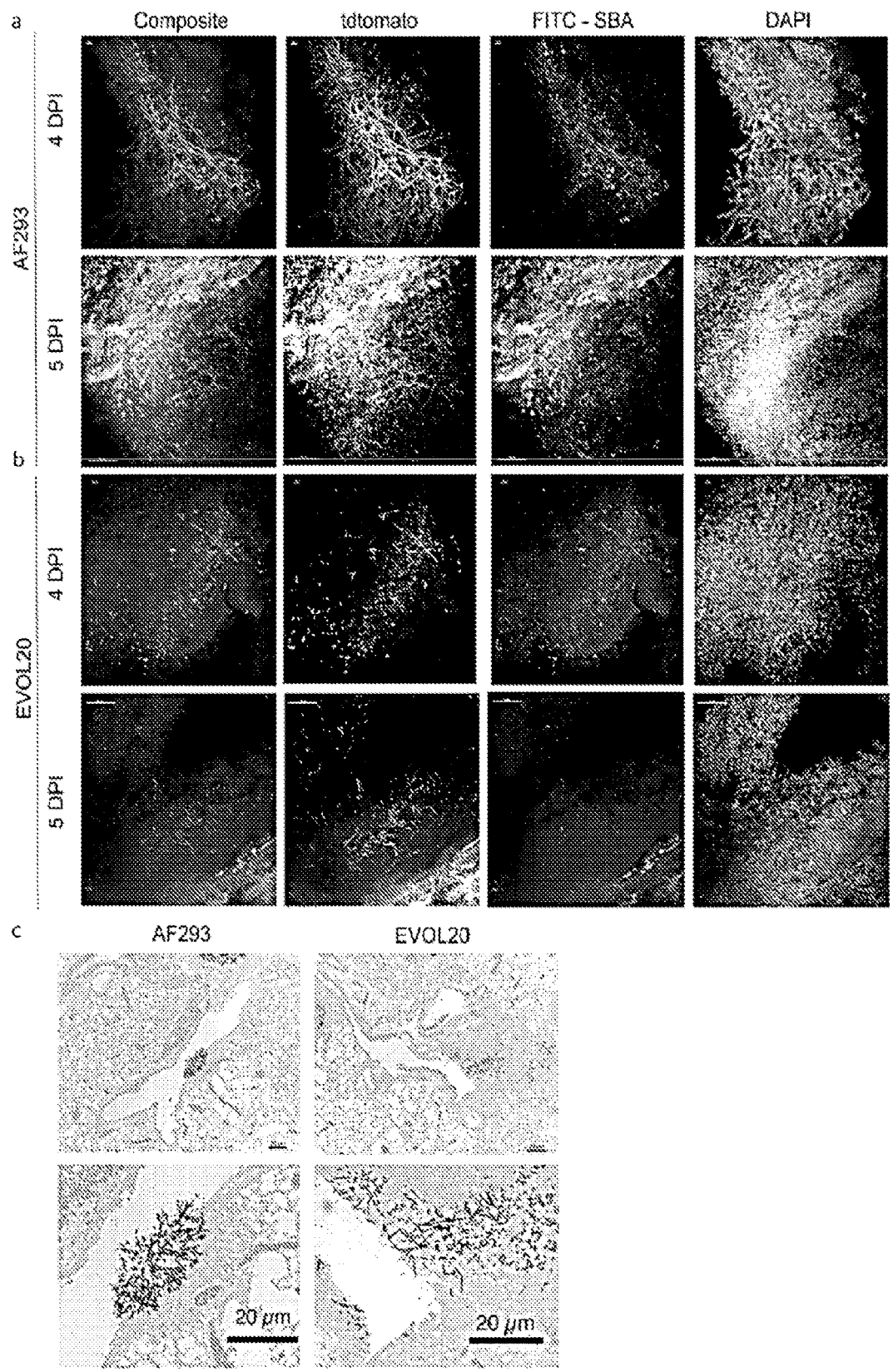
FIG. 18 depicts that FunPact images reflect lesion morphology from histopathology.

It was next determined if the altered filament surface influences the inter-filament interactions in vivo. The miPACT/PACT tissue clearing methods were adopted (microbial identification after passive clarity technique) to visualize in vivo fungal lesions in three dimensions using fluorescently labeled fungi (the technique is termed: fim-PACT: fungal imaging after passive clarity technique) (De-Pas et al. MBio 7, 2016; Yang et al. Cell 158, 945-958, 2014; Chung et al. Nature 497, 332-337, 2013). At 4 dpi and 5 dpi large inflammatory foci with fungal elements are observed within the airways of animals challenged with AF293 or EVOL20. At both time points, AF293 lesions are dense at the center with filaments radiating from the foci of infection, becoming less dense away from the center (FIG. 17a). There is a high degree of connectivity between filaments in AF293 lesions but not in EVOL20 lesions. At 4 dpi and 5 dpi the EVOL20 lesions are visibly more diffuse than those of AF293 (FIG. 17a, FIG. 17b; FIG. 18). There are no dense foci within the EVOL20 lesions, and single filaments can be observed dispersed in distinct locations within the mass of host immune infiltrate (FIG. 17b).

Figure 19:
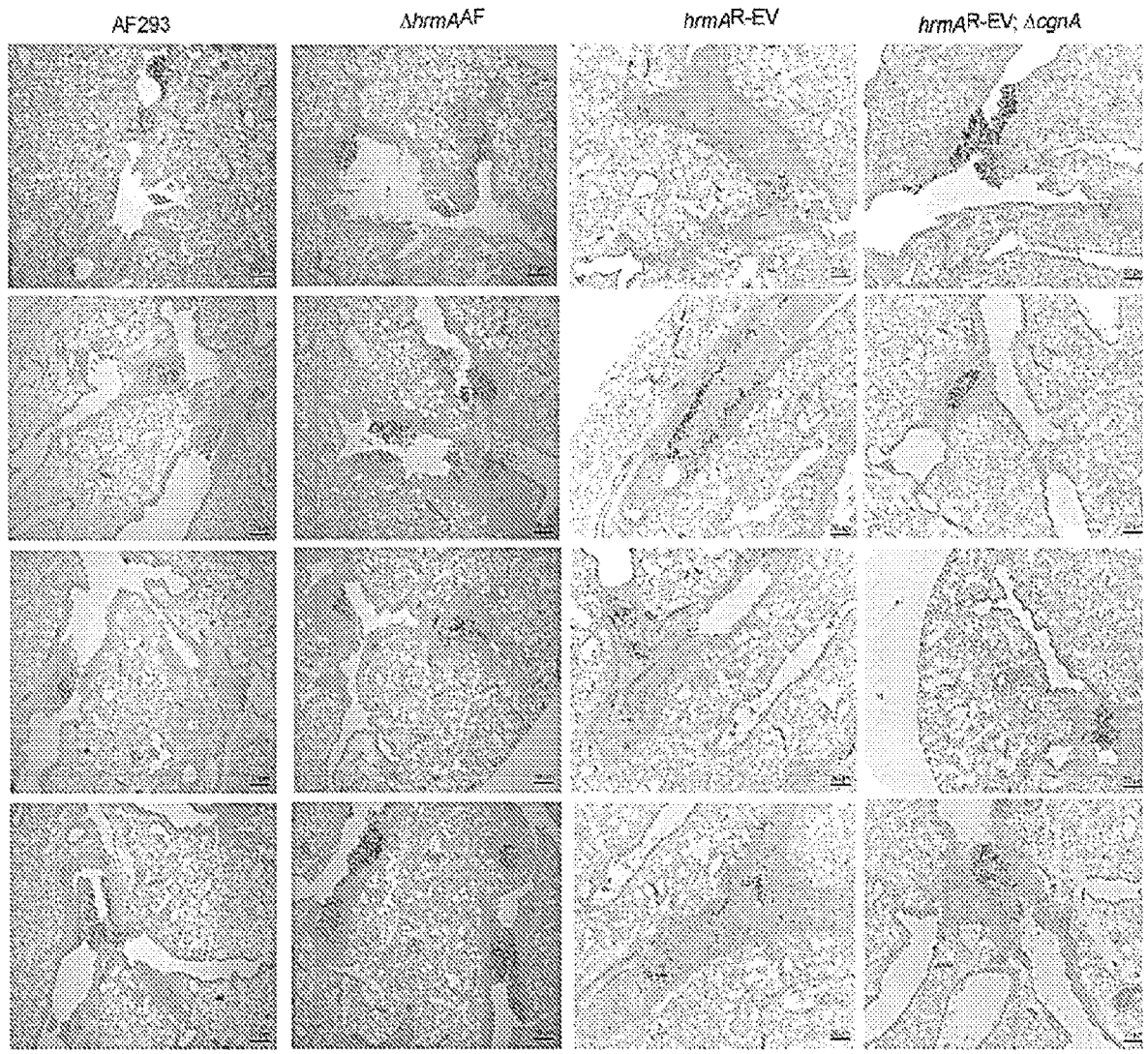
FIG. 19 depicts histopathology slides utilized in the analysis of lesion diffuseness. Four representative images of GMS stained fungal lesions within the murine lung per strain group. Airways inoculated with hrmA$^{R-Ev}$ have more diffuse lesions that spread across the span of the airway and are not localized in a single foci of infection, as observed with AF293, ΔhrmA$^{AF}$, and hrmA$^{R-Ev}$; ΔcgnA. Scale bars: 20 pm. Images are representative of a minimum of 5 biologically independent animals from a 2 independent experiments.

To quantify differences in lesion architecture, we performed Gomori's methenamine silver (GMS) stain and applied a nearest-neighbor algorithm to quantify the "compactness" of fungal lesions within the large airways. The more compact a fungal lesion is, the shorter the distance between each filament and its nearest neighbors; while more diffuse lesions have larger average distances between filaments. Qualitative analysis of the histopathology between N-MORPH AF293 and H-MORPH EVOL20 supported the hypothesis that H-MORPH fungal lesions are more diffuse, and quantification reveals significantly less compact lesions with EVOL20 than AF293 (FIG. 17c). Expansion of this algorithm to lesions of N-MORPHs ΔhrmA$^{AF}$ and hrmA$^{R-Ev}$; ΔcgnA and H-MORPH hrmA$^{R-Ev}$ reveal significantly reduced compactness of hrmA$^{R-Ev}$ compared to the N-MORPH strains (FIG. 17c, FIG. 19, FIG. 18c). The diffuse nature of the hrmA$^{R-Ev}$ lesion is dependent on cgnA and only coincides with H-MORPH.

H-MORPH Facilitate Disease Progression

H-MORPH F11698 (n=7) is significantly increased in murine virulence relative to AF293 (n=5) (p=0.0096) (Supplementary FIG. 5h, FIG. 5i). However, these are non-isogenic strains with an estimated 35759 SNPs between them that could contribute to differences in virulence and morphology. A second comparison between closely related clinical isolates N-MORPH IFM 59356-1 and H-MORPH IFM 59356-3 reveals a 40% increase in survival at 14 dpi, and a 5-day delay before the first mortality event in N-MORPH inoculated animals. By quantitative real-time PCR (qRT-PCR) no significant difference in mRNA levels of hrmA or the HAC gene cgnA is observed between these two strains that contain 51 nonsynonymous SNPs between them. (FIG. 5g).

Loss of hrmA in AF293 does not impact murine mortality, however introduction of the hypoxia-evolved allele of hrmA (hrmA$^{R-Ev}$) and generation of H-MORPH significantly augments virulence in a cgnA-dependent manner (FIG. 17d). Loss of hrmA or cgnA in the H-MORPH EVOL20 significantly attenuates EVOL20 virulence (FIG. 17e). Despite the H-MORPH strains increased virulence, there is no significant difference in fungal burden between AF293, hrmA$^{R-EV}$ ΔhrmA$^{AF}$, and hrmA$^{R-Ev}$;ΔcgnA at 4 dpi (FIG. 170.

Increased 13-glucan exposure in the cell wall of H-MOPRH strains is consistent with observed increases in inflammation at 4 dpi (FIG. 17*g*, FIG. 2*h*, FIG. 2*i*). The airways where H-MORPH hrm$A^{R-Ev}$ is growing are full of immune cell infiltrate that is reduced around lesions of N-MORPH strains (FIG. 17*g*).

Figure 23:
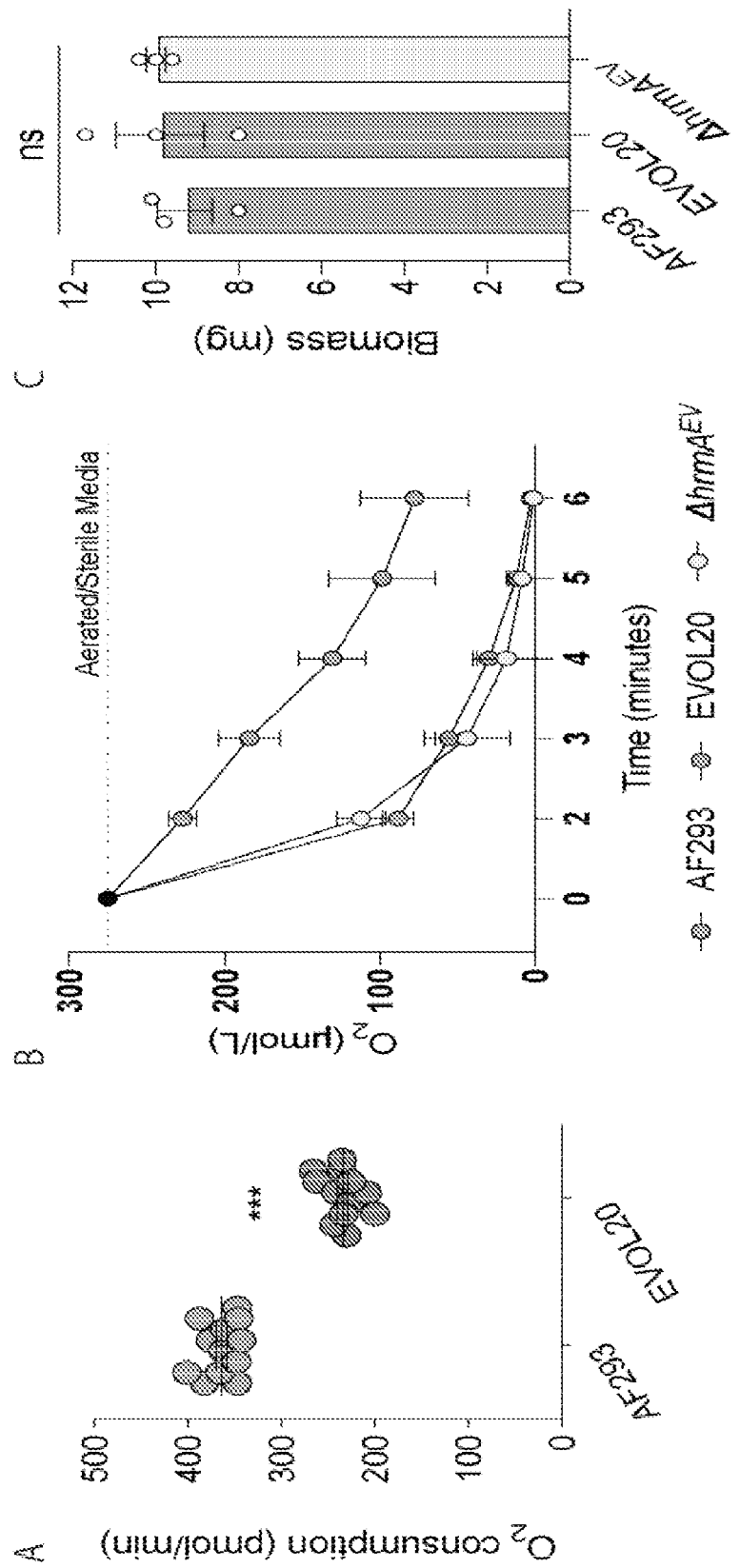
FIG. 23 depicts that an hrmA evolved allele facilitates reduced oxygen consumption in the hypoxia-evolved strain EVOL20.
Figure 24:
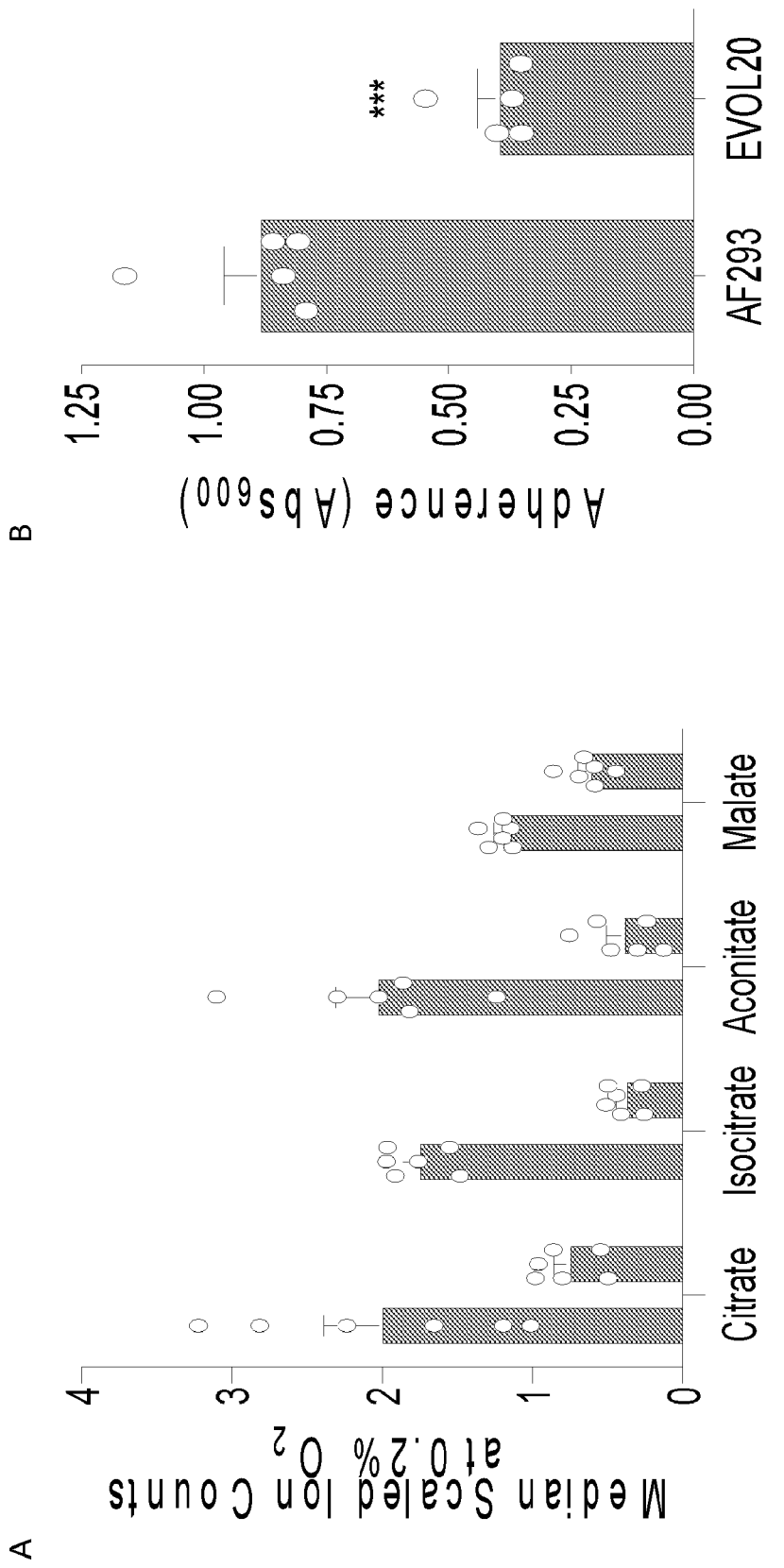
FIG. 24 depicts that the hypoxia evolved strain EVOL20 has increased TCA cycle intermediates and reduces surface adherence.

Host cell damage measured through lactate dehydrogenase (LDH) release in BALF after inoculation with hrm$A^{R-Ev}$ indicates a significant increase in host cell damage (FIG. 17*h*). In both the airways and lung tissue, H-MORPH inoculum is associated with a significant increase in total cells (Supplementary FIG. 20*a*, FIG. 20*e*) and $CD45^+$leukocytes (Supplementary FIG. 20*b*, FIG. 200. A significant increase in the neutrophil chemoattractant KC from BALF is detected (FIG. 6*i*) and corresponds with an increase in airway neutrophils (FIG. 17*j*). The elevated host response to inoculation with H-MORPH hrm$A^{R-Ev}$ is dependent on HAC/cgnA, as loss of cgnA does not reduce hrmA transcripts (Supplementary FIG. 20*h*). These data indicate that localized pulmonary inflammation is elevated following inoculation with H-MORPH; but in addition systemic inflammation, as measured by spleen weight, is significantly increased 60 hpi with hrm$A^{R-EV}$ compared to AF293, ΔhrmA$^{AF}$, and hrm$A^{R-Ev}$; ΔcgnA. (FIG. 17*k*). Together, these data suggest H-MORPH occurs in vivo and significantly impacts disease progression in part through an increase in immunopathogenesis.

As shown in the model of FIG. 21, hypoxic environments, such as the infected host lung, provide an adaptive pressure to the obligate aerobic mold *Aspergillus fumigatus*. This selective pressure can lead to the adoption of certain hypoxia-typic morphological features—furrowing, elevated PVM—and that strains where these morphological traits occur regardless of oxygen tensions have a fitness advantage in low oxygen and simultaneously an increase in virulence. The model disclosed herein shows that the macroscopic morphology (N-MORPH v. H-MORPH) is an indicator of biofilm architecture and hyphal surface characteristics that provide a loose disorganized biofilm and highly inflammatory, diffuse fungal lesions. This disclosure describes a sub-telomeric gene cluster regulator HrmA that promotes expression of CLP cgnA and other genes that alter the fungal surface preventing matrix attachment as one mechanism for the generation of H-MORPH characteristics.

As demonstrated in the above example, forcing an H-MORPH phenotype in a fungal host cell can provide said fungal host cell with growth advantages, such as a reduced oxygen demand. As shown herein, the H-MORPH phenotype in a fungal host cell can be created through the expression (including overexpression) of the sub-telomeric gene cluster regulator HrmA in said fungal host cell. This is a useful mechanism that can be exploited in fungal host cells used in industry for the production of useful products, such as enzymes, secondary metabolites, and citric acid.

Example 2— Reducing Fungal Oxygen Consumption Through Heterologous Expression of a novel sub-telomeric gene cluster from *Aspergillus* species Example 1 above described the discovery and isolation of a novel and useful gene in *Aspergillus fumigatus* for enhancing hypoxia tolerance in fungal host cell.

Identification of *A. fumigatus* gene cluster implicated in fungal oxygen consumption Just as *A. niger* is relatively tolerant to low oxygen concentration (Show 2015, supra), *A. fumigatus* is also able to grow at oxygen tensions as low as 0.2% $O_2$ in both solid-surface and submerged cultures (Kowalski et al. MBio 7, 2016). An in vitro evolution experiment with *A. fumigatus* at 0.2% $O_2$, performed to identify mechanisms of low oxygen adaptation, generated a strain, EVOL20, with improved growth yields at 0.2% $O^2$ compared to the parental reference strain AF293 (Kowalski 2016, supra). Whole genome sequencing of the EVOL20 strain led to the identification of an allele (D304G) in a previously uncharacterized nuclear-localized protein hrmA (Afu5g14900) that was responsible for the increase low-oxygen growth of the strain (Example 1 above). The increased hypoxia fitness conferred by the D304G allele of Afu5g14900/hrmA coincides with a transcriptional profile that is consistent with a hypoxia response being activated in oxygen replete conditions, and this appears to prime the fungus for growth in low oxygen during oxygen fluctuations such as those found in fungal fermentations. It has also been shown that during exposure to low-oxygen conditions, *A. fumigatus* reduces its oxygen consumption, though this usually corresponds with a reduction of growth rate as well (Grahl et al. Mol Microbiol 84, 383-399, 2012). Intriguingly, the strain EVOL20 displays reduced oxygen consumption in oxygen replete conditions both when adhered to a submerged surface (FIG. 23*a*, analyzed with Agilent Seahorse XFe96) or in a planktonic batch culture (FIG. 23*b*, analyzed with Unisense oxygen microelectrode OX-25) at equivalent biomass compared to a wild-type strain (FIG. 23*c*). This is consistent with the strain being constitutively primed for growth in low oxygen. Astoundingly, these data suggest expression of the hrmA evolved allele can reduce oxygen consumption without dramatically impacting fungal biomass yield, by −40%.

The D304G allele of Afu5g14900/hrmA was shown as necessary and sufficient for a number of the phenotypes observed in the EVOL20 strain relative to the parent strain AF293 (Example 1 described above). Similarly, during planktonic batch growth, the reduction in $O^2$ consumption by EVOL20 was dependent on the evolved allele of hrmA (FIG. 23*b*). Intriguingly, the reduction in $O^2$ consumption in EVOL20 co-occured with an accumulation of the TCA cycle intermediates aconitate, malate, isocitrate, and citrate following a shift from 21% $O^2$ to 0.2% $O^2$ for 120 minutes (FIG. 24*a*). Additionally, this low-oxygen consuming strain was poorly adherent to plastic and glass surfaces (FIG. 24*b*), another biotic factor implicated in efficient bioproduction with fungi (Colin et al. AMB Express 3, 27, 2013).

It is proposed herein to utilize the novel hypoxia-evolved hrmA allele (D304G) and associated gene cluster to generate strains of *A. niger, S. cerevisiae*, and other industrial relevant fungi that consume less $O_2$ in production scale fermentations without a detrimental impact on biomass and product yield. Homologous recombination and CRISPR technology will be used to introduce the hrmA evolved allele OR hrmA-associated gene cluster (HAC) in entirety (Afu5g14865-Afu5g14920) into two citric acid producing strains of *A. niger*. ATCC 1015 and ATCC 11414. In addition, haploid *S. cerevisiae* strains will be generated expressing HAC and the hrmA evolved allele. Additional introductions of the evolved allele and associated gene cluster HAC will be introduced into other industrial relevant fungi. It is predicted that this technology being applicable in a diverse group of industrial relevant fungi.

Genome Editing of *A. niger* Strains

Using the sequenced reference strain *A. niger* CBS 513.88 we have identified a site within the sub-terminal chromosomal region of chromosome 8 with homologous gene content to the region 3' of HAC in *A. fumigatus* (Table 4, FungiDB). The HAC gene content will be introduced within this region of the *A. niger* genome using CRISPR technology (Dong et al. J Microbiol Methods 163, 105655, 2019; Leynaud-Kieffer et al. PLoS One 14, e0210243, 2019). The entire HAC loci contains seven ORFs and spans ~18 kb. The cluster will therefore be introduced in segments, beginning with the cluster regulator hrmA evolved allele (D304G) that was evolved experimentally and is important for the reduced oxygen consumption of EVOL20 (FIG. 23*b*). If the introduction of hrmA evolved allele in the absence of the other cluster genes is not sufficient to reduce $O^2$ consumption in *A. niger*, larger portions of HAC within this region of the *A. niger* genome will be introduced and expressed. To facilitate the transformation of such large portions of DNA, XL10-GOLD® Ultracompetent cells (Agilent) will be used to generate and clone the desired constructs.

Table 4— Amino acid identities for HAC adjacent proteins in *A. fumigatus* with their best hits in *A. niger*. Multiple loci 3' to HAC in *A. fumigatus* map with high identity to a group of adjacent proteins (putative orthologs) in the sub-terminal region of *A. niger* CBS 513.88 chromosome 8.

| *A. fumigatus* AF293 | *A. niger* CBS 513.88 | Amino acid identity |
|---|---|---|
| Afu5g14940 | An08g12090 | 60.48% |
| Afu5g14950 | An08g12080 | 38.43% |
| Afu5g14960 | Pseudogene | Not applicable |
| Afu5g14980 | An08g12070 | 50.20% |
| Afu5g14990 | An08g12060 | 48.96% |
| Afu5g14915 | An08g12010 | 41.03% |

Figure 26:
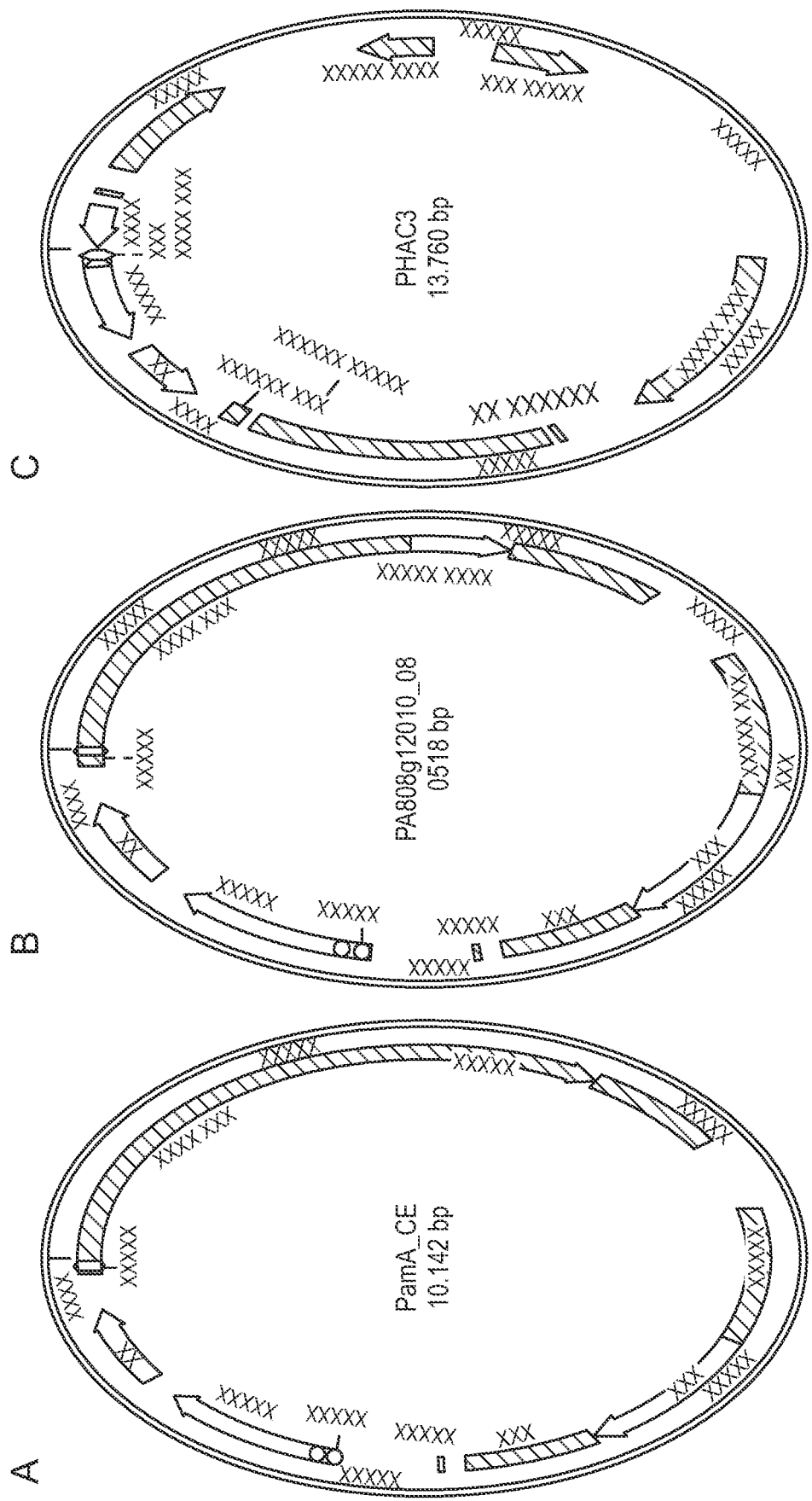
FIG. 26 depicts three example cloning strategies for the engineering of *A. niger*.

There is also a predicted HAC gene homolog within this region (An08g12010) that shares 41% identify with the predicted protein product of an unannotated ORF within *A. fumigatus* AF*293* HAC (proposed *A. fumigatus* gene ID: Afu5g14915) and 38% identify with a protein (AFUB_044360) encoded in an orthologous HAC cluster in *A. fumigatus* strain A1163 (FIG. 25). In both cases higher identity occurs at the c-terminal region (FIG. 25). Afu5g14915 and AFUB_044360 share 78% amino acid identity, and overexpression of AFUB 044360 in a strain where Afu5g14915 has been deleted was sufficient to complement this loss in terms of colony morphology. Therefore, the *A. niger* (An08g12010) and *A. fumigatus* (A1163: AFUB_044360; AF293: Afu5g14915) homologs of this gene will be overexpressed using the well-characterized *Aspergillus nidulans* constitutive promoter gpdA and terminator trpC with the dominant Hygromycin resistance marker to determine if this gene alone, when highly expressed, is sufficient to generate an *A. niger* strain with reduced $O^2$ consumption (sample vector: FIG. 26). All strains will be confirmed through Sanger sequencing, Southern analyses, and qRT-PCR. Finalized strain(s) that show phenotypes of interest (high biomass yield, reduced oxygen consumption, citric acid production) will be sent for whole genome sequencing. Example cloning strategies for *A. niger* are shown in FIG. 26.

Sequences and Vectors are Shown Below.

Sequences and Vectors Utilized in Example 2: Strategy I: Over expression of *A. fumigatus* hrmA hypoxia evolved allele in *A. niger*: the below genomic sequence of hrmA (Insert I) will be amplified with Primer 1 and Primer 2, digested with restriction enzymes Not1-HF and Asc1 and ligated into the below over expression vector sequence with the dominant Hygromycin marker (Vector I) for selection in *A. niger*. The same insert sequence will also be introduced into *Saccharomyces cerevisiae*.

Insert I: *A. fumigatus* hrmA/Afu5g14900 hypoxia evolved genomic sequence

```
ATGGCATCCACAAAGCCCGCTTCGAGTCTCATTTACCAGGCATGGAACAAACTCA

GTATCAACCAAACCATCCCTAGTGACTCCCTTGAATTACTTGGGGAGCGTTTGGC

TATTGCCTTCGCACCCAAACTCAAGGAGCAACGAAGGAATGGCCGGCGTCGGAA

TCTGGAATATGTGGCACAACATCGACGGAAGATTGCTCGAAAAATCTACTTGGA

GATTCTGGAGAAAGACCCAAATATCTTTCTTCCTTTTATCCTGGCTGTTTCCCCTA

GAGCATGCTTATCCTTTGATATCTCGAGCTTTCTTGAACAGCACCAAAGCCAAGG

AAGACATTTCCTCCGCAACAATGCCGAAGCGATCCTCTGGGGTCTCGCAAAGAA

ACATGACATTGATGGCTCCCTCCATTTCAGGAAGCTGATGCGTGAGATTTTCCAA

CTGTCTCCTCCAGCGACAGAAGCCGAAGGCAAGGAGCATTATTCATTGCATTTAA

GCACTCTCCCCGCAATCCGCAATGCCTTCGGTGATGTTATCTTTGACGCAATTGA

ACGTTCCCCTACACAGGTGACAGCGAGAGCTAAAGGTTATTTCTCTGAGAAAAC

CGAAAGTGTTTGGACAAAAGTTCCCTACAGAAGTTCTCAAGACGCAATCATATCT

CTTGAAGTAGGGTCGGCAATCGAGCTTGCGAATGTGTTGTTCCCAATCGCAACCC

AAAAAATTGTCTCTATCCTTTCCGCATGTTCTCCCACTGTGCGCCAGAAGAACTTT

TCTGAGGCTATTCTCGGCCCAGACCCTCAGGATACACCGGCAACATCATCAGAA

ATCGgtatgaagtttaaggtacacatgactgcagttgctaattccaccctgtgctagATGTGGCGTATTTTACTCTG

CGAGGAGCAACGGTCTCGGCAATTGAATCAGTCTTTCGCGCTGATATTTGCGAAG

GTATTAAGGgCAGCGAACTGAGAAACTGGGAAAAGGAGCAGCTGCTCATCGACA

CGACAGATTGTGTCACGATGCAGATATGGCGGGCACAACCTCAACATGGAACCA
```

```
TCAAGTTGCGTATTGGATTCTATGCAGCGGTGAATTTGGCAAATCGGCTGTATGC

AGAAACACCCCAAGATCACATATAG
``` g: the sequence change as a result of in vitro evolution in hypoxia

```
Primer 1:
AAAAAAAAGGCGCGCCATGGCATCCACAAAGCCCGCTT

Primer 2:
AAAAAAAAGCGGCCGCCTATATGTGATCTTGGGGTGTTTCTGCAT
```

Vector I: Overexpression vector with Hygromycin marker

```
ggccgcgaAGCTTGAGATCCACTTAACGTTACTGAAATCATCAAACAGCTTGACG

AATCTGGATATAAGATCGTTGGTGTCGATGTCAGCTCCGGAGTTGAGACAA

ATGGTGTTCAGGATCTCGATAAGATACGTTCATTTGTCCAAGCAGCAAAGAG

TGCCTTCTAGTGATTTAATAGCTCCATGTCAACAAGAATAAAACGCGTTTTC

GGGTTTACCTCTTCCAGATACAGCTCATCTGCAATGCATTAATGCATTGACT

Gcaacctagtaacgccttncaggctccggcgaagagaagaatagcttagcagagctattttcattttcgggagacgagatcaagcag atcaacggtcgtcaagagacctacgagactgaggaatccgctcttggctccacgcgactatatatttgtctctaattgtactttgacatgct cctcttctttactctgatagcttgactatgaaaattccgtcaccagcncctgggttcgcaaagataattgcatgtttcttccttgaactctcaa gcctacaggacacacattcatcgtaggtataaacctcgaaatcanttcctactaagatggtatacaatagtaaccatgcatggttgcctag tgaatgctccgtaacacccaatacgccggccgaaacttttttacaactctcctatgagtcgtttacccagaatgcacaggtacacttgttta gaggtaatccttctttggggatctgacagacgggcaattgattacgggatcccattggtaacgaaatgtaaaagctaggagatcgtccg ccgatgtcaggatgatttcacttgtttcttgtccggctcaccggtcaaagctaaagaggagcaaaaggaacggatagaatcgggtgcc gctgatctatacggtatagtgcccttatcacgttgactcaacccatgctatttaactcaaccctccttctgaaccccaccatcttcttcctttt cctctcatcccacacaattctctatctcagatttgaattccaaaagtcctcggacgaaactgaacaagtcttcctcccttcgataaacctttg gtgattggaataactgaccatcttctatagttcccaaaccaaccgacaatgtaaatacactcctcgattagccctCTAGTatccttgaa gctgtccctgatggtcgtcatctacctgcctggacagcatggcctgcaacgcgggcatcccgatgccgccggaagcgagaagaatca taatggggaaggccatccagcctcgcgtcgagctttgaagttgctgcaagctggcttcaagccatcccatccgaatgtgatgga tgcgttctttctgggccgttgcgactttggggatcgtctttcccgcgcccttggttggaggccctgtctccggtgtccttgtccctt ccaggcaagcgagcgaggtccattcagatggtgctccatcagcgttggctttccgtctccattggctcttggcaattcggtcagc ggggctgactgcctcaggtggggcagtgctagtgtgtgtaccgacccgcaggattggtgctttgcccagagctctacagaatagcgc gcgcatccatatgttagttctgcaattttcttgtatcggtgctgtgactcatacttccccctttggctggccttgcggcaaccaataagaacg cacagtgaaatcttgcgggtggggagtggatccatggcgcctgcattggcttggggacgcgcactgtcgcacacttccatctgacctt cagaagggtttcgtggtgggcaaggaccaaccggttgcgcggccgtgcgtgggtgcctcgcccggcactgccagggccactgcag tggcagtttgctgcctgatacaaaatccttccctccgcccagttttccctctttgaccttccttctcttctctgcaaccaaatccaccctatca aaccaaaacagtatctcgaccgaggtatcaacctgaatcagcaacatcgtagccagcattgtctccgtctctgcagaaccagcgagtt gcaaacattatccaggcaacagggcaccaactcacttcttcggctttcaccaatcggtacagctcttctcagaactcgcgtccgcaaca gttctacgcttcctcagcacctcttcagcttcaatcctgaacactcagaaccgcgcacagcagcgccctcctgttcccttgtttcccaaaa gtaccggtagtatttcgcacggaaagcagggcaacaagatgttctcaggtacccatatgaaaaagcctgaactcaccgcgacgtctgt cgagaagtttctgatcgaaaagttcgacagcgtctccgacctgatgcagctctcggagggcgaagaatctcgtgctttcagcttcgatgt aggagggcgtggatatgtcctgcgggtaaatagctgcgccgatggtttctacaaagatcgttatgtttatcggcactttgcatcggccgc gctcccgattccggaagtgcttgacattggggaattcagcgagagcctgacctattgcatctcccgccgtgcacagggtgtcacgttgc
```

-continued aagacctgcctgaaaccgaactgcccgctgttctgcagccggtcgcggaggccatggatgcgatcgctgcggccgatcttagccag acgagcgggttcggcccattcggaccgcaaggaatcggtcaatacactacatggcgtgatttcatatgcgcgattgctgatcccatgt gtatcactggcaaactgtgatggacgacaccgtcagtgcgtccgtcgcgcaggctctcgatgagctgatgctttgggccgaggactgc cccgaagtccggcacctcgtgcacgcggatttcggctccaacaatgtcctgacggacaatggccgcataacagcggtcattgactgg agcgaggcgatgttcggggattcccaatacgaggtcgccaacatcttcttctggaggccgtggttggcttgtatggagcagcagacgc gctacttcgagcggaggcatccggagcttgcaggatcgccgcggctccgggcgtatatgctccgcattggtcttgaccaactctatca gagcttggttgacggcaatttcgatgatgcagcttgggcgcagggtcgatgcgacgcaatcgtccgatccggagccgggactgtcgg gcgtacacaaatcgcccgcagaagcgcggccgtctggaccgatggctgtgtagaagtactcgccgatagtggaaaccgacgcccc agcactcgtccgagggcaaaggaatagagtagatgccgaccgggatccacttaacgttactgaaatcatcaaacagcttgacgaatct ggatataagatcgttggtgtcgatgtcagctccggagttgagacaaatggtgttcaggatctcgataagatacgttcatttgtccaagcag caaagagtgccttctagtgatttaatagctccatgtcaacaagaataaaacgcgtttcgggtttacctcttccagatacagctcatctgcaa tgcattaatgcattggacctcgcaaccctagtacgccctcaggctccggcgaagcagaagaatagcttagcagagtctattttcattttc gggagacgagatcaagcagatcaacggtcgtcaagagacctacgagactgaggaatccgctcttggctccacgcgactatatatttgt ctctaattgtactttgacatgctcctcttctttactctgatagcttgactatgaaaattccgtcaccagcccctgggttcgcaaagataattgc actgtttcttccttgaactctcaagcctacaggacacacattcatcgtaggtataaacctcgaaaatcattcctactaagatgggtatacaat agtaaccatggttgcctagtgaatgctccgtaacacccaatacgccggccgaaacttttttacaactctcctatgagtcgtttacccagaat gcacaggtacacttgtttagaggtaatccttctttctagctagaggatcctctacgccggacgcatcgtggccggcatcaccggcgcca caggtgcggttgctgActagaataattatgtgtaacaagaaagacagtataatacaaacaaagatgcaagagcggctcatcgtcaccc catgatagctagagcttggcactggccgtcgttttacaacgtcgtgactgggaaaaccctggcgttacccaacttaatcgccttgcagca catcccccttcgccagctggcgtaatagcgaagaggcccgcaccgatcgcccttcccaacagttgcgcagcctgaatggcgaatgg cgcctgatgcggtatttttctccttacgcatctgtgcggtatttcacaccgcatatggtgcactctcagtacaatctgctctgatgccgcatag ttaagccagccccgacacccgccaacacccgctgacgcgccctgacgggcttgtctgctcccggcatccgcttacagacaagctgtg accgtctccgggagctgcatgtgtcagaggttttcaccgtcatcaccgaaacgcgcgagacgaaagggcctcgtgatacgcctatttt ataggttaatgtcatgataataatggtttcttagacgtcaggtggcacttttcggggaaatgtgcgcggaacccctatttgtttatttttctaaa tacattcaaatatgtatccgctcatgagacaataaccctgataaatgcttcaataatattgaaaaaggaagagtatgagtattcaacatttcc gtgtcgcccttattcccttttttgcggcattttgccttcctgttttgctcacccagaaacgctggtgaaagtaaaagatgctgaagatcagtt gggtgcacgagtgggttacatcgaactggatctcaacagcggtaagatccttgagagttttcgccccgaagaacgttttccaatgatga gcacttttaaagttctgctatgtggcgcggtattatcccgtattgacgccgggcaagagcaactcggtcgccgcatacactattctcaga atgacttggttgagtactcaccagtcacagaaaagcatcttacggatggcatgacagtaagagaattatgcagtgctgccataaccatg agtgataacactgcggccaacttacttctgacaacgatcggaggaccgaaggagctaaccgcttttttgcacaacatgggggatcatgt aactcgccttgatcgttgggaaccggagctgaatgaagccataccaaacgacgagcgtgacaccacgatgcctgtagcaatggcaac aacgttgcgcaaactattaactggcgaactacttactctagcttcccggcaacaattaatagactggatggaggcggataaagttgcag gaccacttctgcgctcggcccttccggctggctggtttattgctgataaatctggagccggtgagcgtgggtctcgcggtatcattgcag cactggggccagatggtaagccctcccgtatcgtagttatctacacgacggggagtcaggcaactatggatgaacgaaatagacaga tcgctgagataggtgcctcactgattaagcattggtaactgtcagaccaagtttactcatatatactttagattgatttaaaacttcatttttaat ttaaaaggatctaggtgaagatcctttttgataatctcatgaccaaaatcccttaacgtgagttttcgttccactgagcgtcagacccgta gaaaagatcaaaggatcttcttgagatcctttttttctgcgcgtaatctgctgcttgcaaacaaaaaaaccaccgctaccagcggtggtttg tttgccggatcaagagctaccaactctttttccgaaggtaactggcttcagcagagcgcagataccaaatactgtccttctagtgtagccg tagttaggccaccacttcaagaactctgtagcaccgcctacatacctcgctctgctaatcctgttaccagtggctgctgccagtggcgat aagtcgtgtcttaccgggttggactcaagacgatagttaccggataaggcgcagcggtcgggctgaacggggggttcgtgcacacag -continued cccagcttggagcgaacgacctacaccgaactgagatacctacagcgtgagctatgagaaagcgccacgcttcccgaagggagaa aggcggacaggtatccggtaagcggcagggtcggaacaggagagcgcacgagggagcttccaggggaaacgcctggtatcttt atagtcctgtcgggtttcgccacctctgacttgagcgtcgattttgtgatgctcgtcagggggcggagcctatggaaaaacgccagc aacgcggccttttacggttcctggccttttgctggccttttgctcacatgttctttcctgcgttatcccctgattctgtggataaccgtattacc gcctttgagtgagctgataccgctcgccgcagccgaacgaccgagcgcagcgagtcagtgagcgaggaagcggaagagcgccca atacgcaaaccgcctctccccgcgcgttggccgattcattaatgcagctggcacgacaggtttcccgactggaaagcgggcagtgag cgcaacgcaattaatgtgagttagctcactcattaggcaccccaggctttacactttatgcttccggctcgtatgttgtgtggaattgtgag cggataacaatttcacacaggaaacagctatgaccatgattacg<u>aattcccttgtatctctacacacaggctcaaatcaataagaaga</u>

<u>acggttcgtcttttcgtttatatcttgcatcgtcccaaagctattggcgggatattctgtttgcagttggctgacttgaagtaatctctgca</u>

<u>gatctttcgacactgaaatacgtcgagcctgctccgcttggaagcggcgaggagcctcgtcctgtcacaactaccaacatggagta</u>

<u>cgataagggccagttccgccagctcattaagagccagttcatgggcgttggcatgatggccgtcatgcatctgtacttcaagtacacc</u>

<u>aacgctcttctgatccagtcgatcatccgctgaaggcgctttcgaatctggttaagatccacgtcttcgggaagccagcgactggtgacc</u> tccagcgtccctttaaggctgccaacagctttctcagccagggccagcccaagaccgacaaggcctcctccagaacgccgagaag aactggaggggtggtgtcaaggaggagtaagctccttattgaagtcggaggacggagcggtgtcaagaggatattcttcgactctgta ttatagataagatgatgaggaattggaggtagcatagcttcatttggatttgctttccaggctgagactctagcttggagcatagagggtc ctttggctttcaatattctcaagtatctcgagtttgaacttattccctgtgaaccttttattcaccaatgagcattggaatgaacatgaatctga ggactgcaatcgccatgaggttttcgaaatacatccggatgtcgaaggcttggggcacctgcgttggttgaatttagaacgtggcactat tgatcatccgatagctctgcaaagggcgttgcacaatgcaagtcaaacgttgctagcagttccaggtggaatgttatgatgagcattgtat taaatcaggagatatagcatgatctctagttagctcaccacaaaagtcagacggcgtaaccaaaagtcacacaacacaagctgtaagg atttcggcacggctacggaagacggagaagccaccttcagtggactcgagtaccatttaattctatttgtgtttgatcgagacctaataca gccccctacaacgaccatcaaagtcgtatagctaccagtgaggaagtggactcaaatcgacttcagcaacatctcctggataaactttaa gcctaaactatacagaataagataggtggagagcttataccgagctcccaaatctgtccagatcatggttgaccggtgcctggatcttcc tatagaatcatccttattcgttgacctagctgattctggagtgacccagagggtcatgacttgagcctaaaatccgccgcctccaccatttg tagaaaaatgtgacgaactcgtgagctctgtacagtgaccggtgactcttttctggcatgcggagagacggacggacgcagagagaag ggctgagtaataagccactggccagacagctctggcggctctgaggtgcagtggatgattattaatccgggaccggccgcccctccg ccccgaagtggaaaggctggtgtgcccctcgttgaccaagaatctattgcatcatcggagaatatggagcttcatcgaatcaccggca gtaagcgaaggagaatgtgaagccaggggtgtatagccgtcggcgaaatagcatgccattaacctaggtacagaagtccaattgcttc cgatctggtaaaagattcacgagatagtaccttctccgaagtaggtagagcgagtacccggcgcgtaagctccctaattggcccatcc ggcatctgtagggcgtccaaatatcgtgcctctcctgctttgcccggtgtatgaaaccggaaaggccgctcaggagctggccagcgg cgcagaccgggaacacaagctggcagtcgacccatccggtgctctgcactcgacctgctgaggtccctcagtccctggtaggcagct ttgccccgtctgtccgcccggtgtgtcggcggggttgacaaggtcgttgcgtcagtccaacatttgttgccatattttcctgctctcccac cagctgctcttttctttctctttcttttcccatcttcagtatattcatcttcccatccaagaacctttatttcccctaagtaagtactttgcta catccatactccatccttcccatcccttattcctttgaacctttcagttcgagctttccacttcatcgcagcttgactaacagctaccccgctt gagcagacatcaccatgggg Trpc Terminator
Hygromycin Marker
g: the sequence change as a result of in vitro evolution in hypoxia
Product I: Over expression of *A. fumigatus* hrmA evolved allele with Hygromycin

```
Product I: Over expression of A. fumigatus hrmA evolved allele with Hygromycin
gaattcccttgtatctctacacacaggctcaaatcaataagaagaacggttcgtcttttcgtttatatcttgcatcgtcccaaagctattggc gggatattctgtttgcagttggctgacttgaagtaatctctgcagatctttcgacactgaaatacgtcgagcctgctccgcttggaagcgg cgaggagcctcgtcctgtcacaactaccaacatggagtacgataagggccagttccgccagctcattaagagccagttcatgggcgtt ggcatgatggccgtcatgcatctgtacttcaagtacaccaacgctcttctgatccagtcgatcatccgctgaaggcgctttcgaatctggt taagatccacgtcttcgggaagccagcgactggtgacctccagcgtccctttaaggctgccaacagctttctcagccagggccagccc aagaccgacaaggcctccctccagaacgccgagaagaactggaggggtggtgtcaaggaggagtaagctccttattgaagtcgga ggacggagcggtgtcaagaggatattcttcgactctgtattatagataagatgatgaggaattggaggtagcatagcttcatttggatttg ctttccaggctgagactctagcttggagcatagagggtcctttggctttcaatattctcaagtatctcgagtttgaacttattccctgtgaacc ttttattcaccaatgagcattggaatgaacatgaatctgaggactgcaatcgccatgaggttttcgaaatacatccggatgtcgaaggctt ggggcacctgcgttggttgaattagaacgtggcactattgatcatccgatagctctgcaaagggcgttgcacaatgcaagtcaaacgtt gctagcagttccaggtggaatgttatgatgagcattgtattaaatcaggagatatagcatgatctctagttagctcaccacaaaagtcaga cggcgtaaccaaaagtcacacaacacaagctgtaaggatttcggcacggctacggaagacggagaagccaccttcagtggactcga gtaccatttaattctatttgtgtttgatcgagacctaatacagccctacaacgaccatcaaagtcgtatagctaccagtgaggaagtgga ctcaaatcgacttcagcaacatctcctggataaactttaagcctaaactatacagaataagataggtggagagcttataccgagctccca aatctgtccagatcatggttgaccggtgcctggatcttcctatagaatcatccttattcgttgacctagctgattctggagtgacccagagg gtcatgacttgagcctaaaatccgccgcctccaccatttgtagaaaaatgtgacgaactcgtgagctctgtacagtgaccggtgactcttt ctggcatgcggagagacggacggacgcagagagaagggctgagtaataagccactggccagacagctctggcggctctgaggtg cagtggatgattattaatccgggaccggccgccctccgccccgaagtggaaaggctggtgtgccctcgttgaccaagaatctattg catcatcggagaatatggagcttcatcgaatcaccggcagtaagcgaaggagaatgtgaagccaggggtgtatagccgtcggcgaa atagcatgccattaacctaggtacagaagtccaattgcttccgatctggtaaaagattcacgagatagtaccttctccgaagtaggtaga gcgagtacccggcgcgtaagctccctaattggcccatccggcatctgtagggcgtccaaatatcgtgcctctcctgctttgcccggtgt atgaaaccggaaaggccgctcaggagctggccagcggcgcagaccgggaacacaagctggcagtcgacccatccggtgctctgc actcgacctgctgaggtccctcagtccctggtaggcagctttgcccgtctgtccgcccggtgtgtcggcggggttgacaaggtcgttg cgtcagtccaacatttgttgccatattttcctgctctccccaccagctgctcttttcttttctctttcttttcccatcttcagtatattcatctt cccatccaagaacctttatttcccctaagtaagtactttgctacatccatactccatccttccatcccttattcctttgaacctttcagttcgag ctttcccacttcatcgcagcttgactaacagctacccgcttgagcagacatcaccatggggcgcgccAAAAAAAAGGCGCGC

CATGGCATCCACAAAGCCCGCTTCGAGTCTCATTTACCAGGCATGGAACAAACTC

AGTATCAACCAAACCATCCCTAGTGACTCCCTTGAATTACTTGGGGAGCGTTTGG

CTATTGCCTTCGCACCCAAACTCAAGGAGCAACGAAGGAATGGCCGGCGTCGGA

ATCTGGAATATGTGGCACAACATCGACGGAAGATTGCTCGAAAAATCTACTTGG

AGATTCTGGAGAAAGACCCAAATATCTTTCTTCCTTTTATCCTGGCTGTTTCCCCT

AGAGCATGCTTATCCTTTGATATCTCGAGCTTTCTTGAACAGCACCAAAGCCAAG

GAAGACATTTCCTCCGCAACAATGCCGAAGCGATCCTCTGGGGTCTCGCAAAGA

AACATGACATTGATGGCTCCCTCCATTTCAGGAAGCTGATGCGTGAGATTTTCCA

ACTGTCTCCTCCAGCGACAGAAGCCGAAGGCAAGGAGCATTATTCATTGCATTTA

AGCACTCTCCCCGCAATCCGCAATGCCTTCGGTGATGTTATCTTTGACGCAATTG
```

-continued

```
AACGTTCCCCTACACAGGTGACAGCGAGAGCTAAAGGTTATTTCTCTGAGAAAA

CCGAAAGTGTTTGGACAAAAGTTCCCTACAGAAGTTCTCAAGACGCAATCATATC

TCTTGAAGTAGGGTCGGCAATCGAGCTTGCGAATGTGTTGTTCCCAATCGCAACC

CAAAAAATTGTCTCTATCCTTTCCGCATGTTCTCCCACTGTGCGCCAGAAGAACT

TTTCTGAGGCTATTCTCGGCCCAGACCCTCAGGATACACCGGCAACATCATCAGA

AATCGGTATGAAGTTTAAGGTACACATGACTGCAGTTGCTAATTCCACCCTGTGC

TAGATGTGGCGTATTTTACTCTGCGAGGAGCAACGGTCTCGGCAATTGAATCAGT

CTTTCGCGCTGATATTTGCGAAGGTATTAAGGgCAGCGAACTGAGAAACTGGGAA

AAGGAGCAGCTGCTCATCGACACGACAGATTGTGTCACGATGCAGATATGGCGG

GCACAACCTCAACATGGAACCATCAAGTTGCGTATTGGATTCTATGCAGCGGTGA

ATTTGGCAAATCGGCTGTATGCAGAAACACCCCAAGATCACATATAGgcggccgcgaa gcttgagatccacttaacgttactgaaatcatcaaacagcttgacgaatctggatataagatcgttggtgtcgatgtcagctccggagttg agacaaatggtgttcaggatctcgataagatacgttcatttgtccaagcagcaaagagtgccttctagtgatttaatagctccatgtcaaca agaataaaacgcgttttcggtttacctcttccagatacagctcatctgcaatgcattaatgcattgactgcaacctagtaacgccttncag gctccggcgaagagaagaatagcttagcagagctatttcatttcgggagacgagatcaagcagatcaacggtcgtcaagagaccta cgagactgaggaatccgctcttggctccacgcgactatatatttgtctctaattgtactttgacatgctcctcttctttactctgatagcttgac tatgaaaattccgtcaccagcncctgggttcgcaaagataattgcatgtttcttccttgaactctcaagcctacaggacacacattcatcgt aggtataaacctcgaaatcanttcctactaagatggtatacaatagtaaccatgcatggttgcctagtgaatgctccgtaacacccaatac gccggccgaaacttttttacaactctcctatgagtcgtttacccagaatgcacaggtacacttgtttagaggtaatccttctttctagaggcc tcaaacaatgctcttcaccctcttcgcgggtctgaaataccctcacctggcaacagcaattggcgcttcatggctgtttttccgatctctcta cttgtacggctatgtgtactcgggtaagccacaaggcaagggcagattgctgggaggtttcttctggttttctcaaggcgctctgtgggct ctgagtgtgtttggtgttgccaaagacatgatctcttactgagagttattctgtgtctgacgaaatatgttgtgtatatatatatgtacgttaa aagttccgtggagttaccagtgattgaccaatgttttatcttctacagttctgcctgtctaccccattctagctgtacctgactacagaatagt ttaattgtggttgaccccacagtcggaggcggaggaatacagcaccgatgtggcctgtctccatccagattggcacgcaattttttacac gcggaaaagatcgagatagagtacgactttaaatttagtccccggcggcttctattttagaatatttgagatttgattctcaagcaattgattt ggttgggtcaccctcaattggataatatacctcattgctcggctacttcaactcatcaatcaccgtcataccccgcatataaccctccattc ccacgatgtcgtccaagtcgcaattgacttacggtgctcgagccagcaagcaccccaatcctctggcaaagagacttttttgagattgcc gaagcaaagaagacaaacgttaccgtctctgctgatgtgacgacaacccgagaactcctggacctcgctgaccgtacggaagctgtt ggatccaatacatatgccgtctagcaatggactaatcaacttttgatgatacaggtctcggtccctacatcgccgtcatcaagacacacat cgacatcctcaccgatttcagcgtcgacactatcaatggcctgaatgtgctggctcaaaagcacaacttttttgatcttcgaggaccgcaa attcatcgacatcggcaataccgtccagaagcaataccacgcggtgctctgaggatctccgaatgggcccacattatcaactgcagc gttctccctggcgagggcatcgtcgaggctctggcccagaccgcatctgcgcaagacttcccctatggtcctgagagaggactgttgg tcctggcagagatgacctccaaaggatcgctggctacgggcgagtataccaaggcatcggttgactacgctcgcaaatacaagaactt cgttatgggtttcgtgtcgacgcgggccctgacggaagtgcagtcggatgtgtcttcagcctcggaggatgaagatttcgtggtcttcac gacgggtgtgaacctctcttccaaaggagataagcttggacagcaataccagactcctgcatcggctattggacgcggtgccgacttta tcatcgccggtcgaggcatctacgctgctcccgacccggttgaagctgcacagcggtaccagaaagaaggctgggaagcttatatgg ccagagtatgcggcaagtcatgatttcctcttggagcaaaagtgtagtgccagtacgagtgttgtggaggaaggctgcatacattgtgc ctgtcattaaacgatgagctcgtccgtattggcccctgtaatgccatgttttccgccccaatcgtcaaggttttcccttttgttagattcctac cagtcatctagcaagtgaggtaagctttgccagaaacgccaaggctttatctatgtagtcgataagcaaagtggactgatagcttaatat ggaaggtccctcagggacaagtcgacctgtgcagaagagataacagcttggcatcacgcatcagtgcctcctctcagacagaatcta gagcttggcactggccgtcgttttacaacgtcgtgactgggaaaaccctggcgttacccaacttaatcgccttgcagcacatccccctt
```

-continued

```
cgccagctggcgtaatagcgaagaggcccgcaccgatcgcccttcccaacagttgcgcagcctgaatggcgaatggcgcctgatgc
ggtattttctccttacgcatctgtgcggtatttcacaccgcatatggtgcactctcagtacaatctgctctgatgccgcatagttaagccagc
cccgacacccgccaacacccgctgacgcgccctgacgggcttgtctgctcccggcatccgcttacagacaagctgtgaccgtctccg
ggagctgcatgtgtcagaggttttcaccgtcatcaccgaaacgcgcgagacgaaagggcctcgtgatacgcctattttttataggttaatg
tcatgataataatggtttcttagacgtcaggtggcacttttcggggaaatgtgcgcggaaccccctatttgtttattttttctaaatacattcaaat
atgtatccgctcatgagacaataaccctgataaatgcttcaataatattgaaaaaggaagagtatgagtattcaacatttccgtgtcgccct
tattcccttttttgcggcatttgccttcctgttttgctcacccagaaacgctggtgaaagtaaaagatgctgaagatcagttgggtgcacg
agtgggttacatcgaactggatctcaacagcggtaagatccttgagagttttcgccccgaagaacgttttccaatgatgagcacttttaaa
gttctgctatgtggcgcggtattatcccgtattgacgccgggcaagagcaactcggtcgccgcatacactattctcagaatgacttggtt
gagtactcaccagtcacagaaaagcatcttacggatggcatgacagtaagagaattatgcagtgctgccataaccatgagtgataaca
ctgcggccaacttacttctgacaacgatcggaggaccgaaggagctaaccgcttttttgcacaacatgggggatcatgtaactcgcctt
gatcgttgggaaccggagctgaatgaagccataccaaacgacgagcgtgacaccacgatgcctgtagcaatggcaacaacgttgcg
caaactattaactggcgaactacttactctagcttcccggcaacaattaatagactggatggaggcggataaagttgcaggaccacttct
gcgctcggcccttccggctggctggtttattgctgataaatctggagccggtgagcgtgggtctcgcggtatcattgcagcactgggc
cagatggtaagccctcccgtatcgtagttatctacacgacggggagtcaggcaactatggatgaacgaaatagacagatcgctgagat
aggtgcctcactgattaagcattggtaactgtcagaccaagtttactcatatatactttagattgatttaaaacttcattttttaatttaaaaggat
ctaggtgaagatccttttttgataatctcatgaccaaaatcccttaacgtgagttttcgttccactgagcgtcagaccccgtagaaaagatca
aaggatcttcttgagatcctttttttctgcgcgtaatctgctgcttgcaaacaaaaaaaccaccgctaccagcggtggtttgtttgccggatc
aagagctaccaactctttttccgaaggtaactggcttcagcagagcgcagataccaaatactgtccttctagtgtagccgtagttaggcc
accacttcaagaactctgtagcaccgcctacatacctcgctctgctaatcctgttaccagtggctgctgccagtggcgataagtcgtgtct
taccgggttggactcaagacgatagttaccggataaggcgcagcggtcgggctgaacggggggttcgtgcacacagcccagcttgg
agcgaacgacctacaccgaactgagatacctacagcgtgagctatgagaaagcgccacgcttcccgaagggagaaaggcggaca
ggtatccggtaagcggcagggtcggaacaggagagcgcacgagggagcttccaggggggaaacgcctggtatctttatagtcctgtc
gggtttcgccacctctgacttgagcgtcgatttttgtgatgctcgtcaggggggcggagcctatggaaaaacgccagcaacgcggcct
ttttacggttcctggccttttgctggccttttgctcacatgttctttcctgcgttatcccctgattctgtggataaccgtattaccgcctttgagt
gagctgataccgctcgccgcagccgaacgaccgagcgcagcgagtcagtgagcgaggaagcggaagagcgcccaatacgcaaac
cgcctctccccgcgcgttggccgattcattaatgcagctggcacgacaggtttcccgactggaaagcgggcagtgagcgcaacgcaa
ttaatgtgagttagctcactcattaggcaccccaggctttacactttatgcttccggctcgtatgttgtgtggaattgtgagcggataacaat
ttcacacaggaaacagctatgaccatgattac
```

Strategy II: Over expression of *A. niger* putative HAC ortholog AnO8g12010 in *A. niger*: the below genomic sequence of Ano8g12010(Insert II) will be amplified with Primer 3 and Primer 4, digested with restriction enzymes Not1-HF and Asc1 and ligated into over expression vector sequence with the dominant Hygromycin marker (Vector I) for selection in *A. niger*.

Insert II: *A. niger* AnO8g12010 genomic sequence

```
ATGGCTTGGTACAGTGCTTTACTCCCGTGCATGCTATGGTGGCGGAACCTCCTGT
GGCGTAACAGCACCAATAGGTATAGACAGAGTACAGACGACCTTACTTCACTGA
CTGATAAGATACCTAATCTTGGAGAAAGGgtaagtgtaaatacttttttgaggtcgcttctaggagtctaatca
ctttggaaagacaactcccacagataacatcgatggaaagagcttcgtggcacatactgtcgtgcagaccaggcggattggtgaccga
gaacgttgctgcttcaatgactcggatttgaacagcggcacagTTACCAAATTTATTGAGCTTTGTTAATAG
CATTCCAGATCAGAGTACTACTGCCGGAAAAATTAATCACAAGGCCCTGCGAGA
TCCTGAGCTCTTTGCTATCCGCTCGTCATGCATCGACAAATCAGCCAGCAAGTGG
```

```
ATGGTTAGTCTCTACTACGAACCCCCACCCAGCCTTGATGACCTCGAGATTAAGA

ACTTCGGATCTCGTATTCCAGAGTCGGAGGATGATCCAATTGAGGCTATCTTTCA

CTATGAGGGAGAGAACATTTGGGTATCTGTTCCTTATTTGTATGCTAGAACTAGA

AGCCTTTCAAGCGGTCTGTTCTGA

Primer 3:
AAAAGGCGCGCCATGGCTTGGTACAGTGCTTTACTC

Primer 4:
AAAAGCGGCCGCTCAGAACAGACCGCTTGAAAGGC
```

Product II: Over expression of *A. niger* AnO8g12010 with Hygromycin

```
gaattcccttgtatctctacacacaggctcaaatcaataagaagaacggttcgtcttttttcgtttatatcttgcatcgtcccaaagctattggc gggatattctgtttgcagttggctgacttgaagtaatctctgcagatctttcgacactgaaatacgtcgagcctgctccgcttggaagcgg cgaggagcctcgtcctgtcacaactaccaacatggagtacgataagggccagttccgccagctcattaagagccagttcatgggcgtt ggcatgatggccgtcatgcatctgtacttcaagtacaccaacgctcttctgatccagtcgatcatccgctgaaggcgctttcgaatctggt taagatccacgtcttcgggaagccagcgactggtgacctccagcgtccctttaaggctgccaacagcttctcagccagggccagccc aagaccgacaaggcctccctccagaacgccgagaagaactggaggggtggtgtcaaggaggagtaagctccttattgaagtcgga ggacggagcggtgtcaagaggatattcttcgactctgtattatagataagatgatgaggaattggaggtagcatagcttcatttggatttg cttccaggctgagactctagcttggagcatagagggtcctttggctttcaatattctcaagtatctcgagtttgaacttattccctgtgaacc ttttattcaccaatgagcattggaatgaacatgaatctgaggactgcaatcgccatgaggttttcgaaatacatccggatgtcgaaggctt ggggcacctgcgttggttgaatttagaacgtggcactattgatcatccgatagctctgcaaagggcgttgcacaatgcaagtcaaacgtt gctagcagttccaggtggaatgttatgatgagcattgtattaaatcaggagatatagcatgatctctagttagctcaccacaaaagtcaga cggcgtaaccaaaagtcacacaacacaagctgtaaggattccggcacggctacggaagacggagaagccaccttcagtggactcga gtaccatttaattctatttgtgtttgatcgagacctaatacagccctacaacgaccatcaaagtcgtatagctaccagtgaggaagtgga ctcaaatcgacttcagcaacatctcctggataaactttaagcctaaactatacagaataagataggtggagagcttataccgagctccca aatctgtccagatcatggttgaccggtgcctggatcttcctatagaatcatccttattcgttgacctagctgattctggagtgacccagagg gtcatgacttgagcctaaaatccgccgcctccaccatttgtagaaaaatgtgacgaactcgtgagctctgtacagtgaccggtgactcttt ctggcatgcggagagacggacggacgcagagagaagggctgagtaataagccactggccagacagctctggcggctctgaggtg cagtggatgattattaatccgggaccggccgcccctccgccccgaagtggaaaggctggtgtgcccctcgttgaccaagaatctattg catcatcggagaatatggagcttcatcgaatcaccggcagtaagcgaaggagaatgtgaagccaggggtgtatagccgtcggcgaa atagcatgccattaacctaggtacagaagtccaattgcttccgatctggtaaaagattcacgagatagtaccttctccgaagtaggtaga gcgagtacccggcgcgtaagctccctaattggcccatccggcatctgtagggcgtccaaatatcgtgcctctcctgctttgcccggtgt atgaaaccggaaaggccgctcaggagctggccagcggcgcagaccgggaacacaagctggcagtcgacccatccggtgctctgc actcgacctgctgaggtccctcagtccctggtaggcagctttgccccgtctgtccgcccggtgtgtcggcgggggttgacaaggtcgttg cgtcagtccaacatttgttgccatattttcctgctctccccaccagctgctcttttcttttctcttttcttttcccatcttcagtatattcatcttcc catccaagaacctttatttcccctaagtaagtactttgctacatccatactccatccttcccatcccttattcctttgaaccttcagttcgagcttt cccacttcatcgcagcttgactaacagctaccccgcttgagcagacatcaccatggggCGCGCCATGGCTTGGTACA

GTGCTTTACTCCCGTGCATGCTATGGTGGCGGAACCTCCTGTGGCGTAACAGCAC

CAATAGGTATAGACAGAGTACAGACGACCTTACTTCACTGACTGATAAGATACC

TAATCTTGGAGAAAGGgtaagtgtaaatacttttttgaggtcgcttctaggagtctaatcactttggaaagacaactcccac agataacatcgatggaaagagcttcgtggcacatactgtcgtgcagaccaggcggattggtgaccgagaacgttgctgcttcaatgac tcggatttgaacagcggcacagTTACCAAATTTATTGAGCTTTGTTAATAGCATTCCAGATCA
```

```
GAGTACTACTGCCGGAAAAATTAATCACAAGGCCCTGCGAGATCCTGAGCTCTTT

GCTATCCGCTCGTCATGCATCGACAAATCAGCCAGCAAGTGGATGGTTAGTCTCT

ACTACGAACCCCCACCCAGCCTTGATGACCTCGAGATTAAGAACTTCGGATCTCG

TATTCCAGAGTCGGAGGATGATCCAATTGAGGCTATCTTTCACTATGAGGGAGAG

AACATTTGGGTATCTGTTCCTTATTTGTATGCTAGAACTAGAAGCCTTTCAAGCG

GTCTGTTCTGAGCggccgcgaagcttgagatccacttaacgttactgaaatcatcaaacagcttgacgaatctggatataag
``` atcgttggtgtcgatgtcagctccggagttgagacaaatggtgttcaggatctcgataagatacgttcatttgtccaagcagcaaagagt gccttctagtgatttaatagctccatgtcaacaagaataaaacgcgttttcgggtttacctcttccagatacagctcatctgcaatgcattaat gcattgactgcaacctagtaacgccttncaggctccggcgaagagaagaatagcttagcagagctattttcattttcgggagacgagat caagcagatcaacggtcgtcaagagacctacgagactgaggaatccgctcttggctccacgcgactatatatttgtctctaattgtactt gacatgctcctcttctttactctgatagcttgactatgaaaattccgtcaccagcncctgggttcgcaaagataattgcatgtttcttccttga actctcaagcctacaggacacacattcatcgtaggtataaacctcgaaatcanttcctactaagatggtatacaatagtaaccatgcatgg ttgcctagtgaatgctccgtaacacccaatacgccggccgaaacttttttacaactctcctatgagtcgtttacccagaatgcacaggtac acttgtttagaggtaatccttctttggggatctgacagacgggcaattgattacgggatcccattggtaacgaaatgtaaaagctaggag atcgtccgccgatgtcaggatgatttcacttgtttcttgtccggctcaccggtcaaagctaaagaggagcaaaaggaacggatagaatc gggtgccgctgatctatacggtatagtgcccttatcacgttgactcaacccatgctatttaactcaaccctccttctgaacccaccatctt cttcctttcctctcatcccacacaattctctatctcagatttgaattccaaaagtcctcggacgaaactgaacaagtcttcctcccttcgata aacctttggtgattggaataactgaccatcttctatagttcccaaaccaaccgacaatgtaaatacactcctcgattagccctCTAGTa tccttgaagctgtccctgatggtcgtcatctacctgcctggacagcatggcctgcaacgcgggcatcccgatgccgccggaagcgag aagaatcataatggggaaggccatccagcctcgcgtcgagctttgaagttgctgcaagctggcttcaagccatcccatccgaatgtgat ggatgcgttctttctgggccgttgcgactttggggatcgtctttcccgcgcccttggttggaggccctgtctccggtgtcccttgtcccttc caggcaagcgagcgaggtccattcagatggtgctccatcagcgttggctttccgtctccattggctcttggcaattcggtcagcgggc tgactgcctcaggtggggcagtgctagtgtgtgtaccgacccgcaggattggtgctttgcccagagctctacagaatagcgcgcgcat ccatatgttagttctgcaattttcttgtatcggtgctgtgactcatacttccccctttggctggccttgcggcaaccaataagaacgcacagt gaaatcttgcgggtggggagtggatccatggcgcctgcattggcttggggacgcgcactgtcgcacacttccatctgacctttcagaa gggtttcgtggtgggcaaggaccaaccggttgcgcggccgtgcgtgggtgcctcgcccggcactgccagggccactgcagtggca gtttgctgcctgatacaaaatccttccctccgcccagttttccctctttgaccttccttttctcttctctgcaaccaaatccaccctatcaaacca aaacagtatctcgaccgaggtatcaacctgaatcagcaacatcgtagccagcatttgtctccgtctctgcagaaccagcgagttgcaaa cattatccaggcaacagggcaccaactcacttcttcggcttttcaccaatcggtacagctcttctcagaactcgcgtccgcaacagttctac gcttcctcagcaccttcttcagcttcaatcctgaacactcagaaccgcgcacagcagcgccctcctgttcccttgtttcccaaaagtaccg gtagtatttcgcacggaaagcagggcaacaagatgttctcaggtaccatatgaaaaagcctgaactcaccgcgacgtctgtcgagaa gtttctgatcgaaaagttcgacagcgtctccgacctgatgcagctctcggagggcgaagaatctcgtgctttcagcttcgatgtaggag ggcgtggatatgtcctgcgggtaaatagctgcgccgatggtttctacaaagatcgttatgtttatcggcactttgcatcggccgcgctccc gattccggaagtgcttgacattggggaattcagcgagagcctgacctattgcatctcccgccgtgcacagggtgtcacgttgcaagac ctgcctgaaaccgaactgcccgctgttctgcagccggtcgcggaggccatggatgcgatcgctgcggccgatcttagccagacgag cgggttcggcccattcggaccgcaaggaatcggtcaatacactacatggcgtgatttcatatgcgcgattgctgatccccatgtgtatca ctggcaaactgtgatggacgacaccgtcagtgcgtccgtcgcgcaggctctcgatgagctgatgctttgggccgaggactgccccga agtccggcacctcgtgcacgcggatttcggctccaacaatgtcctgacggacaatggccgcataacagcggtcattgactggagcga ggcgatgttcggggattcccaatacgaggtcgccaacatcttcttctggaggccgtggttggcttgtatggagcagcagacgcgctact tcgagcggaggcatccggagcttgcaggatcgccgcggctccgggcgtatatgctccgcattggtcttgaccaactctatcagagctt -continued

```
ggttgacggcaatttcgatgatgcagcttgggcgcagggtcgatgcgacgcaatcgtccgatccggagccgggactgtcggcgta cacaaatcgcccgcagaagcgcggccgtctggaccgatggctgtgtagaagtactcgccgatagtggaaaccgacgcccagcact cgtccgagggcaaaggaatagagtagatgccgaccgggatccacttaacgttactgaaatcatcaaacagcttgacgaatctggatat aagatcgttggtgtcgatgtcagctccggagttgagacaaatggtgttcaggatctcgataagatacgttcatttgtccaagcagcaaag agtgccttctagtgatttaatagctccatgtcaacaagaataaaacgcgtttcgggtttacctcttccagatacagctcatctgcaatgcatt aatgcattggacctcgcaaccctagtacgcccttcaggctccggcgaagcagaagaatagcttagcagagtctattttcattttcgggag acgagatcaagcagatcaacggtcgtcaagagacctacgagactgaggaatccgctcttggctccacgcgactatatatttgtctctaat tgtactttgacatgctcctcttctttactctgatagcttgactatgaaaattccgtcaccagcccctgggttcgcaaagataattgcactgtttc ttccttgaactctcaagcctacaggacacacattcatcgtaggtataaacctcgaaaatcattcctactaagatgggtatacaatagtaacc atggttgcctagtgaatgctccgtaacacccaatacgccggccgaaactttttacaactctcctatgagtcgtttacccagaatgcacag gtacacttgtttagaggtaatccttctttctagctagaggatcctctacgccggacgcatcgtggccggcatcaccggcgccacaggtg cggttgctgActagaataattatgtgtaacaagaaagacagtataatacaaacaaagatgcaagagcggctcatcgtcacccccatgat agctagagcttggcactggccgtcgttttacaacgtcgtgactgggaaaaccctggcgttacccaacttaatcgccttgcagcacatcc ccctttcgccagctggcgtaatagcgaagaggcccgcaccgatcgcccttcccaacagttgcgcagcctgaatggcgaatggcgcct gatgcggtattttctccttacgcatctgtgcggtatttcacaccgcatatggtgcactctcagtacaatctgctctgatgccgcatagttaag ccagccccgacaccgccaacacccgctgacgcgccctgacgggcttgtctgctcccggcatccgcttacagacaagctgtgaccg tctccgggagctgcatgtgtcagaggttttcaccgtcatcaccgaaacgcgcgagacgaaagggcctcgtgatacgcctattttatag gttaatgtcatgataataatggtttcttagacgtcaggtggcacttttcggggaaatgtgcgcggaacccctatttgtttatttttctaaataca ttcaaatatgtatccgctcatgagacaataaccctgataaatgcttcaataatattgaaaaaggaagagtatgagtattcaactattccgtgt cgcccttattcccttttttgcggcattttgccttcctgttttgctcacccagaaacgctggtgaaagtaaaagatgctgaagatcagttgggt gcacgagtgggttacatcgaactggatctcaacagcggtaagatccttgagagttttcgccccgaagaacgttttccaatgatgagcact tttaaagttctgctatgtggcgcggtattatcccgtattgacgccgggcaagagcaactcggtcgccgcatacactattctcagaatgact tggttgagtactcaccagtcacagaaaagcatcttacggatggcatgacagtaagagaattatgcagtgctgccataaccatgagtgat aacactgcggccaacttacttctgacaacgatcggaggaccgaaggagctaaccgcttttttgcacaacatggggatcatgtaactcg ccttgatcgttgggaaccggagctgaatgaagccataccaaacgacgagcgtgacaccacgatgcctgtagcaatggcaacaacgtt gcgcaaactattaactggcgaactacttactctagcttcccggcaacaattaatagactggatggaggcggataaagttgcaggaccac ttctgcgctcggcccttccggctggctggtttattgctgataaatctggagccggtgagcgtgggtctcgcggtatcattgcagcactgg ggccagatggtaagccctcccgtatcgtagttatctacacgacggggagtcaggcaactatggatgaacgaaatagacagatcgctg agataggtgcctcactgattaagcattggtaactgtcagaccaagtttactcatatatactttagattgatttaaaacttcattttaatttaaaa ggatctaggtgaagatcctttttgataatctcatgaccaaaatcccttaacgtgagttttcgttccactgagcgtcagacccccgtagaaaag atcaaaggatcttcttgagatcctttttttctgcgcgtaatctgctgcttgcaaacaaaaaaaccaccgctaccagcggtggtttgtttgccg gatcaagagctaccaactctttttccgaaggtaactggcttcagcagagcgcagataccaaatactgtccttctagtgtagccgtagttag gccaccacttcaagaactctgtagcaccgcctacatacctcgctctgctaatcctgttaccagtggctgctgccagtggcgataagtcgt gtcttaccgggttggactcaagacgatagttaccggataaggcgcagcggtcgggctgaacggggggttcgtgcacacagcccagc ttggagcgaacgacctacaccgaactgagatacctacagcgtgagctatgagaaagcgccacgcttcccgaagggagaaaggcgg acaggtatccggtaagcggcagggtcggaacaggagagcgcacgagggagcttccaggggaaacgcctggtatctttatagtcct gtcgggtttcgccacctctgacttgagcgtcgatttttgtgatgctcgtcagggggcggagcctatggaaaaacgccagcaacgcgg ccttttacggttcctggccttttgctggccttttgctcacatgttctttcctgcgttatcccctgattctgtggataaccgtattaccgcctttga gtgagctgataccgctcgccgcagccgaacgaccgagcgcagcgagtcagtgagcgaggaagcggaagagcgcccaatacgca
```

```
aaccgcctctccccgcgcgttggccgattcattaatgcagctggcacgacaggtttcccgactggaaagcgggcagtgagcgcaacg
caattaatgtgagttagctcactcattaggcaccccaggctttacactttatgcttccggctcgtatgttgtgtggaattgtgagcggataac
aatttcacacaggaaacagctatgaccatgattac
```

Strategy III: Over expression of *A. fumigatus* 3' HAC region (Afu5g14900-Afu5g14920) in *A. niger*: the below genomic sequence of HAC (Insert III) will be amplified with Primer 5 and Primer 6, digested with restriction enzymes BglII and Not1-HF and ligated into the below over expression vector sequence with the dominant pyrithiamine marker (Vector II) for selection in *A. niger*.

Insert III: *A. fumigatus* hrmA/Afu5g14900 genomic sequence from hypoxia-evolved strain

```
cgccgtaacgtaacaaagcggggttggtagtgtttgcaaatgcattcacatggaccgatcacttttctttccagtctgtccattctgtccaat
ctgtccgatctgacctgcccagtctgtccagtctgtcccttgtgtcgtccgatccaagctggttatcatggcatccacaaagcccgcttcg
agtctcatttaccaggcatggaacaaactcagtatcaaccaaccatccctagtgactcccttgaattacttggggagcgtttggctattg
ccttcgcacccaaactcaaggagcaacgaaggaatggccggcgtcggaatctggaatatgtggcacaacatcgacggaagattgct
cgaaaaatctacttggagattctggagaaagacccaaatatctttcttccttttatcctggctgtttcccctagagcatgcttatcctttgatat
ctcgagctttcttgaacagcaccaaagccaaggaagacatttcctccgcaacaatgccgaagcgatcctctggggtctcgcaaagaaa
catgacattgatggctccctccatttcaggaagctgatgcgtgagattttccaactgtctcctccagcgacagaagccgaaggcaagga
gcattattcattgcatttaagcactctccccgcaatccgcaatgccttcggtgatgttatctttgacgcaattgaacgttccctacacaggt
gacagcgagagctaaaggttatttctctgagaaaaccgaaagtgtttggacaaaagttccctacagaagttctcaagacgcaatcatatc
tcttgaagtagggtcggcaatcgagcttgcgaatgtgttgttcccaatcgcaacccaaaaaattgtctctatcctttccgcatgttctccca
ctgtgcgccagaagaacttttctgaggctattctcggcccagaccctcaggatacaccggcaacatcatcagaaatcggtatgaagttta
aggtacacatgactgcagttgctaattccaccctgtgctagatgtggcgtattttactctgcgaggagcaacggtctcggcaattgaatca
gtctttcgcgctgatatttgcgaaggtattaagggcagcgaactgagaaactgggaaaaggagcagctgctcatcgacacgacagatt
gtgtcacgatgcagatatggcgggcacaacctcaacatggaaccatcaagttgcgtattggattctatgcagcggtgaatttggcaaat
cggctgtatgcagaaacaccccaagatcacatatagtaacctttcatcttttcggccttcttaaatcattgcctttctgtgagtcgcgactttc
caccctttatgaatacaccaataccaggggaagaacgatttcaccgcttcccttggcaatccatatagttcccttctcattctggaacctg
atttcatcgcagttgaagcaatataaattccttcgaggttttctgcattgtagggatggaatgggtgcgtgaaatatttgtcgaaaatagaa
gggtccgaaagttcttccaagctgcgcgctgaaagttgttagcccatctttcgagcatatggtttggcccacatacgagagattcttttgt
gatcggttgagattcttccgtgatcggttctgtcattttcattaagtcagagagccctcttgtatgccggcttttgctgtcggatccggcgag
ataatcgctcctaagccagtcagtcagggaaaagcaaagataaataaaatataggcgaggagtacaaccaggcacgcgtcgtagact
attttctgaagagtttgtcacgtaacctacctcatatggatgggtagttcgaatacttgattgacttgacccgaggttctgaaggcggcgg
aggaaattgcccaacccaccattgcattttcaggtatcaatctctgccacactgtggctaaattcgtctttatcgacacgtgatcacgttc
cctcttccagccctggtatcagagaatcatcgagttatcgcttgtttcaatttcgtcttgcaattagcttagggaataagcatgtggtcacat
caacctacagagcgctaccggtcctttgcgctgagactctcagtgatccgcccaacagacaactagactttgaggttgtcgatataacca
caacaaatggcctgtatateaacgatgtccacgcaattgtctcaagcctcttcacccgacttccagcactagcatccaagcggcctctcc
tcttctcccatgtttctcgtagcgcgcctgcatatacttatatctggagatatgttaaaggagctggaagcctggagcatacgctggaagc
ctggagcatacgcttcaagtgctgccatattcagatagctgagtaggcacaattaggtctaagttcagggaattgcacctctcgcttcatt
gtccgtcgattcgtatcggtctctagttctccccgtttatcactctcactcggtggacagtccgtccagtccgtccagtccgtcgagcctgt
ccaatctgtccaatctgtccaatctgtccaatctgtccaatctgtccaatctgtccaatctgtccaatctgtccaatctgtccaatctgtccaat
ctgtccaatctgtccaatctgtccaatctgtccaatctgtccactctgtccactctgtccactctgtccaatctgtccactctgtc
ccctctgtccactctgtccctctgtccactctgtccctctgtccaatcggtccaatctgtccaatcttgatgatctcgatgatcaataccat
ttagcgagcgctagtgacgccttacagcgttgcggcgtctttatggcttatacatcttccgaatatcagtcgttcgatctccagatcacacct
cggggtgaaacaagcgccatagttcttggtgcgcctgagcttttccctgcccggccactcagtcgtgatggcttcccagagtattccata
```

-continued

```
agtcgaaaccagagataggccagcggacggcaaatctcctctgctccgttctcaaccaatactgccaaagtgagcaatggaaagtgtt
ccaggagcaccgtggcctttaaaagcgccagccttgtcccagatcctcaccgcaattcggcacagaccaacgcagactttcattgacc
attcttcatttccagatcgctgcatagtttccggtatggcttggtatagagccttactcccgtgcataccgttgtggcggaaggttctgggg
cgtaacagcaccgatgaggacggacggagtgaagacgaccttacttcattgagcgataaaatgcctacttttgaagaaacgacaactg
tgagtactgttcgtgaaattgcctccagctgtctaatgtctccgtcggtcagatcacttctgcaaagtacatcaacggtgaaaaaatcatg
gagcataccgttgtggagaccaagcacattgacgaacgtggagacaccagcgtcagtaacggtgattcgaacagcactgcggtaac
cagacattctgggcttagctctgtcagccttttcagatcaaagtacaattgtcgaggacgcgaatgctctggaagaacctgaactctttgct
gttcactctccatatgttgacgactcaaccggcgagcagatggttagactctactacgagctcccagtaagcctcgatgatcttgagatc
ataggccttgaatctcgtattccagagtctgacgatgattcaattgaggcccgctttcgttatcgaggagaggattttttggctacctgttcgt
tattcttatgccaaagctcgaatggttttaacgggtgtatgctgaatggtctgacttcttcactgttgttattttctatttcccggctgctggcca
ctcaatattatcgcaagcactatacaaaataaatagtcctatctctataacagagtacgtcacaaacagcgttcgtccttggcaagaatata
aatagtgtcaatctgctgagaaaaggaggtatgaaatccacttcattcaagcaatggttcccttcgtatacattattatttgtatatggatgg
gaacttttcttgtcttagttgccctgaacgcccgctttaagaagaagcgcattgctgatcctgagtcttctgctgccttcactgatcatcccc
atcaagagtaacatggattctgtatgtccctttgggcatgtttatgtggcagttactaatatattagatggaaactaggaagcggcaaaaca
caggggcaggaagggaaggactcattccaagaaagaaggacaaggaagaacacaagagtgtaaggggtagcaatcctcattggc
gtctactagctgatgggttaaagcaagatacaggtgttcatacgctccaagacaacgatcctgttgtcgagaagccgccattaatttaca
ggagagctggagaagcgccgaaacatgattgggacaagaagtcacccggtttgcgccttagacggtcctgctgtagctgcgggaag
gaagtaccggtaggcctggtctgtcgtatttgtcaccatgagtcttgtcctgagtgcttgaacatgcaaaagcgagattacggatgttgat
cagatacacgggcccctatactaggactagttaccactaggattgtactcaaccttaacagtggcgtttggtacttcgttacagctaaggg
gagaggacagttcctactttcatgtgcttcaaggagaggctcctccaactactgttgctagggaggaaagacactctattcttagctga
gggctgcaggaattcgcatccatgcagtcataccatccatggcatgcaatctatgttgcattagatgcaagaagtaggatagagaaccc
atgtacttgattcacgctagcaggacagagagagataccatacccgacgggagccctgcatgacttcctgtctgcagcttgtcgtgcg
tgtatcattcccatgcgccacgaactcataggcagtggtagttcagaacactctttttttttaaaaaaaaaaagataggaaaataataattt
agggggaagaaaagtaaaaattaaaaagaaaaagttccagatggcgcttctacttctatattcgatcgttattcaataccccagaggcaca
ggcattccgatctctcatcgccaacactgaaaagcagccattttccccgtcttaaagctccaatcctccttcttctcatctacttcctcgct
ccttcaggaccttgagtgttccgttgagctattgggtaacttctcacctgtcaatcatcgattgtcctttctcttgacttgacttcgtgtcgcca
ttctcatttacgatacatatccctggagcagaaaacaaagaaaagggccaattactcttgatctagttccaactctgttgctgcttggaaca
tccgcccatctgtgtggtgaaatcagatgccagcatccatcttgcagcttctcccacttcctgggccgatcttgaatgtttgctctcgaacc
tcgcttagtatttgatctccattctcatctgggtacatcctgtgagtagcatgtcgtcacttgtcacacatactacccgctctcaaatctgtttg
atgggagtcaatctgcctcgaaatggctcgtctgccttcacaagcaaactacagcagatggcgggggcatggactcgagccacagtg
ctggctctcgcttgcatctggaccttcttattctttctcattgctgtatcttttcccccttgaggcttctggcgcgctgcacctttccaagtatc
aaaccaaagctaatcaggggcgtttggcgtcctgccatggcttcactagacctggatctctgcagcctcatcaccatctcggatcacctg
gttctgatcaccttggaagaaagcacaaagacctggagacaatacatattgccgccatcgcagctccctccaatctcgacagcattttc
atgtgtcgggcactatctacctctcggcaattcagtaaccgtactgcctgagaaacatcaacctctcaaattacacaatggtgttcagcgc
acctgctcctggtgtgggctccagtaaaaggccagcgtcatgcatgcaggacgatgttgatgagcgggataatgtcccagtaagtgat
accagcattggaaaggcagatggagctgactcatctcctatatagcccatgggtctatgcgtgcgttcatcgatcaacatcccttacttcc
actacgccatgatctatctcgacaacatgggcagacttaaggtgatggaatctccgtctatccaggagcaaaatgagactgttttcacaa
ccgaagtacgtgaaagattttttggaaatccttggtgccaaggtaggatatcaaccgcccatggttcgaagtatgtaaacactccgcgca
caagtacaatattcttgctgatctcaattgaacagggttgtcagctgccggtgctacaccatacagctatgatcctcaacaaccgcttggtt
gcttgtcttaccgtcaaactaagcgggacagaaattccccagcccactctatgtacggtgtgccgccatccgtccagttctcagccccg
```

-continued

```
gttgaggaatcgccctcttgtggatcagtggacatggtcgggctcgagattggtgatactcctaatgtccttgactactatgagagatcct taaagcactttcggcaggtcaactgtcgccagatcctaaagacattcattaagttcattgagccacgaaagcaagccaagcaccccta t aatggaggtaaaccccctgcaggagcccctcctggtaagaagggcgacccagagaagacaaagcctgaatggtggcccgccaatg tggtccacaaggagcctgaccatcttcgaaaggatcgtacgtgtaacccttcagaaaatcttcagtgtcaagtaactttgctgacagactt agaacgcctgtctctgttaattcatatcatccgcaggcttggaagatttggtatcaccacggatcaattgcaggaaattgcccacgactgc aagcggcggctcagcgaccccca caaactccaaatcttggacgaggtcttcagagtgagaaggattgaagaacgctacgaaagagg agaagttggtaagcggcatcatctttccatgaaattcattttgacagctgttgacgagcctcagatgccaacaagatcgtatatgttgtcaa ccgagagtcgaatcagaaagagaaggatggcgactccaacgtggatccggaccagaagcatgagcaagaagacgataatgcgcg ggaggcacttcccattctccactccgagaagaactcaaccagcccgatgtcgaactcagccgagcacacgggcatggcggcaccaa gtcgtccaatgaatatgggaggtgacagaaaccagttgtttcctttaccggagtggccgagcttcggtgagacaccccaggatgatcg aattttctttcccacgacctctaagtataccgaagattatgcatcgcagcagatgcctagaacacctgcaacaacagcacttgtcagcact aatgagacatgcggcctttgattatatgacacaggagtccatcacctcctcctcccagagcagacttcccaccaccgccaagcac ccctgcccatgcagcactcggccagcctcgacccttggaccctacgttccgacataatttcttcaacccaatggtgtatagtactgcac cccgtcacgccatgtcccaggctactatgttatctcagtttcccaggtccacgacgtctcatggccaggaaatgcctcacatggctcacg gcctgccgaacctgcctcaagacagaccttcaagcatggatggcatgagcatgagaggcccttctttccgcacaggattttt gagtcat ccctgtgacccatcacagcaggctcctcattctagcggatgcggccatcctgacagttggactcaaaatagaccacatgtataatcttaa ctgattgatccttgaccactgttttgaccctcctgcagccttgaagcttcgtttcactgatgattgttcttcgactttgtttctgtccctgactttg ttgtcaatgcggacttatccatgcggcttgttccacgtcaagtgactaccaggacactccgtggttttatatggcaggtactggcgatgac tttccaattcttcttcgtttagtatatatactcgtttcttgttctatgttcgatcatgtcttttccttatacatacctccaaaaatcctgttggag atggcgccagatggcatgagatgcaaatatggatgatgttcttgtgtttgttcatttcaatttctttctcttaatcatgatttgaacaattggcagcg aggtatggcggagctcgttctctttggatgccgatcagctgaataggaggtaacgaggcatgagggtgtttcattatgactctctccggt gtttgtcatttaagggtgcgaggggggaagtgtccgtttcgatgtcctaggatatcgaaaatctgagtagtagccacgtgaccctatgctg acggctgggctggaagacaagcaggttgctgcttacgagaatatgttgaggtattctcgttatcttcgtgaagaatgccgtctccttggcc ctctagccaaagtctgggttgctgaaaggctagctggaattgagaatcgactgtctgcgtccgagtcgcctagaggtgggaaggcccc ctctttctcatacatatgctgactctgcagaccataccaattcgctgcccgaa
``` g: the sequence change as a result of in vitro evolution in hypoxia

```
Primer 5:
AAAAAGATCTgccgtaacgtaacaaagcggg

Primer 6:
AAAAGCGGCCGCttcgggcagcgaattggtatggtc
```

Vector II: Vector for insertion of DNA with pyrithiamine marker

```
CTAAATTGTAAGCGTTAATATTTTGTTAAAATTCGCGTTAAATTTTTGTTAAATCA

GCTCATTTTTTAACCAATAGGCCGAAATCGGCAAAATCCCTTATAAATCAAAAGA

ATAGACCGAGATAGGGTTGAGTGTTGTTCCAGTTTGGAACAAGAGTCCACTATTA

AAGAACGTGGACTCCAACGTCAAAGGGCGAAAAACCGTCTATCAGGGCGATGGC

CCACTACGTGAACCATCACCCTAATCAAGTTTTTTGGGGTCGAGGTGCCGTAAAG

CACTAAATCGGAACCCTAAAGGGAGCCCCCGATTTAGAGCTTGACGGGGAAAGC

CGGCGAACGTGGCGAGAAAGGAAGGGAAGAAAGCGAAAGGAGCGGGCGCTAG

GGCGCTGGCAAGTGTAGCGGTCACGCTGCGCGTAACCACCACACCCGCCGCGCT
```

```
TAATGCGCCGCTACAGGGCGCGTCCCATTCGCCATTCAGGCTGCGCAACTGTTGG
GAAGGGCGATCGGTGCGGGCCTCTTCGCTATTACGCCAGCTGGCGAAAGGGGGA
TGTGCTGCAAGGCGATTAAGTTGGGTAACGCCAGGGTTTTCCCAGTCACGACGTT
GTAAAACGACGGCCAGTGAGCGCGCGTAATACGACTCACTATAGGGCGAATTGG
AGCTCggcgcgccagatctacgcgtttaattaaCCGCGGTGGCGGCCGCTCTAGAACTAGTGGAT
CCCCCGGGCTGCAGGAATTCGATATCAAGCTTATCGATACCGTCGAGgtctgagaggag
gcactgatgcg**tatcatgggtgacgatgagccgctcttgcatctttgtttgtattatactgtctttcttgttacacataattattct
agaatgccccaccgttacatacgggacacagccatttacatatgcatgtggattacgagctaacgagttcattcaaatctcaga
actatcacataatcatcattccctatcgtcaaagaccgtaagacaaatccggttcatgcactgaacccattcgggtagtgagt
catttactc**agcacactcgcgctgacgctcgtcgaacaccttcaatgcctcctcggcagccttgacaccactgagaaccatggcaccg
aaggtagggcccatgcggttaaagccatcaatttcagacagctccataccgccgattatcaagcccttagtaacctcgcgggtgttcttg
acgatggcatcctcggccgagttcatgtcgagaccacgcatgccacctagcttgtcgacgctgcccatggacaccaagcgcttcgca
cagaaggcgccgaatggcccatcgtgaccagtggtactgatgatgacaggagcgttgatagtgttggggtccatgcaggagtgatca
tcgtggtgaagggtgaccagcgtccagttgacgacaacaccagcaatctgggggttgccgttctcggtcggacgggtgatcaagtcct
caacagcggtagcattgaagagcttgacattggggaaggagagaaccttcgacatgagtgtcgaggtaaacagggaggcgtgcttg
acgacaacgtagttggggtttgcgtcctcttcgtaaggaacacccagctcgttcaggaagacttccgcgggacggcgcatgaccatag
cagaaaagagttggccacccaaccaggcaccgccacctattgcacgttagttccggaaagctgagtgcaaggcaatccatcatggac
tactgaccaggagagacgctggcctcgacgatagcaatcttcaggtccggacgagccttggccaagacgtacgcagtgctcagacc
gcaggaaccagcaccaacaatgacaacgtcactttcagcgtacttgtccaggtcctcaaagtaacgtctggtcatggcacgagagacc
tggctttcgcggataggggcgaacttgaactcgtcccacttgccaccgaaatggtccaacagcttggtctgagaagctccctcaacgg
ggacggtctcagaaaccacgaccttacccttgaggccggtagcggccacagtgggttcgtagatggcagctggaggagacatgtttc
aagttgcaatgactatcatctgttagccattccatcaacaggaagaacgagagaaggcatgacccttttcgctggtattatccagatcaa
gttttagccgtataatctcagaacgaacccagtccatcgatgccatgtccttctagactaggatcctagagtctagggcccagcttaggg
agggcatgtgaatgcatcgatgactgggaacgaacaccggcccacgccaaagacgttacctaagatccttgatcattgtgagagtcc
agccaaaagtattccatgacttccatcgtatgccctctagagggctaatcgaggagtgtatttacattgtcggttggtttgggaactataga
agatggtcagttattccaatcaccaaaggtttatcgaagggaggaagacttgttcagtttcgtccgaggacttttggaattcaaatctgag
atagagaattgtgtgggatgagaggaaaaggaagaagatggtggggttcagaaggaggggttgagttaaatagcatgggttgagtca
acgtgataagggcactataccgtatagatcagcggcacccgattctatccgttccttttgctcctcttttagctttgaccggtgagccggac
aagaaacaagtgaaatcatcctgacatcggcggacgatctcctagcttttacatttcgttaccaatgggatcccgtaatcaattgcccgtc
tgtcagatccccagagcattgtttgaggcgaccggtCTCGACCTCGAGGGGGGGCCCGGTACCCAGCT
TTTGTTCCCTTTAGTGAGGGTTAATTGCGCGCTTGGCGTAATCATGGTCATAGCTG
TTTCCTGTGTGAAATTGTTATCCGCTCACAATTCCACACAACATACGAGCCGGAA
GCATAAAGTGTAAAGCCTGGGGTGCCTAATGAGTGAGCTAACTCACATTAATTG
CGTTGCGCTCACTGCCCGCTTTCCAGTCGGGAAACCTGTCGTGCCAGCTGCATTA
ATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCA
GCTCACTCAAAGGCGGTAATACGGTTATCCACAGAATCAGGGGATAACGCAGGA
AAGAACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAAATCGA
CGCTCAAGTCAGAGGTGGCGAAACCCGACAGGACTATAAAGATACCAGGCGTTT
```

-continued

```
CCCCCTGGAAGCTCCCTCGTGCGCTCTCCTGTTCCGACCCTGCCGCTTACCGGAT
ACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAAC
CCCCCGTTCAGCCCGACCGCTGCGCCTTATCCGGTAACTATCGTCTTGAGTCCAA
CCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAGTTACC
TTCGGAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATCTCAAG
AAGATCCTTTGATCTTTTCTACGGGGTCTGACGCTCAGTGGAACGAAAACTCACG
TTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCG
TTCATCCATAGTTGCCTGACTCCCCGTCGTGTAGATAACTACGATACGGGAGGGC
TTACCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTGGTC
CTGCAACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACT
GGTGAGTACTCAACCAAGTCATTCTGAGAATAGTGTATGCGGCGACCGAGTTGCT
CTTGCCCGGCGTCAATACGGGATAATACCGCGCCACATAGCAGAACTTTAAAAG
TGCTCATCATTGGAAAACGTTCTTCGGGGCGAAAACTCTCAAGGATCTTACCGCT
GTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCA
AAAAAGGGAATAAGGGCGACACGGAAATGTTGAATACTCATACTCTTCCTTTTTC
AATATTATTGAAGCATTTATCAGGGTTATTGTCTCATGAGCGGATACATATTTGA
ATGTATTTAGAAAAATAAACAAATAGGGGTTCCGCGCACATTTCCCCGAAAAGT
GCCAC
```

Key:
Pyrithiamine Marker
Product III: Introduction of 3' HAC genes into *A. niger* with pyrithiamine

```
CTAAATTGTAAGCGTTAATATTTTGTTAAAATTCGCGTTAAATTTTTGTTAAATCA
GCTCATTTTTTAACCAATAGGCCGAAATCGGCAAAATCCCTTATAAATCAAAAGA
ATAGACCGAGATAGGGTTGAGTGTTGTTCCAGTTTGGAACAAGAGTCCACTATTA
AAGAACGTGGACTCCAACGTCAAAGGGCGAAAAACCGTCTATCAGGGCGATGGC
CCACTACGTGAACCATCACCCTAATCAAGTTTTTTGGGGTCGAGGTGCCGTAAAG
CACTAAATCGGAACCCTAAAGGGAGCCCCCGATTTAGAGCTTGACGGGGAAAGC
```

```
CGGCGAACGTGGCGAGAAAGGAAGGGAAGAAAGCGAAAGGAGCGGGCGCTAG

GGCGCTGGCAAGTGTAGCGGTCACGCTGCGCGTAACCACCACACCCGCCGCGCT

TAATGCGCCGCTACAGGGCGCGTCCCATTCGCCATTCAGGCTGCGCAACTGTTGG

GAAGGGCGATCGGTGCGGGCCTCTTCGCTATTACGCCAGCTGGCGAAAGGGGGA

TGTGCTGCAAGGCGATTAAGTTGGGTAACGCCAGGGTTTTCCCAGTCACGACGTT

GTAAAACGACGGCCAGTGAGCGCGCGTAATACGACTCACTATAGGGCGAATTGG

AGCTCggcgcgccaGATCTgccgtaacgtaacaaagcggggttggtagtgtttgcaaatgcattcacatggaccgatcacttt tctttccagtctgtccattctgtccaatctgtccgatctgacctgcccagtctgtccagtctgtcccttgtgtcgtccgatccaagctggttat catggcatccacaaagcccgcttcgagtctcatttaccaggcatggaacaaactcagtatcaaccaaaccatccctagtgactcccttga attacttggggagcgtttggctattgccttcgcacccaaactcaaggagcaacgaaggaatggccggcgtcggaatctggaatatgtg gcacaacatcgacggaagattgctcgaaaaatctacttggagattctggagaaagacccaaatatctttcttccttttatcctggctgtttcc cctagagcatgcttatcctttgatatctcgagctttcttgaacagcaccaaagccaaggaagacatttcctccgcaacaatgccgaagcg atcctctggggtctcgcaaagaaacatgacattgatggctccctccatttcaggaagctgatgcgtgagattttccaactgtctcctccag cgacagaagccgaaggcaaggagcattattcattgcatttaagcactctccccgcaatccgcaatgccttcggtgatgttatctttgacg caattgaacgttcccctacacaggtgacagcgagagctaaaggttatttctctgagaaaaccgaaagtgtttggacaaaagttccctaca gaagttctcaagacgcaatcatatctcttgaagtagggtcggcaatcgagcttgcgaatgtgttgttcccaatcgcaacccaaaaaattgt ctctatcctttccgcatgttctcccactgtgcgccagaagaacttttctgaggctattctcggcccagaccctcaggatacaccggcaaca tcatcagaaatcggtatgaagtttaaggtacacatgactgcagttgctaattccaccctgtgctagatgtggcgtattttactctgcgagga gcaacggtctcggcaattgaatcagtctttcgcgctgatatttgcgaaggtattaaggggcagcgaactgagaaactgggaaaaggagc agctgctcatcgacacgacagattgtgtcacgatgcagatatggcgggcacaacctcaacatggaaccatcaagttgcgtattggattc tatgcagcggtgaatttggcaaatcggctgtatgcagaaacaccccaagatcacatatagtaacctttcatcttttcggccttcttaaatcat tgcctttctgtgagtcgcgacttcaccccttatgaatacaccaataccagggggaagaacgatttcaccgcttcccttggcaatccatat agttcccttctcattctggaacctgatttcatcgcagttgaagcaatatatattcctttcgaggttttctgcattgtagggatggaatgggtgc gtgaaatatttgtcgaaaatagaagggtccgaaagttctttccaagctgcgcgctgaaagttgttagcccatctttcgagcatatggtttgg cccacatacgagagattcttttgtgatcggttgagattcttccgtgatcggttctgtcatttctcattaagtcagagagccctcttgtatgccgg cttttgctgtcggatccggcgagataatcgctcctaagccagtcagtcagggaaaagcaaagataaataaaatataggcgaggagtac aaccaggcacgcgtcgtagactattttttctgaagagtttgtcacgtaacctacctcatatggatgggtagttcgaatacttgattgacttga cccgaggttctgaaggcggcggaggaaattgcccaaccccaccattgcattttcaggtatcaatctctgccacactgtggctaaattcgt ctttatcgacacgtgatcacgttccctcttccagccctggtatcagagaatcatcgagttatcgcttgtttcaatttcgtcttgcaattagctta gggaataagcatgtggtcacatcaacctacagagcgctaccggtctttgcgctgagactctcagtgatccgcccaacagacaactaga ctttgaggttgtcgatataaccacaacaaatggcctgtatatcaacgatgtccacgcaattgtctcaagcctcttcacccgacttccagca ctagcatccaagcggcctctcctcttctcccatgtttctcgtagcgcgcctgcatatacttatatctggagatatgttaaaggagctggaag cctggagcatacgctggaagcctggagcatacgcttcaagtgctgccatattcagatagctgagtaggcacaattaggtctaagttcag ggaattgcacctctcgcttcattgtccgtcgattcgtatcggtctctagttctcccgtttatcactctcactcggtggacagtccgtccagt ccgtccagtccgtcgagcctgtccaatctgtccaatctgtccaatctgtccaatctgtccaatctgtccaatctgtccaatctgtccaatctg tccaatctgtccaatctgtccaatctgtccaatctgtccaatctgtccaatctgtccaatctgtccaatctgtccactctgtccactctgtccac tctgtccaatctgtccactctgtccctctgtccactctgtccctctgtccactctgtccctctgtccaatcggtccaatctgtccaatcttg atgatctcgatgatcaataccatttagcgagcgctagtgacgccttacagcgttgcggcgtcttatggcttatacatcttccgaatatcagt cgttcgatctccagatcacacctcggggtgaaacaagcgccatagttcttggtgcgcctgagcttttccctgcccggccactcagtcgtg atggcttcccagagtattccataagtcgaaaccagagataggccagcggacggcaaatctcctctgctccgttctcaaccaatactgcc
```

```
aaagtgagcaatggaaagtgttccaggagcaccgtggcctttaaaagcgccagccttgtcccagatcctcaccgcaattcggcacag
accaacgcagactttcattgaccattcttcatttccagatcgctgcatagtttccggtatggcttggtatagagccttactcccgtgcatacc
gttgtggcggaaggttctggggcgtaacagcaccgatgaggacggacggagtgaagacgaccttacttcattgagcgataaaatgcc
tactttgaagaaacgacaactgtgagtactgttcgtgaaattgcctccagctgtctaatgtctccgtcggtcagatcacttctgcaaagta
catcaacggtgaaaaaatcatggagcataccgttgtggagaccaagcacattgacgaacgtggagacaccagcgtcagtaacggtg
attcgaacagcactgcggtaaccagacattctgggcttagctctgtcagcctttcagatcaaagtacaattgtcgaggacgcgaatgctc
tggaagaacctgaactctttgctgttcactctccatatgttgacgactcaaccggcgagcagatggttagactctactacgagctcccagt
aagcctcgatgatcttgagatcataggccttgaatctcgtattccagagtctgacgatgattcaattgagggcccgctttcgttatcgagga
gaggattttggctacctgttcgttattcttatgccaaagctcgaatggttttaacgggtgtatgctgaatggtctgacttcttcactgttgttat
tttctatttcccggctgctggccactcaatattatcgcaagcactatacaaaataaatagtcctatctctataacagagtacgtcacaaaca
gcgttcgtccttggcaagaatataaatagtgtcaatctgctgagaaaaggaggtatgaaatccacttcattcaagcaatggttcccttcgt
atacattatttgtatatggatgggaacttttcttgtcttagttgccctgaacgcccgctttaagaagaagcgcattgctgatcctgagtctt
ctgctgccttcactgatcatccccatcaagagtaacatggattctgtatgtccctttgggcatgtttatgtggcagttactaatatattagatg
gaaactaggaagcggcaaaacacaggggcaggaagggaaggactcattccaagaaagaaggacaaggaagaacacaagagtgt
aaggggtagcaatcctcattggcgtctactagctgatgggttaaagcaagatacaggtgttcatacgctccaagacaacgatcctgttgt
cgagaagccgccattaatttacaggagagctggagaagcgccgaaacatgattgggacaagaagtcaccggtttgcgccttagacg
gtcctgctgtagctgcgggaaggaagtaccggtaggcctggtctgtcgtatttgtcaccatgagtcttgtcctgagtgcttgaacatgca
aaagcgagattacggatgttgatcagatacacgggcccctatactaggactagttaccactaggattgtactcaaccttaacagtggcgt
ttggtacttcgttacagctaaggggagaggacagttcctactttcatgtgcttcaagggagaggctcctccaactactgttgctagggag
gaaagacactctattcttagctgagggctgcaggaattcgcatccatgcagtcataccatccatggcatgcaatctatgttgcattagatg
caagaagtaggatagagaacccatgtacttgattcacgctagcaggacagagagagataccatacccgacgggagcccctgcatga
cttcctgtctgcagcttgtcgtgcgtgtatcattcccatgcgccacgaactcataggcagtggtagttcagaacactctttttttttaaaaaaa
aaaaagataggaaataataatttaggggaagaaaagtaaaaattaaaaagaaaaagttccagatggcgcttctacttctatattcgatc
gttattcaatacccagaggcacaggcattccgatctctcatcgccaacactgaaaagcagccattttccccgtcttaaagctccaatc
ctccttcttctcatctacttcctgctccttcaggacctgagtgttccgttgagctattgggtaacttctcacctgtcaatcatcgattgtccttt
ctcttgacttgacttcgtgtcgccattctcatttacgatacatatccctggagcagaaaacaaagaaaagggccaattactcttgatctagtt
ccaactctgttgctgcttgaacatccgccatctgtgtggtgaaatcagatgccagcatccatcttgcagcttctcccacttcctgggcc
gatcttgaatgtttgctctcgaacctcgcttagtatttgatctccattctcatctgggtacatcctgtgagtagcatgtcgtcacttgtcacaca
tactacccgctctcaaatctgtttgatgggagtcaatctgcctcgaaatggctcgtctgccttcacaagcaaactacagcagatggcggg
ggcatggactcgagccacagtgctggctctcgcttgcatctggaccttcttattctttctcattgctgtatcttttcccccttgaggcttctgg
cgcgctgcacctttccaagtatcaaaccaaagctaatcaggggcgtttggcgtcctgccatggcttcactagacctggatctctgcagc
ctcatcaccatctcggatcacctggttctgatcaccttggaagaaagcacaaagaccttggagacaatacatattgccgccatcgcagct
ccctccaatctcgacagcattttcatgtgtcgggcactatctacctctcggcaattcagtaaccgtactgcctgagaaacatcaacctctc
aaattacacaatggtgttcagcgcacctgctcctggtgtgggctccagtaaaaggccagcgtcatgcatgcaggacgatgttgatgag
cgggataatgtcccagtaagtgataccagcattggaaaggcagatggagctgactcatcctatatagcccatgggtctatgcgtgcg
ttcatcgatcaacatcccttacttccactacgccatgatctatctcgacaacatgggcagacttaaggtgatggaatctccgtctatccagg
agcaaaatgagactgttttcacaaccgaagtacgtgaaagattttttggaaatccttggtgccaaggtaggatatcaaccgcccatggttc
gaagtatgtaaacactccgcgcacaagtacaatattcttgctgatctcaattgaacagggttgtcagctgccggtgctacaccatacagc
tatgatcctcaacaaccgcttggttgcttgtcttaccgtcaaactaagcgggacagaaattccccagcccactctatgtacggtgtgccg
ccatccgtccagttctcagcccggttgaggaatcgcctcttgtggatcagtggacatggtcgggctcgagattggtgatactcctaat
gtccttgactactatgagagatccttaaagcactttcggcaggtcaactgtcgccagatcctaaagacattcattaagttcattgagccac
```

-continued

```
gaaagcaagccaagcacccctataatggaggtaaaccccctgcaggagcccctcctggtaagaagggcgacccagagaagacaa agcctgaatggtggcccgccaatgtggtccacaaggagcctgaccatcttcgaaaggatcgtacgtgtaacccttcagaaaatcttcag tgtcaagtaactttgctgacagacttagaacgcctgtctctgttaattcatatcatccgcaggcttggaagatttggtatcaccacggatca attgcaggaaattgcccacgactgcaagcggcggctcagcgaccccacaaactccaaatcttggacgaggtcttcagagtgagaag gattgaagaacgctacgaagaggagaagttggtaagcggcatcatctttccatgaaattcattttgacagctgttgacgagcctcagat gccaacaagatcgtatatgttgtcaaccgagagtcgaatcagaaagagaaggatggcgactccaacgtggatccggaccagaagca tgagcaagaagacgataatgcgcgggaggcacttcccattctccactccgagaagaactcaaccagcccgatgtcgaactcagccg agcacacgggcatggcggcaccaagtcgtccaatgaatatgggaggtgacagaaaccagttgtttccttttaccggagtggccgagctt cggtgagacaccccaggatgatcgaattttctttcccacgacctctaagtataccgaagattatgcatcgcagcagatgcctagaacac ctgcaacaacagcacttgtcagcactaatgagacacatgcggcctttgattatatgacacaggagtccatcacctcctcctcccagag cagacttcccaccaccgccaagcacccctgcccatgcagcactcggccagcctcgacccttggaccctacgttccgacataatttctt caacccaatggtgtatagtactgcaccccgtcacgccatgtcccaggctactatgttatctcagtttcccaggtccacgacgtctcatggc caggaaatgcctcacatggctcacggcctgccgaacctgcctcaagacagaccttcaagcatggatggcatgagcatgagaggccct tctttccgcacaggattttttgagtcatccctgtgacccatcacagcaggctcctcattctagcggatgcggccatcctgacagttggactc aaaatagaccacatgtataatcttaactgattgatccttgaccactgttttgaccctcctgcagccttgaagcttcgtttcactgatgattgttc ttcgactttgtttctgtccctgactttgttgtcaatgcggacttatccatgcggcttgttccacgtcaagtgactaccaggacactccgtggtt ttatatggcaggtactggcgatgactttccaattcttcttcgtttagtatatatactcgtttcttgttctatgttcgatcatgtcttttttccttata catacctccaaaaatcctgttggagatggcgccagatggcatgagatgcaaatatggatgatgttcttgtgtttgttcatttcaatttctttctctta atcatgatttgaacaattggcagcgaggtatggcggagctcgttctctttggatgccgatcagctgaataggaggtaacgaggcatgag ggtgtttcattatgactctctccggtgtttgtcatttaagggtgcgaggggggaagtgtccgtttcgatgtcctaggatatcgaaaatctgagt agtagccacgtgaccctatgctgacggctgggctggaagacaagcaggttgctgcttacgagaatatgttgaggtattctcgttatcttc gtgaagaatgccgtctccttggccctctagccaaagtctgggttgctgaaaggctagctggaattgagaatcgactgtctgcgtccgag tcgcctagaggtgggaaggcccccctctttctcatacatatgctgactctgcagaccataccaattcgctgcccgaaGCGGCCGC

TCTAGAACTAGTGGATCCCCCGGGCTGCAGGAATTCGATATCAAGCTTATCGATA

CCGTCGAGgtctgagaggaggcactgatgcgctatcatggggtgacgatgagccgctcttgcatctttgtttgtattatactgtctt tcttgttacacataattattctagaatgccccaccgttacatacgggacacagccatttacatatgcatgtggattacgagctaacgagttc attcaaatctcagaactatcacataatcatcattcccctatcgtcaaagaccgtaagacaaatccggttcatgcactgaacccattcgggt agtgagtcatttactcagcacactcgcgctgacgctcgtcgaacaccttcaatgcctcctcggcagccttgacaccactgagaaccatg gcaccgaaggtagggcccatgcggttaaagccatcaatttcagacagctccataccgccgattatcaagcccttagtaacctcgcggg tgttcttgacgatggcatcctcggccgagttcatgtcgagaccacgcatgccacctagcttgtcgacgctgcccatggacaccaagcg cttcgcacagaaggcgccgaatggcccatcgtgaccagtggtactgatgatgacaggagcgttgatagtgttggggtccatgcagga gtgatcatcgtggtgaagggtgaccagcgtccagttgacgacaacaccagcaatctgggggttgccgttctcggtcggacgggtgat caagtcctcaacagcggtagcattgaagagcttgacattggggaaggagagaaccttcgacatgagtgtcgaggtaaacagggagg cgtgcttgacgacaacgtagttggggtttgcgtcctcttcgtaaggaacacccagctcgttcaggaagacttccgcgggacggcgcat gaccatagcagaaaagagttggccacccaaccaggcaccgccacctattgcacgttagttccggaaagctgagtgcaaggcaatcc atcatggactactgaccaggagagacgctggcctcgacgatagcaatcttcaggtccggacgagccttggccaagacgtacgcagtg ctcagaccgcaggaaccagcaccaacaatgacaacgtcactttcagcgtacttgtccaggtcctcaaagtaacgtctggtcatggcac gagagacctggctttcgcggataggggcgaacttgaactcgtcccacttgccaccgaaatggtccaacagcttggtctgagaagctcc ctcaacggggacggtctcagaaaccacgaccttacccttgaggccggtagcggccacagtgggttcgtagatggcagctggaggag acatgtttcaagttgcaatgactatcatctgttagccattccatcaacaggaagaacgagagaaggcatgacccttttcgctggtattatcc
```

-continued agatcaagtttttagccgtataatctcagaacgaacccagtccatcgatgccatgtccttctagactaggatcctagagtctagggcccag cttagggagggcatgtgaatgcatcgatgactgggaacgaacaccggcccacgccaaagacgttacctaagataccttgatcattgtg agagtccagccaaaagtattccatgacttccatcgtatgccctctagagggctaatcgaggagtgtatttacattgtcggttggtttggga actatagaagatggtcagttattccaatcaccaaaggtttatcgaagggaggaagacttgttcagtttcgtccgaggacttttggaattcaa atctgagatagagaattgtgtgggatgagaggaaaaggaagaagatggtgggggttcagaaggagggggttgagttaaatagcatgggt tgagtcaacgtgataagggcactataccgtatagatcagcggcacccgattctatccgttccttttgctcctctttagctttgaccggtgag ccggacaagaaacaagtgaaatcatcctgacatcggcggacgatctcctagcttttacatttcgttaccaatgggatcccgtaatcaattg cccgtctgtcagatccccagagcattgtttgaggcgaccggtCTCGACCTCGAGGGGGGGCCCGGTACCC

AGCTTTTGTTCCCTTTAGTGAGGGTTAATTGCGCGCTTGGCGTAATCATGGTCATA

GCTGTTTCCTGTGTGAAATTGTTATCCGCTCACAATTCCACACAACATACGAGCC

GGAAGCATAAAGTGTAAAGCCTGGGGTGCCTAATGAGTGAGCTAACTCACATTA

ATTGCGTTGCGCTCACTGCCCGCTTTCCAGTCGGGAAACCTGTCGTGCCAGCTGC

ATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGGT

ATCAGCTCACTCAAAGGCGGTAATACGGTTATCCACAGAATCAGGGGATAACGC

AGGAAAGAACATGTGAGCAAAAGGCCAGCAAAAGGCCAGGAACCGTAAAAAGG

CCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACGC

TGTAGGTATCTCAGTTCGGTGTAGGTCGTTCGCTCCAAGCTGGGCTGTGTGCACG

AACCCCCCGTTCAGCCCGACCGCTGCGCCTTATCCGGTAACTATCGTCTTGAGTC

CAACCCGGTAAGACACGACTTATCGCCACTGGCAGCAGCCACTGGTAACAGGAT

TAGCAGAGCGAGGTATGTAGGCGGTGCTACAGAGTTCTTGAAGTGGTGGCCTAA

CTACGGCTACACTAGAAGGACAGTATTTGGTATCTGCGCTCTGCTGAAGCCAGTT

ACCTTCGGAAAAAGAGTTGGTAGCTCTTGATCCGGCAAACAAACCACCGCTGGT

AGCGGTGGTTTTTTTGTTTGCAAGCAGCAGATTACGCGCAGAAAAAAAGGATCTC

AAGAAGATCCTTTGATCTTTTCTACGGGGTCTGACGCTCAGTGGAACGAAAACTC

ACGTTAAGGGATTTTGGTCATGAGATTATCAAAAAGGATCTTCACCTAGATCCTT

TTAAATTAAAAATGAAGTTTTAAATCAATCTAAAGTATATATGAGTAAACTTGGT

CTGACAGTTACCAATGCTTAATCAGTGAGGCACCTATCTCAGCGATCTGTCTATT

TCGTTCATCCATAGTTGCCTGACTCCCCGTCGTGTAGATAACTACGATACGGGAG

GGCTTACCATCTGGCCCCAGTGCTGCAATGATACCGCGAGACCCACGCTCACCGG

CTCCAGATTTATCAGCAATAAACCAGCCAGCCGGAAGGGCCGAGCGCAGAAGTG

GTCCTGCAACTTTATCCGCCTCCATCCAGTCTATTAATTGTTGCCGGGAAGCTAG

AGTAAGTAGTTCGCCAGTTAATAGTTTGCGCAACGTTGTTGCCATTGCTACAGGC

ATCGTGGTGTCACGCTCGTCGTTTGGTATGGCTTCATTCAGCTCCGGTTCCCAACG

ATCAAGGCGAGTTACATGATCCCCCATGTTGTGCAAAAAAGCGGTTAGCTCCTTC

GGTCCTCCGATCGTTGTCAGAAGTAAGTTGGCCGCAGTGTTATCACTCATGGTTA

TGGCAGCACTGCATAATTCTCTTACTGTCATGCCATCCGTAAGATGCTTTTCTGTG

ACTGGTGAGTACTCAACCAAGTCATTCTGAGAATAGTGTATGCGGCGACCGAGTT

```
GCTCTTGCCCGGCGTCAATACGGGATAATACCGCGCCACATAGCAGAACTTTAA

AAGTGCTCATCATTGGAAAACGTTCTTCGGGGCGAAAACTCTCAAGGATCTTACC

GCTGTTGAGATCCAGTTCGATGTAACCCACTCGTGCACCCAACTGATCTTCAGCA tcttttactttcaccagcgtttctgggtgagcaaaaacaggaaggcaaaatgccg

CAAAAAAGGGAATAAGGGCGACACGGAAATGTTGAATACTCATACTCTTCCTTT

TTCAATATTATTGAAGCATTTATCAGGGTTATTGTCTCATGAGCGGATACATATTT

GAATGTATTTAGAAAAATAAACAAATAGGGGTTCCGCGCACATTTCCCCGAAAA

GTGCCAC
```

Genome Editing of *S. cerevisiae* Strains

Integration of heterologous genes of interest into the chromosome is one method for engineering *S. cerevisiae* for use in industrial scale fermentations and heterologous protein production. Consequently, to demonstrate that the technology disclosed herein can reduce oxygen consumption and requirements in *S. cerevisiae* based fermentations and protein production, the HAC and the evolved allele of hrmA will be integrated into rDNA sites in the *S. cerevisiae* genome using a traditional yeast genetic engineering approach based on homologous recombination. Standard laboratory haploid strains of *S. cerevisiae* will be used for these experiments, BY4741 and BY4742. rDNA sequence will be used as the homologous recombination site flanking HAC or the evolved hrmA allele sequences described above. This will target the heterologous genes for integration at rDNA sites which are commonly used for integration and expression of genes in *S. cerevisiae*. For selection of transformants, the bacterial kanamycin resistance gene, kan, can be utilized. All strains will be confirmed through initial PCR based confirmation of target integration, Southern analyses, and expression levels of the respective integrated genes using qRT-PCR. Finalized strain(s) that show phenotypes of interest (high biomass yield, reduced oxygen consumption, ethanol production) will be sent for whole genome sequencing. Following successful proof of concept in laboratory strains, introduction of HAC and/or associated genes into industrial strains of *S. cerevisiae* will be demonstrated.

Quantification of Fungal Biomass and Morphology

The biomass and morphology of fungi critically impacts the production of fermentation and heterologous protein products in batch cultures (Colin 2013, supra). Genetically-modified *A. niger* and *S. cerevisiae* strains generated as described above will be assayed for: 1) spore germination rate (*A. niger* only), 2) submerged fungal morphology, 3) and relative fungal biomass at a range of oxygen concentrations. A spectrophotometric assay to quantify fungal germination and hyphal extension over 24-36 hours of fungal growth was previously utilized (Beattie 2017, supra). This assay will be used with potato dextrose broth (PDB) to compare differences in early growth rates in normal oxygen (~21% $O_2$) across strains of *A. niger*. To assess morphological changes as a result of the aforementioned genetic modifications, the *A. niger* and *S. cerevisiae* strains will be grown in liquid shaking cultures of 100 mL PDB (*A. niger*) or YPD (yeast) and compare the ability of the strains to form pellets, flocs, or loose filamentous hyphae (*A. niger*). Using this same assay, the mycelia will be collected, flash freeze, and lyophilize the tissue for *A. niger*. This will allow for comparisons of total dry weight of filamentous fungal biomass following, 18, 24, 36, and 48 hours of growth. For *S. cerevisiae*, optical density (.D.) measurements at O.D. 600 will be used to monitor growth rate and total biomass over a 48 hour time period, sampling every hour. Other media conditions relevant to specific fermentations or protein production will be tested as indicated.

Given that the induction of HAC in *A. fumigatus* generates a strain, EVOL20, that is better able to grow in low oxygen environments, the ability of HAC (portions or in entirely) to influence the ability of *A. niger* and *S. cerevisiae* to grow in low oxygen environments (10%, 5%, 2%, and 0.2% $O_2$) will be assayed. These assays will be performed in liquid shaking cultures as described above for biomass quantification using our INVIVO₂ 400 Hypoxia Workstation (Ruskinn Technology Limited, Bridgend, UK) equipped with a gas regulator (Kowalski 2016, supra).

Quantification of Fungal Oxygen Consumption

Fungal oxygen consumption will be quantified using a Unisense Clark-type microsensor (https://www.unisense.com/O₂/) as described above (see FIG. 23b). Currently, the majority of citric acid production by *A. niger* is performed through submerged fermentation, however surface fermentation remains utilized to a lesser extent (Show 2015, supra). Therefore, oxygen consumption of the generated *A. niger* strains in both planktonic (submerged fermentation) and surface-adhered cultures will be assayed. For *S. cerevisiae* batch production cultures will be utilized to monitor oxygen consumption of strains engineered to express HAC in comparison to the parental strains.

For *A. niger* submerged fermentation cultures, strains will be grown to equivalent biomass in 100 mL cultures in PDB. Mycelia will then be collected through vacuum filtration with sterile Miracloth and be resuspended in 20 mL of fresh PDB in a 50 mL plastic conical tubes. Immediately, the Unisense OX-25 electrode will be placed at a depth of 10 mL into the freshly inoculated PDB and will monitor the dissolved oxygen every 120 seconds for minutes. The electrode does not consume oxygen providing fast and accurate readings.

The same protocol will be used for *S. cerevisiae* fermentations, except strains will be grown in YPD or other appropriate media until mid-log phase, collected, washed with sterile PBS, and resuspended in fresh YPD media prior to monitoring of oxygen consumption. For surface-adhered cultures, *A. niger* will be grown in static cultures of 4 mL PDB in sterile 6-well polystyrene plates for 36-48 hours. The spent media will be removed and replaced with fresh PDB before immediately being analyzed for dissolved oxygen using the Unisense OX-system at a depth of 3 mL. Oxygen readings will be recorded as described above. Surface adhered mycelia of genetically modified strains will be collected to compare biomass to the parental strains.

Quantification of *A. niger* Citric Acid Production

Genetically engineered *A. niger* strains that show a reduction in oxygen consumption and a maintenance or increase in fungal biomass yield will be utilized in a colorimetric assay for preliminary quantification of citrate within culture supernatants and within lysed mycelia (BioVision #K655). For supernatant samples, *A. niger* cultures in PDB or fermentation media (Bhattacharjee 2015, supra) will be cultured for 60 hours and mycelia will be removed through sterile Miracloth. For lysed mycelia, collected mycelia through the Miracloth will be flash frozen in liquid nitrogen and ground using a sterile and cold mortar and pestle. Ground tissue will be suspended in PBS and used in the colorimetric assay. Parental strains will be included as references. Strains with reduced oxygen consumption that do not have significant reduction in citric acid production relative to the parental strain will be considered a strain of interest for larger scale assays.

CONCLUSION

Figure 27:
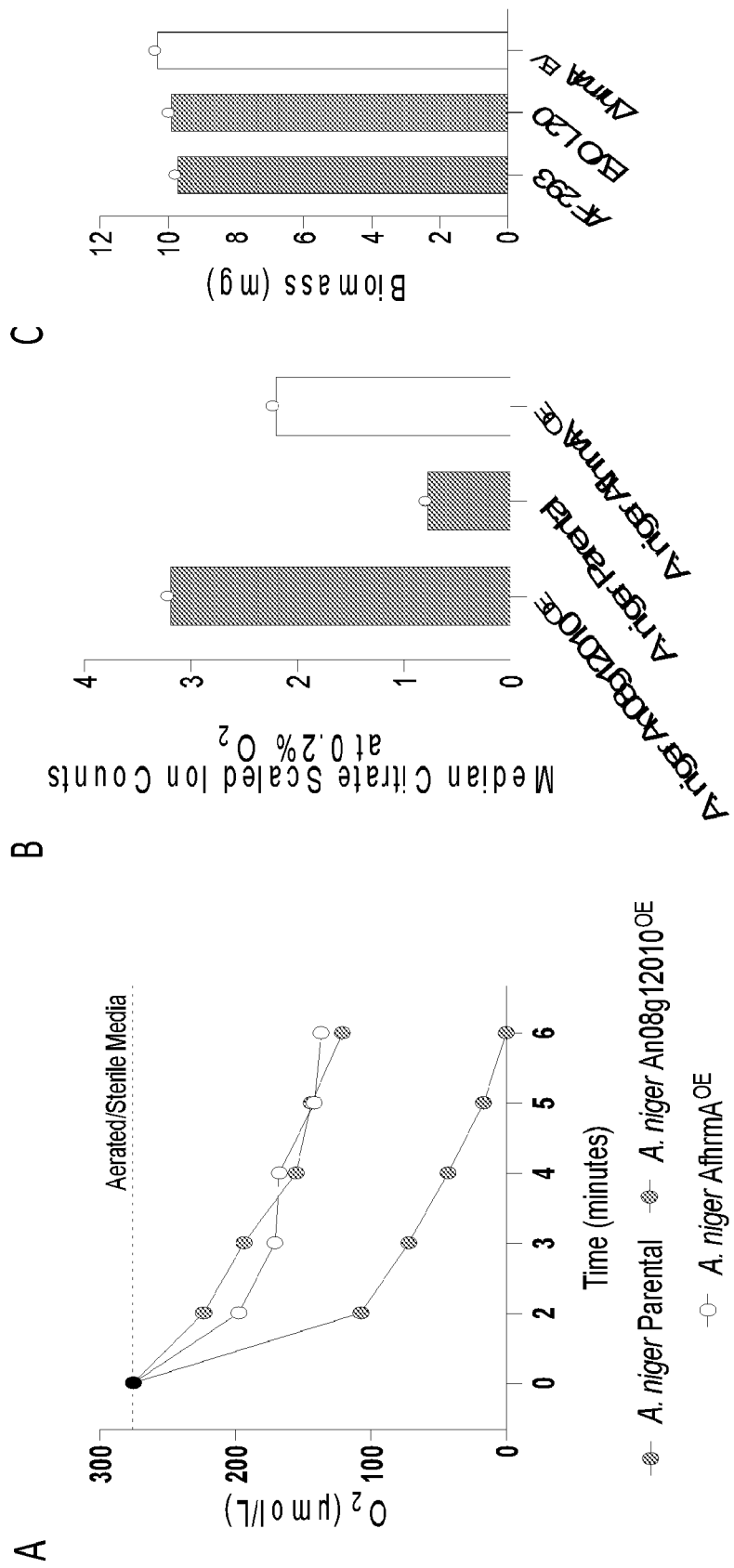
FIG. 27 depicts the predicted results from a successfully engineered *A. niger* strain. The following phenotypes are expected.

Successful engineering of *A. niger* and *S. cerevisiae* strains with the technology described herein will be identified by 1) reduced oxygen consumption in planktonic/submerged culture conditions, 2) an increase in or equivalent production of citric acid in inducing conditions for *A. niger*, and 3) no reduction in fungal biomass compared to the reference *A. niger* or *S. cerevisiae* strains (FIG. 27). Additional engineering of other industrial relevant fungi with our technology is a planned future direction.

Example 3— Introduction of the Cryptic Gene Ortholog is Sufficient to Complement the Loss of cgnA and hrmA in EVOL20

The work described above identified the HAC region as important for hypoxia tolerance. A cryptic subtelomeric gene was identified next. This gene was sufficient to induce the hypoxia-locked colony and biofilm morphology in *A. fumigatus*, and increase low oxygen growth. It is one three putative orthologs present across *A. fumigatus* strains, all of which have the capacity to impact hyphal architecture and biofilm development and are herein named biofilm architecture factors (baf). Introduction of the *A. fumigatus* cryptic gene bafA into *A. niger* generated the hypoxia-locked colony and biofilm morphotypes indicating the potential broad impacts of these previously uncharacterized genes on biofilm architecture and development both naturally and through synthetic introduction.

The Native 5' Sequence to cgnA is Required to Complement the Loss of cgnA in EVOL20

Through an experimental evolution approach, where the reference strain AF293 was serially passaged in a low oxygen (0.2% $O_2$) environment, the strain EVOL20 was generated. As a result of the low oxygen passaging, the EVOL20 strain acquired a hypoxia-locked colony morphology (H-MORPH) characterized by colony furrows and increased vegetative mycelia during normal oxygen growth. Genes were identified the responsible for this morphological transition within a subtelomeric gene cluster. The apparent regulator of this gene cluster, hrmA, induces expression of the surrounding genes in the hrmA-associated cluster (HAC) including the adjacent collagen-like protein encoding gene cgnA. Disruption of the gene cluster by deleting cgnA in EVOL20 reverts the colony morphology from H-MORPH to that of the parent strain AF293 which we termed N-MORPH. However, over expression of cgnA in AF293, where basal HAC expression is low, is unable to generated H-MORPH or the elevated hypoxic growth characteristic of the EVOL20 strain.

Figure 28:
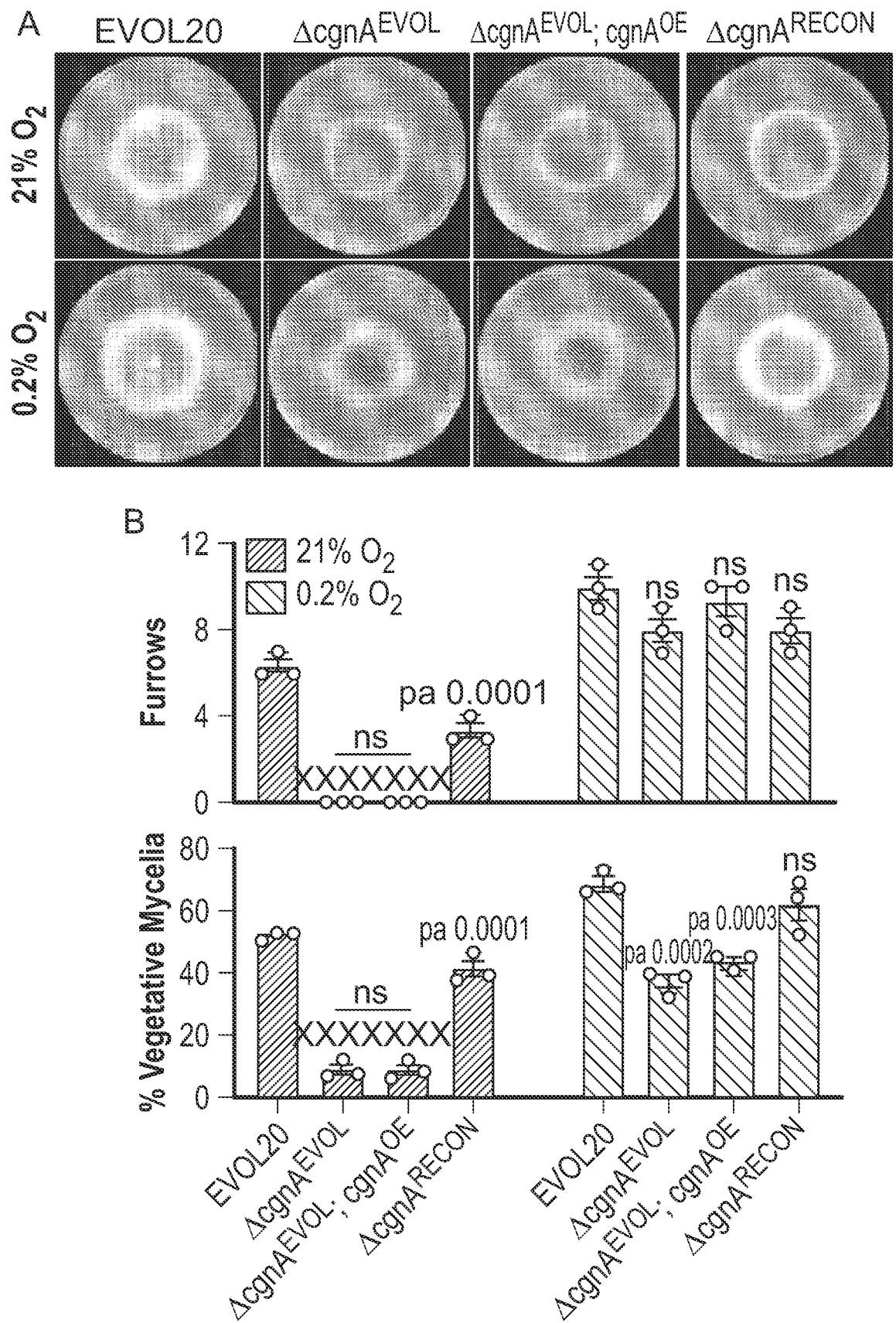
FIG. 28 depicts that a cryptic gene within the hrmA-associated gene cluster is necessary for the hypoxia-evolved phenotypes of EVOL20.
Figure 28:
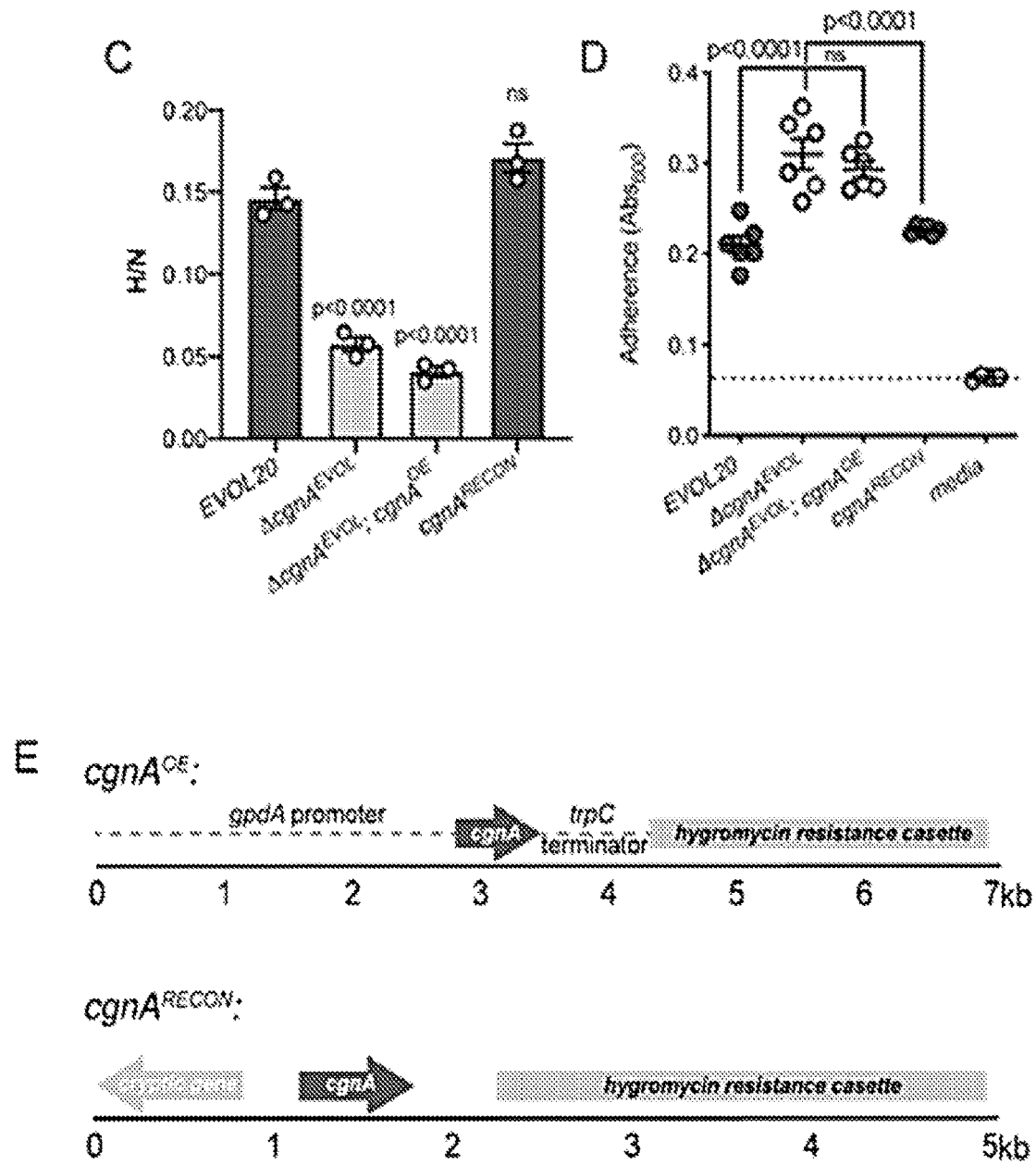

Simultaneous elevated expression of HAC genes may be additionally required for H-MORPH. As the majority of annotated HAC genes, with the exception of Afu5g14920, remain unaltered following the deletion of cgnA in EVOL20, cgnA was overexpressed in this background ($\Delta$cgnAEVOL; cgnA$^{OE}$) (FIG. 28A). This method did not complement the loss of cgnA in EVOL20 and regenerate H-MORPH, where colony furrows and the percent vegetative mycelia were not significantly altered relative to $\Delta$cgnA$^{EVOL}$ (FIG. 28B). We next hypothesized that the ectopic integration of the cgnA allele may prevent complementation. However, ectopic integration of cgnA with its native promoter and 5' sequence is able to complement the loss of cgnA in EVOL20 and restore H-MORPH with elevated colony furrows and an increased percentage of vegetative mycelia (FIG. 28A, 28B). In addition to a transition from H-MORPH to N-MORPH colony morphology, the loss of cgnA in EVOL20 ($\Delta$cgnAEVOL) also significantly reduces the ratio of hypoxic to normoxia growth (hypoxia fitness, H/N) of EVOL20 (FIG. 28C) and significantly increases hyphal adherence (FIG. 28D). Where $\Delta$cgnA EVOL; cgnA$^{OE}$ does not complement either of these phenotypes, cgnA$^{RECO}$N restores both hypoxia fitness and adherence of $\Delta$cgnA$^{EVOL}$ to the levels of EVOL20 (FIG. 28C, 28D). The necessity of the native sequence 5' of cgnA to complement $\Delta$cgnA$^{EVOL}$ prompted the investigation of this region more closely.

A Cryptic Gene is Encoded 5' of cgnA within HAC and is Required for H-MORPH and HAC Related Phenotypes By utilizing previously published RNA-sequencing data, a substantial region of mapped reads 5' to cgnA in EVOL20 that were absent in AF293 were identified. Neither the AF293 assembled reference genome, nor the partially assembled genome of A 1163, annotate a gene within this region. It is unlikely that these reads belong to the same transcript as cgnA as they map to the opposite strand. Therefore, we hypothesize that these reads map to an independent cryptic gene within HAC, and that this gene may be important for H-MORPH and other EVOL20-related phenotypes (i.e. hypoxia fitness, adherence, and biofilm architecture). To determine if our strategies to delete cgnA interrupt the expression of this cryptic gene, we designed primers within the predicted open reading frame (ORF) to quantify relative expression in two isogenic strain sets. Both in EVOL20/$\Delta$cgnAEVOL and in hrmA$^{R-EV}$/hrmA$^{R-EV}$; $\Delta$cgnA. In both cases deletion of the cgnA coding sequence reduces cgnA mRNA levels and mRNA levels corresponding to the cryptic gene.

A two exon ORF of 579 base pairs (bp) from the region corresponding to the cryptic gene was predicted. In the DNA construct used to generate $\Delta$cgnAEVOL;cgnA$^{OE}$, cgnA expression was driven by the constitutive gpdA promoter from *A. nidulans* and therefore the native 5' sequence containing the cryptic gene ORF was not re-introduced (FIG. 28E). In contrast, the DNA construct used to generate the cgnA$^{RECO}$N strain utilized the native sequence 5' to cgnA to drive expression. This region included the entire predicted coding sequence of the cryptic gene (FIG. 28E). Gene expression analysis confirms that both $\Delta$cgnAEVOL; cgnA$^{OE}$ and cgnA RECON have cgnA mRNA levels equivalent to or greater than those of EVOL20, but only cgnA$^{RE}$_{co}$N restores mRNA levels of the cryptic gene similarly to EVOL20 (FIG. 28F). Only with the strain cgnA$^{RECO}$N, where both cgnA and the cryptic gene are expressed, is H-MORPH restored (FIG. 28A, 28B), hypoxic fitness increased (FIG. 28C), and adherence reduced (FIG. 28D) in ΔcgnAEVOL. Thus, the cgnA sequence alone is not sufficient to generate the EVOL20 phenotypes but requires the 5' cryptic gene.

Introduction of the Cryptic Gene Ortholog is Sufficient to Complement the Loss of cgnA and hrmA in EVOL20

Although there has been controversy as to whether a colony grown on a semi-solid surface is in fact a biofilm, there is abundant evidence linking colony morphologies with subsequent biofilm formation and structure phenotypes (Haussler et al. J Bacteriol 195(13):2947-2958, 2013). It was demonstrated in Example 1 with *A. fumigatus* that H-MORPH colony morphology corresponds with architectural changes within submerged biofilms relative to N-MORPH strains. Therefore, the cryptic gene within HAC that is necessary for H-MORPH in EVOL20 with the gene ID Afu5g14915 has been designated biofilm architecture factor A (bafA). Similarly, the uncharacterized genes with high nucleotide and amino acid identity to bafA within HBAC and HCAC will be referred to as bafB (AFUB_044360) and bafC (AFUB_096610), respectively.

Figure 29:
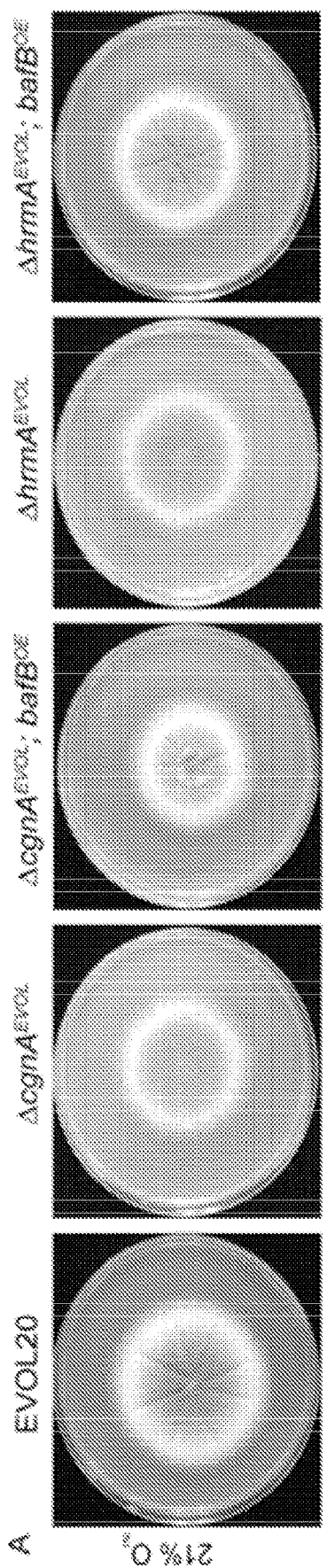
FIG. 29 depicts that the putative ortholog of the cryptic gene, bafB, is sufficient to complement the loss of the HAC genes cgnA and bafA.
Figure 29:
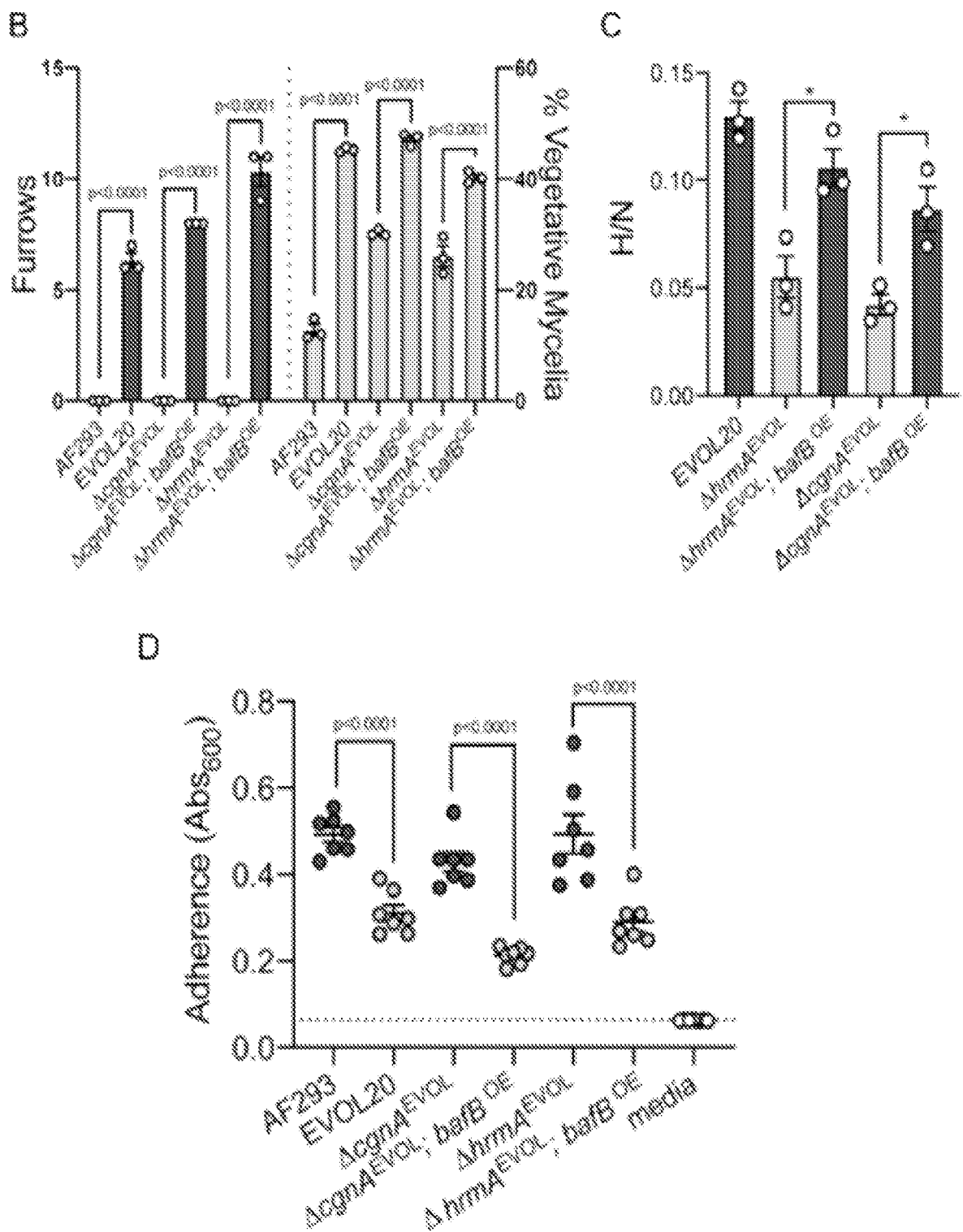
Figure 29:
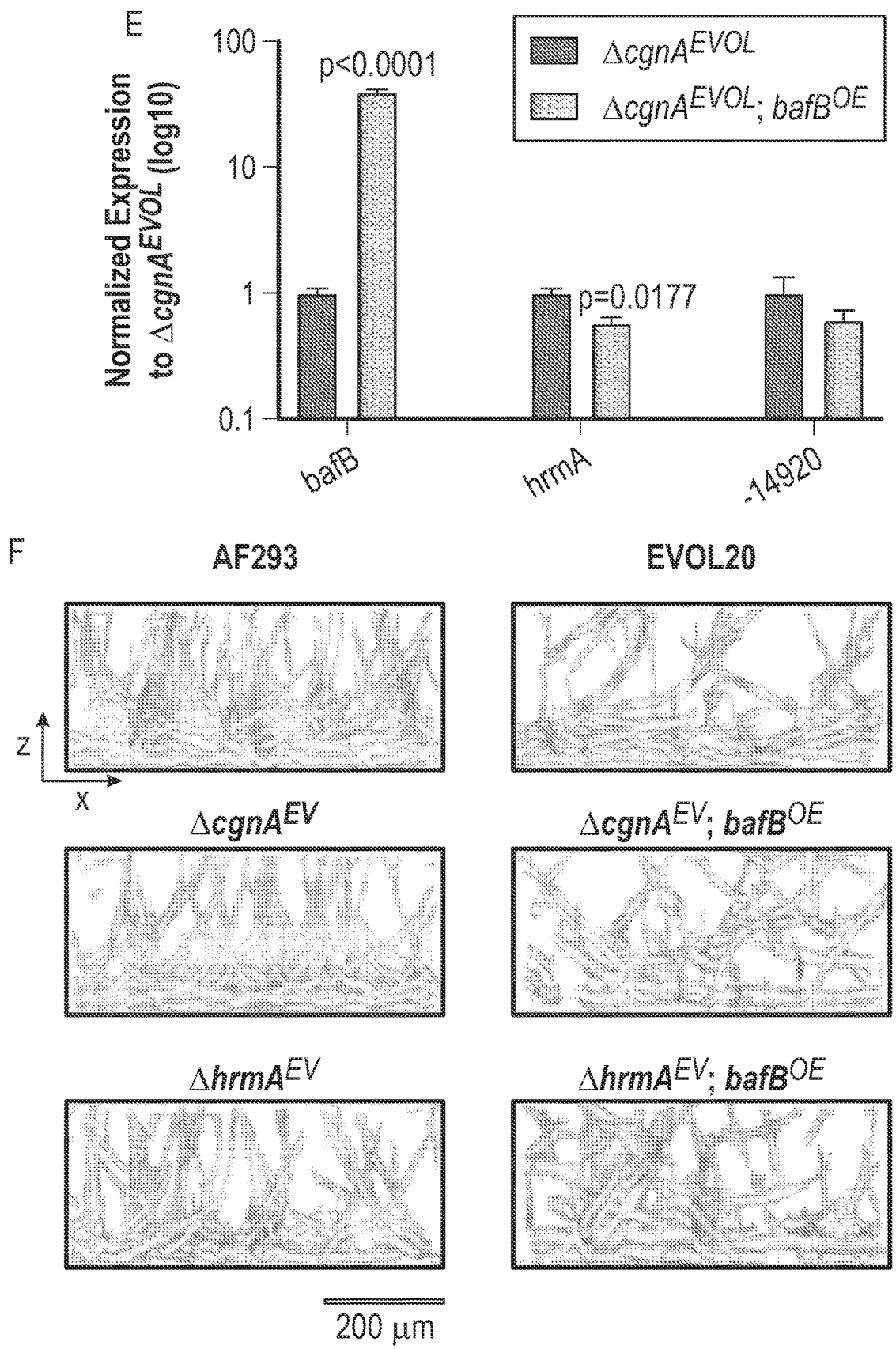

To determine if bafB from CEA10, whose protein sequence is 78.35% identical to bafA, could complement the loss of cgnA in EVOL20 (ΔcgnAEVOL), bafB was introduced with the constitutively active gpdA promoter (ΔcgnAEVOL; bafBOE). The resulting strain reverted the N-MORPH phenotype of ΔcgnAEVOL to the H-MORPH phenotype of EVOL20 with significantly increased colony furrows and percent vegetative mycelia (FIG. 29A, 29B). As mentioned above, the majority of HAC genes are not altered in expression as a result of cgnA deletion, thus the expression of other HAC genes could still be required for bafB to generate H-MORPH. The loss of hrmA in EVOL20 (ΔhrmAEVOL) reverts the colony to N-MORPH and mRNA levels of HAC genes are significantly reduced. To determine if hrmA and subsequently the HAC cluster genes that rely on hrmA for expression are necessary to generate H-MORPH in the presence of bafB, we introduced bafB with the constitutive gpdA promoter into the ΔhrmAEVOL strain (ΔhrmAEVOL; bafBOE). Even in the absence of hrmA, bafB is sufficient to generate H-MORPH and significantly increase colony furrows and percent vegetative mycelia (FIG. 29A, 29B). In addition to H-MORPH, EVOL20 has elevated hypoxic fitness (H/N) and reduced surface adherence relative to AF293 that is dependent on both hrmA and cgnA/bafA (FIG. 28C, 28D). The over expression of bafB significantly increases hypoxic fitness of ΔhrmAEVOL and ΔcgnAEVOL (FIG. 29C); and significantly reduces adherence of these strains to a plastic surface (FIG. 29D). Importantly, bafB is sufficient to complement these phenotypes in EVOL20 without increasing HAC gene mRNA levels (FIG. 29E). In fact, the mRNA levels of hrmA are slightly, but significantly, reduced as a result of constitutive bafB expression (FIG. 29E).

To test whether bafB expression alters biofilm architecture, a HAC-dependent phenotype of EVOL20, we cultured submerged biofilms for 24 hours and imaged the bottom ~300 μm of the biofilm. As a metric for biofilm architecture, we measured the angle of hyphal deviation from the vertical axis. As has been described for the N:MORPH strains AF293, ΔcgnAEVOL, and ΔhrmAEVOL, at 24 hours the bottom ~50 of the biofilm features filaments that grow along the surface and have a high deviation from the vertical. At depths above 50 μm for these N-MORPH strain, the hyphae orient vertically and grow polarized toward the air-liquid interface with little deviation from the vertical axis. In contrast, the H-MORPH strain EVOL20 features hyphae throughout all 300 μm that are oriented with a high deviation from the vertical, in other words more hyphae are oriented horizontally above 50 μm. When bafB is overexpressed in the N-MORPH strains cgnAEVOL and ΔhrmAEVOL, the resulting H-MORPH strains (FIG. 29A) develop biofilms that also resemble the architecture of EVOL20 (FIG. 29F). There is greater hyphal deviation from the vertical axis above 50 μm in the biofilms of ΔcgnAEVOL; bafBOE and ΔhrmAEVOL; bafBOE (FIG. 29F). Thus, introduction of a constitutively expressed bafB is sufficient to complement the HAC-dependent phenotypes of EVOL20.

The BafB protein is predicted to have a signal sequence at its N-terminus (SignalP, FungiDB). To gain insight into how bafB could directly impact the biofilm architecture of the ΔcgnAEVOL strain, a c-terminal green fluorescent protein (GFP) tagged allele of bafB was generated in ΔcgnAEVOL. Introduction of the GFP-tagged allele, like the native bafB allele, is able to revert the N-MORPH colony morphotype of ΔcgnAEVOL to H-MORPH. In mature hyphae, the localization of the GFP signal is present both in the cytosol within circular structures that resemble trafficking vesicles or vacuoles previously described in *A. nidulans*, and concentrated toward the distal hyphal region. At the distal region, the GFP signal is present within circular structures as well as localized along the sides of the hyphae.

Whether the protein is localized on the inner surface or the outer surface remains to be determined. However, the presence of the N-terminal secretion signal peptide and the fact protein secretion occurs at the hyphal tip lends support to the hypothesis that BafB could localize extracellularly. Importantly, the hyphal tip is the region of active fungal growth, and as the colony morphology is a consequence of fungal growth this localization pattern indicates that BafB could be acting as the H-MORPH effector. The high amino acid identity shared between bafB and the HAC-resident gene bafA raise the question of whether bafA is the HAC effector and is sufficient to generate H-MORPH in the parental strain AF293.

Figure 30:
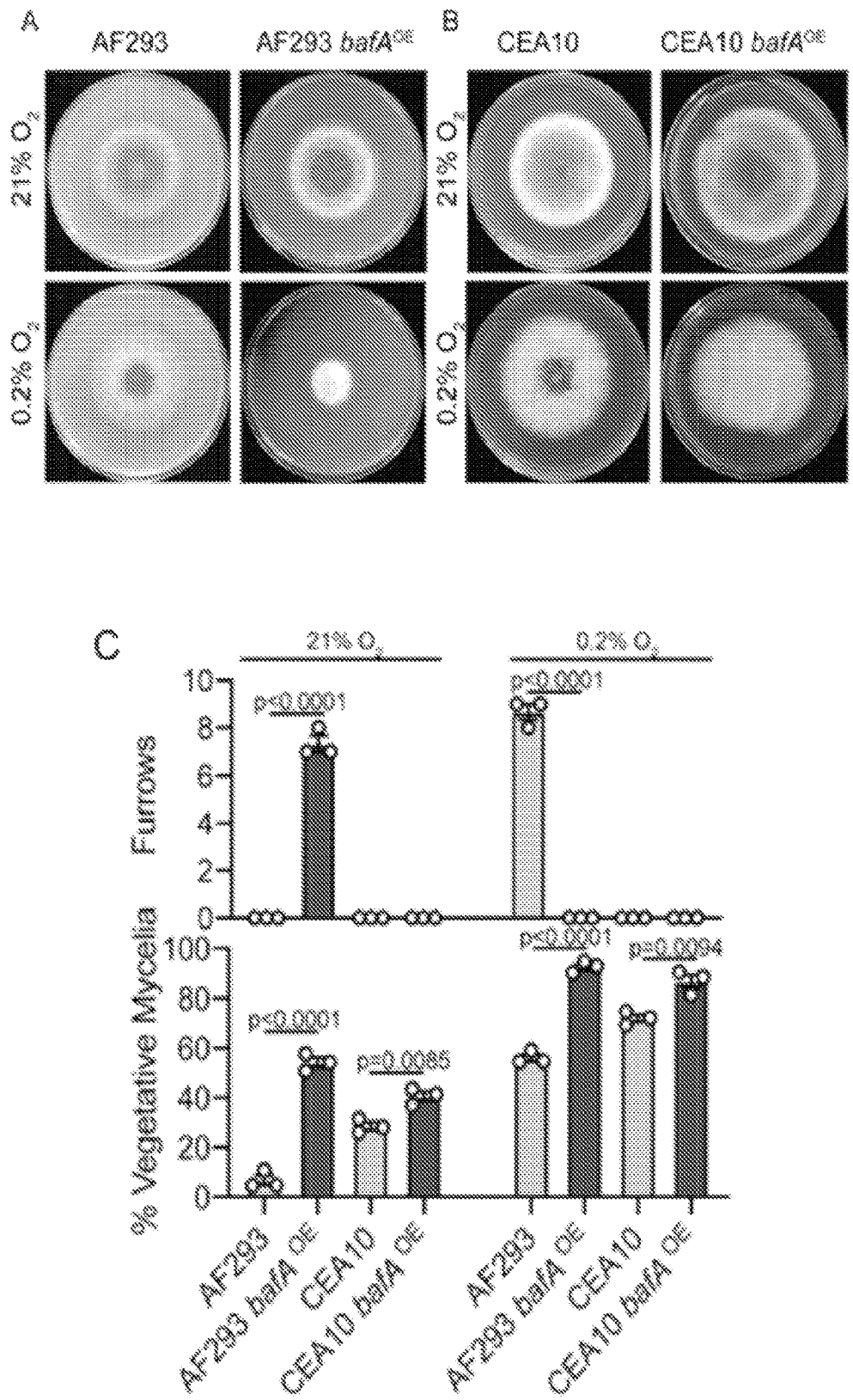
FIG. 30 depicts that the introduction of the HAC cryptic gene bafA is sufficient to generate H-MORPH in AF293 and impacts biofilm architecture in the baf-strain CEA10.
Figure 30:
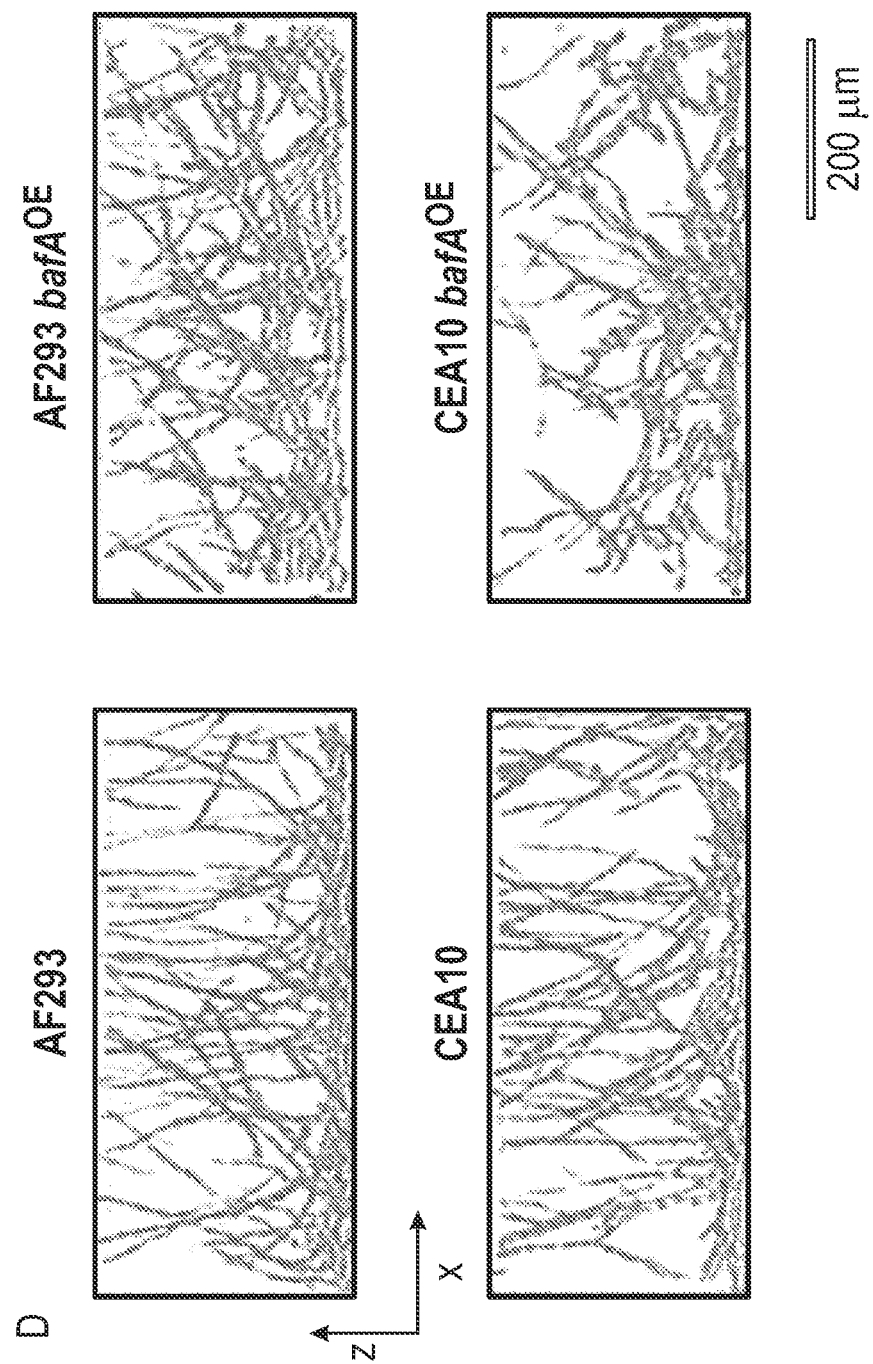
Figure 30:
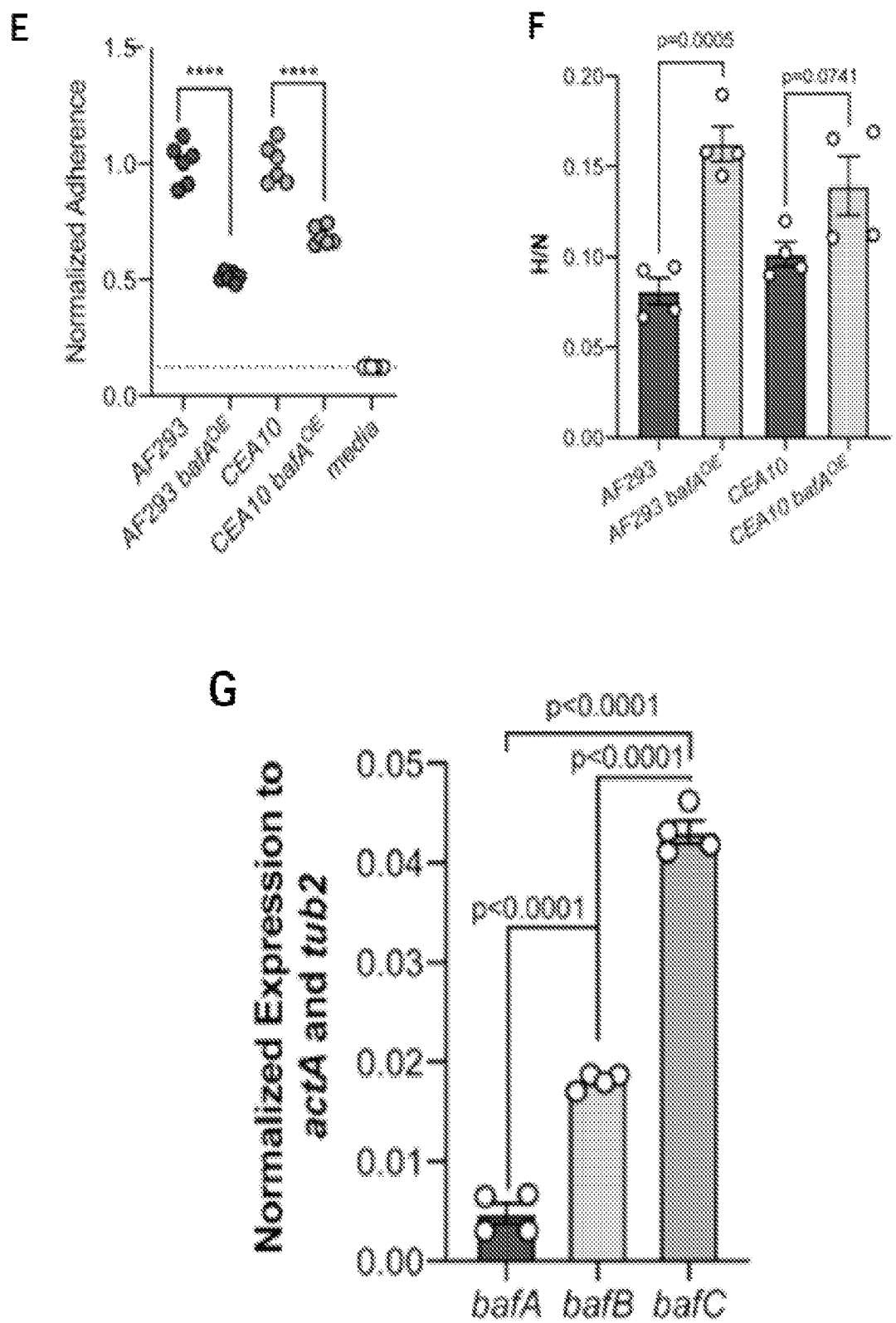

Overexpression of bafA Generates H-MORPH and Elevated Hypoxic Growth in the Absence of HAC Induction in Two Independent Strain Backgrounds In the parental strain AF293, the basal expression of HAC is low, and previous RNA-sequencing data reveals no mapped reads to the predicted bafA ORF in AF293. In addition, qRT-PCR for bafA mRNA revealed no detection above background in AF293, but over expression of an additional bafA allele results in detectable bafA mRNA. The synthetic, elevated expression of bafA in AF293 results in H-MORPH colony morphology with significantly increased colony furrows and percent vegetative mycelia relative to AF293 (FIG. 30A, 30C). Interestingly, the colony morphology in hypoxia (0.2% $O_2$) is also distinctly different as a result of bafA over expression. Unlike AF293, the colony in hypoxia is small, dense and lacks furrows and conidiation (FIG. 31A), resembling the previously published colony morphology resulting from constitutive hrmA expression (Example 1 above).

The strain CEA10 contains HAC, HBAC, and HCAC, but like AF293, bafA expression is below the level of detection by qRT-PCR in biofilm cultures but can be detected following introduction of a second over expressed bafA allele. Elevated expression of bafA in CEA10 qualitatively alters the colony morphology in normal (21% $O_2$) and low oxygen (0.2% $O_2$) and significantly increases the percent vegetative mycelia (FIG. 30B, 30C). However, no colony furrows are present as a result of bafA constitutive expression in CEA10

(FIG. 30C). Despite the absence of this macroscopic H-MORPH feature, over expression of bafA in CEA10, and in AF293, impacts biofilm architecture by increasing the deviation of hyphae from the vertical axis above the bottom 50 µm of the biofilm (FIG. 30D). Unlike AF293, even during hypoxic growth CEA10 colonies do not feature furrows, and instead abundant aerial hyphae develop generating a 'fluffy' colony morphotype. We speculate that perhaps there is a dichotomy among strains of *A. fumigatus* where some respond to low oxygen by forming aerial hyphae (i.e. CEA10) and others develop furrows (i.e. AF293).

H-MORPH in EVOL20, and other clinical isolates, coincides with reduced adherence and increased hypoxic fitness (hypoxic growth relative to normoxia growth, H/N) (Example 1 above). In both CEA10 and AF293, over expression of bafA significantly reduces hyphal adherence to plastic (FIG. 30E). Despite documented differences in hypoxic growth between AF293 and CEA10, bafA over expression also significantly increases the hypoxic fitness of both strains, though to a lesser extent in CEA10 (FIG. 30F). The inability for bafA expression to impact CEA10 colony morphology, and its apparent reduced impact on adherence and hypoxic growth relative to AF293 may be explained by the presence of the other baf genes encoded in the CEA10 genome. While bafA mRNA levels are undetectable in CEA10 during normal oxygen growth, mRNA for both bafB and bafC is detected (FIG. 30G). As the amino acid identity between these three proteins ranges from 45-78%, it was hypothesize that bafB and bafC are also sufficient to impact colony and biofilm morphology.

Figure 31:
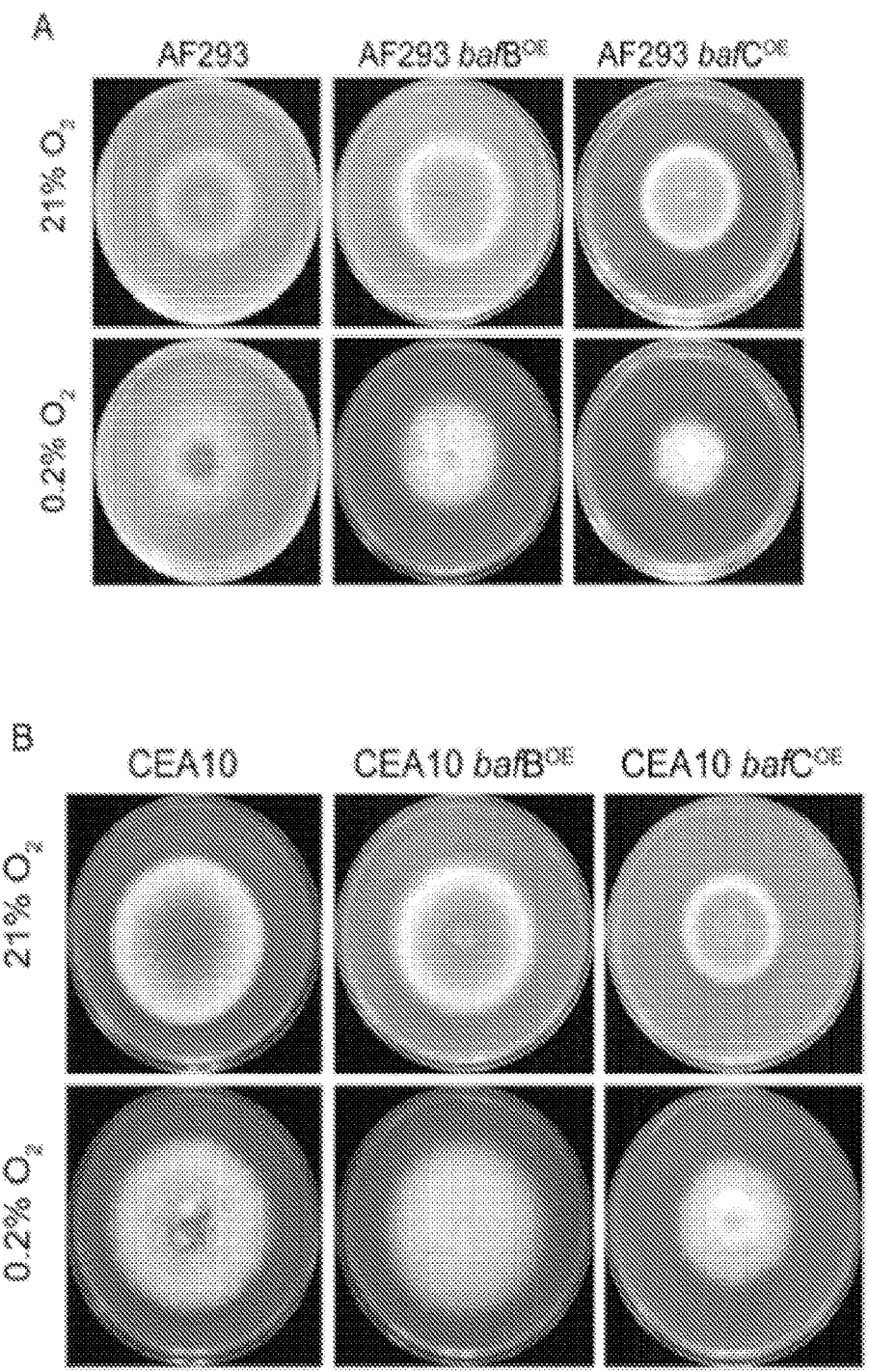
FIG. 31 depicts that the introduction of bafB and bafC impact colony and submerged biofilm morphology in independent strain backgrounds.
Figure 31:
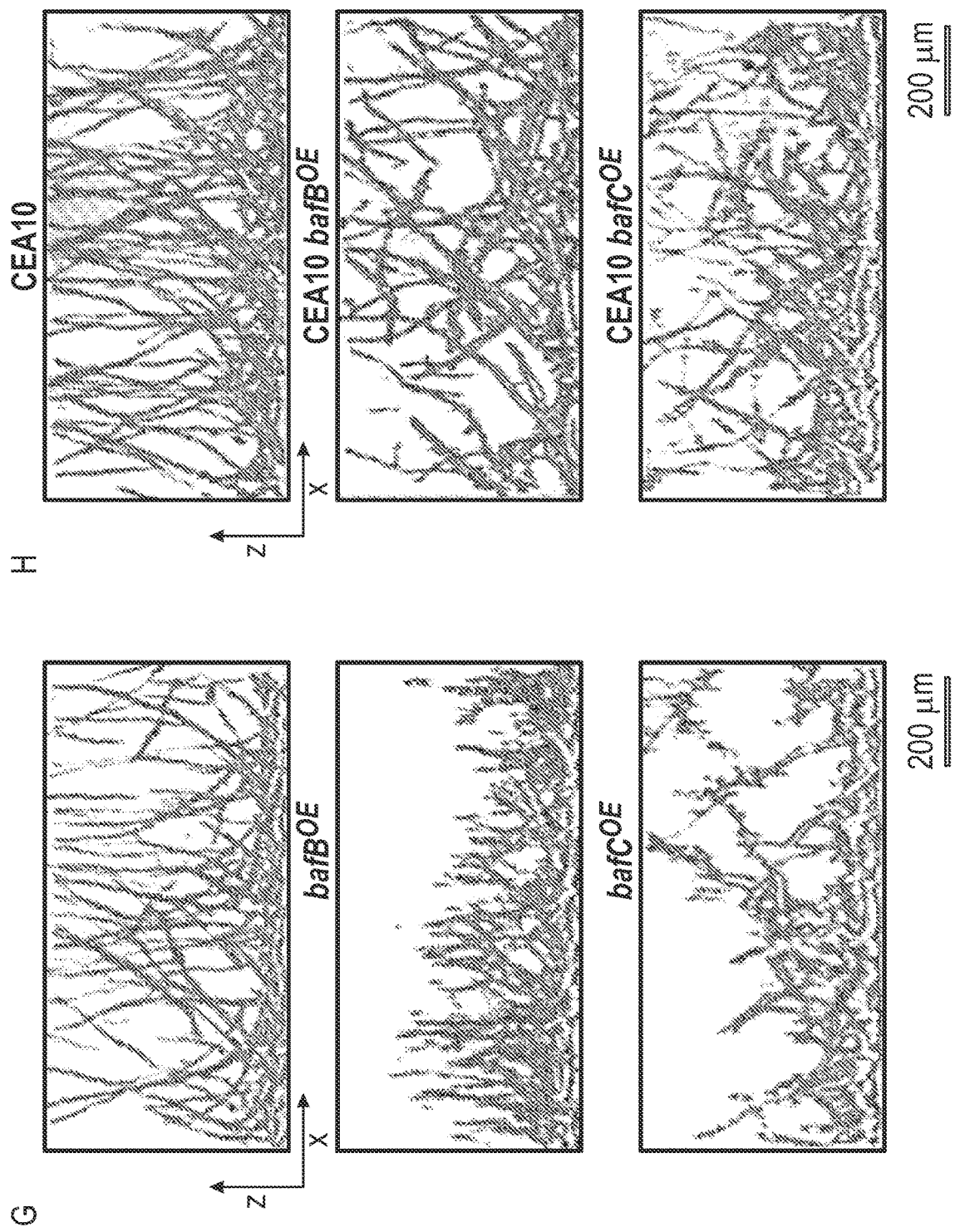

Overexpression of the bafA orthologs bafB and bafC generate H-MORPH-like phenotypes and impact hypoxic growth To determine if bafB and bafC are sufficient to generate H-MORPH phenotypes in the independent reference strains AF293 and CEA10, we used a constitutive promoter to drive expression of these genes and assessed colony morphology, adherence, and biofilm architecture. Introduction of either bafB or bafC in AF293 generates features of H-MORPH in normoxia with significantly increased furrows and percent vegetative mycelia (FIG. 31A, 31C). Similar to bafA over expression in CEA10, bafB overexpression did not induce H-MORPH features of colony furrows and increased percent vegetative mycelia in CEA10 (FIG. 31B, 31D). However, bafB expression significantly reduced overall conidiation in normoxia (21% $O_2$) and hypoxia (0.2% $O_2$), a complimentary metric to percent vegetative mycelia (FIG. 31E). Over expression of bafC in CEA10 is unique in that it does significantly increase colony furrows in normoxia relative to CEA10 (FIG. 31B, 31D). However, the percent vegetative mycelia is not significantly increased (FIG. 31D).

Despite variation in how the baf genes impact colony morphology in the two strain backgrounds, in both AF293 and CEA10 over expression of bafB or bafC results in significantly reduced adherence to plastic (FIG. 31F). CEA10 adheres less well to plastic compared to AF293, and the difference in adherence is smaller as a result of bafB or bafC over expression. As these two genes are already present and expressed in CEA10 (FIG. 30H), it is possible that this native baf expression contributes to this difference between CEA10 and AF293.

As putative biofilm architecture factors, we sought to confirm an impact of bafB and bafC on biofilm architecture, similar to that which we observe with elevated expression of bafA (FIG. 29D, 29E). In AF293, over expression of bafB visibly impacts biofilm architecture and formation in the XZ dimension (FIG. 31G) and XY dimension. The XY dimension reveals dense hyphal growth and abundant hyphal branching. The XZ dimension reveals a stunted 24 hour biofilm that reaches heights of only 200-250 µm (FIG. 31G). Similarly, regions of the 24 hour biofilms generated by the overexpression of bafC in AF293 (AF293 bafC$_{OE}$) are also stunted with evidence of hyphae that are hyper branching (FIG. 31G). In regards to biofilm architecture as defined by hyphal orientation to the vertical axis, over expression of bafC but not bafB in AF293 results in increased deviation above 50 µm. In CEA10, over expression of bafB and bafC results in increased deviation from the vertical axis above 50 µm in 24 hour biofilms (FIG. 31H). There is also no evidence for hyper branching as a result of elevated bafB or bafC expression in CEA10. These data support a role for all three proposed baf genes in biofilm architecture, through multiple metrics, in two independent strain backgrounds of *A. fumigatus*.

Figure 32:
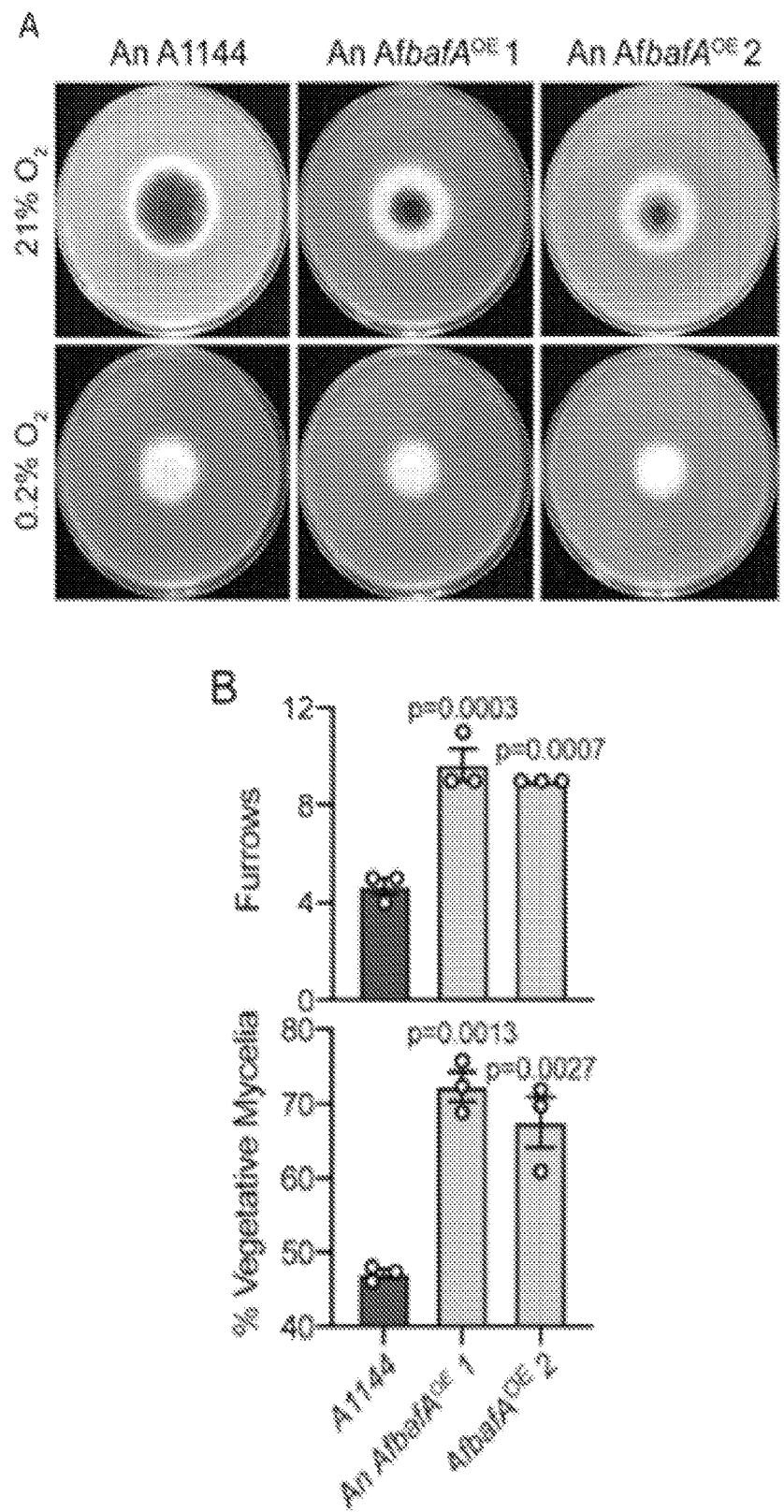
FIG. 32 depicts that the introduction of *A. fumigatus* bafA is sufficient to generate H-MORPH in *Aspergillus niger*.
Figure 32:
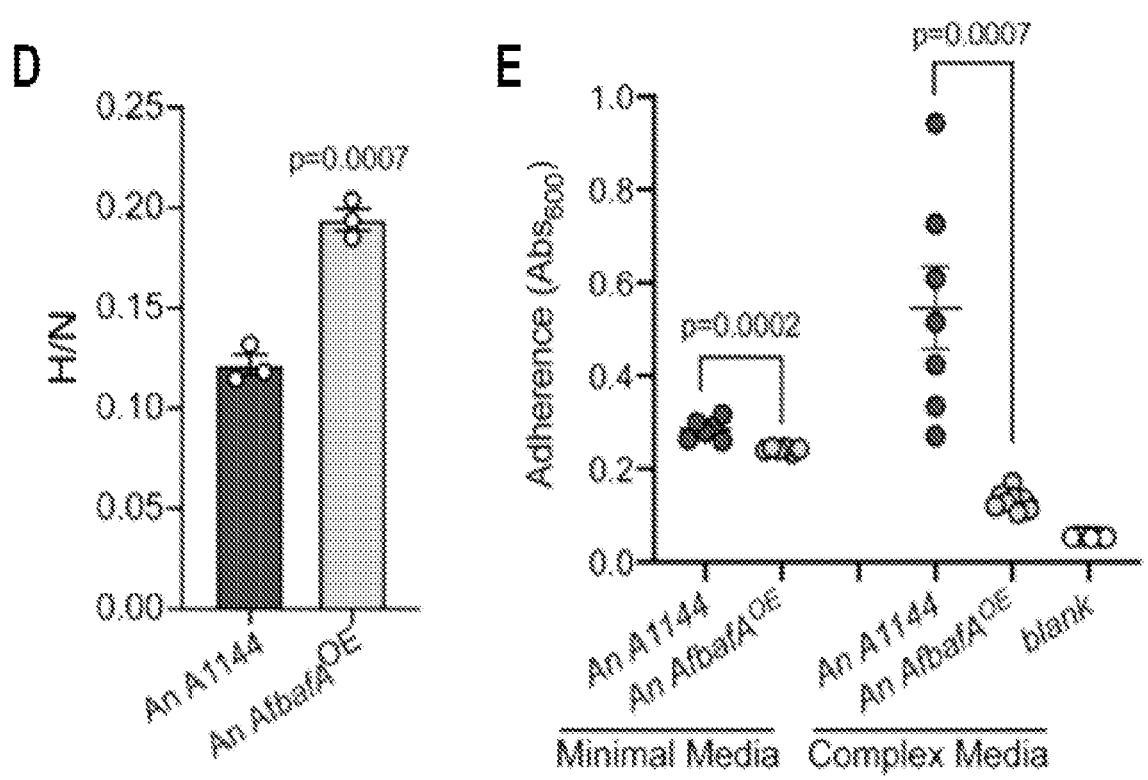

Introduction of *A. fumigatus* bafA into *Aspergillus niger* generates H-MORPH and simultaneously increases hypoxic growth Among the Aspergilli, hrmA is absent from the notable species of *A. nidulans, A. oryzae*, and *A. niger* (Example 1 above). However, *Aspergillus niger* strain CBS 513.88 encodes a gene, An08g12010, with 69% nucleotide identity to *A. fumigatus* bafA and 41.03% amino acid identity to the predicted protein sequence of BafA. This suggests that the role of baf or baf-like genes may be conserved in other Aspergillus species. It was next determined if *A. fumigatus* bafA (AfbafA) could influence colony morphology, biofilm architecture, hypoxic growth, and adherence in the *A. niger* reference strain A1144. This strain was selected for its robust growth at 37° C. and the ease at which it is genetically manipulated. *A. fumigatus* bafA was overexpressed in *A. niger* with the constitutive gpdA promoter to generate An AfbafAOE Over expression of bafA in *A. niger* generated H-MORPH colonies with significantly increased colony furrows and percent vegetative mycelia compared to the control A1144 (FIG. 32A, 32B). Intriguingly, the over expression of AfbafA in *A. niger* resulted in the production of a bright yellow pigment, shown here in two independent transformants (FIG. 32A). The production of yellow pigments by *A. niger* has been noted in the literature for decades as a result of various growth conditions and genetic manipulations.

The reference strain A1144 forms a submerged biofilm with dense filaments within the first 50 µm that are oriented perpendicular to the vertical axis (FIG. 32C). Above the −50 µm at the base of the biofilm, filaments become oriented more closely along the vertical axis, similar to what has been observed with N-MORPH strains of *A. fumigatus* (i.e. AF293) (FIG. 32C). Introduction of the constitutively expressed AfbafA alters the biofilm of A1144. At 24 hours, the hyphae are stunted reaching heights of only 200-250 µm in height (FIG. 32C). These stunted filaments highly deviate from the vertical axis throughout the height of the biofilm indicating that AfbafA is capable of impacting biofilm architecture across species. Not only does AfbafA impact the colony morphology to generate H-MORPH and modulate the biofilm architecture, but it also generates other H-MORPH and EVOL20 associated phenotypes including increased hypoxia fitness and reduced adherence. In AF293 and CEA10 expression of bafA results in increased hypoxia fitness (hypoxic growth normalized to normoxic growth); similarly, the hypoxia fitness of A1144 significantly increases with constitutive expression of AfbafA (FIG. 32D). Adherence of *A. fumigatus* is quantified in minimal media, however, the adherence of the reference *A. niger* strain A1144 is low in minimal media. Thus, the impact of AfbafA on *A. niger* adherence in both minimal and complex media where A1144 adherence is more robust was quantified. In both conditions, adherence was significantly reduced with expression of AfbafA compared to A1144 (FIG. 32E). Not only do reduced adherence and increased hypoxia fitness track with H-MORPH on the macro scale and microscale as has been observed previously, but they do so as a result of bafA expression across different *Aspergillus* species. The ability of bafA alone to generate these phenotypes in the two independent species of *Aspergillus* supports its role as the effector protein of HAC, and supports its application to modify biofilm architecture and function in *Aspergillus* species.

What is claimed:

1. A filamentous fungal host cell, comprising an exogenous nucleotide sequence encoding an Aspergillus fumigatus biofilm architecture factor (baf) protein, wherein the baf protein comprises (a) bafA, or a homolog or ortholog thereof having bafA activity, (b) bafB, or a homolog or ortholog thereof having bafB activity, and (c) bafC, or a homolog or ortholog thereof having bafC activity, the bafA protein or a homolog or ortholog thereof having bafA activity comprising at least 90% identity to the amino acid sequence of SEQ ID NO: 13; the bafB protein or a homolog or ortholog thereof having bafB activity comprising at least 90% identity to the amino acid sequence of SEQ ID NO: 14; and the bafC protein or a homolog or ortholog thereof having bafC activity comprising at least 90% identity to the amino acid sequence of SEQ ID NO: 15.

2. The filamentous fungal host cell of claim 1, wherein the filamentous fungal host cell is not *Aspergillus fumigatus*.

3. The filamentous fungal host cell of claim 1, wherein the bafA protein comprises the amino acid sequence of SEQ ID NO: 13; or the bafB protein comprises the amino acid sequence of SEQ ID NO: 14; or the bafC protein comprises the amino acid sequence of SEQ ID NO: 15.

4. A method of increasing fungal secretion of one or more products of interest, increasing the production of one or more products of interest, and/or reducing oxygen consumption of a filamentous fungal host cell, the method comprising introducing into the filamentous fungal host cell one or more polynucleotide sequences encoding one or both of an hrmA protein and a baf protein to make the filamentous fungal host cell of claim 1.

5. The method of claim 4, wherein
the hrmA protein comprises the amino acid sequence of SEQ ID NO: 12; and/or the baf protein comprises the amino acid sequence of SEQ ID NO: 13, SEQ ID NO: 14, SEQ ID NO: 15, or SEQ ID NO: 16.

6. The method of claim 4, wherein oxygen consumption is reduced by 10% to 90%.

7. The method of claim 4, wherein the polynucleotide sequence is introduced into the filamentous fungal host cell via transformation, optionally wherein the transformation comprises one or more of protoplast-mediated transformation, *Agrobacterium*-mediated transformation, electroporation, biolistic transformation, and shock-wave-mediated transformation.

* * * * *